United States Patent
Bartholomeus et al.

(10) Patent No.: US 11,479,539 B2
(45) Date of Patent: Oct. 25, 2022

(54) SMALL MOLECULE MODULATORS OF THE BTB DOMAIN OF KEAP1

(71) Applicant: MedImmune Limited, Cambridge (GB)

(72) Inventors: Johan Bartholomeus, Montreal (CA); Roland Bürli, Cambridge (GB); Rebecca Jarvis, Cambridge (GB); Shawn Johnstone, Montreal (CA); Thor Ostenfeld, Cambridge (GB); Ina Terstiege, Södertälje (SE); Massimiliano Travagli, Cracow (PL); Stephane Turcotte, Montreal (CA)

(73) Assignee: MedImmune Limited, Cambridge (GB)

( * ) Notice: Subject to any disclaimer, the term of this patent is extended or adjusted under 35 U.S.C. 154(b) by 116 days.

(21) Appl. No.: 16/955,403

(22) PCT Filed: Dec. 20, 2018

(86) PCT No.: PCT/EP2018/086436
§ 371 (c)(1),
(2) Date: Jun. 18, 2020

(87) PCT Pub. No.: WO2019/122265
PCT Pub. Date: Jun. 27, 2019

(65) Prior Publication Data
US 2021/0094931 A1    Apr. 1, 2021

Related U.S. Application Data

(60) Provisional application No. 62/609,463, filed on Dec. 22, 2017.

(51) Int. Cl.
C07D 401/04    (2006.01)
C07D 213/61    (2006.01)
C07D 417/04    (2006.01)

(52) U.S. Cl.
CPC ......... C07D 401/04 (2013.01); C07D 213/61 (2013.01); C07D 417/04 (2013.01)

(58) Field of Classification Search
CPC .............. C07D 401/04; C07D 213/61; C07D 417/04
See application file for complete search history.

(56) References Cited

U.S. PATENT DOCUMENTS

| 4,172,896 | A | 10/1979 | Uno et al. |
|---|---|---|---|
| 5,358,970 | A | 10/1994 | Ruff et al. |
| 5,427,798 | A | 6/1995 | Ludwig et al. |
| 5,541,231 | A | 7/1996 | Ruff et al. |
| 5,731,000 | A | 3/1998 | Ruff et al. |
| 5,763,493 | A | 6/1998 | Ruff et al. |
| 6,119,073 | A | 9/2000 | Havel |
| 6,583,124 | B2 | 6/2003 | Asgharian |
| 2005/0004074 | A1 | 1/2005 | Lyons et al. |
| 2005/0031697 | A1 | 2/2005 | Vehige et al. |
| 2005/0059744 | A1 | 3/2005 | Donello et al. |
| 2005/0080056 | A1 | 4/2005 | Horn |

FOREIGN PATENT DOCUMENTS

| WO | 2013/067036 A1 | 5/2013 |
|---|---|---|
| WO | 2015142218 A1 | 9/2015 |

OTHER PUBLICATIONS

Cancer and Metastasis Reviews (1998), 17(1), 91-106.*
Science (1999), vol. 286, 531-537.*
Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003], Retrieved from the internet, URL;http;//www.cnn/com/2003/HEALTH/conditions/09/24/alzheimers.drug.ap/index.html>.*
Simplicio et al., Prodrugs for Amines, Molecules, (20080000), vol. 13, pp. 519-547, 2008.
Berge et al., "Pharmaceutical Salts", Journal of Pharmaceutical Science, (19770000), vol. 66, doi:doi:10.1002/jps.2600660104, pp. 1-19, XP002675560 DOI: http://dx.doi.org/10.1002/jps.2600660104, 1977.
Jen-Dar Wu et al., An improved general synthetic approach to cisclerodane diterpenoids. A more efficient total synthesis of (+)-6-acetoxy-2-oxokolavenool. Tetrahedron Letters, 2001, 42, pp. 4207-4209.
Fraser F. Fleming et al., Unsaturated Nitriles: A Domino Ozonolysis-Aldol Synthesis of Highly Reactive Oxonitriles. Journal of Organic Chemistry, 1997, 62, pp. 3036-3037.

* cited by examiner

Primary Examiner — Rebecca L Anderson

(57) ABSTRACT

The present application relates to compounds of formula (I') or formula (I), such as formula (Ia), and their pharmaceutical compositions/preparations. This application further relates to methods of treating or preventing neurodegenerative disorders, such as Alzheimer's disease (AD), Parkinson's disease (PD), Huntington disease (HD) and other CAG-triplet repeat (or polyglutamine) diseases, amyotrophic lateral sclerosis (ALS; Lou Gehrig's disease), diffuse Lewy body disease, chorea-acanthocytosis, primary lateral sclerosis, multiple sclerosis (MS), frontotemporal dementia, Friedreich's ataxia, acute head injury, and epilepsy (repression of microglia activation).

15 Claims, No Drawings

SMALL MOLECULE MODULATORS OF THE BTB DOMAIN OF KEAP1

RELATED APPLICATION

This application claims the benefit of priority to U.S. Provisional Patent Application No. 62/609,463, filed Dec. 22, 2017, which application is hereby incorporated by reference in its entirety.

BACKGROUND

Nuclear factor (erythroid-derived 2)-like 2 (Nrf2) is a ubiquitously expressed antioxidant transcription factor which binds to and activates antioxidant response elements (AREs). (Deshmukh, P. et al. (2016). The Keap1-Nrf2 pathway: promising therapeutic target to counteract ROS-mediated damage in cancers and neurodegenerative diseases. Biophysical Reviews, 9(1), 41-56.) Nrf2 is tightly regulated in the cytosol by the repressor protein, Keap1 (Kelch-like ECH-associated protein 1), which is a component of the Cullin 3 (CUL3)-based E3 ubiquitin ligase complex. This complex is known to control the stability and accumulation of Nrf2 by ubiquinating Nrf2 leading to degradation by the proteasome. Under stress conditions, Nrf2 dissociates from Keap1, allowing Nrf2 to migrate to the nucleus, where it can bind AREs and increase the transcription of numerous antioxidative and cytoprotective genes such as heme oxygenase-1, NAD(P)H:quinone reductase, glutathione S-transferase, glutamylcysteine synthetase, and UDP-glucuronosyl transferases. (Sussan T E, et al. Targeting Nrf2 with the triterpenoid CDDO-imidazolide attenuates cigarette smoke-induced emphysema and cardiac dysfunction in mice. Proc Natl Acad Sci USA 2009; 106:250-5.)

The Nrf2 signaling pathway plays a critical role in protecting cells from oxidative stress in various pathophysiological conditions, such as chronic obstructive pulmonary disease (COPD) and cancer; and in neurodegenerative diseases such as Alzheimer's disease, Parkinson's disease, Huntington's disease, Ischaemia and stroke. Activation of Nrf2 induces the expression of numerous cytopreventative and detoxification enzymes, which provide protection from the various pathophysiological conditions. Thus, therapies which target the Nrf2 signaling pathway, including Keap1 inhibitors, may provide treatments for diseases which encompass oxidative stress components.

SUMMARY OF APPLICATION

The present application provides a compound of formula (I')

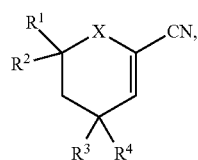

or a pharmaceutically acceptable salt thereof, wherein X is selected from —C(O)— and —S(O)$_2$—; $R^1$ and $R^2$ each independently is selected from H and $C_{1-6}$ alkyl; or $R^1$ and $R^2$ taken together with the carbon to which they are attached form a spirocycloalkyl or spiroheterocycloalkyl ring; $R^3$ is selected from hydroxyl and optionally substituted alkoxy; $R^4$ is selected from optionally substituted aryl and optionally substituted heteroaryl.

In certain embodiments, X is —C(O)—. In certain embodiments, X is —S(O)$_2$—.

In certain embodiments wherein X is —S(O)$_2$—, $R^1$ and $R^2$ each is H.

The present application provides a compound of formula (I),

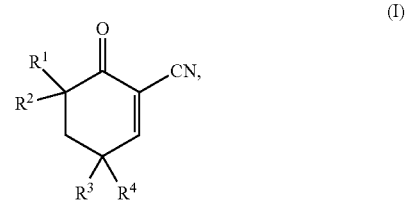

or a pharmaceutically acceptable salt thereof, wherein $R^1$ and $R^2$ each independently is selected from $C_{1-6}$ alkyl; or $R^1$ and $R^2$ taken together with the carbon to which they are attached form a spirocycloalkyl or spiroheterocycloalkyl ring; $R^3$ is selected from hydroxyl and optionally substituted alkoxy; $R^4$ is selected from optionally substituted aryl and optionally substituted heteroaryl. In certain embodiments, the present application provides a compound of formula (I), or a pharmaceutically acceptable salt thereof, wherein $R^1$ and $R^2$ each independently is selected from $C_{1-6}$ alkyl; or $R^1$ and $R^2$ taken together with the carbon to which they are attached form a spirocycloalkyl ring; $R^3$ is selected from hydroxyl and optionally substituted alkoxy; $R^4$ is selected from optionally substituted aryl and optionally substituted heteroaryl.

In certain embodiments, $R^4$ is selected from optionally substituted phenyl, optionally substituted pyridinyl, optionally substituted isoquinolinyl, optionally substituted pyrazinyl, optionally substituted thiophenyl, and optionally substituted thiazolyl, such as optionally substituted pyridinyl.

In certain embodiments, $R^4$ is optionally substituted with one or more $R^5$; and $R^5$, independently for each occurrence, is selected from halogen, CN, optionally substituted alkyl, optionally substituted alkenyl, optionally substituted alkynyl, optionally substituted alkylsulfonyl, optionally substituted alkoxyl, optionally substituted cycloalkyl, optionally substituted cycloalkenyl, optionally substituted heterocycloalkyl, optionally substituted heterocycloalkenyl, optionally substituted aryl, and optionally substituted heteroaryl. In certain such embodiments, $R^4$ is substituted with one or two $R^5$. In certain such embodiments, $R^4$ is substituted with two $R^5$. In certain embodiments, $R^5$, independently for each occurrence, is selected from halogen, optionally substituted alkyl, optionally substituted alkenyl, optionally substituted alkynyl, optionally substituted alkoxyl, optionally substituted cycloalkyl, optionally substituted cycloalkenyl, optionally substituted heterocycloalkyl, optionally substituted heterocycloalkenyl, optionally substituted phenyl, optionally substituted pyrazolyl, optionally substituted pyridinyl, optionally substituted thiazolyl, optionally substituted imidazolyl, optionally substituted pyrimidinyl, optionally substituted isoxazolyl, optionally substituted isothiazolyl, and optionally substituted triazolopyridinyl, such as halogen, optionally substituted alkyl, optionally substituted alkoxyl, optionally substituted aryl, and optionally substituted heteroaryl. In certain embodiments, $R^5$, independently for each occurrence, is selected from halogen, optionally substituted alkyl, optionally substituted alkoxyl, optionally substituted phenyl, optionally substituted pyrazolyl, optionally substituted pyridinyl, and optionally substituted thiazolyl. In certain embodiments, $R^5$, independently for each occurrence, is selected from halogen and optionally substituted alkyl.

In certain embodiments, $R^5$, independently for each occurrence, is optionally substituted with one or more $R^6$; and $R^6$, independently for each occurrence, is selected from halogen, CN, oxo, alkyl, alkenyl, alkynyl, alkoxy, alkylsulfonyl, cycloalkyl, cycloalkenyl, heterocycloalkyl, heterocycloalkenyl, aryl, and heteroaryl. In certain such embodiments, $R^6$, independently for each occurrence, is selected from halogen, CN, oxo, alkyl, alkoxy, alkylsulfonyl, and cycloalkyl, such as halogen, alkyl, and alkylsulfonyl.

The present application further provides a compound of formula (Ia)

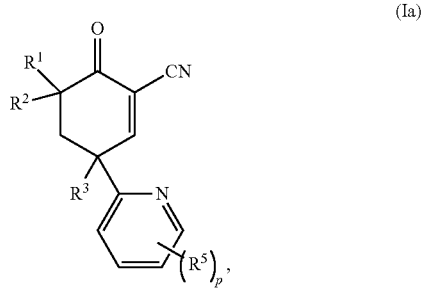

or a pharmaceutically acceptable salt thereof, wherein $R^1$ and $R^2$ each independently is selected from $C_{1-6}$ alkyl; or $R^1$ and $R^2$ taken together with the carbon to which they are attached form a spirocycloalkyl or spiroheterocycloalkyl ring; $R^3$ is selected from hydroxyl and optionally substituted alkoxy; $R^5$, independently for each occurrence, is selected from halogen, CN, optionally substituted alkyl, optionally substituted alkenyl, optionally substituted alkynyl, optionally substituted alkylsulfonyl, optionally substituted alkoxyl, optionally substituted cycloalkyl, optionally substituted cycloalkenyl, optionally substituted heterocycloalkyl, optionally substituted heterocycloalkenyl, optionally substituted aryl, and optionally substituted heteroaryl; and p is selected from 0, 1, 2, 3, and 4. In certain embodiments, the present application provides a compound of formula (Ia), or a pharmaceutically acceptable salt thereof, wherein $R^1$ and $R^2$ each independently is selected from $C_{1-6}$ alkyl; or $R^1$ and $R^2$ taken together with the carbon to which they are attached form a spirocycloalkyl ring; $R^3$ is selected from hydroxyl and optionally substituted alkoxy; $R^5$, independently for each occurrence, is selected from halogen, CN, optionally substituted alkyl, optionally substituted alkenyl, optionally substituted alkynyl, optionally substituted alkylsulfonyl, optionally substituted alkoxyl, optionally substituted cycloalkyl, optionally substituted cycloalkenyl, optionally substituted heterocycloalkyl, optionally substituted heterocycloalkenyl, optionally substituted aryl, and optionally substituted heteroaryl; and p is selected from 0, 1, 2, 3, and 4.

In certain embodiments, p is selected from 1 and 2. In certain embodiments, p is 2.

In certain embodiments, $R^5$, independently for each occurrence, is selected from halogen, optionally substituted alkyl, optionally substituted alkenyl, optionally substituted alkynyl, optionally substituted alkoxyl, optionally substituted cycloalkyl, optionally substituted cycloalkenyl, optionally substituted heterocycloalkyl, optionally substituted heterocycloalkenyl, optionally substituted phenyl, optionally substituted pyrazolyl, optionally substituted pyridinyl, optionally substituted thiazolyl, optionally substituted imidazolyl, optionally substituted pyrimidinyl, optionally substituted isoxazolyl, optionally substituted isothiazolyl, and optionally substituted triazolopyridinyl, such as halogen, optionally substituted alkyl, optionally substituted alkoxyl, optionally substituted aryl, and optionally substituted heteroaryl. In certain embodiments, $R^5$, independently for each occurrence, is selected from halogen, optionally substituted alkyl, optionally substituted alkoxyl, optionally substituted phenyl, optionally substituted pyrazolyl, optionally substituted pyridinyl, and optionally substituted thiazolyl. In certain embodiments, $R^5$, independently for each occurrence, is selected from halogen and optionally substituted alkyl.

In certain embodiments, p is 2 and $R^5$, independently for each occurrence, is selected from halogen and optionally substituted alkyl. In certain embodiments, p is 2 and one occurrence of $R^5$ is halogen and the other occurrence of $R^5$ is optionally substituted alkyl. In certain such embodiments, one occurrence of $R^5$ is —F and the other occurrence of $R^5$ is —CH(F)$_2$.

In certain embodiments, $R^5$, independently for each occurrence, is optionally substituted with one or more $R^6$; and $R^6$, independently for each occurrence, is selected from halogen, CN, oxo, alkyl, alkenyl, alkynyl, alkoxy, alkylsulfonyl, cycloalkyl, cycloalkenyl, heterocycloalkyl, heterocycloalkenyl, aryl, and heteroaryl. In certain such embodiments, $R^6$, independently for each occurrence, is selected from halogen, CN, oxo, alkyl, alkoxy, alkylsulfonyl, and cycloalkyl, such as halogen, alkyl, and alkylsulfonyl.

In certain embodiments, $R^1$ and $R^2$ each independently is selected from $C_{1-4}$ alkyl. In certain such embodiments, $R^1$ and $R^2$ each independently is selected from methyl and ethyl. In certain embodiments, $R^1$ and $R^2$ are both methyl.

In certain embodiments, $R^1$ and $R^2$ taken together with the carbon to which they are attached form a spirocyclopropyl, spirocyclobutyl, or spirocyclopentyl ring. In certain embodiments, $R^1$ and $R^2$ taken together with the carbon to which they are attached form a spirocyclopropyl or spirocyclopentyl ring. In certain such embodiments, $R^1$ and $R^2$ taken together with the carbon to which they are attached form a spirocyclopropyl ring.

In certain embodiments, $R^3$ is optionally substituted alkoxy. In certain such embodiments, $R^3$ is methoxy. In other embodiments, $R^3$ is trifluoromethoxy. In yet other embodiments, $R^3$ is methoxy-$d_3$.

The present application further provides a compound selected from any one of compounds 1-57, 59-94, 96, 98-120, 122-137, 139-158, 160-212, and 214-240, and pharmaceutically acceptable salts thereof.

The present application provides pharmaceutical compositions comprising (a) a compound as disclosed herein; and (b) a pharmaceutically acceptable excipient.

The present application provides a compound a disclosed herein or a pharmaceutical composition as disclosed herein (e.g., a compound of formula (I'), (I), or (Ia), or a pharmaceutically acceptable salt of a compound of formula (I'), (I), or (Ia), or a pharmaceutical composition comprising (a) a compound of formula (I'), (I), or (Ia), or a pharmaceutically acceptable salt of a compound of formula (I'), (I), or (Ia)) for use as a medicament.

The present application further provides methods of treating a disease comprising administering to a subject in need thereof an effective amount of an activator of Nrf2 transcription comprising at least one compound or pharmaceutical composition as disclosed herein (e.g., a compound of formula (I'), (I), or (Ia), or a pharmaceutically acceptable salt of a compound of formula (I'), (I), or (Ia), or a pharmaceutical composition comprising (a) a compound of formula (I'), (I), or (Ia), or a pharmaceutically acceptable salt of a compound of formula (I'), (I), or (Ia)).

The present application further provides methods of inhibiting a Keap1 protein, comprising contacting a cell with an effective amount of at least one compound or pharmaceutical composition as disclosed herein (e.g., a compound of formula (I'), (I), or (Ia), or a pharmaceutically acceptable salt of a compound of formula (I) or (Ia), or a pharmaceutical composition comprising (a) a compound of formula (I'), (I), or (Ia), or a pharmaceutically acceptable salt of a compound of formula (I'), (I), (I'), (I), or (Ia)).

The present application further provides methods of treating a neurodegenerative disorder in a subject, comprising administering to a subject in need thereof an effective amount of at least one compound or pharmaceutical composition as disclosed herein (e.g., a compound of formula (I'), (I), or (Ia), or a pharmaceutically acceptable salt of a compound of formula (I) or (Ia), or a pharmaceutical composition comprising (a) a compound of formula (I'), (I), or (Ia), or a pharmaceutically acceptable salt of a compound of formula (I'), (I), or (Ia)). In certain such embodiments, the neurodegenerative disorder is selected from Alzheimer's disease (AD), Parkinson's disease (PD), Huntington disease (HD) and other CAG-triplet repeat (or polyglutamine) diseases, amyotrophic lateral sclerosis (ALS; Lou Gehrig's disease), diffuse Lewy body disease, chorea-acanthocytosis, primary lateral sclerosis, multiple sclerosis (MS), frontotemporal dementia, Friedreich's ataxia, acute head injury, and epilepsy (repression of microglia activation).

DETAILED DESCRIPTION OF THE APPLICATION

The present application provides a compound of formula (I')

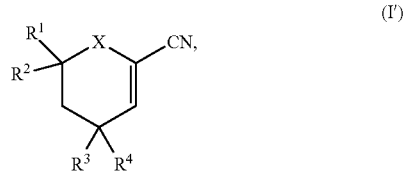

(I')

or a pharmaceutically acceptable salt thereof, wherein:

X is selected from —C(O)— and —S(O)$_2$—;

$R^1$ and $R^2$ each independently is selected from H and $C_{1-6}$ alkyl; or $R^1$ and $R^2$ taken together with the carbon to which they are attached form a spirocycloalkyl or spiroheterocycloalkyl ring;

$R^3$ is selected from hydroxyl and optionally substituted alkoxy;

$R^4$ is selected from optionally substituted aryl and optionally substituted heteroaryl.

In certain embodiments, X is —C(O)—.

In certain embodiments, X is —S(O)$_2$—.

In certain embodiments, X is —S(O)$_2$—, and $R^1$ and $R^2$ each independently is H.

In certain embodiments, X is —C(O)—, and $R^1$ and $R^2$ each independently is selected from $C_{1-6}$ alkyl; or $R^1$ and $R^2$ taken together with the carbon to which they are attached form a spirocycloalkyl or spiroheterocycloalkyl ring. In certain such embodiments, $R^1$ and $R^2$ each independently is selected from $C_{1-6}$ alkyl; or $R^1$ and $R^2$ taken together with the carbon to which they are attached form a spirocycloalkyl ring.

In certain embodiments, $R^1$ and $R^2$ each independently is selected from $C_{1-4}$ alkyl. In certain embodiments, $R^1$ and $R^2$ each independently is selected from methyl and ethyl. In certain embodiments, $R^1$ and $R^2$ are both methyl.

In certain embodiments, $R^1$ and $R^2$ taken together with the carbon to which they are attached form a spirocycloalkyl ring. In certain such embodiments, $R^1$ and $R^2$ taken together with the carbon to which they are attached form a spirocyclopropyl, spirocyclobutyl, or spirocyclopentyl ring. In certain embodiments, $R^1$ and $R^2$ taken together with the carbon to which they are attached form a spirocyclopropyl or spirocyclopentyl ring. In certain embodiments, $R^1$ and $R^2$ taken together with the carbon to which they are attached form a spirocyclopropyl ring.

In certain embodiments, $R^1$ and $R^2$ taken together with the carbon to which they are attached form a spiroheterocycloalkyl ring. In certain such embodiments, $R^1$ and $R^2$ taken together with the carbon to which they are attached form an azetidine or an oxetane ring.

In certain embodiments, $R^3$ is optionally substituted alkoxy. In certain embodiments, $R^3$ is methoxy. In certain embodiments, $R^3$ is trifluoromethoxy. In certain embodiments, $R^3$ is methoxy-d$_3$.

In certain embodiments, $R^4$ is selected from optionally substituted phenyl, optionally substituted pyridinyl, optionally substituted isoquinolinyl, optionally substituted pyrazinyl, optionally substituted thiophenyl, and optionally substituted thiazolyl. In certain embodiments, $R^4$ is optionally substituted pyridinyl.

In certain embodiments, $R^4$ is optionally substituted with one or more $R^5$; and $R^5$, independently for each occurrence, is selected from halogen, CN, optionally substituted alkyl, optionally substituted alkenyl, optionally substituted alkynyl, optionally substituted alkylsulfonyl, optionally substituted alkoxyl, optionally substituted cycloalkyl, optionally substituted cycloalkenyl, optionally substituted heterocycloalkyl, optionally substituted heterocycloalkenyl, optionally substituted aryl, and optionally substituted heteroaryl. In certain embodiments, $R^4$ is substituted with one or two $R^5$. In certain embodiments, $R^4$ is substituted with two $R^5$. In certain embodiments, $R^4$ is substituted with one $R^5$.

In certain embodiments, $R^5$, independently for each occurrence, is selected from halogen, optionally substituted alkyl, optionally substituted alkenyl, optionally substituted alkynyl, optionally substituted alkoxyl, optionally substituted cycloalkyl, optionally substituted cycloalkenyl, optionally substituted heterocycloalkyl, optionally substituted heterocycloalkenyl, optionally substituted phenyl, optionally substituted pyrazolyl, optionally substituted pyridinyl, optionally substituted thiazolyl, optionally substituted imidazolyl, optionally substituted pyrimidinyl, optionally substituted isoxazolyl, optionally substituted isothiazolyl, and optionally substituted triazolopyridinyl. In certain embodiments, $R^5$, independently for each occurrence, is selected from halogen, optionally substituted alkyl, optionally substituted alkoxyl, optionally substituted aryl, and optionally substituted heteroaryl. In certain embodiments, $R^5$, independently for each occurrence, is selected from halogen, optionally substituted alkyl, optionally substituted alkoxyl, optionally substituted phenyl, optionally substituted pyrazolyl, optionally substituted pyridinyl, and optionally substituted thiazolyl. In certain embodiments, $R^5$, independently for each occurrence, is selected from halogen, such as —F, and optionally substituted alkyl, such as fluoro-substituted alkyl (e.g., —CHF$_2$). In certain embodiments, $R^5$, independently for each occurrence, is selected from halogen, optionally substituted phenyl, and optionally substituted pyridinyl. In certain embodiments, $R^5$, independently for each occurrence, is selected from halogen, such as —F, and optionally substituted pyridinyl, such as optionally substituted alkyl-substituted pyridinyl. In certain embodiments, $R^5$, independently for each occurrence, is selected from halogen, such as —F, and optionally substituted phenyl, such as fluoro-substituted phenyl.

In certain embodiments, $R^4$ is substituted with two $R^5$, and $R^5$, independently for each occurrence, is selected from halogen (e.g., —F) and optionally substituted alkyl (e.g., halo-substituted alkyl, such as —CH(F)$_2$).

In certain embodiments, $R^4$ is substituted with one $R^5$, and $R^5$ is halogen (e.g., —Br)

In certain embodiments, $R^5$, independently for each occurrence, is optionally substituted with one or more $R^6$; and $R^6$, independently for each occurrence, is selected from halogen, CN, oxo, alkyl, alkenyl, alkynyl, alkoxy, alkylsulfonyl, cycloalkyl, cycloalkenyl, heterocycloalkyl, heterocycloalkenyl, aryl, and heteroaryl. In certain embodiments, $R^6$, independently for each occurrence, is selected from halogen, CN, oxo, alkyl, alkoxy, alkylsulfonyl, and cycloalkyl. In certain embodiments, $R^6$, independently for each occurrence, is selected from halogen, alkyl, and alkylsulfonyl.

The present application provides a compound of formula (I),

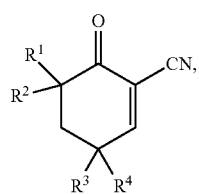

or a pharmaceutically acceptable salt thereof, wherein:
$R^1$ and $R^2$ each independently is selected from $C_{1-6}$ alkyl; or $R^1$ and $R^2$ taken together with the carbon to which they are attached form a spirocycloalkyl or spiroheterocycloalkyl ring;
$R^3$ is selected from hydroxyl and optionally substituted alkoxy; and
$R^4$ is selected from optionally substituted aryl and optionally substituted heteroaryl.

In certain embodiments, $R^1$ and $R^2$ each independently is selected from $C_{1-4}$ alkyl. In certain embodiments, $R^1$ and $R^2$ each independently is selected from methyl and ethyl. In certain embodiments, $R^1$ and $R^2$ are both methyl.

In certain embodiments, $R^1$ and $R^2$ taken together with the carbon to which they are attached form a spirocycloalkyl ring. In certain such embodiments, $R^1$ and $R^2$ taken together with the carbon to which they are attached form a spirocyclopropyl, spirocyclobutyl, or spirocyclopentyl ring. In certain embodiments, $R^1$ and $R^2$ taken together with the carbon to which they are attached form a spirocyclopropyl or spirocyclopentyl ring. In certain embodiments, $R^1$ and $R^2$ taken together with the carbon to which they are attached form a spirocyclopropyl ring.

In certain embodiments, $R^1$ and $R^2$ taken together with the carbon to which they are attached form a spiroheterocycloalkyl ring. In certain such embodiments, $R^1$ and $R^2$ taken together with the carbon to which they are attached form an azetidine or an oxetane ring.

In certain embodiments, $R^3$ is optionally substituted alkoxy. In certain embodiments, $R^3$ is methoxy. In certain embodiments, $R^3$ is trifluoromethoxy. In certain embodiments, $R^3$ is methoxy-d$_3$.

In certain embodiments, $R^4$ is selected from optionally substituted phenyl, optionally substituted pyridinyl, optionally substituted isoquinolinyl, optionally substituted pyrazinyl, optionally substituted thiophenyl, and optionally substituted thiazolyl. In certain embodiments, $R^4$ is optionally substituted pyridinyl.

In certain embodiments, $R^4$ is optionally substituted with one or more $R^5$; and $R^5$, independently for each occurrence, is selected from halogen, CN, optionally substituted alkyl, optionally substituted alkenyl, optionally substituted alkynyl, optionally substituted alkylsulfonyl, optionally substituted alkoxyl, optionally substituted cycloalkyl, optionally substituted cycloalkenyl, optionally substituted heterocycloalkyl, optionally substituted heterocycloalkenyl, optionally substituted aryl, and optionally substituted heteroaryl. In certain embodiments, $R^4$ is substituted with one or two $R^5$. In certain embodiments, $R^4$ is substituted with two $R^5$.

In certain embodiments, $R^5$, independently for each occurrence, is selected from halogen, optionally substituted alkyl, optionally substituted alkenyl, optionally substituted alkynyl, optionally substituted alkoxyl, optionally substituted cycloalkyl, optionally substituted cycloalkenyl, optionally substituted heterocycloalkyl, optionally substituted heterocycloalkenyl, optionally substituted phenyl, optionally substituted pyrazolyl, optionally substituted pyridinyl, optionally substituted thiazolyl, optionally substituted imidazolyl, optionally substituted pyrimidinyl, optionally substituted isoxazolyl, optionally substituted isothiazolyl, and optionally substituted triazolopyridinyl. In certain embodiments, $R^5$, independently for each occurrence, is selected from halogen, optionally substituted alkyl, optionally substituted alkoxyl, optionally substituted aryl, and optionally substituted heteroaryl. In certain embodiments, $R^5$, independently for each occurrence, is selected from halogen, optionally substituted alkyl, optionally substituted alkoxyl, optionally substituted phenyl, optionally substituted pyrazolyl, optionally substituted pyridinyl, and optionally substituted thiazolyl. In certain embodiments, $R^5$, independently for each occurrence, is selected from halogen, such as —F, and optionally substituted alkyl, such as fluoro-substituted alkyl (e.g., —CHF$_2$). In certain embodiments, $R^5$, independently for each occurrence, is selected from halogen, optionally substituted phenyl, and optionally substituted pyridinyl. In certain embodiments, $R^5$, independently for each occurrence, is selected from halogen, such as —F, and optionally substituted pyridinyl, such as optionally substituted alkyl-substituted pyridinyl. In certain embodiments, $R^5$, independently for each occurrence, is selected from halogen, such as —F, and optionally substituted phenyl, such as fluoro-substituted phenyl.

In certain embodiments, $R^4$ is substituted with two $R^5$ and $R^5$, independently for each occurrence, is selected from halogen (e.g., —F) and optionally substituted alkyl (e.g., halo-substituted alkyl, such as —CH(F)$_2$).

In certain embodiments, $R^5$, independently for each occurrence, is optionally substituted with one or more $R^6$; and $R^6$, independently for each occurrence, is selected from halogen, CN, oxo, alkyl, alkenyl, alkynyl, alkoxy, alkylsulfonyl, cycloalkyl, cycloalkenyl, heterocycloalkyl, heterocycloalkenyl, aryl, and heteroaryl. In certain embodiments, $R^6$, independently for each occurrence, is selected from halogen, CN, oxo, alkyl, alkoxy, alkylsulfonyl, and cycloalkyl. In certain embodiments, $R^6$, independently for each occurrence, is selected from halogen, alkyl, and alkylsulfonyl.

The present application provides a compound of formula (I)

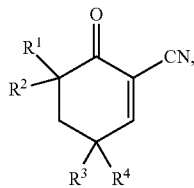

or a pharmaceutically acceptable salt thereof, wherein:

$R^1$ and $R^2$ each independently is selected from $C_{1-6}$ alkyl; or $R^1$ and $R^2$ taken together with the carbon to which they are attached form a spirocycloalkyl ring;

$R^3$ is selected from hydroxyl and optionally substituted alkoxy; and $R^4$ is selected from optionally substituted aryl and optionally substituted heteroaryl.

In certain embodiments, $R^1$ and $R^2$ each independently is selected from $C_{1-4}$ alkyl. In certain embodiments, $R^1$ and $R^2$ each independently is selected from methyl and ethyl. In certain embodiments, $R^1$ and $R^2$ are both methyl.

In certain embodiments, $R^1$ and $R^2$ taken together with the carbon to which they are attached form a spirocycloalkyl ring. In certain such embodiments, $R^1$ and $R^2$ taken together with the carbon to which they are attached form a spirocyclopropyl, spirocyclobutyl, or spirocyclopentyl ring. In certain embodiments, $R^1$ and $R^2$ taken together with the carbon to which they are attached form a spirocyclopropyl or spirocyclopentyl ring. In certain embodiments, $R^1$ and $R^2$ taken together with the carbon to which they are attached form a spirocyclopropyl ring.

In certain embodiments, $R^3$ is optionally substituted alkoxy. In certain embodiments, $R^3$ is methoxy. In certain embodiments, $R^3$ is trifluoromethoxy. In certain embodiments, $R^3$ is methoxy-d$_3$.

In certain embodiments, $R^4$ is selected from optionally substituted phenyl, optionally substituted pyridinyl, optionally substituted isoquinolinyl, optionally substituted pyrazinyl, optionally substituted thiophenyl, and optionally substituted thiazolyl. In certain embodiments, $R^4$ is optionally substituted pyridinyl.

In certain embodiments, $R^4$ is optionally substituted with one or more $R^5$; and $R^5$, independently for each occurrence, is selected from halogen, CN, optionally substituted alkyl, optionally substituted alkenyl, optionally substituted alkynyl, optionally substituted alkylsulfonyl, optionally substituted alkoxyl, optionally substituted cycloalkyl, optionally substituted cycloalkenyl, optionally substituted heterocycloalkyl, optionally substituted heterocycloalkenyl, optionally substituted aryl, and optionally substituted heteroaryl. In certain embodiments, $R^4$ is substituted with one or two $R^5$. In certain embodiments, $R^4$ is substituted with two $R^5$.

In certain embodiments, $R^5$, independently for each occurrence, is selected from halogen, optionally substituted alkyl, optionally substituted alkenyl, optionally substituted alkynyl, optionally substituted alkoxyl, optionally substituted cycloalkyl, optionally substituted cycloalkenyl, optionally substituted heterocycloalkyl, optionally substituted heterocycloalkenyl, optionally substituted phenyl, optionally substituted pyrazolyl, optionally substituted pyridinyl, optionally substituted thiazolyl, optionally substituted imidazolyl, optionally substituted pyrimidinyl, optionally substituted isoxazolyl, optionally substituted isothiazolyl, and optionally substituted triazolopyridinyl. In certain embodiments, $R^5$, independently for each occurrence, is selected from halogen, optionally substituted alkyl, optionally substituted alkoxyl, optionally substituted aryl, and optionally substituted heteroaryl. In certain embodiments, $R^5$, independently for each occurrence, is selected from halogen, optionally substituted alkyl, optionally substituted alkoxyl, optionally substituted phenyl, optionally substituted pyrazolyl, optionally substituted pyridinyl, and optionally substituted thiazolyl. In certain embodiments, $R^5$, independently for each occurrence, is selected from halogen, such as —F, and optionally substituted alkyl, such as fluoro-substituted alkyl (e.g., —CHF$_2$). In certain embodiments, $R^5$, independently for each occurrence, is selected from halogen, optionally substituted phenyl, and optionally substituted pyridinyl. In certain embodiments, $R^5$, independently for each occurrence, is selected from halogen, such as —F, and optionally substituted pyridinyl, such as optionally substituted alkyl-substituted pyridinyl. In certain embodiments, $R^5$, independently for each occurrence, is selected from halogen, such as —F, and optionally substituted phenyl, such as fluoro-substituted phenyl.

In certain embodiments, $R^4$ is substituted with two $R^5$ and $R^5$, independently for each occurrence, is selected from halogen (e.g., —F) and optionally substituted alkyl (e.g., halo-substituted alkyl, such as —CH(F)$_2$).

In certain embodiments, $R^5$, independently for each occurrence, is optionally substituted with one or more $R^6$; and $R^6$, independently for each occurrence, is selected from halogen, CN, oxo, alkyl, alkenyl, alkynyl, alkoxy, alkylsulfonyl, cycloalkyl, cycloalkenyl, heterocycloalkyl, heterocycloalkenyl, aryl, and heteroaryl. In certain embodiments, $R^6$, independently for each occurrence, is selected from halogen, CN, oxo, alkyl, alkoxy, alkylsulfonyl, and cycloalkyl. In certain embodiments, $R^6$, independently for each occurrence, is selected from halogen, alkyl, and alkylsulfonyl.

The present application provides a compound of formula (Ia)

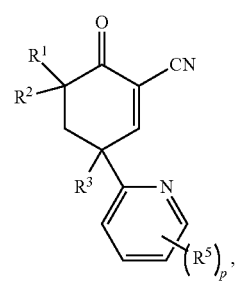

or a pharmaceutically acceptable salt thereof, wherein:

$R^1$ and $R^2$ each independently is selected from $C_{1-6}$ alkyl; or $R^1$ and $R^2$ taken together with the carbon to which they are attached form a spirocycloalkyl or spiroheterocycloalkyl ring;

$R^3$ is selected from hydroxyl and optionally substituted alkoxy;

$R^5$, independently for each occurrence, is selected from halogen, CN, optionally substituted alkyl, optionally substituted alkenyl, optionally substituted alkynyl, optionally substituted alkylsulfonyl, optionally substituted alkoxyl, optionally substituted cycloalkyl, optionally substituted cycloalkenyl, optionally substituted heterocycloalkyl, optionally substituted heterocycloalkenyl, optionally substituted aryl, and optionally substituted heteroaryl; and p is selected from 0, 1, 2, 3, and 4.

In certain embodiments, p is selected from 1 and 2. In certain embodiments, p is 2.

In certain embodiments, $R^5$, independently for each occurrence, is selected from halogen, optionally substituted alkyl, optionally substituted alkenyl, optionally substituted alkynyl, optionally substituted alkoxyl, optionally substituted cycloalkyl, optionally substituted cycloalkenyl, optionally substituted heterocycloalkyl, optionally substituted heterocycloalkenyl, optionally substituted phenyl, optionally substituted pyrazolyl, optionally substituted pyridinyl, optionally substituted thiazolyl, optionally substituted imidazolyl, optionally substituted pyrimidinyl, optionally substituted isoxazolyl, optionally substituted isothiazolyl, and optionally substituted triazolopyridinyl. In certain embodiments, $R^5$, independently for each occurrence, is selected from halogen, optionally substituted alkyl, optionally substituted alkoxyl, optionally substituted aryl, and optionally substituted heteroaryl. In certain embodiments, $R^5$, independently for each occurrence, is selected from halogen, optionally substituted alkyl, optionally substituted alkoxyl, optionally substituted phenyl, optionally substituted pyrazolyl, optionally substituted pyridinyl, and optionally substituted thiazolyl. In certain embodiments, $R^5$, independently for each occurrence, is selected from halogen, such as —F, and optionally substituted alkyl, such as fluoro-substituted alkyl (e.g., —CHF$_2$). In certain embodiments wherein p is 2, one occurrence of $R^5$ is halogen, such as —F, and the other embodiment of $R^5$ is optionally substituted alkyl, such as fluoro-substituted alkyl (e.g., —CHF$_2$). In certain embodiments, $R^5$, independently for each occurrence, is selected from halogen, optionally substituted phenyl, and optionally substituted pyridinyl. In certain embodiments, $R^5$, independently for each occurrence, is selected from halogen, such as —F, and optionally substituted pyridinyl, such as optionally substituted alkyl-substituted pyridinyl. In certain embodiments, $R^5$, independently for each occurrence, is selected from halogen, such as —F, and optionally substituted phenyl, such as fluoro-substituted phenyl.

In certain embodiments, $R^5$, independently for each occurrence, is optionally substituted with one or more $R^6$; and $R^6$, independently for each occurrence, is selected from halogen, CN, oxo, alkyl, alkenyl, alkynyl, alkoxy, alkylsulfonyl, cycloalkyl, cycloalkenyl, heterocycloalkyl, heterocycloalkenyl, aryl, and heteroaryl. In certain embodiments, $R^6$, independently for each occurrence, is selected from halogen, CN, oxo, alkyl, alkoxy, alkylsulfonyl, and cycloalkyl. In certain embodiments, $R^6$, independently for each occurrence, is selected from halogen, alkyl, and alkylsulfonyl.

In certain embodiments, $R^1$ and $R^2$ each independently is selected from $C_{1-4}$ alkyl. In certain embodiments, $R^1$ and $R^2$ each independently is selected from methyl and ethyl. In certain embodiments, $R^1$ and $R^2$ are both methyl.

In certain embodiments, $R^1$ and $R^2$ taken together with the carbon to which they are attached form a spirocycloalkyl ring. In certain embodiments, $R^1$ and $R^2$ taken together with the carbon to which they are attached form a spirocyclopropyl, spirocyclobutyl, or spirocyclopentyl ring. In certain embodiments, $R^1$ and $R^2$ taken together with the carbon to which they are attached form a spirocyclopropyl or spirocyclopentyl ring. In certain embodiments, $R^1$ and $R^2$ taken together with the carbon to which they are attached form a spirocyclopropyl ring.

In certain embodiments, $R^1$ and $R^2$ taken together with the carbon to which they are attached form a spiroheterocycloalkyl ring. In certain such embodiments, $R^1$ and $R^2$ taken together with the carbon to which they are attached form an azetidine or an oxetane ring.

In certain embodiments, $R^3$ is optionally substituted alkoxy. In certain embodiments, $R^3$ is methoxy. In certain embodiments, $R^3$ is trifluoromethoxy. In certain embodiments, $R^3$ is methoxy-d$_3$.

The present application provides a compound of formula (Ia)

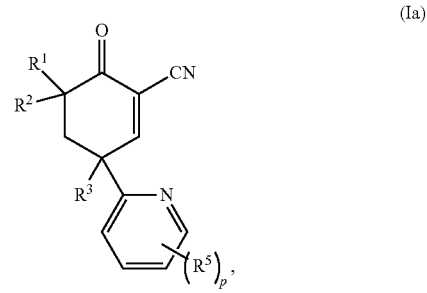

(Ia)

or a pharmaceutically acceptable salt thereof, wherein:

$R^1$ and $R^2$ each independently is selected from $C_{1-6}$ alkyl; or $R^1$ and $R^2$ taken together with the carbon to which they are attached form a spirocycloalkyl ring;

$R^3$ is selected from hydroxyl and optionally substituted alkoxy;

$R^5$, independently for each occurrence, is selected from halogen, CN, optionally substituted alkyl, optionally substituted alkenyl, optionally substituted alkynyl, optionally substituted alkylsulfonyl, optionally substituted alkoxyl, optionally substituted cycloalkyl, optionally substituted cycloalkenyl, optionally substituted heterocycloalkyl, optionally substituted heterocycloalkenyl, optionally substituted aryl, and optionally substituted heteroaryl; and p is selected from 0, 1, 2, 3, and 4.

In certain embodiments, p is selected from 1 and 2.

In certain embodiments, $R^5$, independently for each occurrence, is selected from halogen, optionally substituted alkyl, optionally substituted alkenyl, optionally substituted alkynyl, optionally substituted alkoxyl, optionally substituted cycloalkyl, optionally substituted cycloalkenyl, optionally substituted heterocycloalkyl, optionally substituted heterocycloalkenyl, optionally substituted phenyl, optionally substituted pyrazolyl, optionally substituted pyridinyl, optionally substituted thiazolyl, optionally substituted imidazolyl, optionally substituted pyrimidinyl, optionally substituted isoxazolyl, optionally substituted isothiazolyl, and optionally substituted triazolopyridinyl. In certain embodiments, $R^5$, independently for each occurrence, is selected from halogen, optionally substituted alkyl, optionally substituted alkoxyl, optionally substituted aryl, and optionally substituted heteroaryl. In certain embodiments, $R^5$, independently for each occurrence, is selected from halogen, optionally substituted alkyl, optionally substituted alkoxyl, optionally substituted phenyl, optionally substituted pyrazolyl, optionally substituted pyridinyl, and optionally substituted thiazolyl. In certain embodiments, $R^5$, independently for each occurrence, is selected from halogen, such as —F, and optionally substituted alkyl, such as fluoro-substituted alkyl (e.g., —CHF$_2$). In certain embodiments wherein p is 2, one occurrence of $R^5$ is halogen, such as —F, and the other embodiment of $R^5$ is optionally substituted alkyl, such as fluoro-substituted alkyl (e.g., —CHF$_2$). In certain embodiments, $R^5$, independently for each occurrence, is selected from halogen, optionally substituted phenyl, and optionally substituted pyridinyl. In certain embodiments, $R^5$, independently for each occurrence, is selected from halogen, such as —F, and optionally substituted pyridinyl, such as optionally substituted alkyl-substituted pyridinyl. In certain embodiments, $R^5$, independently for each occurrence, is selected from halogen, such as —F, and optionally substituted phenyl, such as fluoro-substituted phenyl.

In certain embodiments, $R^5$, independently for each occurrence, is optionally substituted with one or more $R^6$; and $R^6$, independently for each occurrence, is selected from halogen, CN, oxo, alkyl, alkenyl, alkynyl, alkoxy, alkylsulfonyl, cycloalkyl, cycloalkenyl, heterocycloalkyl, heterocycloalkenyl, aryl, and heteroaryl. In certain embodiments, $R^6$, independently for each occurrence, is selected from halogen, CN, oxo, alkyl, alkoxy, alkylsulfonyl, and cycloalkyl. In certain embodiments, $R^6$, independently for each occurrence, is selected from halogen, alkyl, and alkylsulfonyl.

In certain embodiments, $R^1$ and $R^2$ each independently is selected from $C_{1-4}$ alkyl. In certain embodiments, $R^1$ and $R^2$ each independently is selected from methyl and ethyl. In certain embodiments, $R^1$ and $R^2$ are both methyl.

In certain embodiments, $R^1$ and $R^2$ taken together with the carbon to which they are attached form a spirocyclopropyl, spirocyclobutyl, or spirocyclopentyl ring. In certain embodiments, $R^1$ and $R^2$ taken together with the carbon to which they are attached form a spirocyclopropyl or spirocyclopentyl ring. In certain embodiments, $R^1$ and $R^2$ taken together with the carbon to which they are attached form a spirocyclopropyl ring.

In certain embodiments, $R^3$ is optionally substituted alkoxy. In certain embodiments, $R^3$ is methoxy. In certain embodiments, $R^3$ is trifluoromethoxy. In certain embodiments, $R^3$ is methoxy-d$_3$.

The present application further provides compound 159,

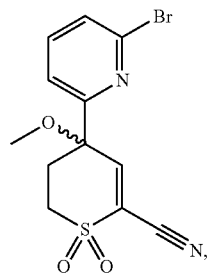 [SMILES: COC1(c2cccc(Br)n2)C=C(C#N)S(=O)(=O)CC1]

or a pharmaceutically acceptable salt thereof.

The present application provides a compound selected from any one of compounds 1-57, 59-94, 96, and 98-108, and pharmaceutically acceptable salts thereof. In certain embodiments, the present application provides a compound selected from any one of compounds 1-57, 59-94, 96, 98-120, 122-137, and 139-196, and pharmaceutically acceptable salts thereof. In certain embodiments, the present application provides a compound selected from any one of compounds 1-57, 59-94, 96, 98-120, 122-137, 139-158, and 160-196, and pharmaceutically acceptable salts thereof. In certain embodiments, the present application provides a compound selected from any one of compounds 1-57, 59-94, 96, 98-120, 122-137, 139-212, and 213-240 and pharmaceutically acceptable salts thereof. In certain embodiments, the present application provides a compound selected from any one of compounds 1-57, 59-94, 96, 98-120, 122-137, 139-158, 160-212, and 213-240 and pharmaceutically acceptable salts thereof.

In certain embodiments wherein alkyl, alkenyl, alkynyl, alkoxy, aryl, heteroaryl, cycloalkyl, heterocycloalkyl, or oxime are substituted, they are substituted, valency permitting, with one or more substituents selected from substituted or unsubstituted alkyl, such as perfluoroalkyl (e.g., trifluoromethyl), alkenyl, alkoxy, alkoxyalkyl, aryl, aralkyl, arylalkoxy, aryloxy, aryloxyalkyl, hydroxyl, halo, alkoxy, such as perfluoroalkoxy (e.g., trifluoromethoxy), alkoxyalkoxy, hydroxyalkyl, hydroxyalkylamino, hydroxyalkoxy, amino, aminoalkyl, alkylamino, aminoalkylalkoxy, aminoalkoxy, acylamino, acylaminoalkyl, such as perfluoro acylaminoalkyl (e.g., trifluoromethylacylaminoalkyl), acyloxy, cycloalkyl, cycloalkylalkyl, cycloalkylalkoxy, heterocyclyl, heterocyclylalkyl, heterocyclyloxy, heterocyclylalkoxy, heteroaryl, heteroarylalkyl, heteroarylalkoxy, heteroaryloxy, heteroaryloxyalkyl, heterocyclylaminoalkyl, heterocyclylaminoalkoxy, amido, amidoalkyl, amidine, imine, oxo, carbonyl (such as carboxyl, alkoxycarbonyl, formyl, or acyl, including perfluoroacyl (e.g., C(O)CF$_3$)), carbonylalkyl (such as carboxyalkyl, alkoxycarbonylalkyl, formylalkyl, or acylalkyl, including perfluoroacylalkyl (e.g., -alkylC(O) CF$_3$)), carbamate, carbamatealkyl, urea, ureaalkyl, sulfate, sulfonate, sulfamoyl, sulfone, sulfonamide, sulfonamidealkyl, cyano, nitro, azido, sulfhydryl, alkylthio, thiocarbonyl (such as thioester, thioacetate, or thioformate), phosphoryl, phosphate, phosphonate or phosphinate.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents, positions of substituents and/or variables are permissible only if such combinations result in stable compounds.

As used in this application, the term "optionally substituted" means that substitution is optional and therefore it is possible for the designated atom or moiety to be unsubstituted.

Compounds of the present application containing one or multiple asymmetrically substituted atoms may be isolated in optically active or racemic forms. It is well known in the art how to prepare optically active forms, such as by resolution of racemic forms, by synthesis from optically active starting materials, or by synthesis using optically active reagents.

In certain embodiments, compounds of the application may be racemic. For example, in embodiments of the application wherein a compound (e.g., a compound of formula (I') or formula (I), such as (Ia)) is disclosed herein as "Enantiomer A" or "Enantiomer B", the application further contemplates the compound in its racemic form. In certain embodiments, compounds of the application may be enriched in one enantiomer. For example, a compound of the application may have greater than 30% ee, 40% ee, 50% ee, 60% ee, 70% ee, 80% ee, 90% ee, or even 95% or greater ee.

In certain embodiments, the therapeutic preparation may be enriched to provide predominantly one enantiomer of a compound (e.g., of formula (I') or formula (I), such as (Ia)). An enantiomerically enriched mixture may comprise, for example, at least 60 mol percent of one enantiomer, or more preferably at least 75, 90, 95, or even 99 mol percent. In certain embodiments, the compound enriched in one enantiomer is substantially free of the other enantiomer, wherein substantially free means that the substance in question makes up less than 10%, or less than 5%, or less than 4%, or less than 3%, or less than 2%, or less than 1% as compared to the amount of the other enantiomer, e.g., in the composition or compound mixture. For example, if a composition or compound mixture contains 98 grams of a first enantiomer and 2 grams of a second enantiomer, it would be said to contain 98 mol percent of the first enantiomer and only 2% of the second enantiomer.

In certain embodiments, compounds of the application may have more than one stereocenter. In certain such embodiments, compounds of the application may be enriched in one or more diastereomer. For example, a compound of the application may have greater than 30% de, 40% de, 50% de, 60% de, 70% de, 80% de, 90% de, or even 95% or greater de.

In certain embodiments, the therapeutic preparation may be enriched to provide predominantly one diastereomer of a compound (e.g., of formula (I') or formula (I), such as (Ia)). A diastereomerically enriched mixture may comprise, for example, at least 60 mol percent of one diastereomer, or more preferably at least 75, 90, 95, or even 99 mol percent.

A variety of compounds in the present application may exist in particular geometric or stereoisomeric forms. The present application takes into account all such compounds, including tautomers, cis- and trans-isomers, R- and S-enantiomers, diastereomers, (D)-isomers, (L)-isomers, the racemic mixtures thereof, and other mixtures thereof, as being covered within the scope of this application. All tautomeric forms are encompassed in the present application. Additional asymmetric carbon atoms may be present in a substituent such as an alkyl group. All such isomers, as well as mixtures thereof, are intended to be included in this application, unless the stereochemistry or isomeric form is specifically indicated.

The present application further includes all pharmaceutically acceptable isotopically labelled compounds (e.g., of formula (I') or formula (I), such as (Ia)). An "isotopically" or "radio-labelled" compound is a compound where one or more atoms are replaced or substituted by an atom having an atomic mass or mass number different from the atomic mass or mass number typically found in nature (i.e., naturally occurring). For example, in certain embodiments, in compounds (e.g., of formula (I') or formula (I), such as (Ia)), hydrogen atoms are replaced or substituted by one or more deuterium or tritium (e.g., hydrogen atoms on a $C_{1-6}$ alkyl or a $C_{1-6}$ alkoxy are replaced with deuterium, such as $d_3$-methoxy or 1,1,2,2-$d_4$-3-methylbutyl).

Certain isotopically labelled compounds (e.g., of formula (I') or formula (I), such as (Ia)), in the application, for example, those incorporating a radioactive isotope, are useful in drug and/or substrate tissue distribution studies. The radioactive isotopes tritium, i.e. $^3H$, and carbon 14, i.e., $^{14}C$, are particularly useful for this purpose in view of their ease of incorporation and ready means of detection.

Substitution with heavier isotopes such as deuterium, i.e., $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$, and $^{13}N$, can be useful in Positron Emission Topography (PET) studies for examining substrate receptor occupancy.

Isotopically labelled compounds (e.g., of formula (I') or formula (I), such as (Ia), or pharmaceutically acceptable salts thereof) can generally be prepared by conventional techniques known to those skilled in the art or by processes analogous to those described in the accompanying examples using an appropriate isotopically labelled reagent in place of the non-labelled reagent previously employed. Suitable isotopes that may be incorporated in compounds of the present application include but are not limited to $^2H$ (also written as D for deuterium), $^3H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$, and $^{131}I$.

In certain embodiments, the present application provides a pharmaceutical preparation suitable for use in a human patient, comprising any of the compounds shown above (e.g., a compound of the application, such as a compound of formula (I') or formula (I), such as (Ia), and one or more pharmaceutically acceptable excipients. In certain embodiments, the pharmaceutical preparations may be for use in treating or preventing a condition or disease as described herein. In certain embodiments, the pharmaceutical preparations have a low enough pyrogen activity to be suitable for use in a human patient.

Compounds of any of the above structures may be used in the manufacture of medicaments for the treatment of any diseases or conditions disclosed herein.

Uses of the Compounds

Compounds of the present application may be administered orally, parenteral, buccal, vaginal, rectal, inhalation, insufflation, sublingually, intramuscularly, subcutaneously, topically, intranasally, intraperitoneally, intrathoracically, intravenously, epidurally, intrathecally, intracerebroventricularly and by injection into the joints.

The dosage will depend on the route of administration, the severity of the disease, age and weight of the patient and other factors normally considered by the attending physician, when determining the individual regimen and dosage level as the most appropriate for a particular patient. The quantity of the compound to be administered will vary for the patient being treated and will vary from about 100 ng/kg of body weight to 100 mg/kg of body weight per day. For instance, dosages can be readily ascertained by those skilled in the art from this disclosure and the knowledge in the art. This, the skilled artisan can readily determine the amount of compound and optional additives, vehicles, and/or carrier in compositions and to be administered in methods of the application. In certain embodiments, the application relates to a compound according to formula (I') or formula (I), such as (Ia), or a pharmaceutically acceptable salt of the compound according to formula (I') or formula (I), such as (Ia), for use as a medicament, e.g., for treatment of any of the disorders disclosed herein.

In certain embodiments, the application relates to a compound according to formula (I') or formula (I), such as (Ia), or a pharmaceutically acceptable salt of the compound according to formula (I') or formula (I), such as (Ia), for use as a medicament.

In certain embodiments, the application relates to a method of inhibiting a Keap1 protein with a compound according to formula (I') or formula (I), such as (Ia), or a pharmaceutically acceptable salt of the compound according to formula (I') or formula (I), such as (Ia).

In certain embodiments, the application relates to a method of activating Nrf2 transcription with a compound according to formula (I') or formula (I), such as (Ia), or a pharmaceutically acceptable salt of the compound according to formula (I') or formula (I), such as (Ia).

In certain embodiments, the application relates to the use of a compound according to formula (I') or formula (I), such as (Ia), or a pharmaceutically acceptable salt of the compound according to formula (I') or formula (I), such as (Ia), in the manufacture of a medicament for treatment of a neurodegenerative disorder in a subject. In certain such embodiments, the neurodegenerative disorder is selected from Alzheimer's disease (AD), Parkinson's disease (PD), Huntington disease (HD) and other CAG-triplet repeat (or polyglutamine) diseases, amyotrophic lateral sclerosis (ALS; Lou Gehrig's disease), diffuse Lewy body disease, chorea-acanthocytosis, primary lateral sclerosis, multiple sclerosis (MS), frontotemporal dementia, Friedreich's ataxia, acute head injury, and epilepsy (repression of microglia activation). In certain embodiments, the application relates to the use of a compound according to formula (I') or formula (I), such as (Ia), or a pharmaceutically acceptable salt of the compound according to formula (I') or formula (I), such as (Ia), in the manufacture of a medicament for treatment of Parkinson's disease in a subject.

In certain embodiments, the application relates to the use of a compound according to formula (I') or formula (I), such as (Ia), or a pharmaceutically acceptable salt of the compound according to formula (I') or formula (I), such as (Ia), in the manufacture of a medicament for treatment of an inflammatory disorder in a subject. In certain such embodiments, the inflammatory disorder is selected from (i) respiratory diseases, such as chronic obstructive pulmonary disease (COPD), asthma (e.g., severe asthma), idiopathic pulmonary fibrosis and radiation pneumonitis; (ii) cardiovascular disease, such as atherosclerotic disease; (iii) metabolic disease, such as acute kidney injury, chronic kidney disease, acute liver injury and chronic liver failure; (iv) multiple-organ failure arising as a consequence of systemic sepsis and/or major trauma, (v) inflammatory arthritis, such as gout, (vi) inflammatory bowel disease (IBD), such as Crohn's disease or ulcerative colitis, and (vii) inflammatory skin diseases, such as atopic dermatitis. In certain embodiments, the respiratory disease is a specified respiratory disease.

In certain embodiments, the application relates to the use of a compound according to formula (I') or formula (I), such as (Ia), or a pharmaceutically acceptable salt of the compound according to formula (I') or formula (I), such as (Ia), in the manufacture of a medicament for treatment of an autoimmune disorder in a subject. In certain such embodiments, the autoimmune disorder is selected from systemic lupus erythematosus (SLE), Sjogren's syndrome, rheumatoid arthritis, psoriatic arthritis, psoriasis, and myositis.

In certain embodiments, the application relates to the use of a compound according to formula (I') or formula (I), such as (Ia), or a pharmaceutically acceptable salt of the compound according to formula (I') or formula (I), such as (Ia), in the manufacture of a medicament for the treatment of cancer in a subject. In certain such embodiments, the cancer is selected from lung cancer, breast cancer, gastric cancer, colorectal cancer, colon cancer, prostate cancer, gallbladder cancer, ovarian cancer, liver cancer, esophageal carcinoma, glioma, esophageal squamous cell carcinoma, pancreatic cancer, endometrial cancer, papillary cancer, head and neck cancers, skin cancer, hepatocellular carcinoma, and renal and urinary bladder carcinoma. In certain embodiments, the application relates to the use of a compound according to formula (I') or formula (I), such as (Ia), or a pharmaceutically acceptable salt of the compound according to formula (I') or formula (I), such as (Ia), in the manufacture of a medicament for treatment of complications or injurious sequelae in a subject arising from the generation of reactive oxidant species (ROS) or oxidative injury. In certain such embodiments, the generation of reactive oxidant species (ROS) or oxidative injury are a result of extracorporeal membrane oxygenation (ECMO), cardio-pulmonary bypass (CBP), renal replacement therapy requiring extracorporeal circuits (e.g., renal dialysis, hemofiltration and hemodiafiltration), or cardiac, kidney or liver transplantation.

In certain embodiments, the application relates to a method of treating or preventing neurodegenerative disorder in a mammal, such as a human being, comprising administering to said patient a therapeutically effective amount of a compound according to formula (I') or formula (I), such as (Ia), or a pharmaceutically acceptable salt of the compound according to formula (I') or formula (I), such as (Ia), and at least one cognitive enhancing agent, memory enhancing agent, or choline esterase inhibitor.

In certain embodiments, the application relates to a pharmaceutical composition comprising as active ingredient a therapeutically effective amount of a compound according to formula (I') or formula (I), such as (Ia), or a pharmaceutically acceptable salt of the compound according to formula (I') or formula (I), such as (Ia), in association with at least one pharmaceutically acceptable excipient, carrier or diluent.

In certain embodiments, the application relates to a pharmaceutical composition comprising (1) a compound according to formula (I') or formula (I), such as (Ia), or a pharmaceutically acceptable salt of the compound of formula (I') or formula (I), such as (Ia), (2) an additional therapeutic agent, or a pharmaceutically acceptable salt thereof, and (3) pharmaceutically acceptable excipients, carriers or diluents.

In certain embodiments, the application relates to a pharmaceutical composition comprising (1) a compound according to formula (I') or formula (I), such as (Ia), or a pharmaceutically acceptable salt of the compound of formula (I') or formula (I), such as (Ia); (2) at least one agent selected from the group consisting of cognitive enhancing agents, memory enhancing agents and choline esterase inhibitors, and (3) pharmaceutically acceptable excipients, carriers or diluents.

In the treatment of any of the disorders disclosed herein, different compounds of the application may be (e.g., conjointly) administered with one or more other compounds of the application. Moreover, compounds of formula (I') or formula (I), such as (Ia), or a pharmaceutically acceptable salt of the compound of formula (I') or formula (I), such as (Ia), or certain combinations thereof, may be conjointly administered with other conventional therapeutic agents in treating one or more disease conditions referred to herein.

In certain embodiments, compounds of the application may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either simultaneously, sequentially, or by separate dosing of the individual components of the treatment. In certain embodiments, the different therapeutic compounds can be administered within one hour, 12 hours, 24 hours, 36 hours, 48 hours, 72 hours, or a week of one another. Thus, an individual who receives such treatment can benefit from a combined effect of different therapeutic compounds.

In certain embodiments, conjoint administration of compounds of the application with one or more additional therapeutic agent(s) provides improved efficacy relative to each individual administration of the compound of the application (e.g., compound of formula (I') or formula (I), such as (Ia), or a pharmaceutically acceptable salt of the compound of formula (I') or formula (I), such as (Ia)) or the one or more additional therapeutic agent(s). In certain such embodiments, the conjoint administration provides an additive effect, wherein an additive effect refers to the sum of each of the effects of individual administration of the compound of the application and the one or more additional therapeutic agent(s).

Such conventional therapeutics may include one or more of the following categories of agents: acetyl cholinesterase inhibitors, anti-inflammatory agents, cognitive and/or memory enhancing agents or atypical antipsychotic agents. Cognitive enhancing agents, memory enhancing agents and acetyl choline esterase inhibitors includes, but not limited to, donepezil (ARICEPT), galantamine (REMINYL or RAzA-DYNE), rivastigmine (EXELON), tacrine (COGNEX) and memantine (NAMENDA, AxuRA or EBIXA). Atypical antipsychotic agents includes, but not limited to, olanzapine (marketed as ZYPREXA), aripiprazole (marketed as ABILIFY), risperidone (marketed as RISPERDAL), quetiapine (marketed as SEROQUEL), clozapine (marketed as CLOZARIL), ziprasidone (marketed as GEODON) and olanzapine/fluoxetine (marketed as SYMBYAX).

Additional conventional therapy may include one or more of the following categories of agents:

(1) antidepressants such as agomelatine, amitriptyline, amoxapine, bupropion, citalopram, clomipramine, desipramine, doxepin duloxetine, elzasonan, escitalopram, fluvoxamine, fluoxetine, gepirone, imipramine, ipsapirone, maprotiline, nortriptyline, nefazodone, paroxetine, phenelzine, protriptyline, ramelteon, reboxetine, robalzotan, sertraline, sibutramine, thionisoxetine, tranylcypromaine, trazodone, trimipramine, venlafaxine and equivalents and pharmaceutically active isomer(s) and metabolite(s) thereof.

(2) atypical antipsychotics including: for example quetiapine and pharmaceutically active isomer(s) and metabolite(s) thereof.

(3) antipsychotics including: for example amisulpride, aripiprazole, asenapine, benzisoxidil, bifeprunox, carbamazepine, clozapine, chlorpromazine, debenzapine, divalproex, duloxetine, eszopiclone, haloperidol, iloperidone, lamotrigine, loxapine, mesoridazine, olanzapine, paliperidone, perlapine, perphenazine, phenothiazine, phenylbutylpiperidine, pimozide, prochlorperazine, risperidone, sertindole, sulpiride, suproclone, suriclone, thioridazine, trifluoperazine, trimetozine, valproate, valproic acid, zopiclone, zotepine, ziprasidone and equivalents and pharmaceutically active isomer(s) and metabolite(s) thereof.

(4) anxiolytics including: for example alnespirone, zapirones, benzodiazepines, barbiturates such as adinazolam, alprazolam, balezepam, bentazepam, bromazepam, brotizolam, buspirone, clonazepam, clorazepate, chlordiazepoxide, cyprazepam, diazepam, diphenhydramine, estazolam, fenobam, flunitrazepam, flurazepam, fosazepam, lorazepam, lormetazepam, meprobamate, midazolam, nitrazepam, oxazepam, prazepam, quazepam, reclazepam, tracazolate, trepipam, temazepam, triazolam, uldazepam, zolazepam and equivalents and pharmaceutically active isomer(s) and metabolite(s) thereof.

(5) anticonvulsants including: for example carbamazepine, clonazepam, ethosuximide, felbamate, fosphenytoin, gabapentin, lacosamide, lamotrogine, levetiracetam, oxcarbazepine, phenobarbital, phenytoin, pregabaline, rufinamide, topiramate, valproate, vigabatrine, zonisamide and equivalents and pharmaceutically active isomer(s) and metabolite(s) thereof.

(6) Alzheimer's therapies including: for example donepezil, rivastigmine, galantamine, memantine, and equivalents and pharmaceutically active isomer(s) and metabolite(s) thereof.

(7) Parkinson's therapies including: for example deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase and equivalents and pharmaceutically active isomer(s) and metabolite(s) thereof.

(8) migraine therapies including: for example almotriptan, amantadine, bromocriptine, butalbital, cabergoline, dichloralphenazone, dihydroergotamine, eletriptan, frovatriptan, lisuride, naratriptan, pergolide, pizotiphen, pramipexole, rizatriptan, ropinirole, sumatriptan, zolmitriptan, zomitriptan, and equivalents and pharmaceutically active isomer(s) and metabolite(s) thereof.

(9) stroke therapies including: for example thrombolytic therapy with eg activase and desmoteplase, abciximab, citicoline, clopidogrel, eptifibatide, minocycline, and equivalents and pharmaceutically active isomer(s) and metabolite(s) thereof.

(10) urinary incontinence therapies including: for example darafenacin, falvoxate, oxybutynin, propiverine, robalzotan, solifenacin, tolterodine and equivalents and pharmaceutically active isomer(s) and metabolite(s) thereof.

(11) neuropathic pain therapies including: for example lidocain, capsaicin, and anticonvulsants such as gabapentin, pregabalin, and antidepressants such as duloxetine, venlafaxine, amitriptyline, klomipramine, and equivalents and pharmaceutically active isomer(s) and metabolite(s) thereof.

(12) nociceptive pain therapies such as paracetamol, NSAIDS and coxibs, such as celecoxib, etoricoxib, lumiracoxib, valdecoxib, parecoxib, diclofenac, loxoprofen, naproxen, ketoprofen, ibuprofen, nabumeton, meloxicam, piroxicam and opioids such as morphine, oxycodone, buprenorfin, tramadol, and equivalents and pharmaceutically active isomer(s) and metabolite(s) thereof.

(13) insomnia therapies including: for example agomelatine, allobarbital, alonimid, amobarbital, benzoctamine, butabarbital, capuride, chloral, cloperidone, clorethate, dexclamol, ethchlorvynol, etomidate, glutethimide, halazepam, hydroxyzine, mecloqualone, melatonin, mephobarbital, methaqualone, midaflur, nisobamate, pentobarbital, phenobarbital, propofol, ramelteon, roletamide, triclofos, secobarbital, zaleplon, zolpidem and equivalents and pharmaceutically active isomer(s) and metabolite(s) thereof.

(14) mood stabilizers including: for example carbamazepine, divalproex, gabapentin, lamotrigine, lithium, olanzapine, quetiapine, valproate, valproic acid, verapamil, and equivalents and pharmaceutically active isomer(s) and metabolite(s) thereof.

Such combination products employ the compounds of this application within the dosage range described herein and the other pharmaceutically active compound or compounds within approved dosage ranges and/or the dosage described in the publication reference.

Definitions

The definitions set forth in this application are intended to clarify terms used throughout this application.

The term "herein" means the entire application.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x\text{-}y}$" when used in conjunction with a chemical moiety, such as, acyl, acyloxy, alkyl, alkenyl, alkynyl, or alkoxy is meant to include groups that contain from x to y carbons in the chain. For example, the term "$C_{x\text{-}y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. $C_0$ alkyl indicates a hydrogen where the group is in a terminal position, a bond if internal. The terms "$C_{2\text{-}y}$alkenyl" and "$C_{2\text{-}y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

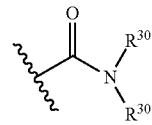

wherein each $R^{30}$ independently represent a hydrogen or hydrocarbyl group, or two $R^{30}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

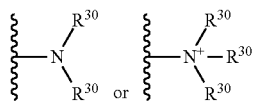

wherein each $R^{30}$ independently represents a hydrogen or a hydrocarbyl group, or two $R^{30}$ are taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

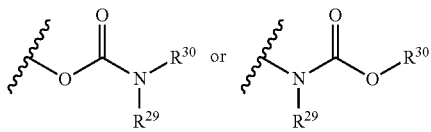

wherein $R^{29}$ and $R^{30}$ independently represent hydrogen or a hydrocarbyl group, such as an alkyl group, or $R^{29}$ and $R^{30}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group $-OCO_2-R^{30}$, wherein $R^{30}$ represents a hydrocarbyl group.

The term "carboxy", as used herein, refers to a group represented by the formula $-CO_2H$.

The term "ester", as used herein, refers to a group $-C(O)OR^{30}$ wherein $R^{30}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Exemplary heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this application, the heteroatoms such as nitrogen may have hydrogen substituents and/or any permissible substituents of organic compounds described herein which satisfy the valences of the heteroatoms.

Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

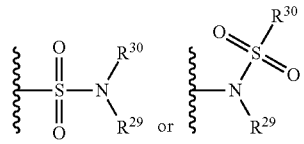

wherein $R^{29}$ and $R^{30}$ independently represents hydrogen or hydrocarbyl, such as alkyl, or $R^{29}$ and $R^{30}$ taken together with the intervening atom(s) complete a heterocycle having from 4 to 8 atoms in the ring structure.

The term "sulfoxide" is art-recognized and refers to the group —S(O)—$R^{30}$, wherein $R^{30}$ represents a hydrocarbyl.

The term "sulfonate" is art-recognized and refers to the group SO$_3$H, or a pharmaceutically acceptable salt thereof.

The term "sulfone" is art-recognized and refers to the group —S(O)$_2$—$R^{30}$, wherein $R^{30}$ represents a hydrocarbyl.

The term "thioalkyl", as used herein, refers to an alkyl group substituted with a thiol group.

The term "thioester", as used herein, refers to a group —C(O)S$R^{30}$ or —SC(O)$R^{30}$ wherein $R^{30}$ represents a hydrocarbyl.

The term "thioether", as used herein, is equivalent to an ether, wherein the oxygen is replaced with asulfur.

The term "urea" is art-recognized and may be represented by the general formula

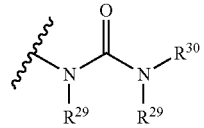

wherein $R^{29}$ and $R^{30}$ independently represent hydrogen or a hydrocarbyl, such as alkyl, or either occurrence of $R^{29}$ taken together with $R^{30}$ and the intervening atom(s) complete a heterocycle having from 4 to 8 atoms in the ring structure.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$ Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxylprotecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

The term "healthcare providers" refers to individuals or organizations that provide healthcare services to a person, community, etc. Examples of "healthcare providers" include doctors, hospitals, continuing care retirement communities, skilled nursing facilities, subacute care facilities, clinics, multispecialty clinics, freestanding ambulatory centers, home health agencies, and HMO's.

The present application includes prodrugs of the compounds formula (I') or formula (I), such as (Ia), or pharmaceutically acceptable salts thereof. The term "prodrug" is intended to encompass compounds which, under physiologic conditions, are converted into the therapeutically active agents of the present application (e.g., a compound of formula (I') or formula (I), such as (Ia)). A common method for making a prodrug is to include one or more selected moieties which are hydrolyzed under physiologic conditions to yield the desired molecule. In certain embodiments, the prodrug is converted by an enzymatic activity of the host animal. For example, a prodrug with a nitro group on an aromatic ring could be reduced by reductase to generate the desired amino group of the corresponding active compound in vivo. In another example, functional groups such as a hydroxyl, carbonate, or carboxylic acid in the parent compound are presented as an ester, which could be cleaved by esterases. Additionally, amine groups in the parent compounds are presented in, but not limited to, carbamate, N-alkylated or N-acylated forms (Simplicio et al, "Prodrugs for Amines," Molecules, (2008), 13:519-547). In certain embodiments, some or all of the compounds of formula (I') or formula (I), such as (Ia), in a formulation represented above can be replaced with the corresponding suitable prodrug.

The present application includes metabolites of the compounds of formula (I') or formula (I), such as (Ia), or pharmaceutically acceptable salts thereof. The term "metabolite" is intended to encompass compounds that are produced by metabolism/biochemical modification of the parent compound under physiological conditions, e.g. through certain enzymatic pathway. For example, an oxidative metabolite is formed by oxidation of the parent compound during metabolism, such as the oxidation of a pyridine ring to pyridine-N-oxide. In another example, an oxidative metabolite is formed by demethylation of a methoxy group to result in a hydroxyl group.

Pharmaceutical Compositions

The compositions and methods of the present application may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the application and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of the application. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a selfemulsifying drug delivery system or a selfmicroemulsifying drug delivery system. The pharmaceutical composition (preparation) also can be a liposome or other polymer matrix, which can have incorporated therein, for example, a compound of the application. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution;

(19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the application, with the carrier and, optionally, one or more accessory ingredients. In general, the formulations are prepared by uniformly and intimately bringing into association a compound of the present application with liquid carriers, or finely divided solid carriers, or both, and then, if necessary, shaping the product.

Formulations of the application suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present application as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in microencapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present application to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this application. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatable with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the application include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this application, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the application. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the application will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present application, the active compound may be administered two or three times daily. In preferred embodiments, the active compound will be administered once daily.

The patient receiving this treatment is any animal in need, including primates, in particular humans, and other mammals such as equines, cattle, swine and sheep; and poultry and pets in general.

This application includes the use of pharmaceutically acceptable salts of compounds of the application in the compositions and methods of the present application. The term "pharmaceutically acceptable salts" includes salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, such as an amine, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, trifluoroacetic, propionic, isobutyric, maleic, malonic, benzoic, succinic, suberic, fumaric, lactic, mandelic, phthalic, benzensulfonic, p-tolylsulfonic, citric, tartaric, methanesulfonic, camphorsulfonic and the like. In certain embodiments, the pharmaceutically acceptable salt is a hydrochloride salt. In certain embodiments, the pharmaceutically acceptable salt is a camsylate salt. In certain embodiments, contemplated salts of the compounds include, but are not limited to, alkyl, dialkyl, trialkyl or tetra-alkyl ammonium salts. In certain embodiments, contemplated salts of compounds include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of compounds include, but are not limited to, Li, Na, Ca, K, Mg, Zn or other metal salts. Also included are the salts of amino acids such as arginate and the like, and salts of organic acids like glucuronic or galactunoric acids and the like (see, for example, Berge et al., "Pharmaceutical Salts", Journal of Pharmaceutical Science, 1977, 66, 1-19). Certain specific compounds of the present invention may contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

The compounds of the application, including their pharmaceutically acceptable salts, can also exist as various solvates, such as with water (also known as hydrates), methanol, ethanol, dimethylformamide, diethyl ether, acetamide, and the like. Mixtures of such solvates can also be prepared. The source of such solvate can be from the solvent of crystallization, inherent in the solvent of preparation or crystallization, or adventitious to such solvent.

The compounds of the application, including their pharmaceutically acceptable salts, can also exist as various polymorphs, pseudo-polymorphs, or in amorphous state. As used herein, the term "polymorph" refers to different crystalline forms of the same compound and other solid state molecular forms including pseudo-polymorphs, such as hydrates, solvates, or salts of the same compound. Different crystalline polymorphs have different crystal structures due to a different packing of molecules in the lattice, as a result of changes in temperature, pressure, or variations in the crystallization process. Polymorphs differ from each other in their physical properties, such as x-ray diffraction characteristics, stability, melting points, solubility, or rates of dissolution in certain solvents. Thus crystalline polymorphic forms are important aspects in the development of suitable dosage forms in pharmaceutical industry.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

In certain embodiments, the application comprises a method for conducting a pharmaceutical business, by determining an appropriate formulation and dosage of a compound of the application for treating or preventing any of the diseases or conditions as described herein, conducting therapeutic profiling of identified formulations for efficacy and toxicity in animals, and providing a distribution network for selling an identified preparation as having an acceptable therapeutic profile. In certain embodiments, the method further includes providing a sales group for marketing the preparation to healthcare providers.

In certain embodiments, the application relates to a method for conducting a pharmaceutical business by determining an appropriate formulation and dosage of a compound of the application for treating or preventing any of the disease or conditions as described herein, and licensing, to a third party, the rights for further development and sale of the formulation.

EXAMPLES

Example 1

Synthetic Protocols

Below follows a number of non-limiting examples of compounds of the application.

General Methods

All temperatures are in degrees Celsius (° C.) and are uncorrected. Reagent grade chemicals and anhydrous solvent were purchased from commercial sources and unless otherwise mentioned, were used without further purification. The names of the products were determined using the naming software included in Dotmatics electronic lab notebook. Silica gel chromatography was performed on Teledyne Isco instruments using pre-packaged disposable $SiO_2$ stationary phase columns with eluent flow rate range of 15 to 200 mL/min, UV detection (254 and 280 nm). Reverse phase preparative HPLC was carried out using C18 columns, UV detection (214 and 254 nm) eluting with gradients of MeCN in $H_2O$ (0.03% $(NH_4)_2CO_3$/0.375% $NH_4OH$) or MeCN in $H_2O$ (0.1% HCOOH).

The analytical HPLC chromatograms were performed using an Agilent 1100 series instrument with DAD detector (190 nm to 300 nm). The mass spectra were recorded with a Waters Micromass ZQ detector at 130° C. The mass spectrometer was equipped with an electrospray ion source (ESI) operated in a positive ion mode and was set to scan between m/z 150-750 with a scan time of 0.3 s. Products and intermediates were analyzed by HPLC/MS on a Gemini-NX (5 μM, 2.0×30 mm) using a high pH buffer gradient of 5% to 100% of MeCN in $H_2O$ (0.03% $(NH_4)_2CO_3$/0.375% $NH_4OH$) over 2.5 min at 1.8 mL/min for a 3.5 min run (B05) and EVO C18 (5 μM, 3.0×50 mm) using a low pH buffer gradient of 5% to 100% of MeCN in $H_2O$ (0.1% HCOOH) over 2.5 min at 2.2 mL/min for a 3.5 min run (A05).

Another analytical HPLC method (C05) was applied for certain compounds: the analytical HPLC analyses were performed using an Shimadzu LC20AD and LC30AD series instrument with PDA detector (190 nm to 400 nm). The mass spectra were recorded with a Shimadzu LCMS2020 detector. The mass spectrometer was equipped with an electrospray ion source (ESI) operated in a positive ion mode and was set to scan between m/z 90-900 with a scan time of 0.5 s. Products and intermediates were analyzed by HPLC/MS on a EVO C18 (2.6 mM, 2.1×50 mm) using a high pH buffer gradient of 10% to 95% of MeCN in $H_2O$ (6.5 mmol ammonium bicarbonate (pH=10) over 2.0 min at 1.0 mL/min for a 3.0 min run (LCMS27) and Xselect CSH C18 (2.5 mM, 3.0×50 mm) using a low pH buffer gradient of 10% to 95% of MeCN in $H_2O$ (0.1% HCOOH) over 2.0 min at 1.2 mL/min for a 3.0 min run or Shim-pack ODS C18 (2.2 mM, 3.0×50 mm) using a low pH buffer gradient of 5% to 95% of MeCN in $H_2O$ (0.05% $CF_3COOH$) over 2.0 min at 1.2 mL/min for a 3.0 min run.

The $^1H$ NMR spectra were either recorded on a Bruker UltraShield 500 MHz/54 mm instrument (BZH 43/500/70B, D221/54-3209) or a ULTRASHIELD™ (300 MHz) or an ASCEND™ (400 MHz) instrument. The chemical shifts were referenced to solvent peaks, which in $^1H$ NMR appears at 7.26 ppm for $CDCl_3$, 2.50 for DMSO-d6, and 3.31 ppm for $CD_3OD$.

Generic Procedure A for Chiral Separation of Enantiomers (Chiral HPLC):

Racemic compounds purified by normal phase or reverse phase column chromatography (>95% purity) were further purified by preparative chiral-HPLC Column. The chiral columns typically used were: (a) CHIRALPAK IC, 2·25 cm, 5 µm; (b) CHIRALPAK AD-H, 2.0 cm I.D. 2·25 cm L, (R,R)Whelk-O 1, 21.1·250 mm, 5 µm; (c) CHIRALPAK IA, 2·25 cm, 5 µm; (d) CHIRAL ART Cellulose-SB, 2*25 cm, 5 µm. Mobile Phase A: Hex, Mobile Phase B: IPA or EtOH; Flow rate: 20 mL/min; gradient: 5 B to 95 B in 10-45 min depending on the compound polarity and column conditions; UV detector: 254/220 nm. The fractions containing each enantiomer were evaporated to dryness, dissolved in CH$_3$CN and water, then lyophilized to afford both enantiomers as solid compounds.

Generic Procedure B for Chiral Separation of Enantiomers (Chiral HPLC):

Racemic compounds purified by normal phase or reverse phase column chromatography (>95% purity) were further purified by preparative chiral-HPLC using a Lux C4 column (150×4.6 mm): mobile phase A (heptane), mobile phase B (EtOH), typical gradient=10% B, UV detector: 230 nm.

Determination/Assignment of the Absolute Configuration:

The crystal structure of several compounds bound to the BTB domain of Keap1 was determined which led to the assignment of the absolute configuration of the molecules. See Example 2 for an exemplary protocol. The compounds for which an Xray has been determined were found to be in the S-configuration and constituted the more active of the enantiomeric pair. For compounds where the enantiomers were separated but for which absolute configuration was not assigned, data is given for the single enantiomer that was tested. For compounds drawn without specified stereochemistry and labeled as "Enantiomer A," all data provided throughout the application for that compound is for the more active enantiomer. For compounds drawn without specified stereochemistry and labeled as "Enantiomer B," all data provided throughout the application for that compound is for the less active enantiomer. For compounds drawn without specified stereochemistry and not labeled as "Enantiomer A" or "Enantiomer B," all data provided throughout the application for that compound is for the racemate.

TABLE 1

| Terms and abbreviations | |
| --- | --- |
| aq | aqueous; |
| (BPin)$_2$ | bis(pinacolato)diboron |
| Comins' reagent | N-bis(trifluoromethanesulfonimide); |
| DBDMH | 1,3-dibromo-5,5-dimethylhydantoin; |
| DMEM | Dulbecco's Modified Eagle's Medium |
| DMF | N,N-dimethyl formamide; |
| DMSO | dimethyl sulfoxide; |
| ee | enantiomeric excess |
| Et$_2$O | diethyl ether |
| EtOAc | ethyl acetate |
| EtOH | ethanol |
| eq. or equiv. | equivalent |
| h | hours |
| HPLC | high performance liquid chromatography |
| LCMS | liquid chromatography mass spectrometry |
| LiHMDS | lithium bis(trimethylsilyl)amide |
| MeOH | methanol |
| MS | mass spectrometry |
| NaHMDS | sodium bis(trimethylsilyl)amide |
| NMP | N-methylpyrrolidone |
| NMR | nuclear magnetic resonance |
| 23° C. | r.t. |
| sat. | saturated |
| SFC | supercritical fluid chromatography |
| tBHQ | tert-butyl hydroquinone |
| THF | tetrahydrofuran |
| OTf | trifluoromethanesulfonate |
| 2nd Generation XPhos | Chloro(2-dicyclohexylphosphino-2',4',6'- |

TABLE 1-continued

| Terms and abbreviations | |
| --- | --- |
| pre-catalyst | triisopropyl-1,1'-biphenyl)[2-(2'-amino-1,1'-biphenyl)]palladium(II) |

Synthesis of Compounds 1A-4A

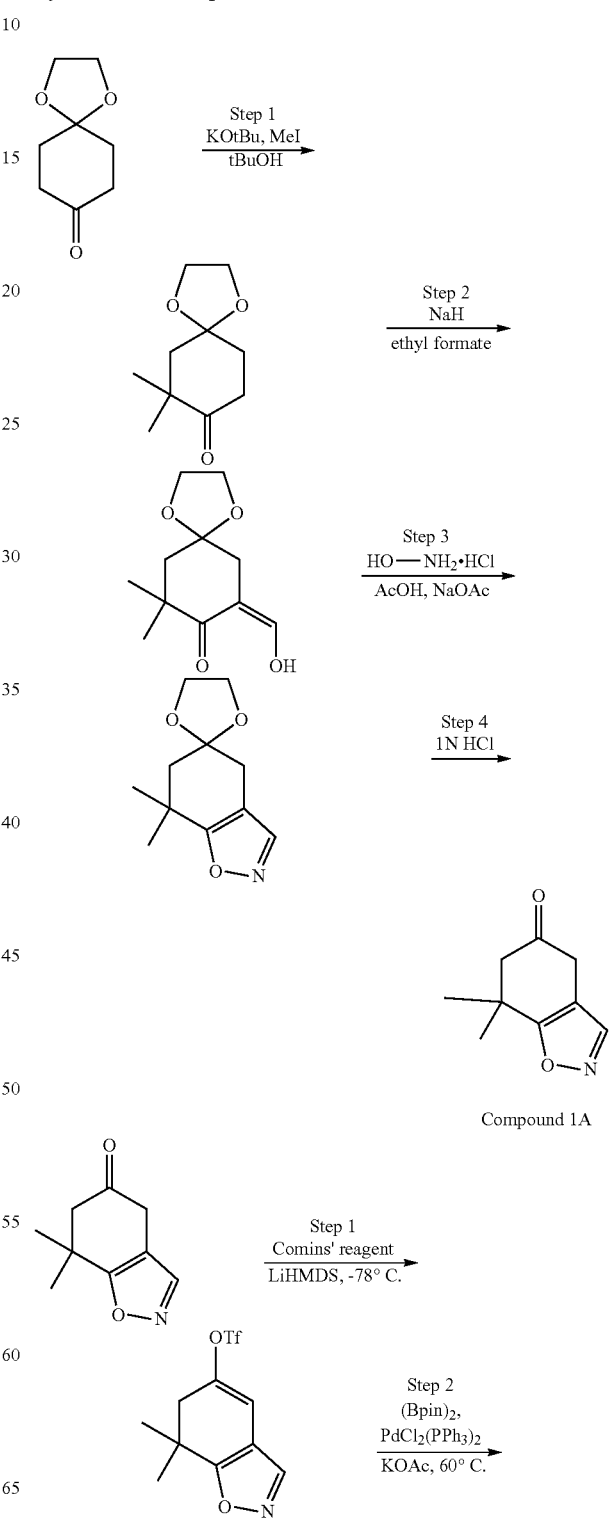

Compound 1A

-continued

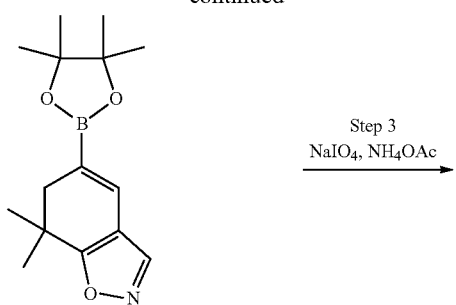

Step 3
NaIO₄, NH₄OAc
→

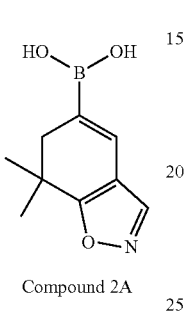

Compound 2A

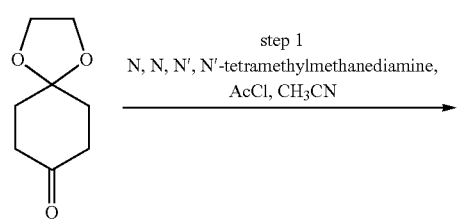

step 1
N, N, N′, N′-tetramethylmethanediamine,
AcCl, CH₃CN
→

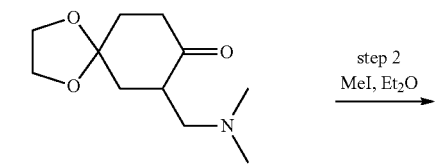

step 2
MeI, Et₂O
→

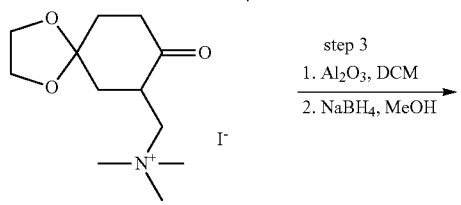

step 3
1. Al₂O₃, DCM
2. NaBH₄, MeOH
→

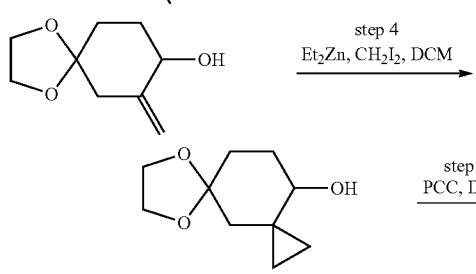

step 4
Et₂Zn, CH₂I₂, DCM
→ step 5
PCC, DCM
→

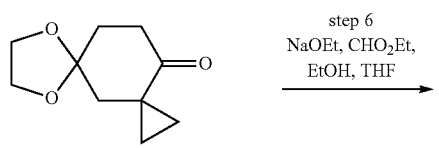

step 6
NaOEt, CHO₂Et,
EtOH, THF
→

-continued

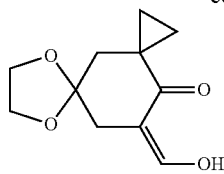

step 7
HO—NH₂(HCl), NaOAc
HOAc, H₂O
→

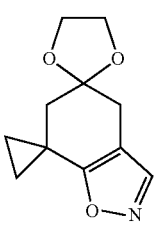

step 8
1N HCl, Acetone
→

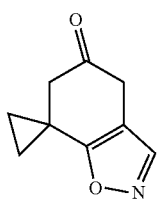

Compound 3A

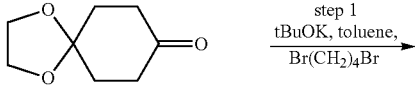

step 1
tBuOK, toluene,
Br(CH₂)₄Br
→ step 2
NaOEt, ethyl formate,
EtOH, THF
→ step 3
HO—NH₂(HCl), NaOAc,
HOAc, H₂O
→

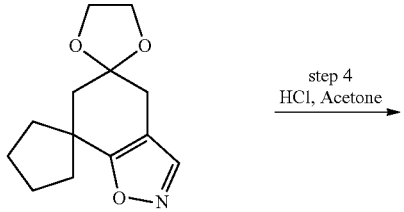

step 4
HCl, Acetone
→

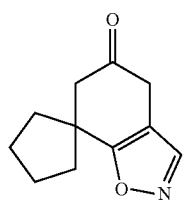

Compound 4A

Compound 1A: 7,7-dimethyl-4,6-dihydro-1,2-benzoxazol-5-one

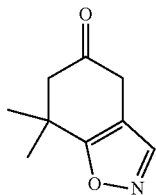

Compound 1A, Step 1: 7,7-dimethyl-1,4-dioxaspiro[4.5]decan-8-one

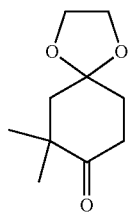

1,4-Dioxaspiro[4.5]decan-8-one (10.0 g, 64.0 mmol) was dissolved in t-butanol (320 mL). Freshly ground KOtBu (18.0 g, 160 mmol) was slowly added. The mixture was stirred at 23° C. for 1 h, and iodomethane (8.50 mL, 137 mmol) was added drop-wise. The mixture was stirred at 23° C. for 2.5 h. Water (400 mL) was added, and the aq phase was extracted with EtOAc (3×400 mL). The combined organic phases were washed with water (400 mL), brine (400 mL), dried (MgSO$_4$), filtered, and concentrated under reduced pressure. The product was purified by silica gel chromatography (220 g cartridge), eluting with hexanes and EtOAc (0-20%), to provide the title compound as an oil (5.18 g, 44%). $^1$H NMR (500 MHz, CDCl$_3$) δ 4.04-3.91 (m, 4H), 2.60-2.52 (m, 2H), 2.0-1.95 (m, 2H), 1.91-1.82 (m, 2H), 1.16 (s, 6H). m/z (ES$^+$), [M+H]$^+$: 185.3. HPLC (B05) t$_R$=1.50 min.

Compound 1A, Step 2: (9Z)-9-(hydroxymethylene)-7,7-dimethyl-1,4-dioxaspiro[4.5]-decan-8-one

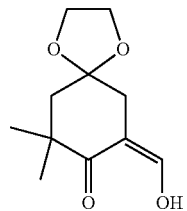

60% NaH in mineral oil (1.39 g, 34.7 mmol) was added portion-wise at 0° C. to a solution of ethyl formate (4.60 mL, 56.9 mmol) and EtOH (10 mL) in dry THF (40 mL). A solution of 7,7-dimethyl-1,4-dioxaspiro[4.5]decan-8-one (5.12 g, 27.8 mmol) in dry THF (20 mL) was added drop-wise. After the addition was complete, the mixture was warmed to 23° C., stirred for 1 h, and then heated to 70° C. for 2 h. After cooling to 23° C., Et$_2$O (200 mL) was added, and the organic phase was extracted with 1N NaOH (3×100 mL). The combined aq phases were washed with Et$_2$O (200 mL), acidified to pH 3 with conc. HCl (~30 mL). The aq phase was extracted with DCM (3×200 mL). The combined organic phases were washed with brine (200 mL), dried (MgSO$_4$), filtered, and concentrated under reduced pressure to provide the title compound as an oil (4.05 g, 69%). $^1$H NMR (500 MHz, CDCl$_3$) δ 14.76 (d, J=3.7 Hz, 1H), 8.54 (d, J=3.6 Hz, 1H), 3.98 (q, J=0.9 Hz, 4H), 2.56 (s, 2H), 1.78 (s, 2H), 1.28 (s, 6H). m/z (ES$^+$), [M+H]$^+$: 213.4. HPLC (A05) t$_R$=1.87 min.

Compound 1A, Step 3: 7',7'-dimethylspiro[1,3-dioxolane-2,5'-4,6-dihydro-1,2-benzoxa-zole]

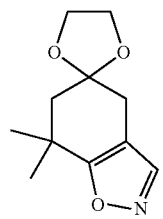

A solution of (9Z)-9-(hydroxymethylene)-7,7-dimethyl-1,4-dioxaspiro[4.5]decan-8-one (3.91 g, 18.4 mmol) in AcOH (150 mL) was added drop-wise to a solution of HO—NH$_2$.HCl (1.41 g, 20.3 mmol) and NaOAc (2.17 mL, 40.5 mmol) in water (10 mL). The mixture was stirred at 60° C. for 3 h. 1N NaOH (300 mL) and sat. NaHCO$_3$ (150 mL) were added. The aq phase was extracted with EtOAc (3×200 mL). The combined organic phases were washed with sat. NaHCO$_3$ (3×200 mL) and brine (200 mL), dried (MgSO$_4$), filtered, and concentrated under reduced pressure. The residue was dissolved in Et$_2$O (100 mL), and the mixture was washed with sat. NaHCO$_3$ (3×100 mL) and brine (100 mL). The organic phase was dried (MgSO$_4$), filtered, and concentrated under reduced pressure to provide the title compound as an oil (3.30 g, 86%). $^1$H NMR (500 MHz, CDCl$_3$) δ 8.06 (s, 1H), 4.05 (s, 4H), 2.75 (s, 2H), 1.97 (s, 2H), 1.45 (s, 6H). m/z (ES$^+$), [M+H]$^+$: 210.4. HPLC (B05) t$_R$=1.73 min.

Compound 1A, Step 4: 7,7-dimethyl-4,6-dihydro-1,2-benzoxazol-5-one

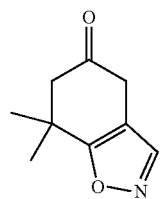

7',7'-Dimethylspiro[1,3-dioxolane-2,5'-4,6-dihydro-1,2-benzoxazole] (3.26 g, 15.6 mmol) was dissolved in acetone (75 mL), and 1M HCl aq. (75 mL, 75.0 mmol) was added. The mixture was heated to 70° C. for 1.5 h. The mixture was cooled to 23° C. and diluted with 1N NaOH (70 mL) and sat. NaHCO$_3$ (50 mL). The aq phase was extracted with Et$_2$O (3×100 mL). The combined organic phases were washed with brine (100 mL), dried (MgSO₄), filtered, and concentrated under reduced pressure. The residue was purified by silica gel chromatography (80 g cartridge), eluting with hexanes and EtOAc (0-30%), followed by trituration from hexanes to provide the title compound as a solid (1.64 g, 64%). $^1$H NMR (500 MHz, CDCl₃) δ 8.10 (s, 1H), 3.33 (s, 2H), 2.61 (s, 2H), 1.39 (s, 6H). m/z (ES⁺), [M+H]⁺: 166.3. HPLC (A05) $t_R$=1.60 min.

Compound 2A:
(7,7-dimethyl-6H-1,2-benzoxazol-5-yl)boronic acid

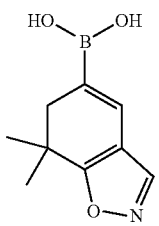

Compound 2A, Step 1:
(7,7-dimethyl-6H-1,2-benzoxazol-5-yl) trifluoromethanesulfonate

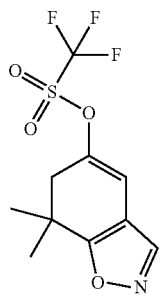 [SMILES: CC1(C)CC(OS(=O)(=O)C(F)(F)F)=Cc2cnoc21]

LiHMDS in THF (1.0 M, 222 mL, 222 mmol) was added to a solution of 7,7-dimethyl-4,6-dihydro-1,2-benzoxazol-5-one (35.0 g, 212 mmol) in THF (2.10 L) at −78° C. The mixture was stirred for 1 h at −78° C., and N-(5-chloro-2-pyridyl)-1,1,1-trifluoro-N-(trifluoromethylsulfonyl)methanesulfonamide (99.8 g, 254 mmol) was added portion-wise. The mixture was stirred at −78° C. for 2.5 h. The mixture was warmed to 23° C. and diluted with sat. NH₄Cl (400 mL). The aq. phase was extracted with DCM (2×400 mL), and the combined organic phases were washed with brine (500 mL), dried (MgSO₄), filtered, and concentrated under reduced pressure. The residue was purified by filtration on silica plug eluting with hexanes and EtOAc (15%), to provide the title compound as an oil (61.9 g; 98%). $^1$H NMR (500 MHz, CDCl₃) δ 8.14 (s, 1H), 6.32 (t, J=1.4 Hz, 1H), 2.72 (d, J=1.4 Hz, 2H), 1.40 (s, 6H). m/z (ES⁺), [M+H]⁺: 298.2. HPLC (A05) $t_R$=2.41 min.

Compound 2A, Step 2: 7-dimethyl-5-(4,4,5,5-tetramethyl-1,3,2-dioxaborolan-2-yl)-6H-1,2-benzoxazole

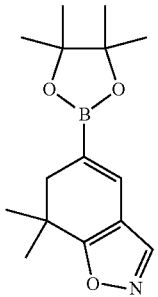 [SMILES: CC1(C)CC(B2OC(C)(C)C(C)(C)O2)=Cc2cnoc21]

Bis(pinacolato)diboron (9.89 g, 39.0 mmol), KOAc (3.82 g, 39.0 mmol), Pd(PPh₃)₂Cl₂ (684 mg, 0.97 mmol), and PPh₃ (510 mg, 1.95 mmol) were dissolved in toluene (100 mL). The solution was purged with N₂ gas for 20 min, and a solution of (7,7-dimethyl-6H-1,2-benzoxazol-5-yl) trifluoromethanesulfonate (5.79 g, 19.48 mmol) in toluene (20 mL) was added. The mixture was stirred at 50° C. for 16 h. The mixture was cooled to 23° C., and water (200 mL) and DCM (200 mL) were added. The aq. phase was extracted with DCM (2×150 mL), and the combined organic phases were washed with brine (200 mL), dried (Na₂SO₄), filtered, and concentrated under reduced pressure. The residue was dissolved in DCM (20 mL) and filtered over a pad of silica gel, washing with DCM (800 mL). The filtrate was concentrated under reduced pressure to provide the title compound as a solid (1:2.8 mixture of title compound and bis(pinacolato)diboron) (9.09 g). $^1$H NMR (500 MHz, CDCl₃) δ 8.09 (s, 1H), 7.00 (t, J=1.8 Hz, 1H), 2.49 (d, J=1.9 Hz, 2H), 1.29 (s, 12H), 1.28 (s, 6H). m/z (ES⁺), [M+H]⁺: 276.3. HPLC (B05) $t_R$=2.22 min.

Compound 2A, Step 3:
(7,7-dimethyl-6H-1,2-benzoxazol-5-yl)boronic acid

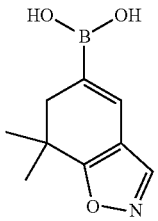

7-Dimethyl-5-(4,4,5,5-tetramethyl-1,3,2-dioxaborolan-2-yl)-6H-1,2-benzoxazole (4.20 g, 15.3 mmol, 26% pure), sodium periodate (19.6 g, 91.6 mmol), and ammonium acetate (7.06 g, 91.6 mmol) were weighed into a flask. A mixture of acetone (180 mL) and water (180 mL) was added, and the mixture was stirred at 23° C. for 16 h. The solution was filtered, and the filtrate was partially concentrated under reduced pressure. The aq phase was extracted with EtOAc (3×200 mL), and the combined organic phases were washed with brine (200 mL), dried (Na₂SO₄), filtered, and concentrated under reduced pressure. The residue was triturated from hexanes (30 mL). The resulting solid was washed with hexanes (30 mL) and dried under high vacuum to provide the title compound as a solid (620 mg, 33%, 2 steps). $^1$H NMR (500 MHz, CDCl$_3$) δ 8.22 (s, 1H), 7.43 (t, J=1.8 Hz, 1H), 2.63 (d, J=1.8 Hz, 2H), 1.35 (s, 6H). m/z (ES+), [M+H]$^+$: 194.0 HPLC (B05) t$_R$=1.53 min.

Compound 3A: 4H-spiro[benzo[d]isoxazole-7,1'-cyclopropan]-5(6H)-one

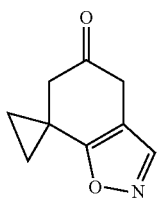 [SMILES: O=C1Cc2cnoc2C2(CC2)C1]

Compound 3A, Step 1: 7,7-dimethyl-1,4-dioxaspiro[4.5]decan-8-one

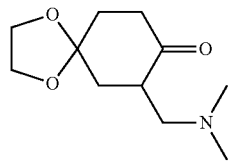

Acetyl chloride (649 g, 8269 mmol) was added to N,N,N',N'-tetramethylmethanediamine (650 g, 6361 mmol) in CH$_3$CN (5 L) at 0° C. The resulting mixture was stirred at 25° C. for 20 h. 1,4-dioxaspiro[4.5]decan-8-one (994 g, 6361 mmol) was added to the above mixture at 0° C. and stirred for 5 h at r.t. Et$_2$O (3 L) was added and stirred for 2 h. The precipitate was collected by filtration, washed with Et$_2$O (1.5 L). The solid was diluted with brine (3 L), treated with Na$_2$CO$_3$ (1011 g) and extracted with DCM (3× with 1.5 L). The combined organic layers were washed with brine. The organic layer was dried over Na$_2$SO$_4$, filtered and evaporated to afford desired product 7-((dimethylamino)methyl)-1,4-dioxaspiro[4.5]decan-8-one (1200 g, 88%) as a light yellow oil. $^1$H NMR (400 MHz, CDCl$_3$) δ 1.64-1.70 (m, 1H), 1.92-2.06 (m, 2H), 2.18 (s, 6H), 2.21-2.29 (m, 1H), 2.32-2.44 (m, 1H), 2.54-2.71 (m, 2H), 2.74-2.87 (m, 1H), 3.91-4.10 (m, 4H), 1H missing. m/z (ES$^+$), [M+H]$^+$: 214. HPLC (C05) t$_R$=0.98 min.

Compound 3A, Step 2: N,N,N-trimethyl-1-(8-oxo-1,4-dioxaspiro[4.5]decan-7-yl)methanaminium

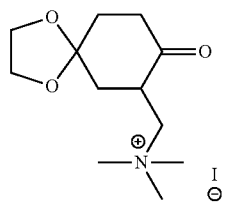 [SMILES: C[N+](C)(C)CC1CC2(CCC1=O)OCCO2 ; [I-]]

Iodomethane (958 g, 6751 mmol) was added to 7-((dimethylamino)methyl)-1,4-dioxaspiro[4.5]decan-8-one (1200 g, 5626 mmol) in Et$_2$O (2.5 L). The resulting mixture was stirred at 20° C. for 16 h. The precipitate was collected by filtration, washed with Et$_2$O (1 L) and dried under vacuum to afford N,N,N-trimethyl-1-(8-oxo-1,4-dioxaspiro[4.5]decan-7-yl)methanaminium (1800 g, 90%) as a white solid, which was used without further purification. $^1$H NMR (400 MHz, DMSO-d$_6$) δ 1.84-1.96 (m, 2H), 1.97-2.07 (m, 1H), 2.06-2.21 (m, 1H), 2.25-2.35 (m, 1H), 2.70-2.83 (m, 1H), 3.03 (s, 9H), 3.26-3.43 (m, 2H), 3.85-3.92 (m, 1H), 3.93-4.09 (m, 4H). m/z (ES$^+$), [M-I$^-$]$^+$: 228. HPLC (C05) t$_R$=0.28 min.

Compound 3A, Step 3: 7-methylene-1,4-dioxaspiro[4.5]decan-8-ol

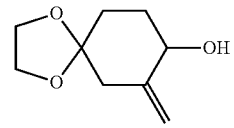

Aluminium oxide (800 g, 7846 mmol) was added to N,N,N-trimethyl-1-(8-oxo-1,4-dioxaspiro[4.5]decan-7-yl)methanaminium iodide (1800 g, 5067 mmol) in DCM (7 L). The resulting mixture was stirred at 20° C. for 1.5 h, cooled to 0° C., treated with MeOH (700 mL) followed by NaBH$_4$ (96 g, 2533 mmol, in batches) and stirred for 30 min at 0° C. The mixture was filtered through Al$_2$O$_3$ and washed with EtOAc and the filtrate concentrated. The crude product was purified by silica gel chromatography, elution gradient 0 to 20% EtOAc in petroleum ether. Pure fractions were evaporated to dryness to afford 7-methylene-1,4-dioxaspiro[4.5]decan-8-ol (750 g, 87%) as a colourless oil. $^1$H NMR (400 MHz, CDCl$_3$) δ 1.68-1.76 (m, 2H), 1.84-2.04 (m, 2H), 2.33 (d, J=13.7 Hz, 1H), 2.60 (d, J=13.7 Hz, 1H), 3.89-4.06 (m, 4H), 4.17-4.25 (m, 1H), 4.85-4.88 (m, 1H), 5.03-5.06 (m, 1H), OH missing. m/z (ES$^+$), [M+H—H$_2$O]$^+$: 153. HPLC (C05) t$_R$=0.75 min.

Compound 3A, Step 4: 6,9-dioxadispiro[2.1.45.33]dodecan-12-ol

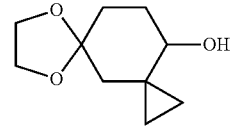

Diethylzinc (hexane solution) (1450 mL, 1450 mmol) was added to 7-methylene-1,4-dioxaspiro[4.5]decan-8-ol (143 g, 840 mmol) in DCM (500 mL) at 0° C. under nitrogen. The resulting mixture was stirred at 0° C. for 20 min, dropwise treated with diiodomethane (650 g, 2427 mmol) at 0° C. and stirred for 20 min at r.t. and for 15 h at 50° C. The mixture was quenched with sat. aq. NH$_4$Cl (500 mL) and combined with other 3 batches (in total 550 g of starting material). The organic layers were separated and washed with aq. NaCl (1×3 L). The combined aqueous layers were extracted with DCM and MeOH (10:1, 5×3 L). The organic layer was dried over Na$_2$SO$_4$, filtered and evaporated. The crude product was purified by silica gel chromatography, elution gradient 0 to 20% EtOAc in petroleum ether. Pure fractions were evaporated to dryness to afford 6,9-dioxadispiro[2.1.45.33]dodecan-12-ol (490 g, 89%) as a pale yellow oil. $^1$H NMR (400 MHz, CDCl$_3$) δ 0.21-0.57 (m, 4H), 1.01-1.10 (m, 1H), 1.61-2.04 (m, 4H), 2.16 (d, J=13.5 Hz, 1H), 3.10-3.19 (m, 1H), 3.83-4.03 (m, 4H), OH missing. m/z (ES$^+$), [M+H—H$_2$O]$^+$: 167. HPLC (C05) t$_R$=0.82 min.

Compound 3A, Step 5: 6,9-dioxadispiro[2.1.45.33]dodecan-12-one

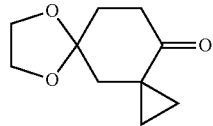 [SMILES: O=C1CCC2(CC13CC3)OCCO2]

Pyridinium chlorochromate (463 g, 2149 mmol) was added in small portions to a mixture of silica gel (560 g, 1791 mmol) and 6,9-dioxadispiro[2.1.45.33]dodecan-12-ol (330 g, 1791 mmol) in DCM (1700 mL). The resulting mixture was stirred at 50° C. for 16 h. This batch was combined with the other two batches (in total 490 g of starting material) for further workup. The combined mixtures were filtered through Celite and washed with DCM. The solvent was removed under reduced pressure. The crude product was purified by silica gel chromatography, elution gradient 0 to 10% EtOAc in petroleum ether. Pure fractions were evaporated to dryness to afford 6,9-dioxadispiro[2.1.45.33]dodecan-12-one (360 g, 73.5%) as a pale yellow oil. $^1$H NMR (300 MHz, CDCl$_3$) δ 0.68-0.75 (m, 2H), 1.24-1.34 (m, 2H), 1.98 (s, 2H), 2.08-2.23 (m, 2H), 2.60 (t, J=7.4, 6.7 Hz, 2H), 3.93-4.15 (m, 4H). m/z (ES$^+$), [M+H]$^+$: 183 HPLC (C05) t$_R$=1.04 min.

Compound 3A, Step 6: (Z)-11-(hydroxymethylene)-6,9-dioxadispiro[2.1.45.33]dodecan-12-one

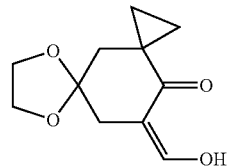 [SMILES: O=C1/C(=C\O)CC2(CC13CC3)OCCO2]

6,9-Dioxadispiro[2.1.45.33]dodecan-12-one (170 g, 932.94 mmol) in THF (600 mL) was added to sodium ethoxide (95 g, 1399 mmol) and ethyl formate (225 mL, 2799 mmol) in THF (1 L) and EtOH (400 mL). The mixture was stirred at r.t. for 1 h and 70° C. for 2 h and combined with two other batches for further workup (total 360 g of starting material). The solvent was removed under reduced pressure and the residue poured into 1M aq. NaOH (3 L) and washed with Et$_2$O (2×1.5 L). The water layer was adjusted to pH 3-4 with conc. HCl and extracted with DCM (2×2 L). The combined organic layers were washed with brine (1×2 L), dried over Na$_2$SO$_4$, filtered and evaporated to afford desired product (380 g, 91%) as a brown oil. $^1$H NMR (400 MHz, CDCl$_3$) δ 0.84 (q, J=3.9, 3.9, 3.9 Hz, 2H), 1.48 (q, J=3.8, 3.8, 3.7 Hz, 2H), 1.88 (s, 2H), 2.66 (s, 2H), 3.96-4.13 (m, 4H), 7.85 (d, J=5.6 Hz, 1H), 14.90 (d, J=7.0 Hz, 1H). m/z (ES$^+$), [M+H]$^+$=211; HPLC (C05) t$_R$=1.13 min.

Compound 3A, Step 7: 4'H,6'H-dispiro[cyclopropane-1,7'-benzo[d]isoxazole-5',2"-[1,3]dioxolane]

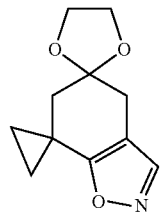 [SMILES: c1noc2c1CC1(CC23CC3)OCCO1]

A solution of (Z)-11-(hydroxymethylene)-6,9-dioxadispiro[2.1.45.33]dodecan-12-one (160 g, 761 mmol) in AcOH (1.4 L) was added to a stirred mixture of hydroxylamine hydrochloride (58.2 g, 837 mmol) and potassium acetate (164 g, 1674 mmol) in water (280 mL). The mixture was stirred at 80° C. for 1 h and worked up together with other batches (375 g of starting material in total). The solvent was removed under reduced pressure and the residue was basified with 1M aq. NaOH solution and sat. aq. NaHCO$_3$. The mixture was extracted with DCM (3×1.2 L). The organic layer was dried over Na$_2$SO$_4$, filtered and evaporated to afford the crude product which was purified by silica gel chromatography (0 to 25% EtOAc in petroleum ether). Pure fractions were evaporated to dryness to afford 4'H,6'H-dispiro[cyclopropane-1,7'-benzo[d]isoxazole-5',2"-[1,3]dioxolane] (300 g, 80%) as a yellow oil. $^1$H NMR (CDCl$_3$, 400 MHz) δ 0.88-0.94 (m, 2H), 1.32-1.38 (m, 2H), 1.97 (s, 2H), 2.79 (s, 2H), 3.98-4.09 (m, 4H), 8.02 (s, 1H). m/z (ES$^+$), [M+H]$^+$=208; HPLC (C05) t$_R$=1.68 min.

Compound 3A, Step 8: 4H-spiro[benzo[d]isoxazole-7,1'-cyclopropan]-5(6H)-one

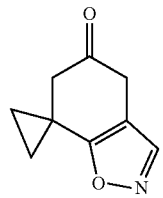 [SMILES: O=C1Cc2cnoc2C2(CC2)C1]

4'H,6'H-dispiro[cyclopropane-1,7'-benzo[d]isoxazole-5',2"-[1,3]dioxolane] (300 g, 203 mmol) was added to 1M aq. HCl (1.2 L) and acetone (600 mL), stirred at 75° C. for 5 h, concentrated, and basified with sat. aq. Na$_2$CO$_3$. The mixture was extracted with EtOAc (3×600 mL) and washed with brine (500 mL). The organic layer was dried over Na$_2$SO$_4$, filtered and evaporated to afford crude product which was purified by silica gel chromatography (0 to 25% EtOAc in petroleum ether). Pure fractions were evaporated to dryness to afford 4H-spiro[benzo[d]isoxazole-7,1'-cyclopropan]-5(6H)-one (175 g, 75%) as a pale yellow solid. $^1$H NMR (300 MHz, CDCl$_3$) δ 0.93-1.01 (m, 2H), 1.34-1.44 (m, 2H), 2.68 (s, 2H), 3.45 (s, 2H), 8.10 (s, 1H). m/z (ES$^+$), [M+H]$^+$=164; HPLC (C05) t$_R$=1.47 min.

Compound 4A: 4H-spiro[benzo[d]isoxazole-7,1'-cyclopropan]-5(6H)-one

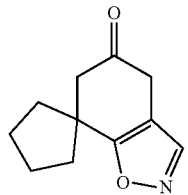 [SMILES: O=C1Cc2cnoc2C2(CCCC2)C1]

Compound 4A, Step 1: 1,4-dioxadispiro[4.1.47.35]tetradecan-12-one

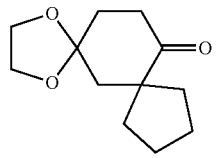 [SMILES: O=C1CCC2(CC13CCCC3)OCCO2]

Potassium tertiary butoxide (21.55 g, 192 mmol) was added to 1,4-dioxaspiro[4.5]decan-8-one (15 g, 96 mmol) and 1,4-dibromobutane (20.74 g, 96.04 mmol). The mixture was stirred for 2 h at 100° C., cooled to r.t., poured into water (300 mL) and extracted with EtOAc (3×200 mL). The organic layer was dried over Na$_2$SO$_4$, filtered and evaporated to afford the crude product, which was purified by silica gel chromatography, elution gradient 0 to 10% EtOAc in petroleum ether. Pure fractions were evaporated to dryness to afford 1,4-dioxadispiro[4.1.47.35]tetradecan-12-one (9.00 g, 44.6%) as a pale yellow oil. m/z (ES$^+$), [M+H]$^+$=211; HPLC (C05) t$_R$=1.30 min.

Compound 4A, Step 2: (Z)-13-(hydroxymethylene)-1,4-dioxadispiro[4.1.47.35]tetradecan-12-one

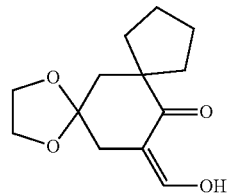 [SMILES: O=C1/C(=C\O)CC2(CC13CCCC3)OCCO2]

1,4-Dioxadispiro[4.1.47.35]tetradecan-12-one (9.00 g, 42.8 mmol) in THF (20 mL) was added to sodium ethoxide (4.37 g, 64.2 mmol), ethyl formate (10.34 mL, 128.40 mmol) in THF (50 mL) and EtOH (20 mL). The mixture was stirred at r.t. for 1 h and at 70° C. for 2 h, quenched with 1M aq. NaOH (500 mL) and washed with Et$_2$O (2×200 mL). The mixture was acidified with HCl and extracted with DCM (3×200 mL). The organic layer was dried over Na$_2$SO$_4$, filtered and evaporated to afford the crude product (Z)-13-(hydroxymethylene)-1,4-dioxadispiro[4.1.47.35]tetradecan-12-one (3.00 g, 29.4%) as a light yellow oil. $^1$H NMR (300 MHz, CDCl$_3$) δ ppm 1.68-1.72 (m, 2H), 1.72-1.78 (m, 2H), 1.80-1.87 (m, 4H), 2.12 (s, 2H), 2.59 (d, J=1.1 Hz, 2H), 4.01 (s, 4H), 8.46 (d, J=2.9 Hz, 1H), 14.80 (d, J=4.0 Hz, 1H). m/z (ES$^+$), [M+H]$^+$=239; HPLC (C05) t$_R$=1.39 min (90%).

Compound 4A, Step 3: 4'H,6'H-dispiro[cyclopropane-1,7'-benzo[d]isoxazole-5',2"-[1,3]dioxolane]

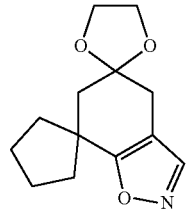 [SMILES: c1noc2c1CC1(CC23CCCC3)OCCO1]

A solution of (Z)-11-(hydroxymethylene)-6,9-dioxadispiro[2.1.45.33]dodecan-12-one (3.00 g, 14.3 mmol) in AcOH (50 mL) was added to a stirred mixture of hydroxylamine hydrochloride (1.09 g, 15.7 mmol) and potassium acetate (3.08 g, 31.39 mmol) in water (10 mL). The resulting mixture was stirred at 80° C. for 1 h. The solvent was removed under reduced pressure. The mixture was basified with sat. aq. NaHCO$_3$ and diluted with EtOAc (200 mL) and washed with water (75 mL) and brine (75 mL). The organic layer was dried over Na$_2$SO$_4$, filtered and evaporated to afford the crude product, which was purified by silica gel chromatography (0 to 15% EtOAc in petroleum ether). Pure fractions were evaporated to dryness to afford 4'H,6'H-dispiro[cyclopropane-1,7'-benzo[d]isoxazole-5',2"-[1,3]dioxolane] (1.30 g, 44%) as a pale yellow oil. $^1$H NMR (300 MHz, CDCl$_3$) δ ppm 1.72-1.86 (m, 4H), 1.89-1.98 (m, 2H), 2.00 (s, 2H), 2.04-2.14 (m, 2H), 2.72 (s, 2H), 4.02 (s, 4H), 8.02 (s, 1H); m/z (ES$^+$), [M+H]$^+$=236; HPLC (C05) t$_R$=1.036 min (100%).

Compound 4A, Step 4: 4'H,6'H-dispiro[cyclopropane-1,7'-benzo[d]isoxazole-5',2"-[1,3]dioxolane]

4'H,6'H-dispiro[cyclopentane-1,7'-benzo[d]isoxazole-5',2"-[1,3]dioxolane] (1.3 g, 5.53 mmol) was added to 1M aq. HCl (50 mL) and acetone (10 mL). The resulting mixture was stirred at 80° C. for 16 h, basified with sat. aq. NaHCO$_3$ and diluted with EtOAc (150 mL) and washed with brine (50 mL). The organic layer was dried over Na$_2$SO$_4$, filtered and evaporated to afford the crude product, which was purified by silica gel chromatography (0 to 10% EtOAc in petroleum ether). Pure fractions were evaporated to dryness to afford 4H-spiro[benzo[d]isoxazole-7,1'-cyclopentan]-5(6H)-one (0.70 g, 66%) as a yellow solid. $^1$H NMR (400 MHz, CDCl$_3$) δ ppm 1.66-1.74 (m, 2H), 1.75-1.87 (m, 2H), 1.88-1.99 (m, 2H), 2.06-2.16 (m, 2H), 2.68 (s, 2H), 3.35 (s, 2H), 8.11 (s, 1H); m/z (ES$^+$), [M+H]$^+$=192; HPLC (C05) t$_R$=1.270 min (100%).

An overview of general synthetic methods applicable to the preparation of compounds of the application is given in the schemes below.
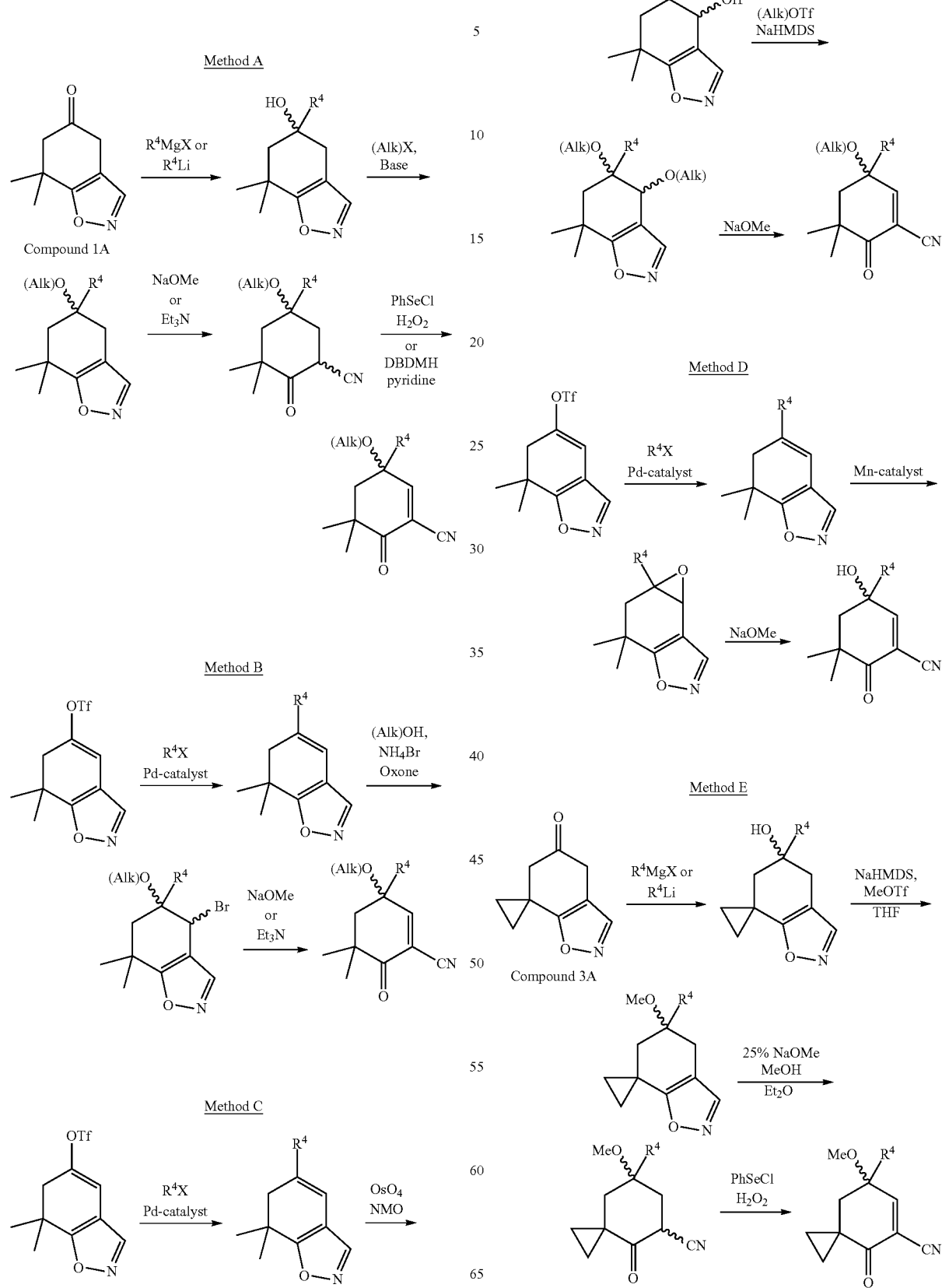

Method F
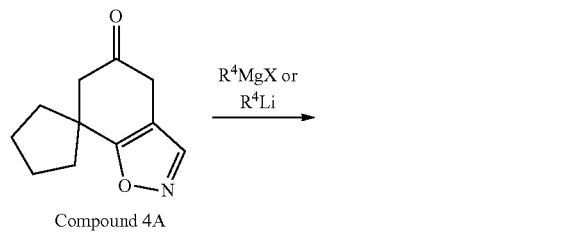
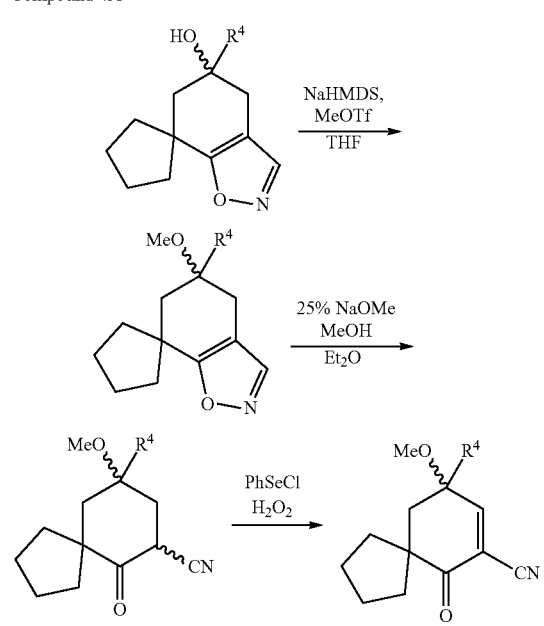
Method G
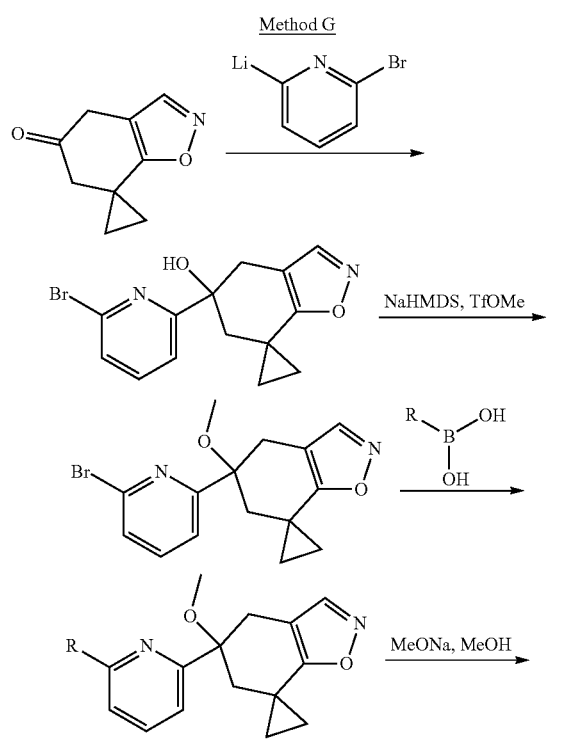
-continued
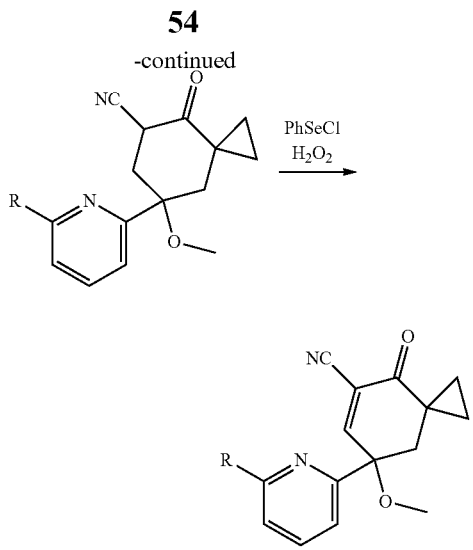
Method H
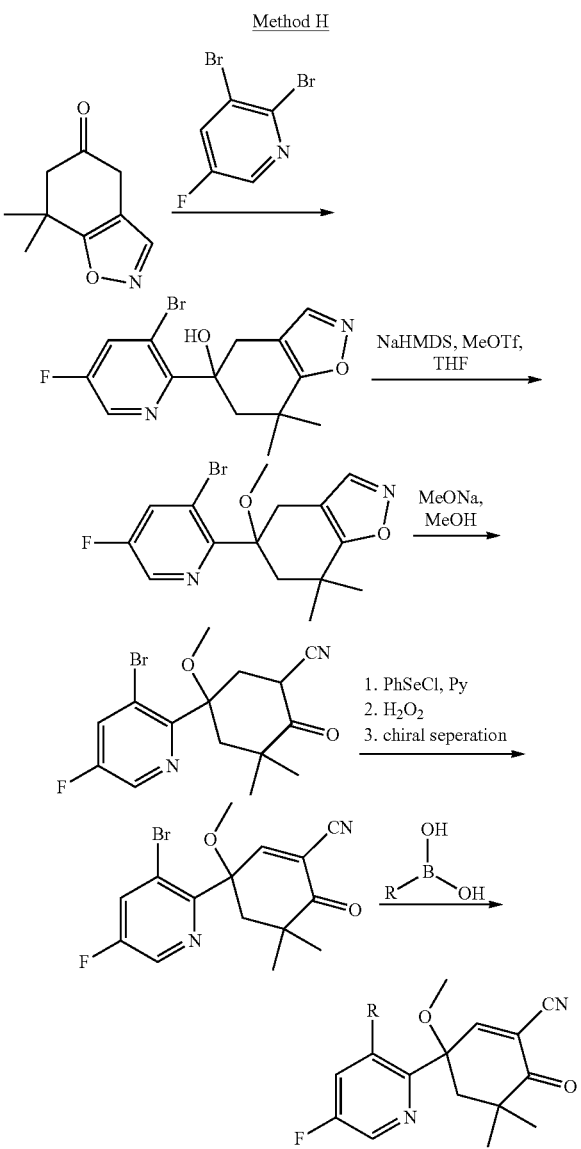

Compound 1: 3-methoxy-5,5-dimethyl-6-oxo-3-[4-(trifluoromethyl)-2-pyridyl]cyclohexene-1-carbonitrile

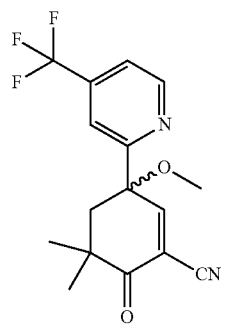 [SMILES: COC1(c2cc(C(F)(F)F)ccn2)C=C(C#N)C(=O)C(C)(C)C1]

Compound 1, Step 1: 7,7-dimethyl-5-[4-(trifluoromethyl)-2-pyridyl]-4,6-dihydro-1,2-benzoxazol-5-ol

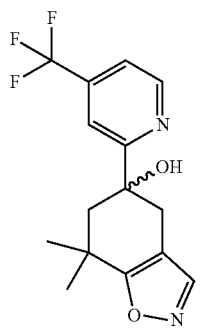 [SMILES: CC1(C)CC(O)(c2cc(C(F)(F)F)ccn2)Cc2cnoc21]

2.50M n-BuLi in hexanes (4.00 mL, 9.99 mmol) was added drop-wise to a solution of 2-bromo-4-(trifluoromethyl)pyridine (2.26 g, 9.99 mmol) in dry DCM (6 mL) at −78° C. under nitrogen, and the mixture was stirred for 30 min. A solution of 7,7-dimethyl-4,6-dihydro-1,2-benzoxazol-5-one (Compound A1, 600 mg, 3.63 mmol) in dry DCM (9.00 mL) was added drop-wise. The solution was stirred at −78° C. for 2 h. The mixture was diluted with MeOH (5.00 mL) at −78° C. and warmed to 23° C. The mixture was diluted with sat. aq. NH$_4$Cl (50 mL), and the aq. phase extracted with EtOAc (3×50 mL). The combined organic phases were washed with brine (50 mL), dried (MgSO$_4$), filtered, and concentrated under reduced pressure. The residue was purified by silica gel chromatography (40 g cartridge), eluting with hexanes and EtOAc (050%), and reverse phase chromatography (25 g, C-18 cartridge), eluting with MeCN (10-100%) and water containing 0.1% (NH$_4$)$_2$CO$_3$ and 0.4% NH$_4$OH, to provide the title compound as an oil (422 mg, 37%). $^1$H NMR (500 MHz, CDCl$_3$) δ 8.76 (d, J=5.1 Hz, 1H), 8.07 (s, 1H), 7.75-7.72 (m, 1H), 7.49 (ddd, J=5.1, 1.5, 0.6 Hz, 1H), 4.32 (s, 1H), 3.13 (d, J=15.9 Hz, 1H), 2.70 (dd, J=15.9, 2.1 Hz, 1H), 2.26 (d, J=14.0 Hz, 1H), 1.94 (dd, J=13.9, 2.1 Hz, 1H), 1.57 (s, 3H), 1.37 (s, 3H). m/z (ES+), [M+H]$^+$: 313.2 HPLC (B05) $t_R$=2.16 min.

Compound 1, Step 2: 5-methoxy-7,7-dimethyl-5-[4-(trifluoromethyl)-2-pyridyl]-4,6-dihydro-1,2-benzoxazole

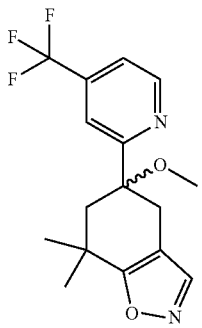 [SMILES: COC1(c2cc(C(F)(F)F)ccn2)Cc2cnoc2C(C)(C)C1]

A solution of 7,7-dimethyl-5-[4-(trifluoromethyl)-2-pyridyl]-4,6-dihydro-1,2-benzoxazol-5-ol (422 mg, 1.35 mmol) in THF (14 mL) was added to a solution of hexamethylphosphoramide (0.470 mL, 2.70 mmol) and NaHMDS (1.62 mL, 1.62 mmol, 1M in THF) in THF (14 mL) at −78° C. After 5 min of stirring, methyl trifluoromethanesulfonate (0.310 mL, 2.70 mmol) was added, and the mixture was stirred at −78° C. for 5 min. The mixture was warmed to 23° C. for 5 min and diluted with water (2.00 mL). Sat. aq. NH$_4$Cl (10 mL) and EtOAc (10 mL) were added, and the aq. phase was extracted with EtOAc (2×10 mL). The combined organic phases were washed with brine (10 mL), dried (Na$_2$SO$_4$), and filtered through a plug of silica, washing with EtOAc (40 mL). The filtrate was concentrated under reduced pressure to provide the title compound as an oil (440 mg, 99%). $^1$H NMR (500 MHz, CDCl$_3$) δ 8.74 (d, J=5.1 Hz, 1H), 8.12 (s, 1H), 7.86-7.81 (m, 1H), 7.44 (dd, J=5.1, 1.0 Hz, 1H), 3.44 (d, J=16.4 Hz, 1H), 3.03 (s, 3H), 2.97 (dd, J=16.5, 1.8 Hz, 1H), 2.13 (d, J=2.0 Hz, 1H), 2.11 (s, 1H), 1.52 (s, 3H), 1.24 (s, 3H). m/z (ES+), [M+H]$^+$: 327.2 HPLC (B05) $t_R$=2.41 min.

Compound 1, Step 3: 5-methoxy-3,3-dimethyl-2-oxo-5-[4-(trifluoromethyl)-2-pyridyl]cyclohexanecarbonitrile

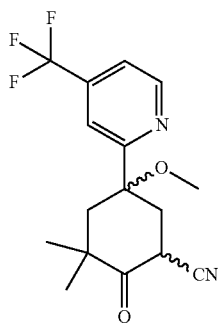 [SMILES: COC1(c2cc(C(F)(F)F)ccn2)CC(C#N)C(=O)C(C)(C)C1]

5-Methoxy-7,7-dimethyl-5-[4-(trifluoromethyl)-2-pyridyl]-4,6-dihydro-1,2-benzoxazole (440 mg, 1.35 mmol) and NaOMe (25 wt. % in MeOH, 1.67 mL, 30.1 mmol) were dissolved in MeOH (15 mL) and Et$_2$O (25 mL), and the mixture was stirred at 23° C. for 2 h. Sat. aq. NH$_4$Cl (50 mL) was added, and the aq. phase was extracted with EtOAc (3×50 mL). The combined organic phases were washed with brine (50 mL), dried (Na₂SO₄), filtered, and concentrated under reduced pressure. The residue was purified by silica gel chromatography (40 g cartridge), eluting with hexanes and EtOAc (0-50%), to provide the title compound as an oil (303 mg, 69%). ¹H NMR (500 MHz, CDCl₃) δ 8.77 (d, J=5.1 Hz, 1H), 7.80-7.77 (m, 1H), 7.50 (ddd, J=5.1, 1.6, 0.6 Hz, 1H), 4.34-4.29 (m, 1H), 3.21 (s, 3H), 2.88-2.84 (m, 2H), 2.27-2.17 (m, 2H), 1.49 (s, 3H), 1.19 (s, 3H). m/z: ES+[M+H]⁺: 327.2 HPLC (B05) $t_R$=1.55 min.

Compound 1, Step 4: 3-methoxy-5,5-dimethyl-6-oxo-3-[4-(trifluoromethyl)-2-pyridyl]-cyclohexene-1-carbonitrile

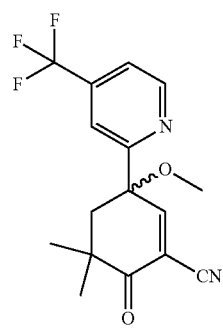 [SMILES: COC1(c2cc(C(F)(F)F)ccn2)C=C(C#N)C(=O)C(C)(C)C1]

A solution of pyridine (150 μL, 1.86 mmol) in DCM (1.00 mL) was added to a solution of phenylselenyl chloride (356 mg, 1.86 mmol) in DCM (3.00 mL) at 0° C. The mixture was stirred at 0° C. for 30 min. A solution of 5-methoxy-3,3-dimethyl-2-oxo-5-[4-(trifluoromethyl)-2-pyridyl]cyclohexanecarbonitrile (303 mg, 0.930 mmol) in DCM (8.70 mL) was added drop-wise, and the solution was stirred at 0° C. for 2.5 h. 1M HCl (2.00 mL) was added, followed by water (5.00 mL), and the phases were separated. Hydrogen peroxide (4.56 mL, 18.6 mmol, 35%) was added drop-wise to the organic phase at 0° C. The mixture was vigorously stirred at 0° C. for 30 min. The mixture was diluted with DCM (50 mL) and sat. aq. NaHCO₃ (20 mL). The aq. phase was extracted with DCM (3×50 mL), and the combined organic phases were washed with brine (20 mL), dried (MgSO₄), filtered, and concentrated under reduced pressure. The residue was purified by silica gel chromatography (25 g cartridge), eluting with hexanes and EtOAc (0-30%), to provide the title compound as a solid (210 mg, 70%). ¹H NMR (500 MHz, CDCl₃) δ 8.76 (d, J=5.1 Hz, 1H), 8.00 (d, J=1.7 Hz, 1H), 7.81-7.77 (m, 1H), 7.53 (dd, J=5.1, 1.0 Hz, 1H), 3.25 (s, 3H), 2.28 (dd, J=14.6, 1.7 Hz, 1H), 2.19 (d, J=14.6 Hz, 1H), 1.40 (s, 3H), 1.06 (s, 3H). m/z: ES+[M+H]⁺: 325.3 HPLC (A05) $t_R$=2.33 min.

Compound 2: 3-(6-bromo-2-pyridyl)-3-methoxy-5,5-dimethyl-6-oxo-cyclohexene-1-carbonitrile

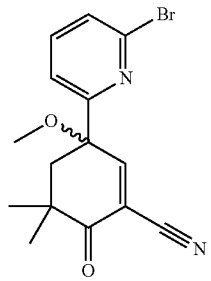 [SMILES: COC1(c2cccc(Br)n2)C=C(C#N)C(=O)C(C)(C)C1]

Compound 2, Step 1: 8-(6-bromo-2-pyridyl)-1,4-dioxaspiro[4.5]decan-8-ol

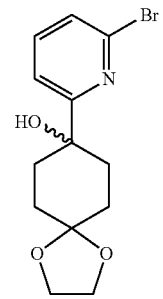 [SMILES: OC1(c2cccc(Br)n2)CCC2(CC1)OCCO2]

2.50 M n-BuLi in hexanes (29.6 mL, 74.1 mmol) was added drop-wise to a solution of 2,6-dibromopyridine (16.1 g, 67.9 mmol) in DCM (80 mL) at −78° C., and the mixture was stirred for 2 h at −78° C. A solution of 1,4-dioxaspiro[4.5]decan-8-one (9.65 g, 61.8 mmol) in DCM (20 mL) was added drop-wise over 30 min. Stirring was continued at −78° C. for 2 h, and the mixture was slowly warmed to 23° C. and stirred for 18 h. Sat. aq. NaHCO₃ (150 mL) was added, and the aq. phase extracted with DCM (3×100 mL). The combined organic phases were washed with brine (100 mL), dried (MgSO₄), filtered, and concentrated under reduced pressure. The product was triturated from hexanes (400 mL) to provide the title compound as a solid (14.7 g, 76%). ¹H NMR (500 MHz, CDCl₃) δ 7.55 (t, J=7.8 Hz, 1H), 7.43-7.32 (m, 2H), 4.18 (s, 1H), 4.08-3.87 (m, 4H), 2.24-1.98 (m, 4H), 1.81-1.64 (m, 4H). m/z (ES+), [M+H]⁺: 314.1. HPLC (B05) $t_R$=1.77 min.

Compound 2, Step 2: 2-bromo-6-(8-methoxy-1,4-dioxaspiro[4.5]decan-8-yl)pyridine

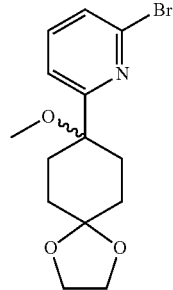 [SMILES: COC1(c2cccc(Br)n2)CCC2(CC1)OCCO2]

60 wt % NaH in mineral oil (3.82 g, 95.5 mmol) was added in portions to a solution of 8-(6-bromo-2-pyridyl)-1,4-dioxaspiro[4.5]decan-8-ol (10.0 g, 31.8 mmol) in THF (75 mL) at 0° C. The mixture was warmed to 23° C. and stirred for 30 min. Iodomethane (6.34 mL, 102 mmol) was added, and the mixture was stirred at 23° C. for 2 h. Sat. aq. NaHCO$_3$ (100 mL) was added, and the aq. Phase was extracted with EtOAc (3×100 mL). The combined organic phases were washed with brine (100 mL), dried (MgSO$_4$), filtered, and concentrated under reduced pressure. The product was purified by silica gel chromatography (120 g cartridge), eluting with hexanes and EtOAc (0-40%), to provide the title compound as a solid (9.80 mg, 94%). $^1$H NMR (500 MHz, CDCl$_3$) δ 7.53 (t, J=7.7 Hz, 1H), 7.46 (dd, J=7.7, 1.0 Hz, 1H), 7.35 (dd, J=7.7, 1.0 Hz, 1H), 4.05-3.86 (m, 4H), 3.07 (s, 3H), 2.33-2.05 (m, 2H), 2.10-1.83 (m, 4H), 1.77-1.60 (m, 2H). m/z (ES+), [M-Ome+H]$^+$: 296.3. HPLC (B05) t$_R$=2.02 min.

Compound 2, Step 3: 4-(6-bromo-2-pyridyl)-4-methoxy-cyclohexanone

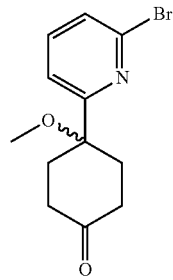 [SMILES: COC1(c2cccc(Br)n2)CCC(=O)CC1]

2-Bromo-6-(8-methoxy-1,4-dioxaspiro[4.5]decan-8-yl)pyridine (9.79 g, 29.8 mmol) was dissolved in 1,4-dioxane (100 mL), and 3M HCl (49.7 mL, 149 mmol) was added. The mixture was stirred at 23° C. for 3 h. 1N NaOH (150 mL) and sat. aq. NaHCO$_3$ (50 mL) were added, and the aq. phase was extracted with EtOAc (3×100 mL). The combined organic phases were washed with brine (100 mL), dried (MgSO$_4$), filtered, and concentrated under reduced pressure. The product was purified by silica gel chromatography (120 g cartridge), eluting with hexanes and EtOAc (0-30%), to provide the title compound as a solid (7.49 g, 89%). $^1$H NMR (500 MHz, CDCl$_3$) δ 7.59 (t, J=7.7 Hz, 1H), 7.53 (dd, J=7.7, 1.0 Hz, 1H), 7.40 (dd, J=7.7, 1.0 Hz, 1H), 3.20 (s, 3H), 2.76-2.61 (m, 2H), 2.45-2.33 (m, 4H), 2.33-2.22 (m, 2H). m/z (ES+), [M+H]$^+$: 284.2. HPLC (B05) t$_R$=1.82 min.

Compound 2, Step 4: 4-(6-bromo-2-pyridyl)-4-methoxy-2,2-dimethyl-cyclohexanone

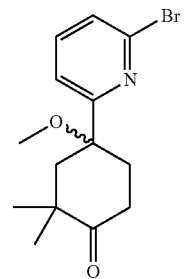 [SMILES: COC1(c2cccc(Br)n2)CCC(=O)C(C)(C)C1]

t-Butanol (20 mL) was added to a mixture of 4-(6-bromo-2-pyridyl)-4-methoxy-cyclohexanone (1.42 g, 5.00 mmol) and KOtBu (1.18 g, 10.5 mmol). The mixture was stirred at 23° C. for 1 h, and iodomethane (0.654 mL, 10.5 mmol) was added. Stirring was continued at 23° C. for 20 h. Water (50 mL) was added, and the aq. phase was extracted with EtOAc (3×50 mL). The combined organic phases were washed with brine (50 mL), dried (MgSO$_4$), filtered, and concentrated under reduced pressure. The product was purified by silica gel chromatography (40 g cartridge), eluting with hexanes and EtOAc (0-30%), to provide the title compound as a solid (0.591 g, 38%). $^1$H NMR (500 MHz, CDCl$_3$) δ 7.57 (t, J=7.7 Hz, 1H), 7.52 (dd, J=7.7, 1.0 Hz, 1H), 7.38 (dd, J=7.7, 1.0 Hz, 1H), 3.14 (s, 3H), 2.96-2.79 (m, 1H), 2.61-2.42 (m, 1H), 2.42-2.25 (m, 2H), 2.10 (d, J=1.7 Hz, 2H), 1.37 (s, 3H), 1.06 (s, 3H). m/z (ES+), [M-OMe+H]$^+$: 280.1. HPLC (A05) t$_R$=2.38 min.

Compound 2, Step 5: (6Z)-4-(6-bromo-2-pyridyl)-6-(hydroxymethylene)-4-methoxy-2,2-dimethyl-cyclohexanone

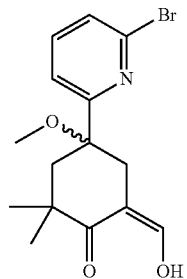 [SMILES: COC1(c2cccc(Br)n2)C/C(=C/O)C(=O)C(C)(C)C1]

A mixture of ethyl formate (5.00 mL, 61.9 mmol) and 4-(6-bromo-2-pyridyl)-4-methoxy-2,2-dimethyl-cyclohexanone (312 mg, 1.00 mmol) was cooled to 0° C. A solution of 25 wt % NaOMe in MeOH (2.50 mL, 11.6 mmol) was added drop-wise. The mixture was warmed to 23° C. and stirred for 3.5 h. Sat. aq. NH$_4$Cl (15 mL) was added, and the aq. phase was extracted with EtOAc (3×20 mL). The combined organic phases were washed with brine (25 mL), dried (MgSO$_4$), filtered, and concentrated under reduced pressure. The product was purified by silica gel chromatography (12 g cartridge), eluting with hexanes and EtOAc (0-20%), to provide the title compound as a solid (245 mg, 72%). ¹H NMR (500 MHz, CDCl₃) δ 14.87 (d, J=5.0 Hz, 1H), 8.39 (d, J=4.7 Hz, 1H), 7.58 (t, J=7.6 Hz, 1H), 7.54 (dd, J=7.7, 1.1 Hz, 1H), 7.39 (dd, J=7.5, 1.1 Hz, 1H), 3.25-3.14 (m, 1H), 3.02 (s, 3H), 2.78 (dt, J=15.8, 1.8 Hz, 1H), 1.95 (d, J=1.7 Hz, 2H), 1.40 (s, 3H), 1.19 (s, 3H). m/z (ES+), [M+H]⁺: 340.5. HPLC (B05) t_R=1.34 min.

Compound 2, Step 6: 5-(6-bromo-2-pyridyl)-5-methoxy-7,7-dimethyl-4,6-dihydro-1,2-benzoxazole

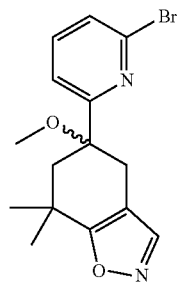 [SMILES: COC1(c2cccc(Br)n2)Cc2cnoc2C(C)(C)C1]

EtOH (27 mL) and water (3.00 mL) were added to (6Z)-4-(6-bromo-2-pyridyl)-6-(hydroxymethylene)-4-methoxy-2,2-dimethyl-cyclohexanone (2.25 g, 6.61 mmol). Hydroxylamine hydrochloride (4.60 g, 66.1 mmol) was added, and the mixture was heated at 85° C. for 1 h. Water (50 mL) was added, and the aq phase was extracted with a 2:1 mixture of Et₂O/DCM (3×50 mL). The combined organic phases were washed with sat. NaHCO₃ (50 mL), brine (50 mL), dried (MgSO₄), filtered, and concentrated under reduced pressure to provide the title compound as an oil (2.18 g, 98%). ¹H NMR (500 MHz, CDCl₃) δ 8.10 (s, 1H), 7.62-7.53 (m, 2H), 7.40 (dd, J=7.3, 1.3 Hz, 1H), 3.38 (d, J=16.6 Hz, 1H), 3.01 (s, 3H), 2.94 (dd, J=16.6, 1.9 Hz, 1H), 2.13-2.03 (m, 2H), 1.49 (s, 3H), 1.27 (s, 3H). m/z (ES+), [M+H]⁺: 337.5. HPLC (B05) t_R=2.39 min.

Compound 2, Step 7: 5-(6-bromo-2-pyridyl)-5-methoxy-3,3-dimethyl-2-oxo-cyclohexanescarbonitrile

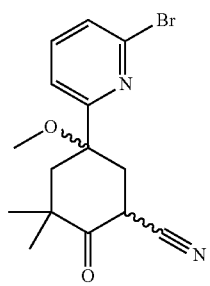 [SMILES: COC1(c2cccc(Br)n2)CC(C#N)C(=O)C(C)(C)C1]

A solution of 5-(6-bromo-2-pyridyl)-5-methoxy-7,7-dimethyl-4,6-dihydro-1,2-benzoxazole (2.18 g, 6.46 mmol) in Et₂O (30 mL) was added to a solution of 25 wt % NaOMe in MeOH (14 mL, 64.8 mmol). The mixture was stirred at 23° C. for 1.5 h. The mixture was diluted with a 2:1 mixture of Et₂O:DCM (50 mL) and acidified to pH 4 with 1N HCl (67 mL). The aq. phase was extracted with a 2:1 mixture of Et₂O:DCM (2×50 mL). The combined organic phases were washed with brine (50 mL), dried (MgSO₄), filtered, and concentrated under reduced pressure. The product was purified by silica gel chromatography (40 g cartridge), eluting with hexanes and EtOAc (0-30%), to provide the title compound as a solid (1.52 g, 72%). ¹H NMR (500 MHz, CDCl₃) δ 7.61 (t, J=5.5 Hz, 1H), 7.49 (d, J=7.6 Hz, 1H), 7.43 (d, J=7.8 Hz, 1H), 4.26 (t, J=9.8 Hz, 1H), 3.18 (d, J=3.3 Hz, 3H), 2.79 (d, J=9.6 Hz, 2H), 2.17 (d, J=3.3 Hz, 2H), 1.44 (d, J=3.2 Hz, 3H), 1.16 (d, J=3.2 Hz, 3H). m/z (ES+), [M+H]⁺: 337.5. HPLC (B05) t_R=1.46 min.

Compound 2, Step 8: 3-(6-bromo-2-pyridyl)-3-methoxy-5,5-dimethyl-6-oxo-cyclohexene-1-carbonitrile

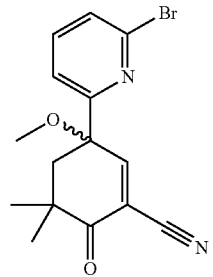 [SMILES: COC1(c2cccc(Br)n2)C=C(C#N)C(=O)C(C)(C)C1]

Phenylselenium chloride (0.575 g, 3.00 mmol) was dissolved in DCM (2.50 mL) at 0° C. A solution of pyridine (0.243 mL, 3.00 mmol) in DCM (1.50 mL) was added drop-wise, and the mixture was stirred at 0° C. for 20 min. A solution of 5-(6-bromo-2-pyridyl)-5-methoxy-3,3-dimethyl-2-oxo-cyclohexanescarbonitrile (0.506 g, 1.50 mmol) in DCM (2.50 mL) was added drop-wise, and the mixture was stirred at 0° C. for 3 h. 1N HCl (1.50 mL) was added, and the phases were separated. H₂O₂ in water (2.92 mL, 30.0 mmol, 35%) was added drop-wise to the organic phase at 0° C., and the mixture was vigorously stirred at 0° C. for 40 min. Water (15 mL) was added, and the aq phase was extracted with DCM (3×15 mL). The combined organic phases were washed with sat. aq. NaHCO₃ (15 mL), brine (15 mL), dried (MgSO₄), filtered, and concentrated under reduced pressure. The product was triturated from hexanes to provide the title compound as a solid (0.413 g, 82%). ¹H NMR (500 MHz, CDCl₃) δ 7.99 (d, J=1.4 Hz, 1H), 7.66 (t, J=7.8 Hz, 1H), 7.52 (dd, J=7.7, 0.9 Hz, 1H), 7.48 (dd, J=7.9, 0.9 Hz, 1H), 3.21 (s, 3H), 2.26 (d, J=14.7 Hz, 1H), 2.21 (dd, J=14.6, 1.6 Hz, 1H), 1.38 (s, 3H), 1.07 (s, 3H). m/z (ES+), [M+H]⁺: 335.8. HPLC (A05) t_R=2.31 min.

Compound 3: 3-methoxy-5,5-dimethyl-6-oxo-3-[5-(trifluoromethyl)-2-pyridyl]cyclohexene-1-carbonitrile

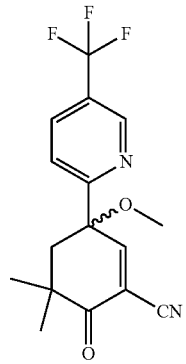 [SMILES: COC1(c2ccc(C(F)(F)F)cn2)C=C(C#N)C(=O)C(C)(C)C1]

Compound 3, Step 1: 7,7-dimethyl-5-[5-(trifluoromethyl)-2-pyridyl]-4,6-dihydro-1,2-benzoxazol-5-ol

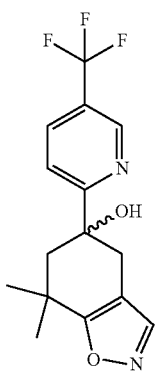 [SMILES: CC1(C)CC(O)(c2ccc(C(F)(F)F)cn2)Cc2cnoc21]

As described for step 1 of example 1, the title compound was prepared from 7,7-dimethyl-4,6-dihydro-1,2-benzoxazol-5-one (600 mg, 3.63 mmol), 2-bromo-5-(trifluoromethyl)pyridine (2.26 g, 9.99 mmol) and 2.50M n-BuLi in hexanes (3.99 mL, 9.99 mmol) in DCM (15 mL). The product was purified by silica gel chromatography (40 g cartridge), eluting with hexanes and EtOAc (0-50%), and reverse phase chromatography (25 g, C-18 cartridge), eluting with MeCN (10-100%) and water containing 0.1% $(NH_4)_2CO_3$ and 0.4% $NH_4OH$, to provide the title compound as an oil (474 mg, 42%). $^1H$ NMR (500 MHz, $CDCl_3$) δ 8.87-8.84 (m, 1H), 8.10 (s, 1H), 8.00 (dd, J=8.3, 1.7 Hz, 1H), 7.61 (d, J=8.3 Hz, 1H), 4.40 (s, 1H), 3.09 (d, J=15.9 Hz, 1H), 2.71 (dd, J=15.8, 2.0 Hz, 1H), 2.24 (d, J=13.9 Hz, 1H), 1.94 (dd, J=13.9, 2.0 Hz, 1H), 1.57 (s, 3H), 1.36 (s, 3H). m/z: ES+[M+H]+: 313.2 HPLC (B05) $t_R$=2.18 min.

Compound 3, Step 2: 5-methoxy-7,7-dimethyl-5-[5-(trifluoromethyl)-2-pyridyl]-4,6-dihydro-1,2-benzoxazole

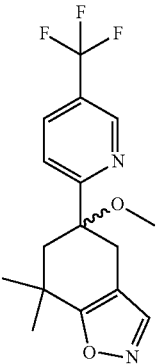

As described for step 2 of example 1, the title compound was prepared from 7,7-dimethyl-5-[5-(trifluoromethyl)-2-pyridyl]-4,6-dihydro-1,2-benzoxazol-5-ol (474 mg, 1.52 mmol), hexamethylphosphoramide (0.53 mL, 3.04 mmol), NaHMDS (1.82 mL, 1.82 mmol, 1M in THF), and methyl trifluoromethanesulfonate (0.34 mL, 3.04 mmol) in THF (1.00 mL) to provide the title compound as an oil (494 mg, 99%). m/z: ES+[M+H]+: 327.1 HPLC (B05) $t_R$=2.42 min.

Compound 3, Step 3: 5-methoxy-3,3-dimethyl-2-oxo-5-[5-(trifluoromethyl)-2-pyridyl]cyclohexanecarbonitrile As described for step 3 of example 1, the title compound was prepared from 5-methoxy-7,7-dimethyl-5-[5-(trifluoromethyl)-2-pyridyl]-4,6-dihydro-1,2-benzoxazole (494 mg, 1.51 mmol) and NaOMe (25 wt. % in MeOH, 1.88 mL, 33.8 mmol) in MeOH (20 mL) and $Et_2O$ (30 mL). The product was purified by silica gel chromatography (40 g cartridge), eluting with hexanes and EtOAc (0-50%), to provide the title compound as an oil (304 mg, 62%). $^1H$ NMR (500 MHz, $CDCl_3$) δ 8.82 (d, J=2.3 Hz, 1H), 8.00 (dd, J=8.3, 1.8 Hz, 1H), 7.69 (d, J=8.3 Hz, 1H), 4.32-4.27 (m, 1H), 3.19 (s, 3H), 2.84-2.78 (m, 2H), 2.22-2.17 (m, 2H), 1.46 (s, 3H), 1.17 (s, 3H). m/z: ES+[M+H]+: 327.2 HPLC (B05) $t_R$=1.54 min.

Compound 3, Step 4: 3-methoxy-5,5-dimethyl-6-oxo-3-[5-(trifluoromethyl)-2-pyridyl]cyclohexene-1-carbonitrile

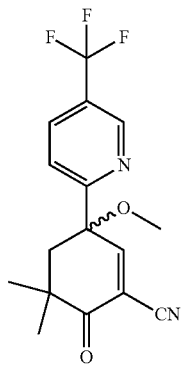 [SMILES: COC1(c2ccc(C(F)(F)F)cn2)C=C(C#N)C(=O)C(C)(C)C1]

As described for step 4 of example 1, the title compound was prepared from 5-methoxy-3,3-dimethyl-2-oxo-5-[5-(trifluoromethyl)-2-pyridyl]cyclohexanecarbonitrile (304 mg, 0.93 mmol), pyridine (0.15 mL, 1.86 mmol), phenylselenyl chloride (357 mg, 1.86 mmol) and hydrogen peroxide (4.58 mL, 18.6 mmol, 35%) in DCM (8.70 mL). The product was purified by silica gel chromatography (40 g cartridge), eluting with hexanes and EtOAc (0-30%), to provide the title compound as a solid (237 mg, 79%). $^1$H NMR (500 MHz, CDCl$_3$) δ 8.85-8.82 (m, 1H), 8.05 (dd, J=8.3, 1.7 Hz, 1H), 8.00 (d, J=1.6 Hz, 1H), 7.72 (d, J=8.3 Hz, 1H), 3.24 (s, 3H), 2.26 (dd, J=14.6, 1.7 Hz, 1H), 2.20 (d, J=14.6 Hz, 1H), 1.39 (s, 3H), 1.06 (s, 3H). m/z: ES+[M+H]$^+$: 325.2 HPLC (A05) $t_R$=2.33 min.

Compound 4: 3-(1-isoquinolyl)-3-methoxy-5,5-dimethyl-6-oxo-cyclohexene-1-carbonitrile

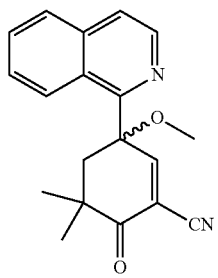 [SMILES: COC1(c2nccc3ccccc23)C=C(C#N)C(=O)C(C)(C)C1]

Compound 4, Step 1: 5-(1-isoquinolyl)-7,7-dimethyl-4,6-dihydro-1,2-benzoxazol-5-ol

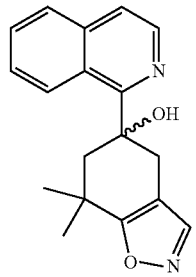 [SMILES: CC1(C)CC(O)(c2nccc3ccccc23)Cc2cnoc21]

As described for step 1 of example 1, the title compound was prepared from 7,7-dimethyl-4,6-dihydro-1,2-benzoxazol-5-one (500 mg, 2.76 mmol), 1-bromoisoquinoline (1.27 g, 6.10 mmol) and 2.50 M n-BuLi in hexanes (2.44 mL, 6.10 mmol) in DCM (10 mL). The product was purified by silica gel chromatography (80 g cartridge), eluting with hexanes and EtOAc (0-50%), and reverse phase chromatography (40 g, C-18 cartridge), eluting with MeCN (10-100%) and water containing 0.1% (NH$_4$)$_2$CO$_3$ and 0.4% NH$_4$OH, to provide the title compound as an oil (294 mg, 36%). $^1$H NMR (500 MHz, CDCl$_3$) δ 8.48 (d, J=5.6 Hz, 1H), 8.21 (d, J=8.7 Hz, 1H), 8.12 (s, 1H), 7.94 (d, J=8.2 Hz, 1H), 7.72 (ddd, J=8.1, 6.9, 1.1 Hz, 1H), 7.68 (d, J=5.4 Hz, 1H), 7.62 (ddd, J=8.4, 6.9, 1.4 Hz, 1H), 6.90 (s, 1H), 3.69 (d, J=16.5 Hz, 1H), 2.79 (dd, J=16.6, 1.6 Hz, 1H), 2.73 (d, J=14.2 Hz, 1H), 1.95 (dd, J=14.2, 1.5 Hz, 1H), 1.66 (s, 3H), 1.45 (s, 3H). m/z: ES+[M+H]$^+$: 295.2 HPLC (B05) $t_R$=2.24 min.

Compound 4, Step 2: 5-(1-isoquinolyl)-5-methoxy-7,7-dimethyl-4,6-dihydro-1,2-benzoxazole

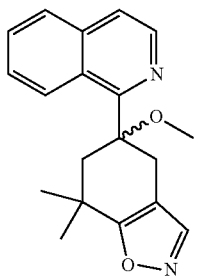 [SMILES: COC1(c2nccc3ccccc23)Cc2cnoc2C(C)(C)C1]

As described for step 2 of example 1, the title compound was prepared from 5-(1-isoquinolyl)-7,7-dimethyl-4,6-dihydro-1,2-benzoxazol-5-ol (147 mg, 0.50 mmol), hexamethyl-phosphoramide (0.17 mL, 1.00 mmol), NaHMDS (0.60 mL, 0.60 mmol, M in THF) and methyl trifluoromethanesulfonate (0.11 mL, 1.00 mmol) in THF (6.00 mL) to provide the title compound as an oil (154 mg, 99%). m/z: ES+[M+H]$^+$: 309.2 HPLC (B05) $t_R$=2.45 min.

Compound 4, Step 3: 5-(1-isoquinolyl)-5-methoxy-3,3-dimethyl-2-oxo-cyclohexanecarbonitrile

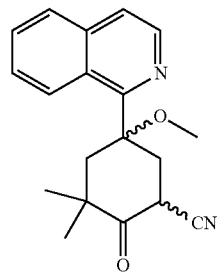 [SMILES: COC1(c2nccc3ccccc23)CC(C#N)C(=O)C(C)(C)C1]

As described for step 3 of example 1, the title compound was prepared from 5-(1-isoquinolyl)-5-methoxy-7,7-dimethyl-4,6-dihydro-1,2-benzoxazole (154 mg, 0.50 mmol) and NaOMe (25 wt. % in MeOH, 0.29 mL, 4.99 mmol) in MeOH (5.00 mL) and Et$_2$O (8.00 mL). The product was purified by silica gel chromatography (12 g cartridge), eluting with hexanes and EtOAc (0-40%), to provide the title compound as an oil (90.0 mg, 58%). $^1$H NMR (500 MHz, CDCl$_3$) $^1$H NMR (500 MHz, CDCl$_3$) δ 9.00 (dd, J=8.7, 0.9 Hz, 1H), 8.43 (d, J=5.6 Hz, 1H), 7.87 (d, J=7.5 Hz, 1H), 7.71 (ddd, J=8.2, 6.8, 1.2 Hz, 1H), 7.65 (ddd, J=8.4, 6.8, 1.4 Hz, 1H), 7.62 (d, J=5.2 Hz, 1H), 4.41 (dd, J=14.0, 4.4 Hz, 1H), 3.22 (dt, J=14.6, 4.3 Hz, 1H), 3.13 (s, 3H), 3.00 (d, J=11.9 Hz, 1H), 2.71 (dd, J=15.0, 4.1 Hz, 1H), 2.12 (d, J=16.1 Hz, 1H), 1.55 (s, 3H), 1.14 (s, 3H). m/z: ES+[M+H]$^+$: 309.2 HPLC (B05) $t_R$=1.72 min.

Compound 4, Step 4: 3-(1-isoquinolyl)-3-methoxy-5,5-dimethyl-6-oxo-cyclohexene-1-carbonitrile

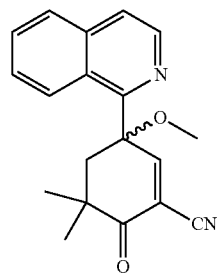 [SMILES: COC1(c2nccc3ccccc23)C=C(C#N)C(=O)C(C)(C)C1]

As described for step 4 of example 1, the title compound was prepared from 5-(1-isoquinolyl)-5-methoxy-3,3-dimethyl-2-oxo-cyclohexanecarbonitrile (90.0 mg, 0.29 mmol), pyridine (47.2 μL, 0.58 mmol), phenylselenyl chloride (112 mg, 0.58 mmol) and hydrogen peroxide (1.43 mL, 5.84 mmol, 35%) in DCM (3.00 mL). The product was purified by silica gel chromatography (12 g cartridge), eluting with hexanes and EtOAc (0-40%), to provide the title compound as a solid (64.5 mg, 72%). $^1$H NMR (500 MHz, CDCl$_3$) δ 8.87-8.82 (m, 1H), 8.44 (d, J=5.6 Hz, 1H), 8.41 (s, 1H), 7.93 (d, J=8.2 Hz, 1H), 7.78 (td, J=6.9, 3.4 Hz, 1H), 7.73-7.67 (m, 2H), 3.25 (s, 3H), 2.74 (dd, J=14.6, 1.3 Hz, 1H), 2.48 (d, J=14.6 Hz, 1H), 1.40 (s, 3H), 0.89 (s, 3H). m/z: ES+[M+H]$^+$: 307.2 HPLC (A05) $t_R$=2.54 min.

Compound 5: 3-(3-(difluoromethyl)pyridin-2-yl)-3-methoxy-5,5-dimethyl-6-oxocyclohex-1-enecarbonitrile (Enantiomer A)

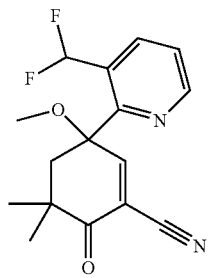

Enantiomer A

Compound 5, Step 1: 5-[3-(difluoromethyl)-2-pyridyl]-7,7-dimethyl-4,6-dihydro-1,2-benzoxazol-5-ol

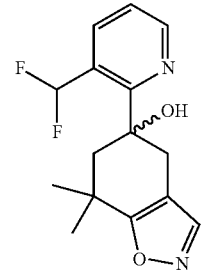 [SMILES: CC1(C)CC(O)(c2ncccc2C(F)F)Cc2cnoc21]

As described for step 1 of example 1, the title compound was prepared from 7,7-dimethyl-4,6-dihydro-1,2-benzoxazol-5-one (225 mg, 1.24 mmol) 2-bromo-3-(difluoromethyl)pyridine (571 mg, 2.74 mmol) and n-BuLi (1.10 mL, 2.74 mmol, 2.50 M in hexanes) in DCM (4.50 mL). The product was purified by silica gel chromatography (25 g cartridge), eluting with hexanes and EtOAc (0-50%), and reverse phase chromatography (40 g, C-18 cartridge), eluting with MeCN (10-100%) and water containing 0.1% (NH$_4$)$_2$CO$_3$ and 0.4% NH$_4$OH, to provide the title compound as an oil (153 mg, 42%. $^1$H NMR (500 MHz, CDCl$_3$) δ 8.64-8.59 (m, 1H), 8.14 (d, J=6.6 Hz, 1H), 8.11 (s, 1H), 7.64 (t, J=55.3 Hz, 1H), 7.37 (dd, J=7.9, 4.7 Hz, 1H), 3.59 (d, J=16.3 Hz, 1H), 2.88 (s, 1H), 2.71 (dd, J=16.3, 2.1 Hz, 1H), 2.36 (d, J=14.4 Hz, 1H), 2.07 (dd, J=14.4, 2.2 Hz, 1H), 1.57 (s, 3H), 1.36 (s, 3H). m/z: ES+[M+H]$^+$: 295.2 HPLC (B05) $t_R$=2.09 min.

Compound 5, Step 2: 5-[3-(difluoromethyl)-2-pyridyl]-5-methoxy-7,7-dimethyl-4,6-dihydro-1,2-benzoxazole

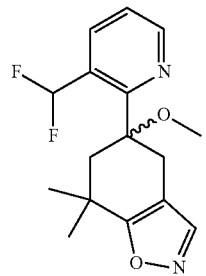 [SMILES: COC1(c2ncccc2C(F)F)Cc2cnoc2C(C)(C)C1]

As described for step 2 of example 1, the title compound was prepared from 5-[3-(difluoromethyl)-2-pyridyl]-7,7-dimethyl-4,6-dihydro-1,2-benzoxazol-5-ol (70.0 mg, 0.24 mmol) hexamethylphosphoramide (83.0 μL, 0.48 mmol), NaHMDS (0.29 mL, 0.29 mmol, 1M in THF) and methyl trifluoromethanesulfonate (54.0 μL, 1.00 mmol) in THF (3.00 mL) to provide the title compound as an oil (73.0 mg, 99%). m/z: ES+[M+H]$^+$: 309.1 HPLC (B05) $t_R$=2.36 min.

Compound 5, Step 3: 5-[3-(difluoromethyl)-2-pyridyl]-5-methoxy-3,3-dimethyl-2-oxo-cyclohexanecarbonitrile

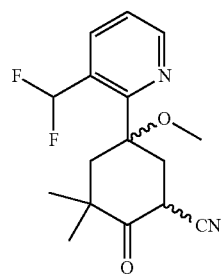 [SMILES: COC1(c2ncccc2C(F)F)CC(C#N)C(=O)C(C)(C)C1]

As described for step 3 of example 1, the title compound was prepared from 5-[3-(difluoromethyl)-2-pyridyl]-5-methoxy-7,7-dimethyl-4,6-dihydro-1,2-benzoxazole (73.0 mg, 0.24 mmol) and NaOMe (25 wt. % in MeOH, 0.14 mL, 2.37 mmol) in MeOH (2.50 mL) and Et$_2$O (4.00 mL). The product was purified by silica gel chromatography (12 g cartridge), eluting with hexanes and EtOAc (0-40%), to provide the title compound as an oil (49.0 mg, 67%). $^1$H NMR (500 MHz, CDCl$_3$) δ 8.63 (dd, J=4.7, 1.7 Hz, 1H), 8.14 (dd, J=8.0, 1.6 Hz, 1H), 7.64 (t, J=55.0 Hz, 2H), 7.42 (dd, J=7.9, 4.7 Hz, 1H), 4.22 (dd, J=14.1, 4.5 Hz, 1H), 3.17 (s, 3H), 3.06 (dd, J=14.4, 14.8 Hz, 1H), 2.96-2.90 (m, 1H), 2.23 (dd, J=15.1, 4.0 Hz, 1H), 2.06 (d, J=14.9 Hz, 1H), 1.46 (s, 3H), 1.14 (s, 3H). m/z: ES+[M+H]$^+$: 309.2 HPLC (B05) $t_R$=1.53 min.

Compound 5, Step 4: 3-[3-(difluoromethyl)-2-pyridyl]-3-methoxy-5,5-dimethyl-6-oxo-cyclohex-ene-1-carbonitrile

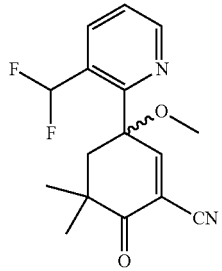 [SMILES: COC1(c2ncccc2C(F)F)C=C(C#N)C(=O)C(C)(C)C1]

As described for step 4 example 1, the title compound was prepared from 5-[3-(difluoromethyl)-2-pyridyl]-5-methoxy-3,3-dimethyl-2-oxo-cyclohexanecarbonitrile (49.0 mg, 0.16 mmol), pyridine (26.0 μL, 0.32 mmol), phenylselenyl chloride (60.8 mg, 0.32 mmol) and hydrogen peroxide (0.78 mL, 3.18 mmol, 35%) in DCM (1.66 mL). The product was purified by silica gel chromatography (12 g cartridge), eluting with hexanes and EtOAc (0-50%), to provide the title compound as a solid (31.0 mg, 64%). $^1$H NMR (500 MHz, CDCl$_3$) δ 8.65-8.62 (m, 1H), 8.18 (d, J=8.0 Hz, 1H), 8.12 (d, J=1.7 Hz, 1H), 7.50 (t, J=55.5 Hz, 1H), 7.49-7.43 (m, J=4.7 Hz, 1H), 3.26 (d, J=0.9 Hz, 3H), 2.37 (dd, J=14.7, 1.7 Hz, 1H), 2.18 (d, 14.7 Hz, 1H), 1.38 (s, 3H), 1.03 (s, 3H). m/z: ES+[M+H]$^+$: 307.2 HPLC (A05) $t_R$=2.43 min.

Compound 5, Step 5: 3-(3-(difluoromethyl)pyridin-2-yl)-3-methoxy-5,5-dimethyl-6-oxocyclohex-1-enecarbonitrile (Enantiomer A)

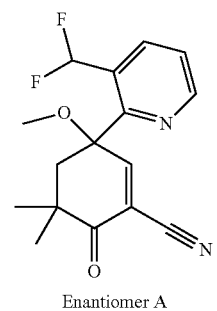 [SMILES: COC1(c2ncccc2C(F)F)C=C(C#N)C(=O)C(C)(C)C1]

Enantiomer A

Enantiomers were separated using Generic Procedure B for chiral separation of enantiomers (starting from 20.8 mg racemate), yielding Isomer 1 (7 mg, ee=99%) and Isomer 2 (5 mg, ee=92%, Enantiomer A).

Compound 6: 3-[3-(difluoromethyl)-2-pyridyl]-3-hydroxy-5,5-dimethyl-6-oxo-cyclohexene-1-carbonitrile

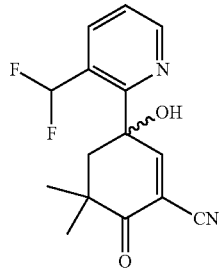 [SMILES: CC1(C)CC(O)(c2ncccc2C(F)F)C=C(C#N)C1=O]

Compound 6, Step 1: 5-[3-(difluoromethyl)-2-pyridyl]-5-hydroxy-3,3-dimethyl-2-oxo-cyclohexanecarbonitrile

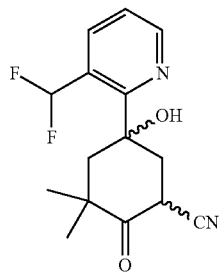 [SMILES: CC1(C)CC(O)(c2ncccc2C(F)F)CC(C#N)C1=O]

As described for step 3 example 1, the title compound was prepared from 5-[3-(difluoromethyl)-2-pyridyl]-7,7-dimethyl-4,6-dihydro-1,2-benzoxazol-5-ol (75.0 mg, 0.25 mmol) and NaOMe (25% wt in MeOH, 0.15 mL, 2.55 mmol) in MeOH (2.50 mL) and Et$_2$O (4.00 mL). The product was purified by silica gel chromatography (12 g cartridge), eluting with hexanes and EtOAc (0-40%), to provide the title compound as an oil (27.0 mg, 36%). $^1$H NMR (500 MHz, CDCl$_3$) δ 8.63 (d, J=3.1 Hz, 1H), 8.15-8.09 (m, 1H), 7.52 (t, J=54.9 Hz, 1H), 7.41 (dd, J=7.7, 5.2 Hz, 1H), 4.56 (dd, J=13.8, 4.9 Hz, 1H), 3.14 (t, J=13.9 Hz, 1H), 2.52 (ddd, J=14.0, 4.9, 3.9 Hz, 1H), 2.35 (d, J=14.9 Hz, 1H), 2.03 (m, 2H), 1.51 (s, 3H), 1.17 (s, 3H). m/z: ES+[M+H]$^+$: 295.2 HPLC (B05) t$_R$=1.31 min.

Compound 6, Step 2: 3-[3-(difluoromethyl)-2-pyridyl]-3-hydroxy-5,5-dimethyl-6-oxo-cyclohexene-1-carbonitrile

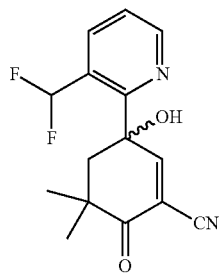 [SMILES: CC1(C)CC(O)(c2ncccc2C(F)F)C=C(C#N)C1=O]

As described for step 4 of example 1, the title compound was prepared from 5-[3-(difluoromethyl)-2-pyridyl]-5-hydroxy-3,3-dimethyl-2-oxo-cyclohexanecarbonitrile (27.0 mg, 0.09 mmol), pyridine (14.8 μL, 0.18 mmol), phenylselenyl chloride (35.1 mg, 0.18 mmol) and hydrogen peroxide (0.45 mL, 1.83 mmol, 35%) in DCM (1.00 mL). The product was purified by silica gel chromatography (12 g cartridge), eluting with hexanes and EtOAc (0-50%), to provide the title compound as a solid (10.3 mg, 38%). $^1$H NMR (500 MHz, CDCl$_3$) δ 8.67 (d, J=4.0 Hz, 1H), 8.16 (d, J=7.2 Hz, 1H), 7.53-7.48 (m, 2H), 7.21 (t, J=54.4 Hz, 1H), 4.68 (s, 1H), 2.34 (d, J=14.9 Hz, 1H), 2.23 (dd, J=14.9, 2.0 Hz, 1H), 1.47 (s, 3H), 1.14 (s, 3H). m/z: ES+[M+H]$^+$: 293.1 HPLC (A05) t$_R$=2.24 min.

Compound 7: 3-methoxy-5,5-dimethyl-6-oxo-3-(3-phenyl-2-pyridyl)cyclohexene-1-carbonitrile

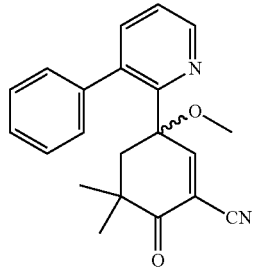 [SMILES: COC1(c2ncccc2-c2ccccc2)C=C(C#N)C(=O)C(C)(C)C1]

Phenyl magnesium bromide (1M in THF, 0.45 mL, 0.45 mmol) was added to a solution of ZnCl$_2$ (1M in Et$_2$O, 0.52 mL, 0.52 mmol) and Pd(dppf)Cl$_2$ (15.2 mg, 0.02 mmol) in THF (0.75 mL) under Ar. The mixture was stirred for 20 m, and NMP (0.60 mL) and 3-(3-bromo-2-pyridyl)-3-methoxy-5,5-dimethyl-6-oxo-cyclohexene-1-carbonitrile (125 mg, 0.37 mmol) were added. The mixture was stirred at 60° C. for 16 h. Sat. aq. NaHCO$_3$ (2.00 mL) and EtOAc (2.00 mL) were added, and the aq phase was extracted with EtOAc (2×5.00 mL). The combined organic phases were washed with brine (10 mL), dried (Na$_2$SO$_4$), filtered, and concentrated under reduced pressure. The product was purified by silica gel chromatography (12 g cartridge), eluting with hexanes and EtOAc (0-40%), to provide the title compound as a solid (21.3 mg, 21%). $^1$H NMR (500 MHz, CDCl$_3$) δ 8.58 (dd, J=4.7, 1.8 Hz, 1H), 8.03 (d, J=1.0 Hz, 1H), 7.58 (dd, J=7.7, 1.8 Hz, 1H), 7.47-7.43 (m, 3H), 7.35 (dd, J=7.7, 4.7 Hz, 1H), 7.32-7.28 (m, 2H), 3.15 (s, 3H), 2.29 (dd, J=14.5, 1.1 Hz, 1H), 2.13 (dd, J=14.5, 0.9 Hz, 1H), 1.09 (s, 3H), 0.80 (s, 3H). m/z: ES+[M+H]$^+$: 333.3 HPLC (A05) t$_R$=2.50 min.

Compound 8: 3-methoxy-3-[6-(3-methoxyazetidin-1-yl)-2-pyridyl]-5,5-dimethyl-6-oxo-cyclohexene-1-carbonitrile

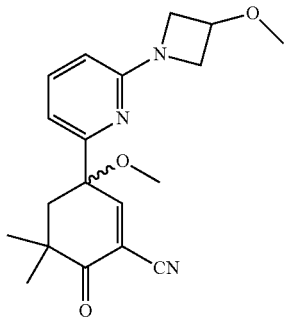

3-(6-Bromo-2-pyridyl)-3-methoxy-5,5-dimethyl-6-oxo-cyclohexene-1-carbonitrile (50.3 mg, 0.15 mmol), 3-methoxyazetidine hydrochloride (92.7 mg, 0.75 mmol), Pd(dppf)Cl$_2$.DCM (12.3 mg, 0.02 mmol), and Cs$_2$CO$_3$ (122 mg, 0.38 mmol) were weighed into a microwave vessel. The mixture was purged with N$_2$ gas for 5 m, and water (0.30 mL) and monoglyme (2.00 mL) were added. The mixture was purged with N$_2$ gas for 5 min. The mixture was heated to 125° C. under microwave irradiation for 1.5 h and concentrated under reduced pressure. Water (15 mL) was added, and the aq phase was extracted with EtOAc (3×15 mL). The combined organic phases were washed with brine (2×10 mL), dried (MgSO$_4$), filtered, and concentrated under reduced pressure. The product was purified twice by silica gel chromatography (12 g cartridge), eluting with hexanes and EtOAc (0-30%), and (4 g cartridge), eluting with hexanes and DCM (20-100%), to provide the title compound as a solid (12.5 mg, 24%). $^1$H NMR (500 MHz, CDCl$_3$) δ 8.06 (t, J=0.8 Hz, 1H), 7.51 (dd, J=8.2, 7.5 Hz, 1H), 6.81 (dd, J=7.4, 0.7 Hz, 1H), 6.23 (dd, J=8.3, 0.7 Hz, 1H), 4.34 (tt, J=6.2, 4.3 Hz, 1H), 4.17 (dddd, J=8.9, 6.3, 5.4, 1.0 Hz, 2H), 3.83 (dddd, J=13.1, 8.9, 4.3, 1.0 Hz, 2H), 3.35 (s, 3H), 3.19 (s, 3H), 2.35-2.13 (m, 2H), 1.33 (s, 3H), 1.00 (s, 3H). m/z: ES+[M+H]$^+$: 342.4 HPLC (A05) t$_R$=2.22 min.

Compound 9: 3-methoxy-5,5-dimethyl-3-(6-methyl-2-pyridyl)-6-oxo-cyclohexene-1-carbonitrile

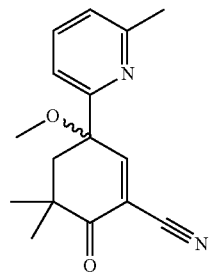 [SMILES: COC1(c2cccc(C)n2)C=C(C#N)C(=O)C(C)(C)C1]

3-(6-Bromo-2-pyridyl)-3-methoxy-5,5-dimethyl-6-oxo-cyclohexene-1-carbonitrile (134 mg, 0.400 mmol), Cs$_2$CO$_3$ (261 mg, 0.800 mmol), potassium methyltrifluoroborate (97.6 mg, 0.800 mmol), water (0.75 mL), and monoglyme (5 mL) were mixed in a microwave vessel, and the mixture was purged with N$_2$ gas for 5 min. Pd(dppf)Cl$_2$.DCM (32.7 mg, 0.040 mmol) was added, and the mixture was purged with N$_2$ gas was for 5 min. The mixture was heated at 120° C. with microwave irradiation for 1.5 h. The mixture was concentrated under reduced pressure. Water (25 mL) was added, and the aq phase was extracted with EtOAc (3×25 mL). The combined organic phases were washed with brine (25 mL), dried (MgSO$_4$), filtered, and concentrated under reduced pressure. The product was purified by silica gel chromatography (12 g cartridge), eluting with hexanes and EtOAc (0-30%), to provide the title compound as a solid (48.6 mg, 45%). $^1$H NMR (500 MHz, CDCl$_3$) δ 8.10 (t, J=1.0 Hz, 1H), 7.66 (t, J=7.8 Hz, 1H), 7.32 (dt, J=7.8, 0.8 Hz, 1H), 7.11 (dt, J=7.7, 0.8 Hz, 1H), 3.19 (s, 3H), 2.52 (s, 3H), 2.34-2.15 (m, 2H), 1.37 (s, 3H), 1.01 (s, 3H). m/z (ES+), [M-OMe+H]$^+$: 239.4. HPLC (A05) t$_R$=2.24 min.

Compound 10: 3-(6-ethyl-2-pyridyl)-3-methoxy-5,5-dimethyl-6-oxo-cyclohexene-1-carbonitrile

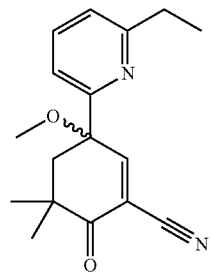 [SMILES: CCc1cccc(C2(OC)C=C(C#N)C(=O)C(C)(C)C2)n1]

3-(6-Bromo-2-pyridyl)-3-methoxy-5,5-dimethyl-6-oxo-cyclohexene-1-carbonitrile (201 mg, 0.600 mmol), potassium ethyltrifluoroborate (163 mg, 1.20 mmol), cataCXium® A (43.0 mg, 0.120 mmol) and Cs$_2$CO$_3$ (391 mg, 1.20 mmol) were weighed into a microwave vessel. Toluene (8.10 mL) and water (0.900 mL) were added, and the mixture was purged with N$_2$ gas for 5 min. Pd(OAc)$_2$ (13.5 mg, 0.0600 mmol) was added, and the mixture was purged with N$_2$ gas for 5 min. The mixture was heated at 100° C. for 18 h. After cooling to 23° C., the mixture was concentrated under reduced pressure. Water (25 mL) was added, and the aq phase was extracted with EtOAc (3×25 mL). The combined organic phases were washed with brine (25 mL), dried (MgSO$_4$), filtered, and concentrated under reduced pressure. The product was purified twice by silica gel chromatography (12 g cartridge), eluting with hexanes and EtOAc (0-30%), and (12 g cartridge), eluting with hexanes and DCM (0-100%), to provide the title compound as a solid (122 mg, 72%). $^1$H NMR (500 MHz, CDCl$_3$) δ 8.14 (t, J=1.0 Hz, 1H), 7.71 (t, J=7.7 Hz, 1H), 7.36 (dd, J=7.9, 0.9 Hz, 1H), 7.14 (dd, J=7.7, 0.9 Hz, 1H), 3.21 (s, 3H), 2.81 (q, J=7.6 Hz, 2H), 2.35-2.22 (m, 2H), 1.38 (s, 3H), 1.30 (t, J=7.6 Hz, 3H), 1.01 (s, 3H). m/z (ES+), [M-OMe+H]$^+$: 253.3. HPLC (A05) t$_R$=2.35 min.

75

Compound 11: 3-methoxy-5,5-dimethyl-6-oxo-3-(2-pyridyl)cyclohexene-1-carbonitrile

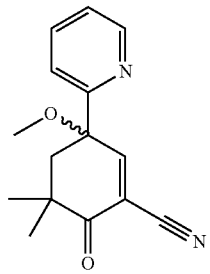 [SMILES: COC1(c2ccccn2)C=C(C#N)C(=O)C(C)(C)C1]

3-(6-Bromo-2-pyridyl)-3-methoxy-5,5-dimethyl-6-oxo-cyclohexene-1-carbonitrile (100 mg, 0.300 mmol), Xant-Phos (25.9 mg, 0.0400 mmol), Pd(OAc)$_2$ (3.35 mg, 0.0100 mmol), dimethylammonium chloride (23.7 uL, 0.360 mmol), and Cs$_2$CO$_3$ (292 mg, 0.890 mmol) were weighed into a microwave vial. 1,4-Dioxane (1.50 mL) was purged with N$_2$ gas and added. The mixture was heated at 95° C. for 18 h. After cooling to 23° C., the mixture was filtered through a pad of celite, washing with EtOAc. The filtrate was concentrated under reduced pressure. The product was purified by silica gel chromatography (12 g cartridge), eluting with hexanes and EtOAc (0-30%), followed by HPLC, eluting with MeCN and water containing 0.1% (NH$_4$)$_2$CO$_3$ and 0.4% NH$_4$OH, to provide the title compound as a solid (11.6 mg, 13%). $^1$H NMR (500 MHz, CDCl$_3$) δ 8.56 (ddd, J=4.8, 1.8, 0.9 Hz, 1H), 8.07 (t, J=1.0 Hz, 1H), 7.80 (td, J=7.7, 1.8 Hz, 1H), 7.55 (dt, J=8.0, 1.1 Hz, 1H), 7.29 (ddd, J=7.5, 4.9, 1.1 Hz, 1H), 3.20 (s, 3H), 2.27 (d, J=1.0 Hz, 2H), 1.37 (s, 3H), 1.00 (s, 3H). m/z (ES+), [M+H]$^+$: 257.3. HPLC (B05) t$_R$=2.08 min.

Compound 12: 3-methoxy-5,5-dimethyl-3-[6-(2-methylimidazol-1-yl)-2-pyridyl]-6-oxo-cyclohexene-1-carbonitrile

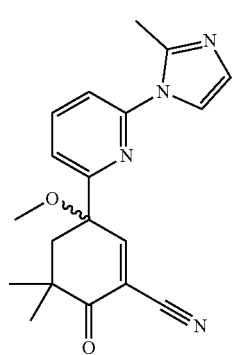 [SMILES: COC1(c2cccc(-n3ccnc3C)n2)CC(C#N)C(=O)C(C)(C)C1]

76

Compound 12, Step 1: 5-methoxy-3,3-dimethyl-5-[6-(2-methylimidazol-1-yl)-2-pyridyl]-2-oxo-cyclohexanescarbonitrile

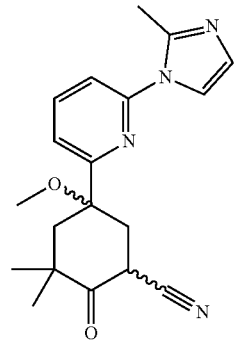

A mixture of 5-(6-bromo-2-pyridyl)-5-methoxy-3,3-dimethyl-2-oxo-cyclohexanescarbonitrile (52.7 mg, 0.160 mmol), 2-methylimidazole (25.7 mg, 0.310 mmol), CuI (5.95 mg, 0.0300 mmol), 1,10-Phenanthroline (5.63 mg, 0.0300 mmol), and Cs$_2$CO$_3$ (153 mg, 0.470 mmol) were combined in a microwave vessel. DMF (0.600 mL) was purged with N$_2$ gas and added to the vessel. The vessel was evacuated and back-filled with N$_2$ gas (3 times). The mixture was stirred at 23° C. for 30 m, and then heated at 90° C. for 18 h. Brine (25 mL) was added, and the aq phase was extracted with EtOAc (3×25 mL). The combined organic phases were washed with brine (25 mL), dried (MgSO$_4$), filtered, and concentrated under reduced pressure. The product was purified by silica gel chromatography (12 g cartridge), eluting with hexanes and EtOAc (50-100%), to provide the title compound as a solid (18.7 mg, 35%). $^1$H NMR (500 MHz, CDCl$_3$) δ 7.93 (t, J=7.9 Hz, 1H), 7.54 (dd, J=7.8, 0.8 Hz, 1H), 7.29-7.26 (m, 2H), 7.04 (d, J=3.0 Hz, 1H), 4.32 (dd, J=13.9, 4.7 Hz, 1H), 3.21 (s, 3H), 2.85 (ddd, J=14.3, 4.7, 3.8 Hz, 1H), 2.73 (t, J=14.1 Hz, 1H), 2.60 (s, 3H), 2.27 (dd, J=15.0, 3.8 Hz, 1H), 2.21-2.13 (m, 1H), 1.46 (s, 3H), 1.17 (s, 3H). m/z (ES+), [M+H]$^+$: 339.6. HPLC (B05) t$_R$=1.38 min.

Compound 12, Step 2: 3-methoxy-5,5-dimethyl-3-[6-(2-methylimidazol-1-yl)-2-pyridyl]-6-oxo-cyclohexene-1-carbonitrile

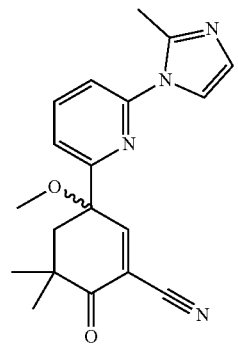

5-Methoxy-3,3-dimethyl-5-[6-(2-methylimidazol-1-yl)-2-pyridyl]-2-oxo-cyclohexanescarbonitrile (28.5 mg, 0.0800 mmol) was dissolved in DMF (1.00 mL), and the mixture was cooled to 0° C. 1,3-Dibromo-5,5-dimethylhydantoin (14.5 mg, 0.0500 mmol) was added, and the mixture was stirred at 0° C. for 2 h. Pyridine (100 uL, 1.24 mmol) was added, and the mixture was heated at 55° C. for 18 h. Sat. NaHCO$_3$ (15 mL) was added, and the aq phase was extracted with EtOAc (3×20 mL). The combined organic phases were washed with brine (25 mL), dried (MgSO$_4$), filtered, and concentrated under reduced pressure. The product was purified by HPLC (eluting with MeCN and water containing 0.1% (NH$_4$)$_2$CO$_3$ and 0.4% NH$_4$OH) to provide the title compound as a solid (3.30 mg, 12%). $^1$H NMR (500 MHz, CDCl$_3$) δ 7.98 (d, J=7.4 Hz, 2H), 7.56 (d, J=7.8 Hz, 1H), 7.33 (d, J=8.0 Hz, 1H), 7.28 (s, 1H), 7.05 (s, 1H), 3.27 (s, 3H), 2.61 (s, 3H), 2.32 (d, J=15.2 Hz, 1H), 2.27 (d, J=14.8 Hz, 1H), 1.39 (s, 3H), 1.05 (s, 3H). m/z (ES+), [M+H]$^+$: 337.6. HPLC (A05) $t_R$=1.50 min.

Compound 13: 3-methoxy-5,5-dimethyl-6-oxo-3-(6-phenyl-2-pyridyl)cyclohexene-1-carbonitrile

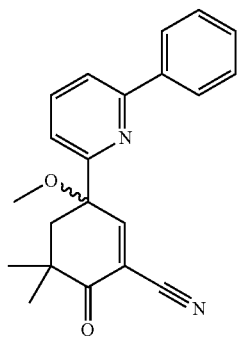 [SMILES: COC1(c2cccc(-c3ccccc3)n2)C=C(C#N)C(=O)C(C)(C)C1]

3-(6-Bromo-2-pyridyl)-3-methoxy-5,5-dimethyl-6-oxo-cyclohexene-1-carbonitrile (50.0 mg, 0.150 mmol), Cs$_2$CO$_3$ (97.2 mg, 0.300 mmol), phenylboronic acid (36.4 mg, 0.300 mmol), monoglyme (1.75 mL), and water (0.250 mL) were weighed into a microwave vessel, and the mixture was purged with N$_2$ gas for 10 min. Pd(dppf)Cl$_2$.DCM (12.2 mg, 0.0100 mmol) was added, and the mixture was purged with N$_2$ gas for 10 min. The vessel was heated at 100° C. with microwave irradiation for 30 min. Water (10 mL) was added, and the aq phase was extracted with EtOAc (3×10 mL). The combined organic phases were washed with brine (10 mL), dried (MgSO$_4$), filtered, and concentrated under reduced pressure. The product was purified by silica gel chromatography (4 g cartridge), eluting with hexanes and EtOAc (0-20%), to provide the title compound as a solid (33.2 mg, 67%). $^1$H NMR (500 MHz, CDCl$_3$) δ 8.23 (d, J=1.0 Hz, 1H), 8.00 (d, J=1.6 Hz, 1H), 7.98 (t, J=1.4 Hz, 1H), 7.87 (t, J=7.8 Hz, 1H), 7.75 (dd, J=7.9, 0.9 Hz, 1H), 7.50 (ddd, J=7.7, 6.8, 1.1 Hz, 3H), 7.47-7.42 (m, 1H), 3.25 (s, 3H), 2.33 (d, J=1.0 Hz, 2H), 1.39 (s, 3H), 1.02 (s, 3H). m/z (ES+), [M+H]$^+$: 334.0. HPLC (A05) $t_R$=2.52 min.

Compound 14: 5,5-Dimethyl-3-[6-(1-methylpyrazol-4-yl)-2-pyridyl]-6-oxo-3-(trideuterio-methoxy)cyclohexene-1-carbonitrile (Enantiomer A)

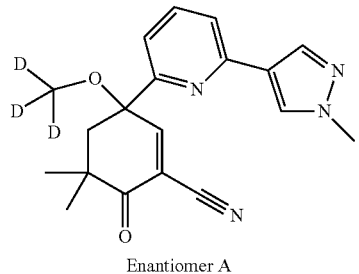 [SMILES: [2H]C([2H])([2H])OC1(c2cccc(-c3cnn(C)c3)n2)C=C(C#N)C(=O)C(C)(C)C1]

Enantiomer A

Compound 14, Step 1: 2-bromo-6-[8-(trideuteriomethoxy)-1,4-dioxaspiro[4.5]decan-8-yl]pyridine

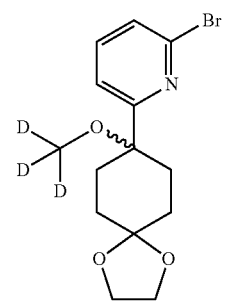 [SMILES: [2H]C([2H])([2H])OC1(c2cccc(Br)n2)CCC2(CC1)OCCO2]

As described for step 2 of Compound 2, the title compound was prepared from 8-(6-bromo-2-pyridyl)-1,4-dioxaspiro[4.5]decan-8-ol (1.00 g, 3.18 mmol), 60 wt % NaH in mineral oil (0.255 g, 6.37 mmol), and iodomethane-d$_3$ (0.426 mL, 6.84 mmol) in THF (10 mL) to provide the title compound as a solid. $^1$H NMR (500 MHz, CDCl$_3$) δ 7.53 (t, J=7.7 Hz, 1H), 7.46 (dd, J=7.7, 1.0 Hz, 1H), 7.34 (dd, J=7.7, 1.0 Hz, 1H), 4.00-3.94 (m, 4H), 2.25-2.15 (m, 2H), 2.02-1.90 (m, 4H), 1.71-1.64 (m, 2H). m/z (ES+), [M-OCD$_3$+H]$^+$: 296.4. HPLC (B05) $t_R$=2.13 min.

Compound 14, Step 2: 4-(6-bromo-2-pyridyl)-4-(trideuteriomethoxy)cyclohexanone

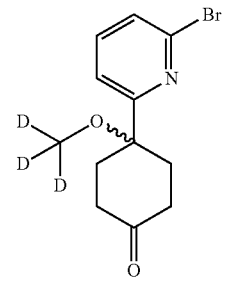

As described for step 3 of Compound 2, the title compound was prepared from 2-bromo-6-[8-(trideuteriomethoxy)-1,4-dioxaspiro[4.5]decan-8-yl]pyridine (1.05 g, 3.17 mmol) and 3M HCl (5.00 mL) in 1,4-Dioxane (10 mL). The product was purified by silica gel chromatography (25 g cartridge), eluting with hexanes and EtOAc (0-30%), to provide the title compound as a solid (0.681 g, 75%). $^1$H NMR (500 MHz, CDCl$_3$) δ 7.58 (dd, J=7.8, 3.1 Hz, 1H), 7.53 (d, J=7.8 Hz, 1H), 7.40 (d, J=7.9 Hz, 1H), 2.76-2.61 (m, 2H), 2.36 (d, J=13.7 Hz, 4H), 2.30 (d, J=8.7 Hz, 2H). m/z (ES+), [M+H]$^+$: 287.5. HPLC (B05) $t_R$=1.89 min.

Compound 14, Step 3: 4-(6-bromo-2-pyridyl)-2,2-dimethyl-4-(trideuteriomethoxy)cyclohexanone

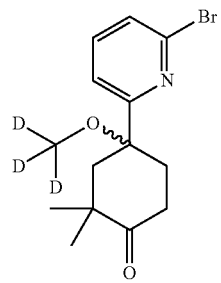

As described for step 4 of Compound 2, the title compound was synthesized from 4-(6-bromo-2-pyridyl)-4-(trideuteriomethoxy)cyclohexanone (661 mg, 2.30 mmol), KOtBu (646 mg, 5.75 mmol), and iodomethane (0.301 mL, 4.83 mmol) in tert-butanol (10 mL). The product was purified by silica gel chromatography (25 g cartridge), eluting with hexanes and EtOAc (0-20%), to provide the title compound as a solid (189 mg, 26%). $^1$H NMR (500 MHz, CDCl$_3$) δ 7.57 (t, J=7.7 Hz, 1H), 7.52 (dd, J=7.7, 1.1 Hz, 1H), 7.38 (dd, J=7.6, 1.0 Hz, 1H), 2.94-2.81 (m, 1H), 2.59-2.47 (m, 1H), 2.40-2.31 (m, 2H), 2.09 (d, J=1.6 Hz, 2H), 1.37 (s, 3H), 1.06 (s, 3H). m/z (ES+), [M-OCD$_3$+H]+: 280.7. HPLC (B05) $t_R$=2.26 min.

Compound 14, Step 4: (6Z)-4-(6-bromo-2-pyridyl)-6-(hydroxymethylene)-2,2-dimethyl-4-(trideuteriomethoxy)cyclohexanone

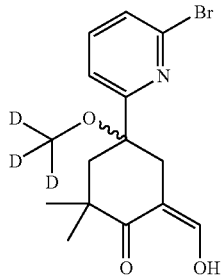 [SMILES: [2H]C([2H])([2H])OC1(c2cccc(Br)n2)C/C(=C/O)C(=O)C(C)(C)C1]

As described for step 5 of Compound 2, the title compound was prepared from 4-(6-bromo-2-pyridyl)-2,2-dimethyl-4-(trideuteriomethoxy)cyclohexanone (185 mg, 0.590 mmol) and 25 wt % NaOMe in MeOH (1.25 mL, 5.79 mmol) in ethyl formate (2.50 mL, 31.0 mmol). The product was purified by silica gel chromatography (12 g cartridge), eluting with hexanes and EtOAc (0-20%), to provide the title compound as an oil (119 mg, 59%). $^1$H NMR (500 MHz, CDCl$_3$) δ 14.88 (d, J=5.0 Hz, 1H), 8.39 (d, J=4.7 Hz, 1H), 7.58 (t, J=7.6 Hz, 1H), 7.54 (dd, J=7.7, 1.2 Hz, 1H), 7.39 (dd, J=7.6, 1.1 Hz, 1H), 3.20 (dd, J=15.8, 0.8 Hz, 1H), 2.77 (ddd, J=15.9, 2.4, 1.3 Hz, 1H), 1.97-1.92 (m, 2H), 1.40 (s, 3H), 1.19 (s, 3H). m/z (ES+), [M+H]$^+$: 343.9. HPLC (B05) $t_R$=1.28 min.

Compound 14, Step 5: 5-(6-bromo-2-pyridyl)-7,7-dimethyl-5-(trideuteriomethoxy)-4,6-dihydro-1,2-benzoxazole

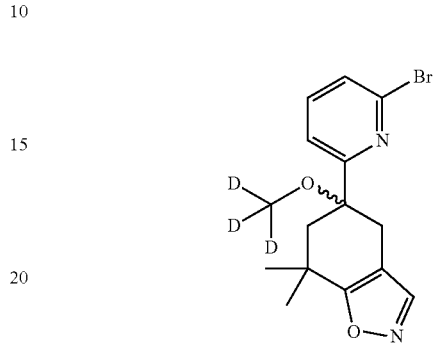

As described for step 6 of Compound 2, the title compound was prepared from (6Z)-4-(6-bromo-2-pyridyl)-6-(hydroxymethylene)-2,2-dimethyl-4-(trideuterio-methoxy)cyclohexanone (115 mg, 0.340 mmol) and hydroxylamine hydrochloride (233 mg, 3.35 mmol) in EtOH (1.60 mL) and water (0.200 mL) to provide the title compound as a solid. $^1$H NMR (500 MHz, CDCl$_3$) δ 8.10 (s, 1H), 7.62-7.58 (m, 1H), 7.57 (dd, J=7.8, 1.4 Hz, 1H), 7.40 (dd, J=7.3, 1.4 Hz, 1H), 3.38 (d, J=16.5 Hz, 1H), 2.94 (dd, J=16.6, 2.0 Hz, 1H), 2.11 (d, J=14.3 Hz, 1H), 2.07 (dd, J=14.4, 2.1 Hz, 1H), 1.50 (s, 3H), 1.27 (s, 3H). m/z (ES+), [M-OCD$_3$+H]+: 307.8. HPLC (B05) $t_R$=2.38 min.

Compound 14, Step 6: 5-(6-bromo-2-pyridyl)-3,3-dimethyl-2-oxo-5-(trideuteriomethoxy)cyclo-hexanes-carbonitrile

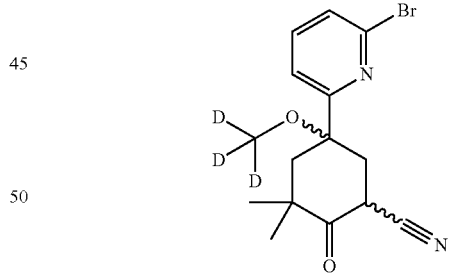

As described for step 7 of Compound 2, the title compound was prepared from 5-(6-bromo-2-pyridyl)-7,7-dimethyl-5-(trideuteriomethoxy)-4,6-dihydro-1,2-benzoxazole (100 mg, 0.290 mmol) and 25 wt % NaOMe in MeOH (0.640 mL, 2.95 mmol) in Et$_2$O (1.50 mL). The product was purified by silica gel chromatography (4 g cartridge), eluting with hexanes and EtOAc (0-20%), to provide the title compound as a solid (61.1 mg, 61%). $^1$H NMR (500 MHz, CDCl$_3$) δ 7.61 (t, J=7.8 Hz, 1H), 7.49 (dd, J=7.7, 0.9 Hz, 1H), 7.43 (dd, J=7.7, 0.9 Hz, 1H), 4.31-4.21 (m, 1H), 2.82-2.72 (m, 2H), 2.17 (d, J=1.5 Hz, 2H), 1.43 (s, 3H), 1.16 (s, 3H). m/z (ES+), [M+H]$^+$: 340.8. HPLC (B05) $t_R$=1.49 min.

Compound 14, Step 7: 3-(6-bromo-2-pyridyl)-5,5-dimethyl-6-oxo-3-(trideuteriomethoxy)cyclohexene-1-carbonitrile

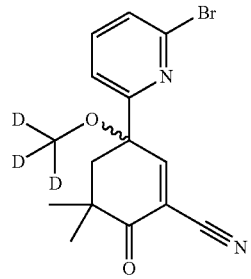 [SMILES: [2H]C([2H])([2H])OC1(c2cccc(Br)n2)CC(C#N)C(=O)C(C)(C)C1]

As described for step 8 of Compound 2, the title compound was prepared from phenylselenium chloride (67.6 mg, 0.350 mmol), pyridine (28.5 μL, 0.350 mmol), 5-(6-bromo-2-pyridyl)-3,3-dimethyl-2-oxo-5-(trideuteriomethoxy)cyclohexanescarbonitrile (60.0 mg, 0.180 mmol), and 35 wt % $H_2O_2$ in water (0.340 mL, 3.53 mmol) in DCM (2.50 mL). The product was triturated from hexanes to provide the title compound as a solid (40.9 mg, 69%). $^1$H NMR (500 MHz, $CDCl_3$) δ 7.98 (d, J=1.5 Hz, 1H), 7.66 (t, J=7.8 Hz, 1H), 7.52 (dd, J=7.7, 0.9 Hz, 1H), 7.48 (dd, J=7.9, 0.9 Hz, 1H), 2.26 (d, J=14.6 Hz, 1H), 2.21 (dd, J=14.6, 1.6 Hz, 1H), 1.38 (s, 3H), 1.07 (s, 3H). m/z (ES+), [M+H]$^+$: 338.9. HPLC (A05) $t_R$=2.31 min.

Compound 14, Step 8: 5,5-dimethyl-3-[6-(1-methylpyrazol-4-yl)-2-pyridyl]-6-oxo-3-(trideuteriomethoxy)cyclohexene-1-carbonitrile

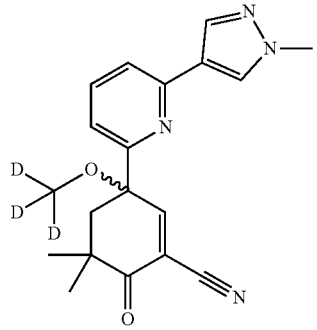 [SMILES: [2H]C([2H])([2H])OC1(c2cccc(-c3cnn(C)c3)n2)C=C(C#N)C(=O)C(C)(C)C1]

As described for Compound 13, the title compound was prepared from 3-(6-bromo-2-pyridyl)-5,5-dimethyl-6-oxo-3-(trideuteriomethoxy)cyclohexene-1-carbonitrile (39.0 mg, 0.120 mmol), $Cs_2CO_3$ (75.0 mg, 0.230 mmol), (1-methylpyrazol-4-yl)boronic acid (29.0 mg, 0.230 mmol), and Pd(dppf)$Cl_2$.DCM (9.40 mg, 0.0100 mmol) in monoglyme (1.75 mL) and water (0.250 mL). The product was purified by silica gel chromatography (4 g cartridge), eluting with hexanes and EtOAc (0-60%), to provide the title compound as a solid (24.4 mg, 62%). $^1$H NMR (500 MHz, $CDCl_3$) δ 8.15 (q, J=0.6 Hz, 1H), 7.91-7.87 (m, 2H), 7.75 (t, J=7.8 Hz, 1H), 7.42 (dd, J=7.9, 0.9 Hz, 1H), 7.34 (dd, J=7.8, 0.9 Hz, 1H), 3.98 (s, 3H), 2.31-2.28 (m, 1H), 2.28-2.24 (m, 1H), 1.38 (s, 3H), 1.02 (s, 3H). m/z (ES+), [M+H]$^+$: 341.0. HPLC (A05) $t_R$=2.14 min.

Compound 14, Step 9: 5,5-dimethyl-3-[6-(1-methylpyrazol-4-yl)-2-pyridyl]-6-oxo-3-(trideuteriomethoxy)cyclohexene-1-carbonitrile (Enantiomer A)

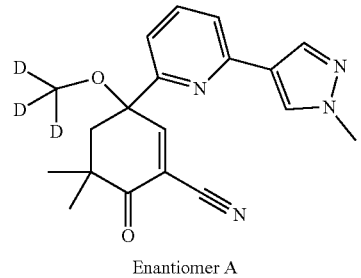 [SMILES: [2H]C([2H])([2H])OC1(c2cccc(-c3cnn(C)c3)n2)C=C(C#N)C(=O)C(C)(C)C1]

Enantiomer A

Enantiomers were separated using Generic Procedure B for chiral separation of enantiomers (starting from 23 mg racemate), yielding Isomer 1 (11 mg, ee=95%) and Isomer 2 (11 mg, ee=99.7%; Enantiomer A).

Compound 15: 3-methoxy-5,5-dimethyl-6-oxo-3-(3-(trifluoromethyl)pyridin-2-yl)cyclohex-1-enecarbonitrile (Enantiomer A)

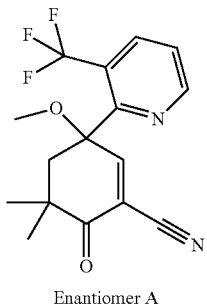 [SMILES: COC1(c2ncccc2C(F)(F)F)C=C(C#N)C(=O)C(C)(C)C1]

Enantiomer A

Compound 15, Step 1: 5-methoxy-7,7-dimethyl-5-[3-(trifluoromethyl)-2-pyridyl]-4,6-dihydro-1,2-benzoxazole

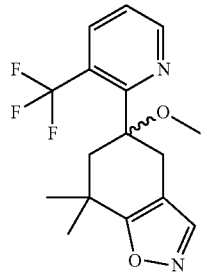 [SMILES: COC1(c2ncccc2C(F)(F)F)Cc2cnoc2C(C)(C)C1]

A mixture of 7,7-dimethyl-5-[3-(trifluoromethyl)-2-pyridyl]-4,6-dihydro-1,2-benzoxazol-5-ol (201 mg, 0.640 mmol) in THF (6.50 mL) was added to a solution of HMPA (224 uL, 1.29 mmol) and 1.0 M NaHMDS in THF (772 uL, 0.770 mmol) in THF (6.50 mL) at −78° C. After 5 m of stirring, MeOTf (146 uL, 1.29 mmol) was added. The mixture was stirred at −78° C. for 1 h. After warming the mixture to 23° C., sat. NH$_4$Cl (20 mL) was added, and the aq phase was extracted with EtOAc (3×20 mL). The combined organic phases were washed with brine (20 mL), dried (MgSO$_4$), filtered, and concentrated under reduced pressure. The product was purified by silica gel chromatography (12 g cartridge), eluting with hexanes and EtOAc (0-40%), to provide the title compound as an oil (113 mg, 54%). $^1$H NMR (500 MHz, CDCl$_3$) δ 8.67 (dd, J=4.7, 1.7 Hz, 1H), 8.12 (d, J=9.2 Hz, 2H), 7.39-7.34 (m, 1H), 3.73 (d, J=16.4 Hz, 1H), 2.99 (dd, J=16.5, 2.5 Hz, 1H), 2.93 (q, J=0.9 Hz, 3H), 2.43 (dd, J=14.2, 2.5 Hz, 1H), 1.95 (d, J=14.2 Hz, 1H), 1.52 (s, 3H), 1.20 (s, 3H). m/z (ES+), [M+H]$^+$: 327.2. HPLC (B05) t$_R$=2.47 min.

Compound 15, Step 2: 5-methoxy-3,3-dimethyl-2-oxo-5-[3-(trifluoromethyl)-2-pyridyl]cyclohexanescarbonitrile

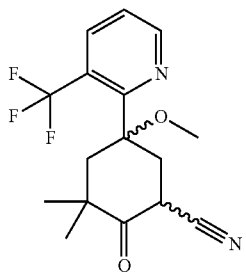 [SMILES: COC1(c2ncccc2C(F)(F)F)CC(C#N)C(=O)C(C)(C)C1]

As described for step 2 of Compound 24, the title compound was prepared from 25 wt % NaOMe in MeOH (0.360 mL, 1.67 mmol) and 5-methoxy-7,7-dimethyl-5-[3-(trifluoromethyl)-2-pyridyl]-4,6-dihydro-1,2-benzoxazole (109 mg, 0.330 mmol) in Et$_2$O (1.50 mL). The product was purified by silica gel chromatography (4 g cartridge), eluting with hexanes and EtOAc (0-40%), to provide the title compound as a solid (65.6 mg, 60%). $^1$H NMR (500 MHz, CDCl$_3$) δ 8.69 (dd, J=4.6, 1.6 Hz, 1H), 8.13 (dd, J=8.2, 1.7 Hz, 1H), 7.43-7.38 (m, 1H), 4.17 (dd, J=14.1, 4.3 Hz, 1H), 3.21 (t, J=14.5 Hz, 1H), 3.15 (q, J=1.1 Hz, 3H), 2.93 (dt, J=14.8, 4.2 Hz, 1H), 2.52 (dd, J=14.8, 4.1 Hz, 1H), 1.89 (d, J=14.8 Hz, 1H), 1.45 (s, 3H), 1.11 (s, 3H). m/z (ES+), [M+H]$^+$: 327.3. HPLC (B05) t$_R$=1.71 min.

Compound 15, Step 3: 3-methoxy-5,5-dimethyl-6-oxo-3-[3-(trifluoromethyl)-2-pyridyl]cyclohexene-1-carbonitrile

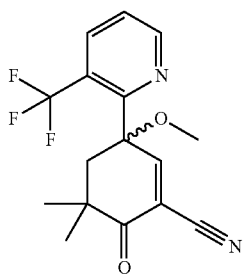 [SMILES: COC1(c2ncccc2C(F)(F)F)C=C(C#N)C(=O)C(C)(C)C1]

As described for step 8 of Compound 2, the title compound was prepared from phenylselenium chloride (114 mg, 0.600 mmol), pyridine (48.3 uL, 0.600 mmol), 5-methoxy-3,3-dimethyl-2-oxo-5-[3-(trifluoromethyl)-2-pyridyl]cyclohexanescarbonitrile (97.5 mg, 0.300 mmol), and 35 wt % H$_2$O$_2$ in water (0.580 mL, 5.98 mmol) in DCM (2.00 mL). The product was purified by silica gel chromatography (4 g cartridge), eluting with hexanes and EtOAc (0-40%), to provide the title compound as a solid (69.0 mg, 71%). $^1$H NMR (500 MHz, CDCl$_3$) δ 8.71 (dd, J=4.8, 1.6 Hz, 1H), 8.15 (dd, J=8.1, 1.6 Hz, 1H), 8.03 (d, J=2.0 Hz, 1H), 7.48-7.42 (m, 1H), 3.25 (t, J=0.9 Hz, 3H), 2.58 (dd, J=14.8, 2.1 Hz, 1H), 2.09 (d, J=14.8 Hz, 1H), 1.40 (s, 3H), 1.09 (s, 3H). m/z (ES+), [M+H]$^+$: 325.2. HPLC (A05) t$_R$=2.33 min.

Compound 15, Step 4: 3-methoxy-5,5-dimethyl-6-oxo-3-(3-(trifluoromethyl)pyridin-2-yl)cyclohex-1-enecarbonitrile (Enantiomer A)

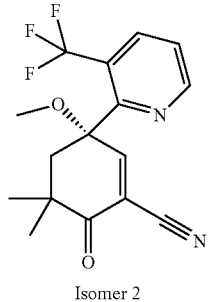 [SMILES: CO[C@]1(c2ncccc2C(F)(F)F)C=C(C#N)C(=O)C(C)(C)C1]

Isomer 2

Enantiomers were separated using Generic Procedure B for chiral separation of enantiomers (starting from 40.6 mg racemate), yielding Isomer 1 (20 mg, ee=99.5%) and Isomer 2 (20 mg, ee=98.6%, Enantiomer A).

Compound 16: 3-methoxy-5,5-dimethyl-3-(6-methyl-3-pyridyl)-6-oxo-cyclohexene-1-carbonitrile

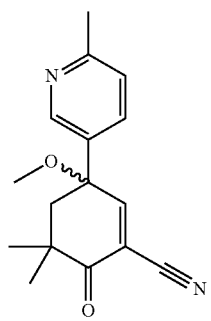 [SMILES: COC1(c2ccc(C)nc2)C=C(C#N)C(=O)C(C)(C)C1]

Compound 16, Step 1: 7,7-dimethyl-5-(6-methyl-3-pyridyl)-6H-1,2-benzoxazole

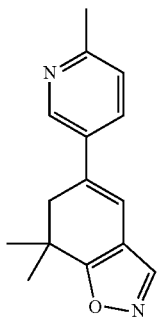 [SMILES: Cc1ccc(C2=Cc3cnoc3C(C)(C)C2)cn1]

As described for step 1 of Compound 17, the title compound was prepared from (7,7-dimethyl-6H-1,2-benzoxazol-5-yl) trifluoromethanesulfonate (0.500 g, 1.68 mmol), 2-methylpyridine-5-boronic acid (0.280 g, 2.02 mmol), $Cs_2CO_3$ (1.10 g, 3.36 mmol), and $Pd(dppf)Cl_2$ (36.9 mg, 0.0500 mmol) in monoglyme (4.00 mL) and water (1.00 mL). The product was purified by silica gel chromatography (40 g cartridge), eluting with hexanes and EtOAc (0-60%), to provide the title compound as a solid (186 mg; 46%). $^1$H NMR (500 MHz, $CDCl_3$) δ 8.60 (d, J=2.0 Hz, 1H), 8.17 (s, 1H), 7.61 (dd, J=8.1, 2.4 Hz, 1H), 7.15 (d, J=8.1 Hz, 1H), 6.57 (t, J=1.5 Hz, 1H), 2.78 (d, J=1.5 Hz, 2H), 2.57 (s, 3H), 1.39 (s, 6H). m/z (ES+), [M+H]$^+$: 241.2. HPLC (A05) $t_R$=1.36 min.

Compound 16, Step 2: 7,7-dimethyl-5-(6-methyl-3-pyridyl)-4,6-dihydro-1,2-benzoxazole-4,5-diol

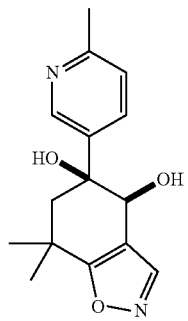 [SMILES: Cc1ccc([C@@]2(O)CC(C)(C)c3oncc3[C@@H]2O)cn1]

4-Methylmorpholine N-oxide (24.4 mg, 0.210 mmol) and 4 wt % $OsO_4$ in water (0.166 mL, 0.0300 mmol) were added to a solution of 7,7-dimethyl-5-(6-methyl-3-pyridyl)-6H-1,2-benzoxazole (25.0 mg, 0.100 mmol) in THF (5.50 mL) and water (1.00 mL). The mixture was stirred at 23° C. for 1.5 h. Brine (20 mL) was added, and the aq phase was extracted with EtOAc (3×20 mL). The combined organic phases were washed with brine (20 mL), dried ($MgSO_4$), filtered, and concentrated under reduced pressure. The product was purified by silica gel chromatography (4 g cartridge), eluting with hexanes and EtOAc (0-100%), to provide the title compound as a solid (22.8 mg; 80%). $^1$H NMR (500 MHz, $CDCl_3$) δ 8.34 (s, 1H), 8.23 (s, 1H), 7.78 (d, J=6.3 Hz, 1H), 6.91 (d, J=7.9 Hz, 1H), 5.13 (s, 1H), 3.45 (s, 1H), 2.19 (s, 3H), 2.06 (d, J=14.7 Hz, 1H), 2.01 (d, J=14.7 Hz, 1H), 1.56 (s, 3H), 1.35 (s, 3H). m/z (ES+), [M+H]$^+$: 275.3. HPLC (A05) $t_R$=1.08 min.

Compound 16, Step 3: 3-methoxy-5,5-dimethyl-3-(6-methyl-3-pyridyl)-6-oxo-cyclohexene-1-carbonitrile 1.0 M NaHMDS in THF (0.310 mL, 0.310 mmol) was added to a solution of 7,7-dimethyl-5-(6-methyl-3-pyridyl)-4,6-dihydro-1,2-benzoxazole-4,5-diol (40.0 mg, 0.150 mmol) in THF (2.00 mL) at −78° C. After 10 m of stirring at −78° C., MeOTf (34.7 uL, 0.310 mmol) was added to the solution. The mixture was stirred at −78° C. for 15 min. Sat. $NH_4Cl$ (2.00 mL) was added, and the mixture was warmed to 23° C. Brine (10 mL) was added, and the aq phase was extracted with EtOAc (3×10 mL). The combined organic phases were washed with brine (20 mL), dried ($MgSO_4$), filtered and concentrated under reduced pressure. The residue was dissolved in DCM (2.00 mL), and 25 wt % NaOMe in MeOH (34.6 uL, 0.160 mmol) was added. The mixture was stirred at 0° for 30 min. Sat. $NH_4Cl$ (2.00 mL) was added, and the mixture was warmed to 23° C. Brine (10 mL) was added, and the aq phase was extracted with DCM (3×10 mL). The combined organic phases were washed with brine (20 mL), dried ($MgSO_4$), filtered and concentrated under reduced pressure. The product was purified by silica gel chromatography (4 g cartridge), eluting with hexanes and EtOAc (0-100%), to provide the title compound as a solid (8.04 mg; 20%). $^1$H NMR (500 MHz, $CDCl_3$) δ 8.46 (dd, J=2.4, 0.5 Hz, 1H), 7.78 (d, J=1.3 Hz, 1H), 7.52 (dd, J=8.1, 2.5 Hz, 1H), 7.23 (d, J=8.1 Hz, 1H), 3.18 (s, 3H), 2.59 (s, 3H), 2.35 (dd, J=14.7, 1.5 Hz, 1H), 2.15 (d, J=14.7 Hz, 1H), 1.35 (s, 3H), 1.01 (s, 3H). m/z (ES+), [M+H]$^+$: 270.9. HPLC (A05) $t_R$=0.14 min.

Compound 17: 3-methoxy-5,5-dimethyl-6-oxo-3-(p-tolyl)cyclohexene-1-carbonitrile

Compound 17, Step 1:
7,7-dimethyl-5-(p-tolyl)-6H-1,2-benzoxazole

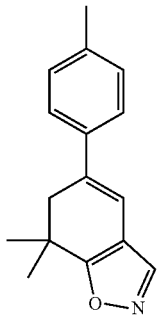 [SMILES: Cc1ccc(C2=Cc3cnoc3C(C)(C)C2)cc1]

(7,7-Dimethyl-6H-1,2-benzoxazol-5-yl) trifluoromethanesulfonate (297 mg, 1.00 mmol), p-tolylboronic acid (163 mg, 1.20 mmol) and Cs$_2$CO$_3$ (652 mg, 2.00 mmol) were mixed in a microwave vessel. Monoglyme (4.00 mL) and water (1.00 mL) were added, and the mixture was purged with N$_2$ gas for 20 min. Pd(dppf)Cl$_2$.DCM (40.8 mg, 0.0500 mmol) was added. The mixture was purged with N$_2$ gas for 10 min. The mixture was heated at 60° C. for 1 h. After cooling to 23° C., sat. NH$_4$Cl (20 mL) was added, and the aq phase was extracted with EtOAc (3×30 mL). The combined organic phases were washed with brine (30 mL), dried (MgSO$_4$), filtered, and concentrated under reduced pressure. The product was purified by silica gel chromatography (25 g cartridge), eluting with hexanes and EtOAc (0-10%), to provide the title compound as a solid (157 mg, 66%). $^1$H NMR (500 MHz, CDCl$_3$) δ 8.15 (s, 1H), 7.40-7.31 (m, 2H), 7.18 (dd, J=8.5, 0.6 Hz, 2H), 6.52 (t, J=1.4 Hz, 1H), 2.79 (d, J=1.5 Hz, 2H), 2.36 (s, 3H), 1.37 (s, 6H). m/z (ES+), [M+H]$^+$: 240.2. HPLC (A05) t$_R$=2.60 min.

Compound 17, Step 2: 3-methoxy-5,5-dimethyl-6-oxo-3-(p-tolyl)cyclohexene-1-carbonitrile

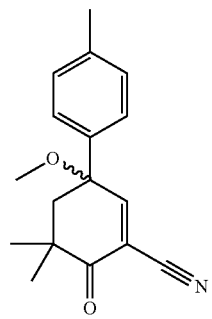

Methanol (2.00 mL) was added to a mixture of 7,7-dimethyl-5-(p-tolyl)-6H-1,2-benzoxazole (50.0 mg, 0.210 mmol), ammonium bromide (24.6 mg, 0.250 mmol), and ozone (77.1 mg, 0.250 mmol). The mixture was stirred at 23° C. for 3 h. Sat. Na$_2$S$_2$O$_3$ (20 mL) was added, and the aq phase was extracted with EtOAc (3×20 mL). The combined organic phases were washed with brine (20 mL), dried (MgSO$_4$), filtered, and concentrated under reduced pressure. The residue was dissolved in DCM (2.00 mL). NEt$_3$ (0.150 mL, 1.04 mmol) was added, and the mixture was stirred at 23° C. for 18 h. Brine (20 mL) was added, and the aq phase was extracted with DCM (3×20 mL). The combined organic phases were washed with brine (20 mL), dried (MgSO$_4$), filtered, and concentrated under reduced pressure. The product was purified by HPLC (eluting with MeCN (10-100%) and water containing 0.1% (NH$_4$)$_2$CO$_3$ and 0.4% NH$_4$OH), to provide the title compound as a solid (26.1 mg, 46%). $^1$H NMR (500 MHz, CDCl$_3$) δ 7.83 (dd, J=1.3, 0.6 Hz, 1H), 7.25-7.21 (m, 2H), 7.21-7.16 (m, 2H), 3.14 (s, 3H), 2.37 (s, 3H), 2.31 (dd, J=14.6, 1.4 Hz, 1H), 2.18 (d, J=14.6 Hz, 1H), 1.33 (s, 3H), 0.96 (s, 3H). m/z (ES+), [M+H—OMe]$^+$: 238.1. HPLC (A05) t$_R$=2.46 min.

Compound 18: 3-(2-chloro-3-pyridyl)-3-methoxy-5,5-dimethyl-6-oxo-cyclohexene-1-carbonitrile

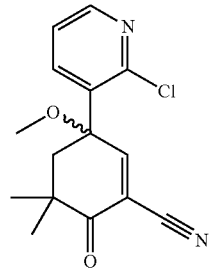 [SMILES: COC1(c2cccnc2Cl)C=C(C#N)C(=O)C(C)(C)C1]

Compound 18, Step 1: 5-(2-chloro-3-pyridyl)-7,7-dimethyl-4,6-dihydro-1,2-benzoxazol-5-ol

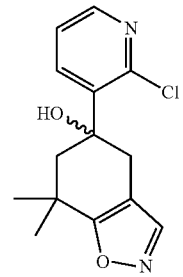 [SMILES: CC1(C)CC(O)(c2cccnc2Cl)Cc2cnoc21]

As described for step 1 of Compound 1, the title compound was prepared from 2.50 M n-BuLi in hexanes (1.60 mL, 4.00 mmol), 3-bromo-2-chloropyridine (0.720 g, 3.75 mmol), and 7,7-dimethyl-4,6-dihydro-1,2-benzoxazol-5-one (0.410 g, 2.50 mmol) in DCM (10 mL). The product was purified by silica gel chromatography (25 g cartridge), eluting with hexanes and EtOAc (0-70%), to provide the title compound as a solid (218 mg; 31%). $^1$H NMR (500 MHz, CDCl$_3$) δ 8.35 (dd, J=4.7, 1.9 Hz, 1H), 8.12 (s, 1H), 8.03 (dd, J=7.8, 1.9 Hz, 1H), 7.29 (dd, J=7.8, 4.7 Hz, 1H), 3.56 (d, J=16.3 Hz, 1H), 2.87 (d, J=14.2 Hz, 1H), 2.79 (dd, J=16.3, 1.7 Hz, 1H), 2.64 (d, J=0.5 Hz, 1H), 2.03 (dd, J=14.2, 1.7 Hz, 1H), 1.52 (s, 3H), 1.27 (s, 3H). m/z (ES+), [M+H]$^+$: 279.2. HPLC (A05) t$_R$=1.88 min.

Compound 18, Step 2: 5-(2-chloro-3-pyridyl)-5-methoxy-7,7-dimethyl-4,6-dihydro-1,2-benzoxazole

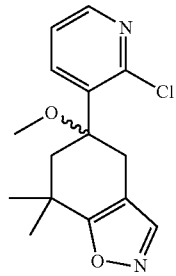 [SMILES: COC1(c2cccnc2Cl)Cc2cnoc2C(C)(C)C1]

1.0 M NaHMDS in THF (0.930 mL, 0.930 mmol) was added to a solution of 1,3-dimethyl-2-imidazolidinone (0.170 mL, 1.55 mmol) in THF (3.75 mL) at −78° C. A solution of 5-(2-chloro-3-pyridyl)-7,7-dimethyl-4,6-dihydro-1,2-benzoxazol-5-ol (216 mg, 0.770 mmol) in THF (3.75 mL) was added. After 10 m of stirring at −78° C., MeOTf (0.180 mL, 1.55 mmol) was added to the solution. The mixture was stirred at −78° C. for 20 min. After warming the solution to 23° C., sat. NH$_4$Cl (20 mL) was added, and the aq phase was extracted with EtOAc (3×20 mL). The combined organic phases were washed with brine (20 mL), dried (MgSO$_4$), filtered, and concentrated under reduced pressure. The product was purified by silica gel chromatography (12 g cartridge), eluting with hexanes and EtOAc (0-50%), to provide the title compound as a solid (132 mg; 58%). $^1$H NMR (500 MHz, CDCl$_3$) δ 8.35 (dd, J=4.6, 1.8 Hz, 1H), 8.12 (s, 1H), 7.66 (dd, J=7.8, 1.9 Hz, 1H), 7.23 (dd, J=7.8, 4.6 Hz, 1H), 3.33 (d, J=16.0 Hz, 1H), 3.13 (dd, J=16.0, 1.5 Hz, 1H), 3.03 (s, 3H), 2.58 (dd, J=14.1, 0.7 Hz, 1H), 2.31 (dd, J=14.1, 1.6 Hz, 1H), 1.47 (s, 3H), 1.10 (s, 3H). m/z (ES+), [M+H]$^+$: 293.1. HPLC (A05) t$_R$=2.08 min.

Compound 18, Step 3: 5-(2-chloro-3-pyridyl)-5-methoxy-3,3-dimethyl-2-oxo-cyclohexanescarbonitrile

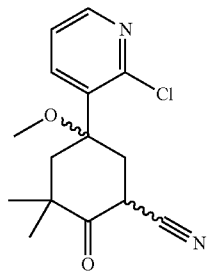 [SMILES: COC1(c2cccnc2Cl)CC(C#N)C(=O)C(C)(C)C1]

As described for step 2 of Compound 24, the title compound was prepared from 25 wt % NaOMe in MeOH (120 uL, 2.15 mmol) and 5-(2-chloro-3-pyridyl)-5-methoxy-7,7-dimethyl-4,6-dihydro-1,2-benzoxazole (126 mg, 0.430 mmol) in Et$_2$O (2.50 mL). The product was purified by silica gel chromatography (12 g cartridge), eluting with hexanes and EtOAc (0-60%), to provide the title compound as a solid (82.7 mg; 66%). $^1$H NMR (500 MHz, CDCl$_3$) δ 8.40 (dd, J=4.7, 1.8 Hz, 1H), 7.68 (dd, J=7.9, 1.8 Hz, 1H), 7.30 (dd, J=7.8, 4.6 Hz, 1H), 4.35 (dd, J=13.6, 4.5 Hz, 1H), 3.19-3.15 (m, 1H), 3.14 (s, 3H), 2.72 (dd, J=14.7, 3.9 Hz, 1H), 2.65 (t, J=13.6 Hz, 1H), 1.93 (d, J=14.6 Hz, 1H), 1.47 (s, 3H), 1.18 (s, 3H). m/z (ES+), [M+H]$^+$: 293.1. HPLC (A05) t$_R$=2.06 min.

Compound 18, Step 4: 3-(2-chloro-3-pyridyl)-3-methoxy-5,5-dimethyl-6-oxo-cyclohexene-1-carbonitrile

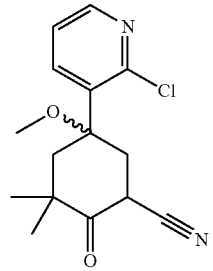 [SMILES: COC1(c2cccnc2Cl)CC(C#N)C(=O)C(C)(C)C1]

As described for step 8 of Compound 2, the title compound was prepared from phenylselenium chloride (103 mg, 0.540 mmol), pyridine (43.7 uL, 0.540 mmol), 5-(2-chloro-3-pyridyl)-5-methoxy-3,3-dimethyl-2-oxo-cyclohexanescarbonitrile (79.0 mg, 0.270 mmol), and 35 wt % H$_2$O$_2$ in water (0.520 mL, 5.40 mmol) in DCM (2.00 mL). The product was purified by silica gel chromatography (4 g cartridge), eluting with hexanes and EtOAc (0-60%), to provide the title compound as a solid (53.4 mg; 68%). $^1$H NMR (500 MHz, CDCl$_3$) δ 8.43 (dd, J=4.7, 1.9 Hz, 1H), 7.95 (dd, J=7.8, 1.9 Hz, 1H), 7.84 (d, J=2.2 Hz, 1H), 7.39 (dd, J=7.8, 4.7 Hz, 1H), 3.30 (s, 3H), 2.46 (d, J=14.8 Hz, 1H), 2.08 (dd, J=14.8, 2.2 Hz, 1H), 1.41 (s, 3H), 1.18 (s, 3H). m/z (ES+), [M+H]$^+$: 291.1. HPLC (A05) t$_R$=2.15 min.

Compound 19: 3-methoxy-5,5-dimethyl-6-oxo-3-[2-(trifluoromethyl)phenyl]cyclohexene-1-carbonitrile

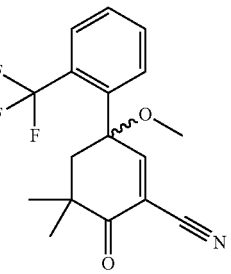

Compound 19, Step 1: 5-methoxy-7,7-dimethyl-5-[2-(trifluoromethyl)phenyl]-4,6-dihydro-1,2-benzoxazole

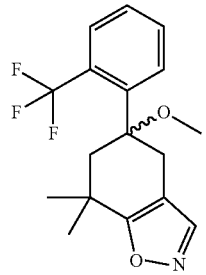 [SMILES: COC1(c2ccccc2C(F)(F)F)Cc2cnoc2C(C)(C)C1]

As described for step 1 of Compound 15, the title compound was prepared from 7,7-dimethyl-5-[2-(trifluoromethyl)phenyl]-4,6-dihydro-1,2-benzoxazol-5-ol (150 mg, 0.480 mmol), HMPA (168 uL, 0.960 mmol), 1.0 M NaHMDS in THF (578 uL, 0.580 mmol), and MeOTf (109 uL, 0.960 mmol) in THF (10 mL). The product was dissolved in a minimal amount of EtOAc, and the mixture was passed through a plug of silica gel washing with EtOAc. The filtrate was concentrated under reduced pressure to provide the title compound as an oil (148 mg, 94%). $^1$H NMR (500 MHz, CDCl$_3$) δ 8.15 (s, 1H), 7.85 (dd, J=7.9, 1.4 Hz, 1H), 7.51-7.41 (m, 3H), 3.25 (d, J=15.4 Hz, 1H), 3.06 (dd, J=15.6, 2.0 Hz, 1H), 2.92 (d, J=0.8 Hz, 3H), 2.42 (dd, J=14.3, 2.0 Hz, 1H), 2.12 (d, J=14.3 Hz, 1H), 1.48 (s, 3H), 1.09 (s, 3H). m/z (ES+), [M+H]$^+$: 326.3. HPLC (B05) $t_R$=2.52 min.

Compound 19, Step 2: 5-methoxy-3,3-dimethyl-2-oxo-[2-(trifluoromethyl)phenyl]cyclohexanes-carbonitrile

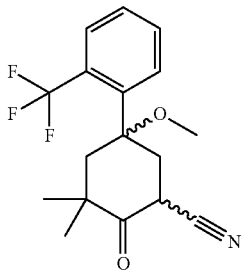 [SMILES: COC1(c2ccccc2C(F)(F)F)CC(C#N)C(=O)C(C)(C)C1]

As described for step 2 of Compound 24, the title compound was prepared from 25 wt % NaOMe in MeOH (0.460 mL, 2.14 mmol) and 5-methoxy-7,7-dimethyl-5-[2-(trifluoromethyl)phenyl]-4,6-dihydro-1,2-benzoxazole (139 mg, 0.430 mmol) in Et$_2$O (2.00 mL). The product was purified by silica gel chromatography (12 g cartridge), eluting with hexanes and EtOAc (0-40%), to provide the title compound as a solid (98.4 mg, 71%). $^1$H NMR (500 MHz, CDCl$_3$) δ 7.86 (dd, J=8.2, 1.5 Hz, 1H), 7.57 (td, J=7.6, 1.4 Hz, 1H), 7.49-7.44 (m, 2H), 4.25 (dd, J=13.5, 4.1 Hz, 1H), 3.11 (d, J=0.8 Hz, 3H), 2.97 (dt, J=13.7, 4.2 Hz, 1H), 2.81 (t, J=13.6 Hz, 1H), 2.55 (dd, J=15.0, 4.3 Hz, 1H), 1.82 (d, J=14.9 Hz, 1H), 1.45 (s, 3H), 1.12 (s, 3H). m/z (ES+), [M+H]$^+$: 326.3. HPLC (B05) $t_R$=1.72 min.

Compound 19, Step 3: 3-methoxy-5,5-dimethyl-6-oxo-3-[2-(trifluoromethyl)phenyl]cyclohexene-1-carbonitrile

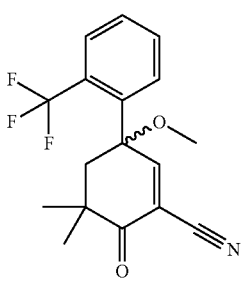 [SMILES: COC1(c2ccccc2C(F)(F)F)C=C(C#N)C(=O)C(C)(C)C1]

As described for step 8 of Compound 2, the title compound was prepared from phenylselenium chloride (115 mg, 0.600 mmol), pyridine (48.7 uL, 0.600 mmol), 5-methoxy-3,3-dimethyl-2-oxo-5-[2-(trifluoromethyl)phenyl]cyclohexanescarbonitrile (98.0 mg, 0.300 mmol), and 35 wt % H$_2$O$_2$ in water (0.590 mL, 6.02 mmol) in DCM (2.00 mL). The product was purified by silica gel chromatography (4 g cartridge), eluting with hexanes and EtOAc (0-40%), to provide the title compound as a solid (39.7 mg, 41%). $^1$H NMR (500 MHz, CDCl$_3$) δ 7.83-7.79 (m, 2H), 7.64 (d, J=4.3 Hz, 2H), 7.50 (dt, J=8.4, 4.1 Hz, 1H), 3.25 (s, 3H), 2.32 (dd, J=15.2, 2.2 Hz, 1H), 2.21 (d, J=15.1 Hz, 1H), 1.41 (s, 3H), 1.12 (s, 3H). m/z (ES+), [M+H]$^+$: 324.1. HPLC (A05) $t_R$=2.45 min.

Compound 20: 3-methoxy-5,5-dimethyl-6-oxo-3-[6-(trifluoromethyl)-2-pyridyl]cyclo-hexene-1-carbonitrile

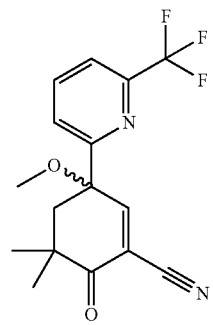 [SMILES: COC1(c2cccc(C(F)(F)F)n2)C=C(C#N)C(=O)C(C)(C)C1]

Compound 20, Step 1: 5-methoxy-7,7-dimethyl-5-[6-(trifluoromethyl)-2-pyridyl]-4,6-dihydro-1,2-benzoxazole

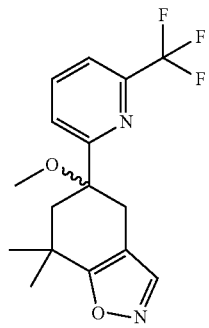 [SMILES: COC1(c2cccc(C(F)(F)F)n2)Cc2cnoc2C(C)(C)C1]

As described for step 1 of Compound 15, the title compound was prepared from 7,7-dimethyl-5-[6-(trifluoromethyl)-2-pyridyl]-4,6-dihydro-1,2-benzoxazol-5-ol (165 mg, 0.530 mmol), HMPA (184 uL, 1.06 mmol), 1.0 M NaHMDS in THF (634 uL, 0.630 mmol), and MeOTf (120 uL, 1.06 mmol) in THF (10 mL). The product was dissolved in a minimal amount of EtOAc and, the mixture was passed through a plug of silica gel washing with EtOAc. The filtrate was concentrated under reduced pressure to provide the title compound as an oil (150 mg, 87%). $^1$H NMR (500 MHz, CDCl$_3$) δ 8.12 (s, 1H), 7.94-7.89 (m, 1H), 7.82 (d, J=8.0 Hz, 1H), 7.60 (dd, J=7.7, 1.0 Hz, 1H), 3.48 (d, J=16.6 Hz, 1H), 3.01 (s, 3H), 2.97 (dt, J=16.6, 1.3 Hz, 1H), 2.10 (d, J=1.3 Hz, 2H), 1.51 (s, 3H), 1.26 (s, 3H). m/z (ES+), [M+H]$^+$: 327.3. HPLC (B05) $t_R$=2.45 min.

Compound 20, Step 2: 5-methoxy-3,3-dimethyl-2-oxo-5-[6-(trifluoromethyl)-2-pyridyl]cyclohexanescarbonitrile

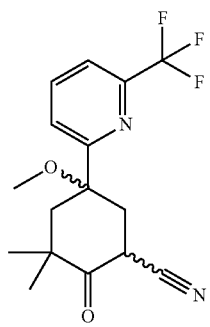 [SMILES: COC1(c2cccc(C(F)(F)F)n2)CC(C#N)C(=O)C(C)(C)C1]

As described for step 2 of Compound 24, the title compound was prepared from 25 wt % NaOMe in MeOH (0.500 mL, 2.30 mmol) and 5-methoxy-7,7-dimethyl-5-[6-(trifluoromethyl)-2-pyridyl]-4,6-dihydro-1,2-benzoxazole (150 mg, 0.460 mmol) in Et$_2$O (2.50 mL). The product was purified by silica gel chromatography (4 g cartridge), eluting with hexanes and EtOAc (0-40%), to provide the title compound as an oil (104 mg, 69%). $^1$H NMR (500 MHz, CDCl$_3$) δ 7.95 (td, J=7.9, 0.7 Hz, 1H), 7.75 (d, J=8.0 Hz, 1H), 7.63 (dd, J=7.7, 0.9 Hz, 1H), 4.31-4.26 (m, 1H), 3.17 (s, 3H), 2.85-2.83 (m, 1H), 2.82 (d, J=1.8 Hz, 1H), 2.24-2.15 (m, 2H), 1.45 (s, 3H), 1.17 (s, 3H). m/z (ES+), [M+H]$^+$: 327.2. HPLC (B05) $t_R$=1.65 min.

Compound 20, Step 3: 3-methoxy-5,5-dimethyl-6-oxo-3-[6-(trifluoromethyl)-2-pyridyl]cyclohexene-1-carbonitrile

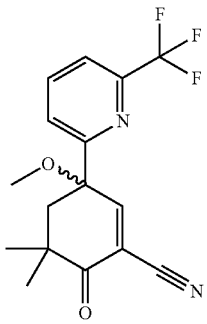 [SMILES: COC1(c2cccc(C(F)(F)F)n2)C=C(C#N)C(=O)C(C)(C)C1]

As described for step 8 of Compound 2, the title compound was prepared from phenylselenium chloride (113 mg, 0.590 mmol), pyridine (47.6 uL, 0.590 mmol), 5-methoxy-3,3-dimethyl-2-oxo-5-[6-(trifluoromethyl)-2-pyridyl]cyclohexanescarbonitrile (96.0 mg, 0.290 mmol), and 35 wt % H$_2$O$_2$ in water (0.570 mL, 5.88 mmol) in DCM (2.00 mL). The product was purified by silica gel chromatography (4 g cartridge), eluting with hexanes and EtOAc (0-40%), to provide the title compound as a solid (43.7 mg, 46%). $^1$H NMR (500 MHz, CDCl$_3$) δ 8.04-7.98 (m, 2H), 7.78 (d, J=8.0 Hz, 1H), 7.69 (dd, J=7.8, 0.9 Hz, 1H), 3.21 (s, 3H), 2.29 (dd, J=14.6, 1.5 Hz, 1H), 2.25 (d, J=14.5 Hz, 1H), 1.39 (s, 3H), 1.05 (s, 3H). m/z (ES+), [M+H]$^+$: 325.2. HPLC (A05) $t_R$=2.34 min.

Compound 21: 3-(2-bromo-3-pyridyl)-3-methoxy-5,5-dimethyl-6-oxo-cyclohexene-1-carbonitrile

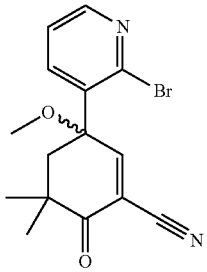 [SMILES: COC1(c2cccnc2Br)C=C(C#N)C(=O)C(C)(C)C1]

Compound 21, Step 1: 5-(2-bromo-3-pyridyl)-5-methoxy-7,7-dimethyl-4,6-dihydro-1,2-benzoxazole

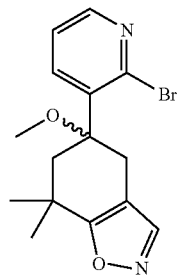 [SMILES: COC1(c2cccnc2Br)Cc2cnoc2C(C)(C)C1]

As described for step 1 of Compound 15, the title compound was prepared from 5-(2-bromo-3-pyridyl)-7,7-dimethyl-4,6-dihydro-1,2-benzoxazol-5-ol (200 mg, 0.620 mmol), HMPA (215 uL, 1.24 mmol), 1.0 M NaHMDS in THF (743 uL, 0.740 mmol), and MeOTf (140 uL, 1.24 mmol) in THF (12 mL). The product was dissolved in a minimal amount of EtOAc and passed through a plug of silica gel washing with EtOAc. The filtrate was concentrated under reduced pressure to provide the title compound as a solid (190 mg, 91%). $^1$H NMR (500 MHz, CDCl$_3$) δ 8.32 (dd, J=4.6, 1.9 Hz, 1H), 8.13 (s, 1H), 7.59 (dd, J=7.8, 1.9 Hz, 1H), 7.24 (dd, J=7.8, 4.6 Hz, 1H), 3.31 (d, J=15.9 Hz, 1H), 3.16 (dd, J=15.9, 1.4 Hz, 1H), 3.03 (s, 3H), 2.62 (d, J=14.1 Hz, 1H), 2.36 (dd, J=14.1, 1.5 Hz, 1H), 1.47 (s, 3H), 1.09 (s, 3H). m/z (ES+), [M+H]$^+$: 337.2. HPLC (B05) $t_R$=2.00 min.

Compound 21, Step 2: 5-(2-bromo-3-pyridyl)-5-methoxy-3,3-dimethyl-2-oxo-cyclohexanescarbonitrile

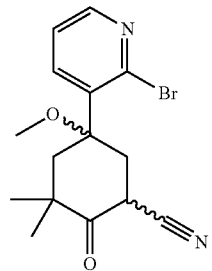 [SMILES: COC1(c2cccnc2Br)CC(C#N)C(=O)C(C)(C)C1]

As described for step 2 of Compound 24, the title compound was prepared from 25 wt % NaOMe in MeOH (0.590 mL, 2.71 mmol) and 5-(2-bromo-3-pyridyl)-5-methoxy-7,7-dimethyl-4,6-dihydro-1,2-benzoxazole (183 mg, 0.540 mmol) in Et$_2$O (3.00 mL). The product was purified by silica gel chromatography (12 g cartridge), eluting with hexanes and EtOAc (0-50%), to provide the title compound as a solid (121 mg, 66%). $^1$H NMR (500 MHz, CDCl$_3$) δ 8.37 (dd, J=4.6, 1.8 Hz, 1H), 7.61 (dd, J=7.9, 1.9 Hz, 1H), 7.31 (dd, J=7.8, 4.6 Hz, 1H), 4.36 (dd, J=13.6, 4.4 Hz, 1H), 3.22-3.15 (m, 1H), 3.13 (s, 3H), 2.84 (d, J=14.5 Hz, 1H), 2.62 (t, J=13.6 Hz, 1H), 1.89 (d, J=14.7 Hz, 1H), 1.47 (s, 3H), 1.18 (s, 3H). m/z (ES+), [M+H]$^+$: 337.2. HPLC (B05) $t_R$=1.18 min.

Compound 21, Step 3: 3-(2-bromo-3-pyridyl)-3-methoxy-5,5-dimethyl-6-oxo-cyclohexene-1-carbonitrile

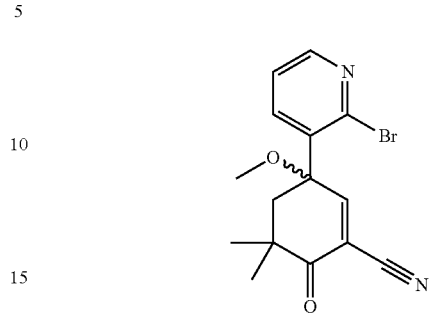

As described for step 8 of Compound 2, the title compound was prepared from phenylselenium chloride (139 mg, 0.720 mmol), pyridine (58.5 uL, 0.720 mmol), 5-(2-bromo-3-pyridyl)-5-methoxy-3,3-dimethyl-2-oxo-cyclohexanescarbonitrile (122 mg, 0.360 mmol), and 35 wt % H$_2$O$_2$ in water (703 uL, 7.24 mmol) in DCM (4.00 mL). The product was purified by silica gel chromatography (4 g cartridge), eluting with hexanes and EtOAc (0-50%), to provide the title compound as a solid (91.3 mg, 75%). $^1$H NMR (500 MHz, CDCl$_3$) δ 8.40 (dd, J=4.6, 1.9 Hz, 1H), 7.93 (dd, J=7.8, 1.9 Hz, 1H), 7.88 (d, J=2.2 Hz, 1H), 7.42 (dd, J=7.8, 4.6 Hz, 1H), 3.28 (s, 3H), 2.54 (d, J=14.8 Hz, 1H), 2.09 (dd, J=14.8, 2.2 Hz, 1H), 1.42 (s, 3H), 1.19 (s, 3H). m/z (ES+), [M+H]$^+$: 335.1. HPLC (A05) $t_R$=2.27 min.

Compound 22: 3-(3-bromo-2-pyridyl)-3-methoxy-5,5-dimethyl-6-oxo-cyclohexene-1-carbonitrile

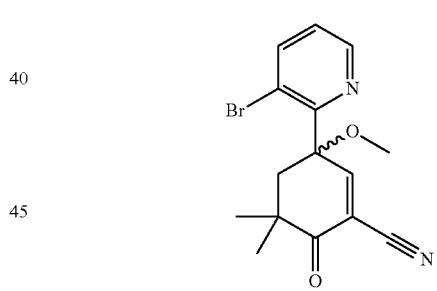

Compound 22, Step 1: 5-(3-bromo-2-pyridyl)-5-methoxy-7,7-dimethyl-4,6-dihydro-1,2-benzoxazole

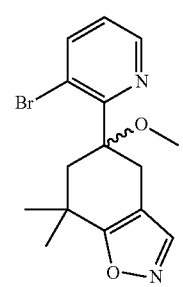

As described for step 1 of Compound 15, the title compound was prepared from 5-(3-bromo-2-pyridyl)-7,7-dimethyl-4,6-dihydro-1,2-benzoxazol-5-ol (200 mg, 0.620 mmol), HMPA (215 uL, 1.24 mmol), 1.0 M NaHMDS in THF (743 uL, 0.740 mmol), and MeOTf (140 uL, 1.24 mmol) in THF (12 mL). The product was purified by silica gel chromatography (12 g cartridge), eluting with hexanes and EtOAc (0-40%), to provide the title compound as a solid (125 mg; 60%). $^1$H NMR (500 MHz, CDCl$_3$) δ 8.45 (dd, J=4.5, 1.5 Hz, 1H), 8.11 (s, 1H), 7.94 (dd, J=8.0, 1.5 Hz, 1H), 7.09 (dd, J=8.0, 4.5 Hz, 1H), 3.42 (d, J=15.7 Hz, 1H), 3.13 (dd, J=15.8, 1.7 Hz, 1H), 2.99 (s, 3H), 2.59 (dd, J=14.3, 1.8 Hz, 1H), 2.38 (d, J=14.3 Hz, 1H), 1.49 (s, 3H), 1.09 (s, 3H). m/z (ES+), [M+H]$^+$: 337.2. HPLC (B05) $t_R$=2.31 min.

Compound 22, Step 2: 5-(3-bromo-2-pyridyl)-5-methoxy-3,3-dimethyl-2-oxo-cyclohexanescarbonitrile

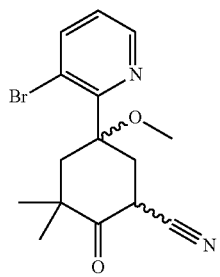 [SMILES: COC1(c2ncccc2Br)CC(C#N)C(=O)C(C)(C)C1]

As described for step 2 of Compound 24, the title compound was prepared from 25 wt % NaOMe in MeOH (0.390 mL, 1.81 mmol) and 5-(3-bromo-2-pyridyl)-5-methoxy-7,7-dimethyl-4,6-dihydro-1,2-benzoxazole (122 mg, 0.360 mmol) in Et$_2$O (2.00 mL). The product was purified by silica gel chromatography (12 g cartridge), eluting with hexanes and EtOAc (0-50%), to provide the title compound as a solid (36.7 mg, 30%). $^1$H NMR (500 MHz, CDCl$_3$) δ 8.48 (dd, J=4.5, 1.5 Hz, 1H), 7.95 (dd, J=8.0, 1.5 Hz, 1H), 7.13 (dd, J=8.0, 4.5 Hz, 1H), 4.31 (dd, J=14.0, 4.5 Hz, 1H), 3.17 (dt, J=14.5, 4.3 Hz, 1H), 3.12 (s, 3H), 2.84-2.73 (m, 2H), 2.01 (d, J=14.8 Hz, 1H), 1.45 (s, 3H), 1.15 (s, 3H). m/z (ES+), [M+H]$^+$: 337.2. HPLC (B05) $t_R$=1.50 min.

Compound 22, Step 3: 3-(3-bromo-2-pyridyl)-3-methoxy-5,5-dimethyl-6-oxo-cyclohexene-1-carbonitrile

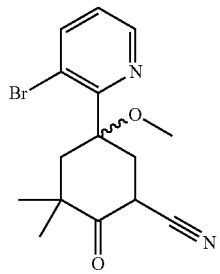 [SMILES: COC1(c2ncccc2Br)CC(C#N)C(=O)C(C)(C)C1]

As described for step 8 of Compound 2, the title compound was prepared from phenylselenium chloride (142 mg, 0.740 mmol), pyridine (60.0 uL, 0.740 mmol), 5-(3-bromo-2-pyridyl)-5-methoxy-3,3-dimethyl-2-oxo-cyclohexanescarbonitrile (125 mg, 0.370 mmol), and 35 wt % H$_2$O$_2$ in water (720 uL, 7.41 mmol) in DCM (4.00 mL). The product was purified by silica gel chromatography (4 g cartridge), eluting with hexanes and EtOAc (0-50%), and reverse phase chromatography (25 g, C-18 cartridge), eluting with water (0.1% HCOOH) and MeCN (10-90%), to provide the title compound as a solid (78.4 mg, 63%). $^1$H NMR (500 MHz, CDCl$_3$) δ 8.49 (dd, J=4.6, 1.5 Hz, 1H), 8.16 (t, J=1.0 Hz, 1H), 7.99 (dd, J=8.0, 1.5 Hz, 1H), 7.20 (dd, J=8.0, 4.6 Hz, 1H), 3.21 (s, 3H), 2.62 (dd, J=14.6, 1.2 Hz, 1H), 2.52 (dd, J=14.6, 0.8 Hz, 1H), 1.33 (s, 3H), 0.91 (s, 3H). m/z (ES+), [M+H]$^+$: 335.1. HPLC (A05) $t_R$=2.41 min.

Compound 23: 3-methoxy-5,5-dimethyl-3-(3-(1-methyl-1H-pyrazol-4-yl)pyridin-2-yl)-6-oxocyclohex-1-enecarbonitrile (Enantiomer A)

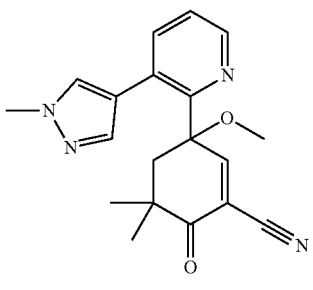

Enantiomer A 3-(3-Bromo-2-pyridyl)-3-methoxy-5,5-dimethyl-6-oxo-cyclohexene-1-carbonitrile (500 mg, 1.49 mmol), (1-methylpyrazol-4-yl)boronic acid (282 mg, 2.24 mmol), and Cs$_2$CO$_3$ (972 mg, 2.98 mmol) were mixed in a microwave vessel. Monoglyme (4.00 mL) and water (1.00 mL) were added, and the mixture was degassed for 10 min. Pd(dppf)Cl$_2$ (109 mg, 0.150 mmol) was added. Degassing was continued for 10 min. The mixture was stirred at 60° C. for 2 h. After cooling to 23° C., water (50 mL) was added, and the aq phase was extracted with EtOAc (3×50 mL). The combined organic phases were washed with brine (50 mL), dried (MgSO$_4$), filtered, and concentrated under reduced pressure. The product was purified by silica gel chromatography (25 g cartridge), eluting with hexanes and EtOAc (0-100%), and reverse phase chromatography (25 g cartridge), eluting with water (0.1% HCOOH) and MeCN (5-100%), to provide the title compound as a solid (0.187 g; 37%). $^1$H NMR (500 MHz, CDCl$_3$) δ 8.46 (dd, J=4.7, 1.7 Hz, 1H), 8.25 (d, J=1.4 Hz, 1H), 7.71 (dd, J=7.8, 1.7 Hz, 1H), 7.67-7.65 (m, 2H), 7.32 (dd, J=7.8, 4.7 Hz, 1H), 4.00 (s, 3H), 3.23 (s, 3H), 2.40 (dd, J=14.4, 1.6 Hz, 1H), 2.15 (d, J=14.4 Hz, 1H), 1.10 (s, 3H), 0.63 (s, 3H). m/z (ES+), [M+H]$^+$: 336.8. HPLC (A05) $t_R$=1.62 min.

Enantiomers were separated using Generic Procedure B for chiral separation of enantiomers (starting from 51 mg racemate), yielding Isomer 1 (16 mg, ee=98.5%) and Isomer 2 (13 mg, ee=96.1%, Enantiomer A).

Compound 24: 3-hydroxy-5,5-dimethyl-6-oxo-3-[5-(trifluoromethyl)-2-pyridyl]cyclo-hexene-1-carbonitrile

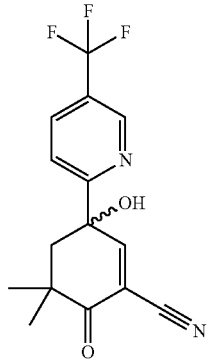 [SMILES: CC1(C)CC(O)(c2ccc(C(F)(F)F)cn2)C=C(C#N)C1=O]

Compound 24, Step 1: 7,7-dimethyl-5-[5-(trifluoromethyl)-2-pyridyl]-4,6-dihydro-1,2-benzoxazol-5-ol

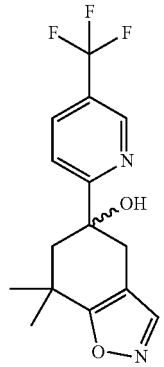 [SMILES: CC1(C)CC(O)(c2ccc(C(F)(F)F)cn2)Cc2cnoc21]

As described for step 1 of Compound 2, the title compound was prepared from 2.50 M nBuLi in hexanes (2.52 mL, 6.30 mmol), 2-bromo-5-(trifluoromethyl)-pyridine (1.36 g, 6.00 mmol), and 7,7-dimethyl-4,6-dihydro-1,2-benzoxazol-5-one (0.500 g, 3.00 mmol) in DCM (7.50 mL). The product was purified by silica gel chromatography (25 g cartridge), eluting with hexanes and EtOAc (0-50%), and reverse phase chromatography (40 g, C-18 cartridge), eluting with MeCN (20-100%) and water (0.03% $(NH_4)_2CO_3$/ 0.375% $NH_4OH$), to provide the title compound as a solid (296 mg, 32%). $^1$H NMR (500 MHz, $CDCl_3$) δ 8.76 (dd, J=4.8, 1.6 Hz, 1H), 8.14 (dd, J=8.1, 1.6 Hz, 1H), 7.47 (ddd, J=8.0, 4.6, 0.9 Hz, 1H), 5.30 (s, 1H), 4.63 (dd, J=13.4, 5.0 Hz, 1H), 3.08 (t, J=13.4 Hz, 1H), 2.44 (ddd, J=13.3, 5.0, 3.5 Hz, 1H), 2.39 (d, J=14.5 Hz, 1H), 1.92 (dd, J=14.5, 3.6 Hz, 1H), 1.50 (s, 3H), 1.15 (s, 3H). m/z (ES+), [M+H]$^+$: 313.1. HPLC (B05) $t_R$=2.19 min.

Compound 24, Step 2: 5-hydroxy-3,3-dimethyl-2-oxo-5-[5-(trifluoromethyl)-2-pyridyl]cyclohexanes-carbonitrile

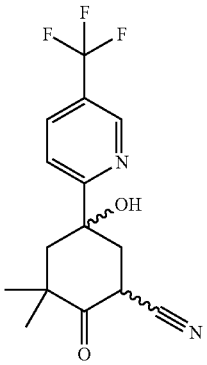 [SMILES: CC1(C)CC(O)(c2ccc(C(F)(F)F)cn2)CC(C#N)C1=O]

25 wt % NaOMe in MeOH (0.35 mL, 1.60 mmol) was added drop-wise at 0° C. to a solution of 7,7-dimethyl-5-[5-(trifluoromethyl)-2-pyridyl]-4,6-dihydro-1,2-benzoxazol-5-ol (100 mg, 0.320 mmol) in $Et_2O$ (1.50 mL). The mixture was stirred at 0° C. for 45 m. Sat. $NH_4Cl$ (20 mL) was added, and the aq phase was extracted with EtOAc (3×20 mL). The combined organic phases were washed with brine (20 mL), dried ($MgSO_4$), filtered, and concentrated under reduced pressure. The product was purified by silica gel chromatography (4 g cartridge), eluting with hexanes and EtOAc (0-40%), to provide the title compound as a solid (84.9 mg, 85%). $^1$H NMR (500 MHz, $CDCl_3$) δ 8.86 (dq, J=1.7, 0.9 Hz, 1H), 8.03 (ddd, J=8.3, 2.2, 0.7 Hz, 1H), 7.51 (dt, J=8.4, 0.8 Hz, 1H), 5.31 (s, 1H), 4.62 (dd, J=13.4, 4.9 Hz, 1H), 2.61 (t, J=13.3 Hz, 1H), 2.44 (ddd, J=13.2, 5.0, 3.7 Hz, 1H), 2.15 (d, J=14.3 Hz, 1H), 1.96 (dd, J=14.3, 3.7 Hz, 1H), 1.53 (s, 3H), 1.18 (s, 3H). m/z (ES+), [M+H]$^+$: 313.3. HPLC (B05) $t_R$=1.45 min.

Compound 24, Step 3: 3-hydroxy-5,5-dimethyl-6-oxo-3-[5-(trifluoromethyl)-2-pyridyl]cyclohexene-1-carbonitrile

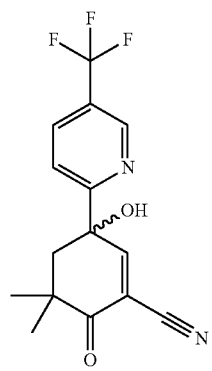 [SMILES: CC1(C)CC(O)(c2ccc(C(F)(F)F)cn2)C=C(C#N)C1=O]

As described for step 8 of Compound 2, the title compound was prepared from phenylselenium chloride (104 mg, 0.540 mmol), pyridine (44.0 µL, 0.260 mmol), 35 wt % $H_2O_2$ in water (0.530 mL, 5.44 mmol), and 5-hydroxy-3,3-dimethyl-2-oxo-5-[5-(trifluoromethyl)-2-pyridyl]-cyclohexanescarbonitrile (85.0 mg, 0.270 mmol) in DCM (1.00 mL). The product was purified by silica gel chromatography (4 g cartridge), eluting with hexanes and EtOAc (0-40%), to provide the title compound as an oil (62.5 mg, 74%). $^1$H NMR (500 MHz, CDCl$_3$) δ 8.88 (dt, J=2.0, 1.0 Hz, 1H), 8.08 (ddd, J=8.2, 2.3, 0.7 Hz, 1H), 7.54 (dt, J=8.2, 0.8 Hz, 1H), 7.26 (d, J=2.1 Hz, 1H), 5.32 (s, 1H), 2.34 (d, J=14.7 Hz, 1H), 2.16 (dd, J=14.7, 2.1 Hz, 1H), 1.49 (s, 3H), 1.19 (s, 3H). m/z (ES+), [M+H]$^+$: 311.1. HPLC (A05) t$_R$=2.13 min.

Compound 25: 3-methoxy-5,5-dimethyl-3-[2-(1-methylpyrazol-4-yl)-3-pyridyl]-6-oxo-cyclohexene-1-carbonitrile

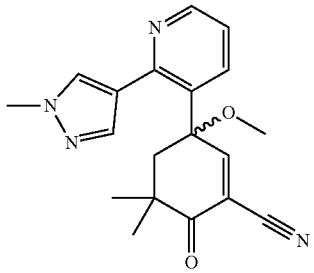 [SMILES: COC1(c2cccnc2-c2cnn(C)c2)C=C(C#N)C(=O)C(C)(C)C1]

As described for Compound 13, the title compound was prepared from 3-(2-bromo-3-pyridyl)-3-methoxy-5,5-dimethyl-6-oxo-cyclohexene-1-carbo-nitrile (63.0 mg, 0.190 mmol), Cs$_2$CO$_3$ (122 mg, 0.380 mmol), (1-methylpyrazol-4-yl)boronic acid (47.3 mg, 0.380 mmol), and Pd(dppf)Cl$_2$.DCM (15.4 mg, 0.0200 mmol) in monoglyme (1.75 mL) and water (0.250 mL). The product was purified by silica gel chromatography (4 g cartridge), eluting with hexanes and EtOAc (0-60%), to provide the title compound as a solid (5 mg, 8%). $^1$H NMR (500 MHz, CDCl$_3$) δ 8.40 (dd, J=4.6, 1.9 Hz, 1H), 7.93 (dd, J=7.8, 1.9 Hz, 1H), 7.88 (d, J=2.2 Hz, 1H), 7.42 (dd, J=7.8, 4.6 Hz, 1H), 3.28 (s, 3H), 2.54 (d, J=14.8 Hz, 1H), 2.09 (dd, J=14.8, 2.2 Hz, 1H), 1.42 (s, 3H), 1.19 (s, 3H). m/z (ES+), [M+H]$^+$: 337.2. HPLC (A05) t$_R$=1.71.

Compound 42: (3S)-3-[3-(difluoromethyl)-5-fluoropyridin-2-yl]-3-methoxy-5,5-dimethyl-6-oxocyclohex-1-ene-1-carbonitrile Compound 42, step 1: 5-(3-(Difluoromethyl)-5-fluoropyridin-2-yl)-7,7-dimethyl-4,5,6,7-tetrahydrobenzo[d]isoxazol-5-ol

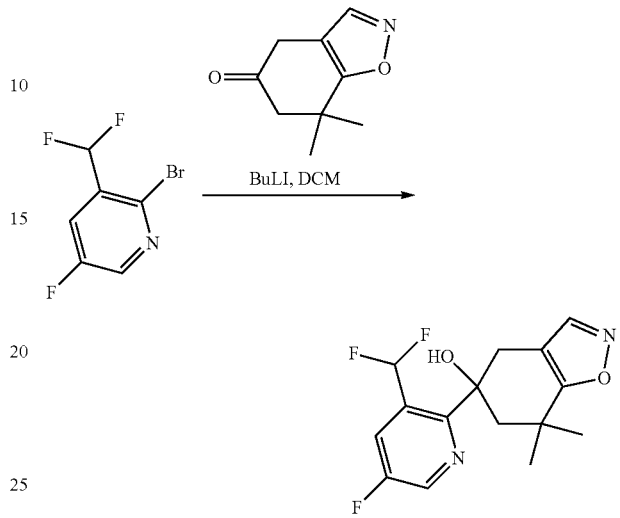

A solution of n-Butyllithium in hexane (67.8 mL, 169.5 mmol) was added to a mixture of 2-bromo-3-(difluoromethyl)-5-fluoropyridine (35.6 g, 157 mmol) in DCM (300 mL) at −78° C. under N$_2$. The resulting solution was stirred at −78° C. for 5 min and dropwise treated with a solution of 7,7-dimethyl-6,7-dihydrobenzo[d]isoxazol-5(4H)-one (20 g, 121.07 mmol) in DCM (60 mL). The resulting mixture was stirred at −78° C. for 1 h, quenched with sat. aq. NH$_4$Cl (100 mL) and water (400 mL) and extracted with DCM (2×400 mL). 100 mL MeOH and 3.8 g NaBH$_4$ were added to the combined organic layers and stirred for 30 min at rt. The mixture was washed with water (300 mL) and brine (300 mL), dried over Na$_2$SO$_4$, filtered and evaporated to afford a yellow residue. The crude product was purified by flash silica chromatography (elution gradient 0 to 10% EtOAc in petroleum ether) to give title compound (14.80 g, 39.1%) as a yellow solid. $^1$H NMR (400 MHz, CDCl$_3$) δ 1.36 (s, 3H), 1.60 (s, 3H), 2.03-2.12 (m, 1H), 2.37 (d, J=14.5 Hz, 1H), 2.71 (dd, J=16.3, 2.2 Hz, 1H), 3.62 (d, J=16.3 Hz, 1H), 7.54-7.72 (m, 1H), 7.85 (dd, J=9.1, 2.5 Hz, 1H), 8.13 (s, 1H), 8.48 (d, J=2.8 Hz, 1H). m/z (ES+), [M+H]$^+$=313.

Compound 42, step 2: 5-(3-(Difluoromethyl)-5-fluoropyridin-2-yl)-5-methoxy-7,7-dimethyl-4,5,6,7-tetrahydrobenzo[d]isoxazole

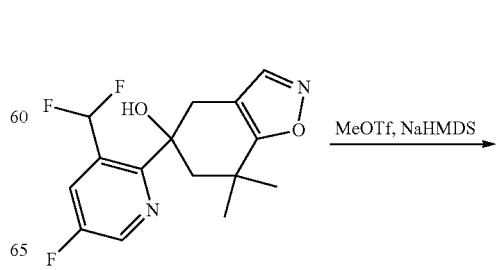

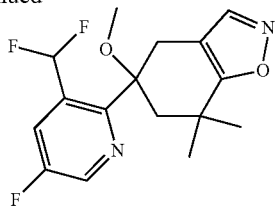

NaHMDS (52.1 mL, 52.13 mmol) was added dropwise to 5-(3-(difluoromethyl)-5-fluoropyridin-2-yl)-7,7-dimethyl-4,5,6,7-tetrahydrobenzo[d]isoxazol-5-ol (14.8 g, 47.39 mmol) and HMPA (16.49 mL, 94.78 mmol) in THF (300 mL) at −78° C. under $N_2$. Methyl trifluoromethanesulfonate (15.55 g, 94.78 mmol) was added dropwise after the reaction was stirred for 5 min at −78° C. The resulting mixture was warmed to rt, stirred for 20 min, and quenched with sat. aq. $NH_4Cl$ (100 mL) and water (400 mL) and extracted with EtOAc (2×500 mL). The combined organic layers were dried over $Na_2SO_4$, filtered and evaporated to afford a yellow residue. The crude product was purified by flash silica chromatography (elution gradient 0 to 10% EtOAc in petroleum ether) to give title compound (11.0 g, 71.1%) as a white solid. $^1$H NMR (400 MHz, $CDCl_3$) δ 1.14 (s, 3H), 1.53 (s, 3H), 2.09 (d, J=14.5 Hz, 1H), 2.26 (dd, J=14.5, 2.1 Hz, 1H), 2.95 (dd, J=16.3, 2.1 Hz, 1H), 2.99 (s, 3H), 3.58 (d, J=16.3 Hz, 1H), 7.5-7.74 (m, 1H), 7.82-7.89 (m, 1H), 8.14 (s, 1H), 8.47 (d, J=2.8 Hz, 1H). m/z (ES+), [M+H]$^+$=327.

Compound 42, step 3: 5-(3-(Difluoromethyl)-5-fluoropyridin-2-yl)-5-methoxy-3,3-dimethyl-2-oxo-cyclohexanecarbonitrile

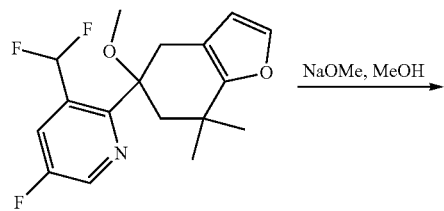

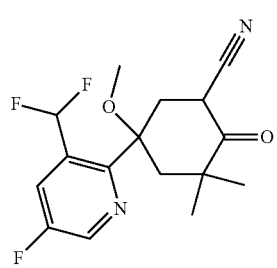

A solution of NaOMe in MeOH (31.3 mL, 168.6 mmol) was added to 5-(3-(difluoromethyl)-5-fluoropyridin-2-yl)-5-methoxy-7,7-dimethyl-4,5,6,7-tetrahydrobenzo[d]isoxazole (11 g, 33.7 mmol) in $Et_2O$ (200 mL) at 0° C. The resulting mixture was stirred at 0° C. for 1 h, quenched with sat. aq. $NH_4Cl$ (50 mL) and water (50 mL) and extracted with EtOAc (2×100 mL). The combined organic layers were dried over $Na_2SO_4$, filtered and evaporated to afford title compound (10.80 g, 98%) as a yellow oil which was used without further purification. $^1$H NMR (400 MHz, $CDCl_3$) δ 1.16 (s, 3H), 1.50 (s, 3H), 2.00-2.10 (m, 1H), 2.18-2.27 (m, 1H), 2.92 (dt, J=14.9, 4.4 Hz, 1H), 3.02 (d, J=13.9 Hz, 1H), 3.18 (s, 3H), 4.17-4.26 (m, 1H), 7.48-7.79 (m, 1H), 7.86 (dd, J=8.6, 2.8 Hz, 1H), 8.50 (d, J=2.8 Hz, 1H). m/z (ES+), [M+H]$^+$=327.

Compound 42, step 4: 3-(3-(Difluoromethyl)-5-fluoropyridin-2-yl)-3-methoxy-5,5-dimethyl-6-oxo-cyclohex-1-enecarbonitrile

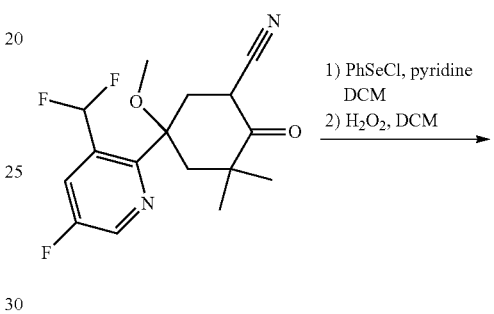

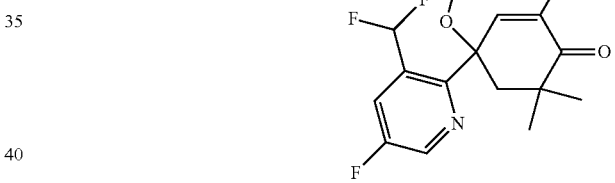

A solution of pyridine (5.35 mL, 66.19 mmol) in DCM (10 mL) was added dropwise to phenylselenyl chloride (12.68 g, 66.19 mmol) in DCM (100 mL) at 0° C. The mixture was stirred for 20 min and treated dropwise with a solution of rac-(5R)-5-(3-(difluoromethyl)-5-fluoropyridin-2-yl)-5-methoxy-3,3-dimethyl-2-oxocyclohexane-1-carbonitrile (10.8 g, 33.10 mmol) in DCM (100 mL). The resulting mixture was stirred at 0° C. for 2 h, treated with 1M aq. HCl (80 mL) and water (160 mL), and the phases were separated. Hydrogen peroxide (67.6 mL, 661.93 mmol) was added dropwise to the DCM layer at 0° C. and the mixture was vigorously stirred at 0° C. for 40 min. Water (200 mL) was added and the mixture was extracted with DCM (2×200 mL). The combined organic phases were washed with brine (2×150 mL), dried ($Na_2SO_4$), filtered, and concentrated under reduced pressure to afford a pale yellow residue. The crude product was purified by flash silica chromatography (elution gradient 0 to 10% EtOAc in petroleum ether) to give title compound (10.2 g, 95%) as a white solid. $^1$H NMR (400 MHz, $CDCl_3$) δ 1.05 (s, 3H), 1.39 (s, 3H), 2.17 (d, J=14.7 Hz, 1H), 2.39 (dd, J=14.7, 1.8 Hz, 1H), 3.28 (d, J=0.9 Hz, 3H), 7.37-7.65 (m, 1H), 7.91 (dd, J=8.5, 2.8 Hz, 1H), 8.07 (d, J=1.7 Hz, 1H), 8.50-8.55 (m, 1H). m/z (ES+), [M+H]$^+$=325.

Compound 42, step 5: (3S)-3-[3-(difluoromethyl)-5-fluoropyridin-2-yl]-3-methoxy-5,5-dimethyl-6-oxo-cyclohex-1-ene-1-carbonitrile

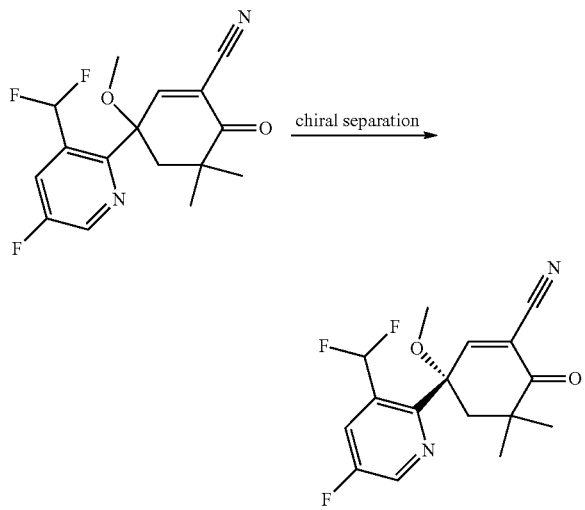

10.2 g of the racemate was purified by preparative chiral-HPLC under the following conditions: CHIRAL ART Cellulose-SB S-5 um column, 2·25 cm, 5 um (mobile phase A: hexane (HPLC), mobile phase B: IPA (HPLC), flow rate: 20 mL/min, gradient: 20 B to 20 B in 15 min; 254/220 nm detection; isomer 1 (retention time 8.9 min), isomer 2 (retention time 11.5 min). The fractions containing the desired compound (isomer 2) were evaporated to dryness to afford title compound (3.1 g, 30%) as white solid. $^1$H NMR (400 MHz, CDCl$_3$) δ 1.05 (s, 3H), 1.39 (s, 3H), 2.17 (d, J=14.7 Hz, 1H), 2.39 (dd, J=14.7, 1.8 Hz, 1H), 3.28 (d, J=0.9 Hz, 3H), 7.52 (ddd, J=55.4, 53.8, 1.7 Hz, 1H), 7.91 (dd, J=8.5, 2.8 Hz, 1H), 8.07 (d, J=1.7 Hz, 1H), 8.52 (d, J=2.7 Hz, 1H); m/z (ES+), [M+H]+=325; ee=97.3%. Determination of the absolute configuration of Compound 42 is provided in Example 2 below.

The compounds provided in Table 2 have been prepared by analogy to the synthesis described for Compound 1, starting from Compound A1 (Method A: addition, alkylation, isoxazole opening, oxidation). All pure enantiomers in the following Table were separated as described in the Generic Procedure A for chiral separation of enantiomers (chiral HPLC). The absolute configuration of compounds 38 and 40 were assigned based on the crystal structure of the compounds bound to the BTB domain of Keap1. For compounds where the enantiomers were separated but for which absolute configuration was not assigned, data is given for the single enantiomer that was tested. For compounds drawn without specified stereochemistry and labeled as "Enantiomer A," all data provided throughout the application for that compound is for the more active enantiomer. For compounds drawn without specified stereochemistry and labeled as "Enantiomer B," all data provided throughout the application for that compound is for the less active enantiomer. For compounds drawn without specified stereochemistry and not labeled as "Enantiomer A" or "Enantiomer B," all data provided throughout the application for that compound is for the racemate.

TABLE 2

Compounds 26-41 and 43-48

| Cmpd # | Structure | Name | Analytical data |
|---|---|---|---|
| 26 | 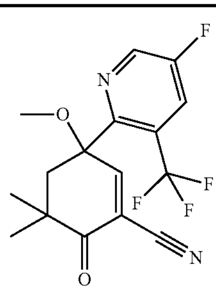 | 3-(5-fluoro-3-(trifluoromethyl)pyridin-2-yl)-3-methoxy-5,5-dimethyl-6-oxocyclohex-1-enecarbonitrile (Enantiomer A) | $^1$H NMR (400 MHz, CDCl$_3$) δ ppm 1.11 (s, 3H), 1.41 (s, 3H), 2.07 (d, J = 14.8, 1H), 2.58 (dd, J = 14.8, 2.1 Hz, 1H), 3.27 (s, 3H), 7.91 (dd, J = 8.7, 2.7 Hz, 1H), 7.99 (d, J = 2.0 Hz, 1H), 8.61 (d, J = 2.7 Hz, 1H). m/z (ES+), [M + H]+ = 343; HPLC (C05) t$_R$ = 2.20 min (99.6%). ee = 99.9%. |
| 27 | 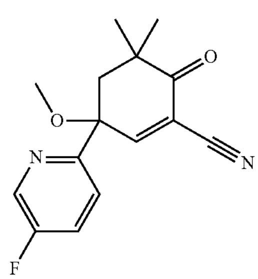 | 3-(5-fluoropyridin-2-yl)-3-methoxy-5,5-dimethyl-6-oxocyclohex-1-enecarbonitrile (Enantiomer A) | $^1$H NMR (400 MHz, CDCl$_3$) δ ppm 1.03 (s, 3H), 1.39 (s, 3H), 2.24 (d, J = 14.5 Hz, 1H), 2.29 (dd, J = 14.6, 1.3 Hz, 1H), 3.22 (s, 3H), 7.50-7.65 (m, 2H), 8.04 (d, J = 1.3 Hz, 1H), 8.44 (d, J = 2.7 Hz, 1H); m/z (ES+), [M + H]+ = 275; HPLC (C05) t$_R$ = 1.88 min (99.1%). ee = 98.4%. |

TABLE 2-continued

Compounds 26-41 and 43-48

| Cmpd # | Structure | Name | Analytical data |
|---|---|---|---|
| 28 | 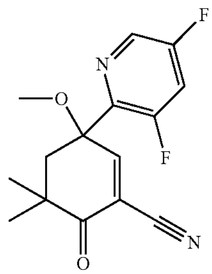 [SMILES: COC1(c2ncc(F)cc2F)C=C(C#N)C(=O)C(C)(C)C1] | 3-(3,5-difluoropyridin-2-yl)-3-methoxy-5,5-dimethyl-6-oxocyclohex-1-enecarbonitrile | $^1$H NMR (400 MHz, CDCl$_3$) δ ppm 0.92 (s, 3H), 1.34 (s, 3H), 2.51 (d, J = 1.1 Hz, 2H), 3.22 (s, 3H), 7.34 (ddd, J =10.4, 7.9, 2.4 Hz, 1H), 8.13 (d, J = 1.1 Hz, 1H), 8.34 (d, J = 2.3 Hz, 1H); m/z (ES$^+$), [M + H]$^+$ = 293; HPLC (C05) t$_R$ = 2.492 min (98.7%). |
| 29 | 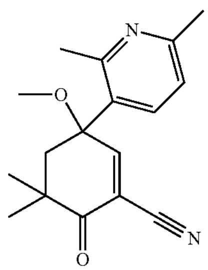 | 3-(2,6-dimethylpyridin-3-yl)-3-methoxy-5,5-dimethyl-6-oxocyclohex-1-enecarbonitrile | $^1$H NMR (400 MHz, CDCl$_3$) δ ppm 1.11 (s, 3H), 1.41 (s, 3H), 2.16 (d, J = 14.9 Hz, 1H), 2.43 (dd, J = 14.9, 1.8 Hz, 1H), 2.85 (s, 3H), 2.97 (s, 3H), 3.29 (s, 3H), 7.49 (d, J = 8.3 Hz, 1H), 7.79 (d, J = 1.8 Hz, 1H), 7.98 (d, J = 8.3 Hz, 1H); m/z (ES$^+$), [M + H]$^+$ = 285; HPLC (C05) t$_R$ = 1.168 min (96.3%). |
| 30 | 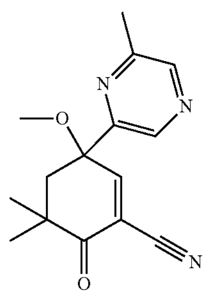 [SMILES: COC1(c2cncc(C)n2)C=C(C#N)C(=O)C(C)(C)C1] | 3-methoxy-5,5-dimethyl-3-(6-methylpyrazin-2-yl)-6-oxocyclohex-1-enecarbonitrile | $^1$H NMR (400 MHz, CDCl$_3$) δ ppm 1.08 (s, 3H), 1.42 (s, 3H), 2.26 (d, J = 14.6 Hz, 1H), 2.34 (dd, J = 14.7, 1.6 Hz, 1H), 2.59 (s, 3H), 3.28 (s, 3H), 8.01 (d, J = 1.5 Hz, 1H), 8.48 (s, 1H), 8.68 (s, 1H); m/z (ES$^+$), [M + H]$^+$ = 272; HPLC (C05) t$_R$ = 1.725 min (98.5%). |
| 31 | 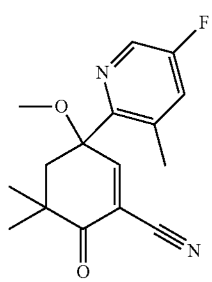 | 3-(5-fluoro-3-methylpyridin-2-yl)-3-methoxy-5,5-dimethyl-6-oxocyclohex-1-enecarbonitrile (Enantiomer A) | $^1$H NMR (300 MHz, CDCl$_3$) δ ppm 0.96 (s, 3H), 1.35 (s, 3H), 2.26 (d, J = 14.5, 0.8 Hz, 1H), 2.47 (dd, J = 14.5, 1.3 Hz, 1H), 2.61 (s, 3H), 3.22 (s, 3H), 7.30-7.35 (m, 1H), 8.18 (br. s, 1H), 8.25 (d, J = 2.8 Hz, 1H); m/z (ES$^+$), [M + H]$^+$ = 289; HPLC (C05) t$_R$ = 1.471 min (99.5%). |
|  | Enantiomer A |  |  |
| 32 | 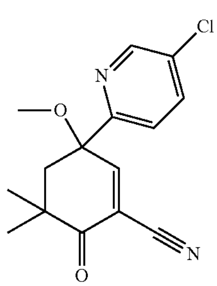 | 3-(5-chloropyridin-2-yl)-3-methoxy-5,5-dimethyl-6-oxocyclohex-1-enecarbonitrile (Enantiomer A) | $^1$H NMR (400 MHz, CDCl$_3$) δ ppm 1.04 (s, 3H), 1.39 (s, 3H), 2.23 (d, J = 14.6 Hz, 1H), 2.28 (dd, J = 14.6, 1.5 Hz, 1H), 3.23 (s, 3H), 7.55 (dd, J = 8.4, 0.7 Hz, 1H), 7.81 (dd, J = 8.5, 2.4 Hz, 1H), 8.02 (d, J = 1.3 Hz, 1H), 8.53-8.55 (m, 1H) m/z (ES$^+$), [M + H]$^+$ = 291; HPLC (C05) t$_R$ = 2.02 min (99.3%). ee = 99%. |
|  | Enantiomer A |  |  |

TABLE 2-continued

Compounds 26-41 and 43-48

| Cmpd # | Structure | Name | Analytical data |
|---|---|---|---|
| 33 | Enantiomer A | 3-methoxy-5,5-dimethyl-6-oxo-3-(4-(trifluoromethyl)thiazol-2-yl)cyclohex-1-enecarbonitrile (Enantiomer A) | $^1$H NMR (300 MHz, DMSO-$d_6$) δ ppm 0.95 (s, 3H), 1.25 (s, 3H), 2.43-2.48 (m, 2H), 3.27 (s, 3H), 8.43 (s, 1H), 8.73 (s, 1H). m/z (ES$^+$), [M + H]$^+$ = 331; HPLC (C05) $t_R$ = 2.10 min (96%). ee = 99%. |
| 34 | Enantiomer A | 3-methoxy-5,5-dimethyl-3-(3-methylthiophen-2-yl)-6-oxocyclohex-1-enecarbonitrile (Enantiomer A) | $^1$H NMR (300 MHz, DMSO-$d_6$) δ ppm 0.92 (s, 3H), 1.22 (s, 3H), 2.26 (s, 3H), 2.38 (d, J = 1.1 Hz, 2H), 3.14 (s, 3H), 6.94 (d, J = 5.1 Hz, 1H), 7.45 (d, J = 5.1 Hz, 1H), 8.42 (d, J = 1.1 Hz, 1H). m/z (ES$^+$), [M + H]$^+$ = 276; HPLC (C05) $t_R$ = 2.11 min (97%). ee = 99%. |
| 35 | Enantiomer A | 3-ethoxy-5,5-dimethyl-6-oxo-3-(3-(trifluoromethyl)pyridin-2-yl)cyclohex-1-enecarbonitrile (Enantiomer A) | $^1$H NMR (300 MHz, DMSO-$d_6$) δ ppm 0.93 (s, 3H), 1.10 (t, J = 6.8 Hz, 3H), 1.27 (s, 3H), 2.15 (d, J = 14.6 Hz, 1H), 2.54 (d, J = 1.7 Hz, 1H), 3.19-3.32 (m, 1H), 3.51-3.68 (m, 1H), 7.68 (ddd, J = 8.1, 4.7, 0.9 Hz, 1H), 8.35 (dd, J = 8.1, 1.6 Hz, 1H), 8.52 (s, 1H), 8.85 (dd, J = 4.7, 1.5 Hz, 1H). m/z (ES$^+$), [M + H]$^+$ = 339; HPLC (C05) $t_R$ = 1.81 min (99%). ee = 99%. |
| 36 | Enantiomer A | 3-methoxy-5,5-dimethyl-3-(4-methylthiazol-2-yl)-6-oxocyclohex-1-enecarbonitrile (Enantiomer A) | $^1$H NMR (300 MHz, DMSO-$d_6$) δ ppm 0.89 (s, 3H), 1.22 (s, 3H), 2.37 (s, 3H), 2.40-2.47 (m, 2H), 3.20 (s, 3H), 7.48 (s, 1H), 8.42 (s, 1H). m/z (ES$^+$), [M + H]$^+$ = 277; HPLC (C05) $t_R$ = 2.00 min (96%). ee = 98%. |
| 37 | Enantiomer A | 3-ethoxy-3-(5-fluoropyridin-2-yl)-5,5-dimethyl-6-oxocyclohex-1-enecarbonitrile (Enantiomer A) | $^1$H NMR (300 MHz, DMSO-$d_6$) δ ppm 0.81 (s, 3H), 1.08 (t, J = 6.9 Hz, 3H), 1.24 (s, 3H), 2.30 (d, J = 1.1 Hz, 2H), 3.17 (dq, J = 9.0, 6.9 Hz, 1H), 3.47 (dq, J = 9.0, 6.9 Hz, 1H), 7.73 (ddd, J = 8.8, 4.5, 0.7 Hz, 1H), 7.87 (td, J = 8.8, 2.9 Hz, 1H), 8.51 (s, 1H), 8.59 (d, J = 2.9 Hz, 1H). m/z (ES$^+$), [M + H]$^+$ = 289; HPLC (C05) $t_R$ = 2.13 min (98%). ee = 99%. |

TABLE 2-continued

Compounds 26-41 and 43-48

| Cmpd # | Structure | Name | Analytical data |
|---|---|---|---|
| 38 | 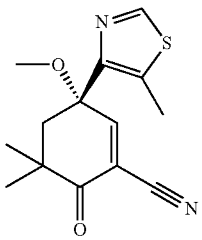 [SMILES: CO[C@]1(c2ncsc2C)C=C(C#N)C(=O)C(C)(C)C1] | (S)-3-methoxy-5,5-dimethyl-3-(5-methylthiazol-4-yl)-6-oxocyclohex-1-enecarbonitrile | $^1$H NMR (300 MHz, DMSO-d$_6$) δ ppm 0.73 (s, 3H), 1.18 (s, 3H), 2.33-2.46 (m, 2H), 2.56 (s, 3H), 3.11 (s, 3H), 8.48 (d, J = 0.9 Hz, 1H), 8.88 (s, 1H). m/z (ES$^+$), [M + H]$^+$ = 277; HPLC (C05) t$_R$ = 1.99 min (97%). ee = 98%. |
| 39 | Enantiomer A | 3-methoxy-5,5-dimethyl-6-oxo-3-(thiazol-2-yl)cyclohex-1-enecarbonitrile (Enantiomer A) | $^1$H NMR (300 MHz, DMSO-d$_6$) δ ppm 0.85 (s, 3H), 1.22 (s, 3H), 2.44-2.52 (m, 2H), 3.19 (s, 3H), 7.85 (d, J = 3.2 Hz, 1H), 7.95 (d, J = 3.2 Hz, 1H), 8.47 (d, J = 1.0 Hz, 1H). m/z (ES$^+$), [M + H]$^+$ = 263; HPLC (C05) t$_R$ = 1.92 min (96%). ee = 98%. |
| 40 | 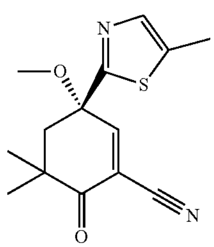 | (S)-3-methoxy-5,5-dimethyl-3-(5-methylthiazol-2-yl)-6-oxocyclohex-1-enecarbonitrile | $^1$H NMR (300 MHz, DMSO-d$_6$) δ ppm 0.86 (s, 3H), 1.21 (s, 3H), 2.41-2.45 (m, 2H), 2.48 (s, 3H), 3.18 (s, 3H), 7.52 (q, J = 1.1 Hz, 1H), 8.42 (d, J = 1.0 Hz, 1H). m/z (ES$^+$), [M + H]$^+$ = 277; HPLC (C05) t$_R$ = 2.11 min (95%). ee = 99%. |
| 41 | Enantiomer A | 3-methoxy-5,5-dimethyl-6-oxo-3-(3-(trifluoromethoxy)pyridin-2-yl)cyclohex-1-enecarbonitrile (Enantiomer A) | $^1$H NMR (400 MHz, DMSO-d$_6$) δ ppm 0.68 (s, 3H), 1.19 (s, 3H), 2.51 (d, J = 3.9 Hz, 2H), 3.16 (s, 3H), 7.66 (dd, J = 8.5, 4.6 Hz, 1H), 8.00 (dp, J = 8.5, 1.7 Hz, 1H), 8.57-8.64 (m, 2H). m/z (ES$^+$), [M + H]$^+$ = 341; HPLC (C05) t$_R$ = 2.04 min (99%). ee = 97%. |
| 43 | Enantiomer A | 3-methoxy-5,5-dimethyl-3-(4-methylthiazol-5-yl)-6-oxocyclohex-1-enecarbonitrile (Enantiomer A) | $^1$H NMR (300 MHz, DMSO-d$_6$) δ ppm 0.94 (s, 3H), 1.21 (s, 3H), 2.33-2.40 (m, 2H), 2.42 (s, 3H), 3.15 (s, 3H), 8.43 (d, J = 0.8 Hz, 1H), 8.99 (s, 1H). m/z (ES$^+$), [M + H]$^+$ = 277; HPLC (C05) t$_R$ = 1.89 min (95%). ee = 98%. |

TABLE 2-continued

Compounds 26-41 and 43-48

| Cmpd # | Structure | Name | Analytical data |
|---|---|---|---|
| 44 | (Enantiomer A) | 3-(3,5-difluoropyridin-2-yl)-3-methoxy-5,5-dimethyl-6-oxocyclohex-1-enecarbonitrile (Enantiomer A) | 1H NMR (400 MHz, DMSO-$d_6$) δ ppm 0.71 (s, 3H), 1.19 (s, 3H), 2.48 (br. s, 2H), 3.15 (s, 3H), 8.13 (ddd, J = 11.3, 8.9, 2.4 Hz, 1H), 8.58 (d, J = 2.4 Hz, 2H). m/z (ES$^+$), [M + H]$^+$ = 293; HPLC (C05) $t_R$ = 1.59 min; ee = 98%. |
| 45 | (Enantiomer A) | 3-(5-chloro-3-(difluoromethyl)pyridin-2-yl)-3-methoxy-5,5-dimethyl-6-oxocyclohex-1-enecarbonitrile (Enantiomer A) | $^1$H NMR (400 MHz, DMSO-$d_6$) δ ppm 0.91 (s, 3H), 1.28 (s, 3H), 2.16 (d, J = 14.6 Hz, 1H), 2.55 (dd, J = 14.5, 1.7 Hz, 1H), 3.22 (s, 3H), 7.62 (t, J = 53.8 Hz, 1H), 8.41 (d, J = 2.4 Hz, 1H), 8.50 (d, J = 1.4 Hz, 1H), 8.87 (d, J = 2.2 Hz, 1H). m/z (ES$^+$), [M + H]$^+$ = 341; HPLC (C05) $t_R$ = 1.99 min (99.7%). ee = 95.5% |
| 46 | 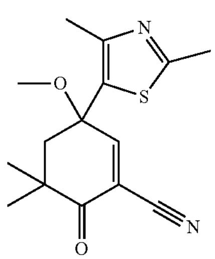 | 3-(2,4-dimethylthiazol-5-yl)-3-methoxy-5,5-dimethyl-6-oxocyclohex-1-enecarbonitrile | $^1$H NMR (400 MHz, DMSO-$d_6$) δ ppm 0.96 (s, 3H), 1.21 (s, 3H), 2.31 (d, J = 14.4 Hz, 1H), 2.34 (s, 3H), 2.39 (d, J = 14.4 Hz, 1H), 2.58 (s, 3H), 3.17 (s, 3H), 8.42 (s, 1H); m/z (ES$^+$), [M + H]$^+$ = 291; HPLC (C05) $t_R$ = 3.60 min (97%). |
| 47 | (Enantiomer A) | 3-(3-(difluoromethoxy)-5-fluoropyridin-2-yl)-3-methoxy-5,5-dimethyl-6-oxocyclohex-1-enecarbonitrile (Enantiomer A) | $^1$H NMR (400 MHz, DMSO-$d_6$) δ ppm 0.66 (s, 3H), 1.16 (s, 3H), 2.44 (d, J = 14.3 Hz, 1H), 2.59 (dd, J = 14.4, 1.5 Hz, 1H), 3.12 (s, 3H), 7.45 (t, J = 72.6 Hz, 1H), 7.94 (dd, J = 9.8, 2.4 Hz, 1H), 8.55 (d, J = 2.5 Hz, 2H). m/z (ES$^+$), [M + H]$^+$ = 341; HPLC (C05) $t_R$ = 1.61 min (99%). ee = 98%. |

TABLE 2-continued

Compounds 26-41 and 43-48

| Cmpd # | Structure | Name | Analytical data |
|---|---|---|---|
| 48 | 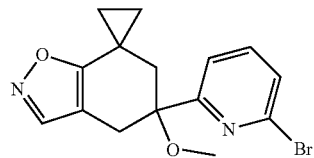<br>Enantiomer A | 3-(3-bromo-5-fluoropyridin-2-yl)-3-methoxy-5,5-dimethyl-6-oxocyclohex-1-enecarbonitrile (Enantiomer A) | $^1$H NMR (400 MHz, DMSO-$d_6$) δ ppm 0.73 (s, 3H), 1.20 (s, 3H), 2.53-2.66 (m, 2H), 3.16 (s, 3H), 8.39 (dd, J = 8.3, 2.5 Hz, 1H), 8.58 (s, 1H), 8.71 (d, J = 2.5 Hz, 1H). m/z (ES$^+$), [M + H]$^+$ = 353; HPLC (C05) $t_R$ = 1.73 min (99.3%). ee = 99.7%. |

Compound 49: 7-methoxy-7-(6-(1-methyl-1H-pyrazol-4-yl)pyridin-2-yl)-4-oxospiro[2.5]oct-5-ene-5-carbonitrile (Enantiomer A)

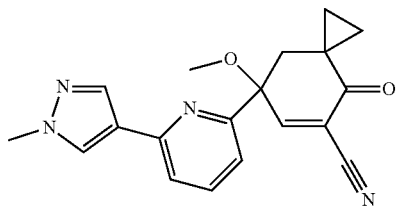

Enantiomer A

Compound 49, Step 1: 5-(6-bromopyridin-2-yl)-5,6-dihydro-4H-spiro[benzo[d]isoxazole-7,1'-cyclopropan]-5-ol

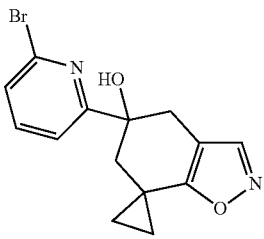 [SMILES: OC1(c2cccc(Br)n2)Cc2cnoc2C2(CC2)C1]

n-Butyllithium, 2.5 M solution in hexanes (4.90 mL, 12.3 mmol) was added dropwise to 2,6-dibromopyridine (2.90 g, 12.3 mmol) in DCM (40 mL) at −78° C. under nitrogen. 4H-spiro[benzo[d]isoxazole-7,1'-cyclopropan]-5(6H)-one (1 g, 6.13 mmol) in DCM (8 mL) was added dropwise after the reaction had been stirred for 30 min. The resulting mixture was stirred at −78° C. for 1.5 h under N$_2$, quenched with sat. aq. NaHCO$_3$ (70 mL) and extracted with DCM (3×60 mL). The organic layers were combined and washed with brine (1×75 mL). The organic layer was dried over Na$_2$SO$_4$, filtered and evaporated to afford the crude product, which was purified by silica gel chromatography (0 to 25% EtOAc in petroleum ether). Pure fractions were evaporated to dryness to afford 5-(6-bromopyridin-2-yl)-5,6-dihydro-4H-spiro[benzo[d]isoxazole-7,1'-cyclopropan]-5-ol (1.45 g, 74%) as a yellow solid. $^1$H NMR (300 MHz, CDCl$_3$) δ ppm 0.70-0.78 (m, 1H), 0.99-1.07 (m, 1H), 1.34-1.40 (m, 2H), 1.74 (dd, J=13.7, 1.5 Hz, 1H), 2.62 (d, J=13.6 Hz, 1H), 2.82 (dd, J=16.0, 1.5 Hz, 1H), 3.22 (d, J=16.0 Hz, 1H), 7.45 (ddd, J=7.7, 5.8, 0.9 Hz, 2H), 7.59 (t, J=7.7 Hz, 1H), 8.11 (s, 1H); m/z (ES+), [M+H]$^+$=321; HPLC (C05) $t_R$=1.304 min (97%).

Compound 49, Step 2: 5-(6-bromopyridin-2-yl)-5-methoxy-5,6-dihydro-4H-spiro[benzo[d]isoxazole-7,1'-cyclopropane]

HMPA (1.14 mL, 6.54 mmol) in THF (5 mL) and 1M NaHMDS (3.27 mL, 3.27 mmol) were added to 5-(6-bromopyridin-2-yl)-5,6-dihydro-4H-spiro[benzo[d]isoxazole-7,1'-cyclopropan]-5-ol (1.05 g, 3.27 mmol) in THF (10 mL) at −78° C. under nitrogen. Methyl trifluoromethanesulfonate (1.07 g, 6.54 mmol) in THF (5 mL) was added after the reaction had been stirred for 5 min at −78° C. The resulting mixture was stirred at −78° C. for 5 min and warmed up to r.t. for 15 min. The mixture was diluted with water (10 mL), sat. aq. NH$_4$Cl (30 mL), and EtOAc (40 mL), and the aq. phase was extracted with EtOAc (2×40 mL). The combined organic phases were washed with brine (50 mL), dried (Na$_2$SO$_4$), filtered and evaporated to afford the crude product, which was purified by silica gel chromatography (0 to 20% EtOAc in petroleum ether). Pure fractions were evaporated to dryness to afford 5-(6-bromopyridin-2-yl)-5-methoxy-5,6-dihydro-4H-spiro[benzo[d]isoxazole-7,1'-cyclopropane] (0.500 g, 45.6%) as a pale yellow solid. $^1$H NMR (400 MHz, CDCl$_3$) δ ppm 0.83 (ddd, J=10.3, 6.3, 4.1 Hz, 1H), 0.98 (ddd, J=9.5, 6.1, 4.0 Hz, 1H), 1.32 (ddd, J=9.9, 6.1, 4.1 Hz, 1H), 1.39 (ddd, J=10.1, 6.1, 3.9 Hz, 1H), 1.94 (dd, J=14.2, 1.9 Hz, 1H), 2.72 (d, J=14.3 Hz, 1H), 2.93 (dd, J=16.1, 1.9 Hz, 1H), 3.13 (s, 3H), 3.29 (d, J=16.1 Hz, 1H), 7.43 (dd, J=7.6, 1.1 Hz, 1H), 7.55 (dd, J=7.7, 1.0 Hz, 1H), 7.61 (t, J=7.7 Hz, 1H), 8.09 (s, 1H); m/z (ES+), [M+H]⁺=335; HPLC (C05) t_R=1.40 min (97%).

Compound 49, Step 3: 5-methoxy-5-(6-(1-methyl-1H-pyrazol-4-yl)pyridin-2-yl)-5,6-dihydro-4H-spiro[benzo[d]isoxazole-7,1'-cyclopropane]

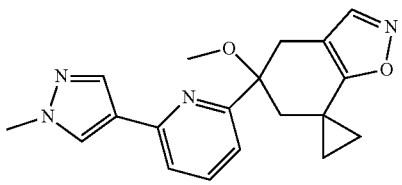 [SMILES: COC1(c2cccc(-c3cnn(C)c3)n2)Cc2cnoc2C2(CC2)C1]

2nd Generation XPhos pre-catalyst (73.9 mg, 0.09 mmol) was added to a mixture of Cs₂CO₃ (612 mg, 1.88 mmol), 5-(6-bromopyridin-2-yl)-5-methoxy-5,6-dihydro-4H-spiro[benzo[d]isoxazole-7,1'-cyclopropane] (210 mg, 0.63 mmol) and 1-methyl-4-(4,4,5,5-tetramethyl-1,3,2-dioxaborolan-2-yl)-1H-pyrazole (391 mg, 1.88 mmol) in 1,4-dioxane (10 mL) and water (2 mL). The resulting mixture was stirred at 80° C. for 2 h under N₂. The mixture was concentrated under reduced pressure, poured into water (30 mL), extracted with EtOAc (3×40 mL), the organic layer was dried over Na₂SO₄, filtered and evaporated to afford the crude product, which was purified by silica gel chromatography (0 to 45% EtOAc in petroleum ether). Pure fractions were evaporated to dryness to afford 5-methoxy-5-(6-(1-methyl-1H-pyrazol-2-yl)pyridin-2-yl)-5,6-dihydro-4H-spiro[benzo[d]isoxazole-7,1'-cyclopropane] (145 mg, 69%) as a yellow foam. ¹H NMR (400 MHz, CDCl₃) δ ppm 0.71 (ddd, J=9.4, 6.8, 4.5 Hz, 1H), 0.97 (ddd, J=9.5, 6.7, 4.5 Hz, 1H), 1.22 (ddd, J=9.8, 6.7, 4.5 Hz, 1H), 1.38 (ddd, J=11.1, 6.8, 4.5 Hz, 1H), 2.10 (dd, J=14.1, 1.5 Hz, 1H), 2.66 (d, J=14.1 Hz, 1H), 2.95 (dd, J=16.0, 1.5 Hz, 1H), 3.17 (s, 3H), 3.45 (d, J=15.9 Hz, 1H), 3.97 (s, 3H), 7.39 (ddd, J=7.7, 4.8, 0.9 Hz, 2H), 7.72 (t, J=7.8 Hz, 1H), 7.89 (s, 1H), 7.93 (s, 1H), 8.13 (s, 1H); m/z (ES⁺), [M+H]⁺=337; HPLC (C05) t_R=0.85 min (82%).

Compound 49, Step 4: 7-methoxy-7-(6-(1-methyl-1H-pyrazol-4-yl)pyridin-2-yl)-4-oxospiro[2.5]octane-5-carbonitrile

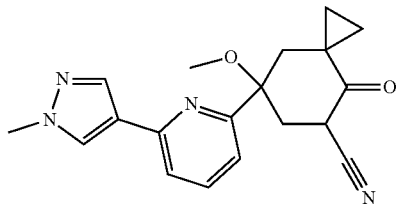 [SMILES: COC1(c2cccc(-c3cnn(C)c3)n2)CC(C#N)C(=O)C2(CC2)C1]

Sodium methylate in methanol (0.40 mL, 2.16 mmol) was added dropwise to 5-methoxy-5-(3-(1-methyl-1H-pyrazol-4-yl)pyridin-2-yl)-5,6-dihydro-4H-spiro[benzo[d]isoxazole-7,1'-cyclopropane] (145 mg, 0.43 mmol) in Et₂O (4 mL) at 0° C. The mixture was stirred at 0° C. for 2 h, quenched with sat. aq. NH₄Cl (25 mL), extracted with EtOAc (3×25 mL) and the organic layer was dried over Na₂SO₄, filtered and evaporated to afford the crude product, which was purified by silica gel chromatography (0 to 50% EtOAc in petroleum ether). Pure fractions were evaporated to dryness to afford 7-methoxy-7-(3-(1-methyl-1H-pyrazol-4-yl)pyridin-2-yl)-4-oxospiro[2.5]octane-5-carbonitrile (115 mg, 79%) as a pale yellow foam. ¹H NMR (400 MHz, CDCl₃) δ ppm 0.57 (ddd, J=8.8, 7.1, 4.0 Hz, 1H), 1.01 (ddd, J=8.8, 7.1, 4.0 Hz, 1H), 1.18 (ddd, J=10.4, 7.2, 3.8 Hz, 1H), 1.63 (ddd, J=10.0, 7.2, 4.1 Hz, 1H), 2.02 (d, J=14.7 Hz, 1H), 2.62 (d, J=14.7 Hz, 1H), 2.88 (ddd, J=14.1, 6.4, 2.8 Hz, 1H), 3.03 (dd, J=14.1, 12.7 Hz, 1H), 3.20 (d, J=11.7 Hz, 3H), 4.02 (d, J=0.9 Hz, 3H), 4.05 (dd, J=12.6, 6.4 Hz, 1H), 7.36 (ddd, J=8.9, 7.8, 0.9 Hz, 1H), 7.43 (ddd, J=14.5, 7.8, 0.9 Hz, 1H), 7.71-7.79 (m, 1H), 7.94-7.97 (m, 1H), 8.01 (s, 1H); m/z (ES⁺), [M+H]⁺=337; HPLC (C05) t_R=0.558 min (93%).

Compound 49, Step 5: 7-methoxy-7-(6-(1-methyl-1H-pyrazol-4-yl)pyridin-2-yl)-4-oxospiro[2.5]oct-5-ene-5-carbonitrile

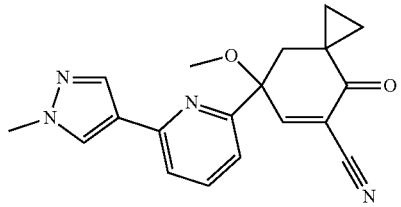 [SMILES: COC1(c2cccc(-c3cnn(C)c3)n2)C=C(C#N)C(=O)C2(CC2)C1]

Pyridine (0.055 mL, 0.68 mmol) in DCM (1 mL) was added dropwise to phenylselenyl chloride (131 mg, 0.68 mmol) in DCM (1.5 mL) at 0° C. 7-methoxy-7-(6-(1-methyl-1H-pyrazol-4-yl)pyridin-2-yl)-4-oxospiro[2.5]octane-5-carbonitrile (115 mg, 0.34 mmol) in DCM (2 mL) was added dropwise after the reaction had been stirred for 20 min and the resulting mixture was stirred at 0° C. for 2 h. 1 aq. HCl (1.5 mL) and water (4 mL) were added, and the phases were separated. H₂O₂ (0.698 mL, 6.84 mmol) was added dropwise to the DCM layer at 0° C., and the mixture was vigorously stirred at 0° C. for 40 min. Water (20 mL) was added and the mixture was extracted with DCM (3×20 mL). The combined organic phases were washed with brine (2×20 mL), dried (MgSO₄), filtered, and concentrated under reduced pressure. The crude product was purified by preparative HPLC using standard conditions. Fractions containing the desired compound were evaporated to dryness to afford 7-methoxy-7-(6-(1-methyl-1H-pyrazol-4-yl)pyridin-2-yl)-4-oxospiro[2.5]oct-5-ene-5-carbonitrile (36 mg, 32%) as a white solid. ¹H NMR (400 MHz, CDCl₃) δ 0.46 ppm (ddd, J=9.2, 7.3, 4.0 Hz, 1H), 0.94 (ddd, J=9.1, 7.3, 4.0 Hz, 1H), 1.25 (ddd, J=9.9, 7.3, 4.0 Hz, 1H), 1.51 (ddd, J=9.9, 7.3, 4.0 Hz, 1H), 2.29 (d, J=13.9 Hz, 1H), 2.41 (d, J=13.9 Hz, 1H), 3.34 (s, 3H), 4.00 (s, 3H), 7.34 (dd, J=7.8, 0.9 Hz, 1H), 7.44 (dd, J=7.8, 0.9 Hz, 1H), 7.76 (t, J=7.8 Hz, 1H), 7.87 (s, 1H), 7.92 (d, J=0.7 Hz, 1H), 8.14 (d, J=1.0 Hz, 1H). m/z (ES⁺), [M+H]⁺=335; HPLC (C05) t_R=1.73 min (98%).

Compound 49, Step 6: 7-methoxy-7-(6-(1-methyl-1H-pyrazol-4-yl)pyridin-2-yl)-4-oxospiro[2.5]oct-5-ene-5-carbonitrile (Enantiomer A)

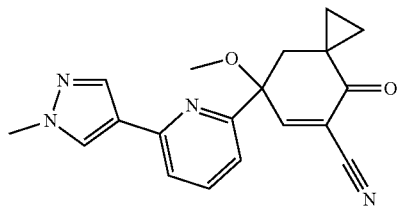

Enantiomer A

Enantiomers were separated using Generic Procedure B for chiral separation of enantiomers (starting from 27 mg racemate), yielding Isomer 1 (11 mg, ee=99.7%) and Isomer 2 (12 mg, ee=96.5%, Enantiomer A).

The compounds provided in Table 3 have been prepared by analogy to the synthesis described for Compound 49, starting from Compound A3 (addition, alkylation, Suzuki reaction, isoxazole opening, oxidation). All pure enantiomers in the following Table were separated as described in the Generic Procedure A for chiral separation of enantiomers (chiral HPLC). For compounds where the enantiomers were separated but for which absolute configuration was not assigned, data is given for the single enantiomer that was tested. For compounds drawn without specified stereochemistry and labeled as "Enantiomer A," all data provided throughout the application for that compound is for the more active enantiomer. For compounds drawn without specified stereochemistry and labeled as "Enantiomer B," all data provided throughout the application for that compound is for the less active enantiomer. For compounds drawn without specified stereochemistry and not labeled as "Enantiomer A" or "Enantiomer B," all data provided throughout the application for that compound is for the racemate.

TABLE 3

Compounds 50-53

| Cmpd # | Structure | Name | Analytical data |
|---|---|---|---|
| 50 | Enantiomer A | 7-methoxy-7-(6-(2-methylpyrimidin-5-yl)pyridin-2-yl)-4-oxospiro[2.5]oct-5-ene-5-carbonitrile (Enantiomer A) | $^1$H NMR (400 MHz, CDCl$_3$) δ ppm 0.52 (ddd, J = 9.2, 7.3, 4.0 Hz, 1H), 0.99 (ddd, J = 9.1, 7.3, 4.0 Hz, 1H), 1.30 (ddd, J = 10.0, 7.3, 4.0 Hz, 1H), 1.53 (ddd, J = 9.9, 7.3, 4.0 Hz, 1H), 2.36 (d, J = 14.0 Hz, 1H), 2.44 (d, J = 14.0 Hz, 1H), 2.85 (s, 3H), 3.34 (s, 3H), 7.61 (dd, J = 7.8, 0.7 Hz, 1H), 7.78 (dd, J = 7.8, 0.9 Hz, 1H), 7.96 (t, J = 7.8, 7.8 Hz, 1H), 8.13 (s, 1H), 9.22 (s, 2H); m/z (ES+), [M + H]$^+$ = 347; HPLC (C05) $t_R$ = 1.66 min (98.8%). ee = 99.6%. |
| 51 | Enantiomer A | 7-methoxy-4-oxo-7-(6-(pyrimidin-5-yl)pyridin-2-yl)spiro[2.5]oct-5-ene-5-carbonitrile (Enantiomer A) | $^1$H NMR (400 MHz, CDCl$_3$) δ ppm 0.54 (ddd, J = 9.2, 7.3, 3.9 Hz, 1H), 1.01 (ddd, J = 9.1, 7.3, 4.0 Hz, 1H), 1.33 (ddd, J = 9.9, 7.2, 3.9 Hz, 1H), 1.53 (ddd, J = 9.9, 7.2, 4.0 Hz, 1H), 2.35 (dd, J = 14.4, 0.9 Hz, 1H), 2.47 (d, J = 14.1 Hz, 1H), 3.35 (s, 3H), 7.65 (dd, J = 7.9, 0.9 Hz, 1H), 7.82 (dd, J = 7.8, 0.9 Hz, 1H), 7.99 (t, J = 7.8, 7.8 Hz, 1H), 8.15 (d, J = 1.0 Hz, 1H), 9.32 (s, 1H), 9.33 (s, 2H); m/z (ES$^+$), [M + H]$^+$ = 333; HPLC (C05) $t_R$ = 2.20 min (98.9%). ee = 98.9%. |
| 52 | Enantiomer A | 7-(6-(3,5-dimethylisoxazol-4-yl)pyridin-2-yl)-7-methoxy-4-oxospiro[2.5]oct-5-ene-5-carbonitrile (Enantiomer A) | $^1$H NMR (400 MHz, CDCl$_3$) δ ppm 0.45 (ddd, J = 9.1, 7.2, 4.0 Hz, 1H), 0.96 (ddd, J = 9.1, 7.2, 4.0 Hz, 1H), 1.22 (ddd, J = 10.2, 7.2, 3.9 Hz, 1H), 1.52 (ddd, J = 11.0, 7.2, 4.0 Hz, 1H), 2.33 (d, J = 14.1 Hz, 1H), 2.40 (d, J = 14.1 Hz, 1H), 2.45 (s, 3H), 2.60 (s, 3H), 3.33 (s, 3H), 7.38 (dd, J = 7.8, 0.9 Hz, 1H), 7.48 (dd, J = 7.9, 0.9 Hz, 1H), 7.88 (t, J = 7.8, 7.8 Hz, 1H), 8.12 (s, 1H) m/z (ES$^+$), [M + H]$^+$ = 350; HPLC (C05) $t_R$ = 1.32 min (97.7%). ee = 99%. |

TABLE 3-continued

Compounds 50-53

| Cmpd # | Structure | Name | Analytical data |
|---|---|---|---|
| 53 | 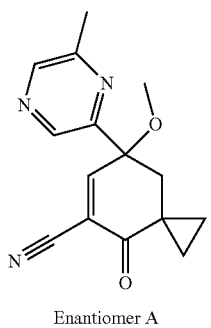 [SMILES: COC1(c2cncc(C)n2)C=C(C#N)C(=O)C2(CC2)C1]

Enantiomer A | 7-methoxy-7-(6-(1-methyl-1H-pyrazol-5-yl)pyridin-2-yl)-4-oxospiro[2.5]oct-5-ene-5-carbonitrile (Enantiomer A) | $^1$H NMR (400 MHz, CDCl$_3$) δ ppm 0.43 (ddd, J = 9.3, 7.3, 4.0 Hz, 1H), 0.95 (ddd, J = 9.2, 7.2, 4.1 Hz, 1H), 1.21 (ddd, J = 9.9, 7.2, 4.0 Hz, 1H), 1.54 (ddd, J = 10.0, 7.3, 4.1 Hz, 1H), 2.30 (d, J = 14.0 Hz, 1H), 2.46 (d, J = 14.0 Hz, 1H), 3.34 (s, 3H), 4.21 (s, 3H), 6.68 (d, J = 2.1 Hz, 1H), 7.52 (dd, J = 7.9, 0.9 Hz, 1H), 7.57 (d, J = 2.1 Hz, 1H), 7.64 (dd, J = 7.9, 0.9 Hz, 1H), 7.90 (t, J = 7.9, 7.9 Hz, 1H), 8.12 (d, J = 1.0 Hz, 1H) m/z (ES$^+$), [M + H]$^+$ = 335; HPLC (C05) t$_R$ = 1.20 min (97.6%). ee = 99% |

Compound 54: 7-methoxy-7-(6-methylpyrazin-2-yl)-4-oxospiro[2.5]oct-5-ene-5-carbonitrile (Enantiomer A)

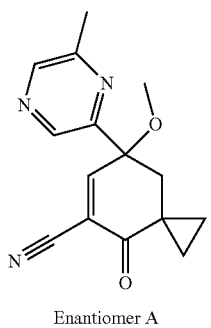 [SMILES: COC1(c2cncc(C)n2)C=C(C#N)C(=O)C2(CC2)C1]

Enantiomer A

Compound 54, Step 1: 3-hydroxy-5,5-dimethyl-6-oxo-3-[5-(trifluoromethyl)-2-pyridyl]cyclohexene-1-carbonitrile n-Butyllithium (2.5M solution in hexane, 2.57 mL, 6.43 mmol) was added dropwise to 2-bromo-6-methylpyrazine (1060 mg, 6.13 mmol) in DCM (6 mL) at −78° C. under nitrogen. 4H-spiro[benzo[d]isoxazole-7,1'-cyclopropan]-5(6H)-one (500 mg, 3.06 mmol) in DCM (1.5 mL) was added dropwise after the mixture had been stirred for 30 min. The mixture was stirred at −78° C. for 1.5 h under N$_2$, quenched with sat. aq. NaHCO$_3$ (20 mL) and extracted with DCM (3×20 mL). The combined organic layers were washed with brine (1×25 mL), dried over Na$_2$SO$_4$, filtered and evaporated. The crude product was purified by silica gel chromatography (45 to 50% EtOAc in petroleum ether). Pure fractions were evaporated to dryness to afford 5-(6-methylpyrazin-2-yl)-5,6-dihydro-4H-spiro[benzo[d]isoxazole-7,1'-cyclopropan]-5-ol (200 mg, 25.4%) as a yellow foam. $^1$H NMR (400 MHz, CDCl$_3$) δ ppm 0.58 (ddd, J=9.2, 7.3, 4.0 Hz, 1H), 1.01 (ddd, J=9.1, 7.3, 4.0 Hz, 1H), 1.35 (ddd, J=9.8, 7.3, 3.9 Hz, 1H), 1.76 (ddd, J=9.9, 7.3, 3.9 Hz, 1H), 2.58 (d, J=7.5 Hz, 1H), 2.61 (s, 3H), 2.63 (d, J=4.4 Hz, 1H), 2.85 (dd, J=16.0, 1.5 Hz, 1H), 3.22 (d, J=16.0 Hz, 1H), 4.14 (s, 1H), 8.13 (s, 1H), 8.45 (s, 1H), 8.61 (s, 1H). m/z (ES$^+$), [M+H]$^+$=258; HPLC (C05) t$_R$=0.663 min (92.3%).

Compound 54, Step 2: 5-methoxy-5-(6-methylpyrazin-2-yl)-5,6-dihydro-4H-spiro[benzo[d]isoxazole-7,1'-cyclopropane]

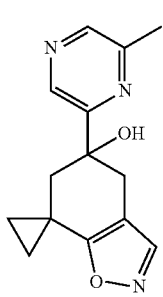 [SMILES: Cc1cncc(C2(O)Cc3cnoc3C3(CC3)C2)n1]

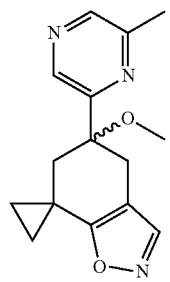

HMPA (0.27 mL, 1.55 mmol) and NaHMDS (0.777 mL, 0.78 mmol) were added to 5-(6-methylpyrazin-2-yl)-5,6-dihydro-4H-spiro[benzo[d]isoxazole-7,1'-cyclopropan]-5-ol (200 mg, 0.78 mmol) in THF (3 mL) at −78° C. under nitrogen. Methyl trifluoromethanesulfonate (255 mg, 1.55 mmol) was added after the mixture had been stirred for 5 min at −78° C. The mixture was stirred at −78° C. for 5 min, warmed to r.t. for 10 min, diluted with water (6 mL), sat. NH$_4$Cl (30 mL) and EtOAc (30 mL). The layers were separated and the aq. phase was extracted with EtOAc (2×30 mL). The combined organic phases were washed with brine (40 mL), dried (Na$_2$SO$_4$), filtered and evaporated to afford the crude product, which was purified by silica gel chromatography (25 to 30% EtOAc in petroleum ether). Pure fractions were evaporated to dryness to afford 5-methoxy-5-(6-methylpyrazin-2-yl)-5,6-dihydro-4H-spiro[benzo[d]isoxazole-7,1'-cyclopropane] (51 mg, 24%) as a yellow oil. $^1$H NMR (400 MHz, CDCl$_3$) δ ppm 0.77 (ddd, J=9.6, 6.8, 4.5 Hz, 1H), 0.99 (ddd, J=9.5, 6.6, 4.5 Hz, 1H), 1.26 (ddd, J=9.5, 6.6, 4.5 Hz, 1H), 1.40 (ddd, J=9.6, 6.8, 4.5 Hz, 1H), 2.06 (dd, J=14.1, 1.7 Hz, 1H), 2.57 (s, 3H), 2.62 (d, J=14.1 Hz, 1H), 2.97 (dd, J=16.0, 1.6 Hz, 1H), 3.16 (s, 3H), 3.34 (d, J=16.0 Hz, 1H), 8.11 (s, 1H), 8.39 (s, 1H), 8.65 (s, 1H). m/z (ES$^+$), [M+H]$^+$=272; HPLC (C05) t$_R$=0.721 min (93.3%).

Compound 54, Step 3: 5-methoxy-5-(6-methylpyrazin-2-yl)-5,6-dihydro-4H-spiro[benzo[d]isoxazole-7,1'-cyclopropane]

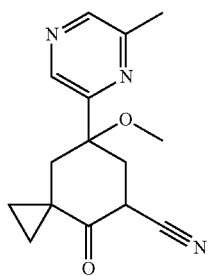 [SMILES: COC1(c2cncc(C)n2)CC(C#N)C(=O)C2(CC2)C1]

Sodium methoxide in methanol (0.175 mL, 0.94 mmo) was added to 5-methoxy-5-(6-methylpyrazin-2-yl)-5,6-dihydro-4H-spiro[benzo[d]isoxazole-7,1'-cyclopropane] (51 mg, 0.19 mmol) in Et$_2$O (1.5 mL) at 0° C. The resulting solution was stirred at 0° C. for 45 min, poured into sat. NH$_4$Cl (20 mL) and extracted with EtOAc (3×25 mL). The organic layer was dried over Na$_2$SO$_4$, filtered and evaporated to afford a yellow oil, which was purified by silica gel chromatography (35 to 45% EtOAc in petroleum ether) to afford 7-methoxy-7-(6-methylpyrazin-2-yl)-4-oxospiro[2.5]octane-5-carbonitrile (32 mg, 63%) as a yellow oil. $^1$H NMR (400 MHz, CDCl$_3$) δ ppm 0.70 (ddd, J=9.1, 7.2, 4.2 Hz, 1H), 1.01 (ddd, J=9.1, 7.2, 4.2 Hz, 1H), 1.19 (ddd, J=10.0, 7.2, 4.2 Hz, 1H), 1.74 (ddd, J=10.0, 7.2, 4.2 Hz, 1H), 2.59 (s, 3H), 2.59 (s, 1H), 2.73 (d, J=14.8 Hz, 1H), 2.84 (d, J=1.8 Hz, 1H), 2.87 (d, J=1.0 Hz, 1H), 3.20 (s, 1H), 3.23 (s, 3H), 8.44 (s, 1H), 8.64 (s, 1H). m/z (ES$^+$), [M+H]$^+$=272; HPLC (C05) t$_R$=1.175 min (95%).

Compound 54, Step 4: 7-methoxy-7-(6-methylpyrazin-2-yl)-4-oxospiro[2.5]oct-5-ene-5-carbonitrile (Enantiomer A)

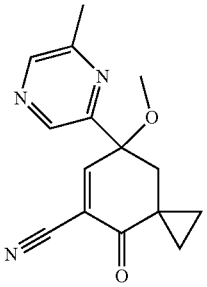

Enantiomer A

Pyridine (0.019 mL, 0.24 mmol) in DCM (0.25 mL) was added dropwise to phenylselenyl chloride (45.2 mg, 0.24 mmol) in DCM (0.5 mL) at 0° C. 7-Methoxy-7-(6-methylpyrazin-2-yl)-4-oxospiro[2.5]octane-5-carbonitrile (32 mg, 0.12 mmol) in DCM (0.25 mL) was added dropwise after the mixture had been stirred for 20 min. The mixture was stirred at 0° C. for 2 h, treated with 1M aq. HCl (0.6 mL) and water (1 mL), and the phases were separated. H$_2$O$_2$ (0.241 mL, 2.36 mmol) was added dropwise to the DCM layer at 0° C., and the mixture was vigorously stirred at 0° C. for 40 min. Water (20 mL) was added, and the mixture was extracted with DCM (3×20 mL). The combined organic phases were washed with brine (2×20 mL), dried (MgSO$_4$), filtered, and concentrated under reduced pressure. The crude product was purified by preparative HPLC under standard conditions to give 7-methoxy-7-(6-methylpyrazin-2-yl)-4-oxospiro[2.5]oct-5-ene-5-carbonitrile (23 mg, 72%), followed by chiral separation as described in the Generic Procedure A to afford the titled compound (8 mg) as a grey solid. $^1$H NMR (400 MHz, CDCl$_3$) δ ppm 0.58 (ddd, J=9.2, 7.3, 4.0 Hz, 1H), 1.01 (ddd, J=9.1, 7.3, 4.0 Hz, 1H), 1.35 (ddd, J=9.8, 7.3, 3.9 Hz, 1H), 1.54 (ddd, J=9.9, 7.3, 3.9 Hz, 1H), 2.38 (d, J=3.2 Hz, 2H), 2.59 (s, 3H), 3.33 (s, 3H), 8.02 (s, 1H), 8.48 (s, 1H), 8.65 (s, 1H). m/z (ES$^+$), [M+H]$^+$=270; HPLC (C05) t$_R$=1.24 min (95.0%). ee=97.0%.

The compounds provided in Table 4 have been prepared by analogy to the synthesis described for Compound 54, starting from Compound A3 (addition, alkylation, isoxazole opening, oxidation). All pure enantiomers in the following Table were separated as described in the Generic Procedure A for chiral separation of enantiomers (chiral HPLC). The absolute configuration of compound 55 was assigned based on the crystal structure of the compound bound to the BTB domain of Keap1. For compounds where the enantiomers were separated but for which absolute configuration was not assigned, data is given for the single enantiomer that was tested. For compounds drawn without specified stereochemistry and labeled as "Enantiomer A," all data provided throughout the application for that compound is for the more active enantiomer. For compounds drawn without specified stereochemistry and labeled as "Enantiomer B," all data provided throughout the application for that compound is for the less active enantiomer. For compounds drawn without specified stereochemistry and not labeled as "Enantiomer A" or "Enantiomer B," all data provided throughout the application for that compound is for the racemate.

TABLE 4

Compounds 55-57 and 59-65

| Cmpd # | Structure | Name | Analytical data |
|---|---|---|---|
| 55 | 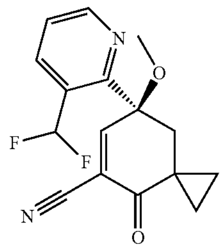 [SMILES: CO[C@]1(c2ncccc2C(F)F)C=C(C#N)C(=O)C2(CC2)C1] | (S)-7-[3-(difluoromethyl)pyridin-2-yl]-7-methoxy-4-oxospiro[2.5]oct-5-ene-5-carbonitrile | ¹H NMR (400 MHz, CDCl₃) δ ppm 0.47 (ddd, J = 9.2, 7.2, 4.0 Hz, 1H), 1.01 (ddd, J = 9.2, 7.2, 4.0 Hz, 1H), 1.34 (ddd, J = 9.9, 7.2, 4.0 Hz, 1H), 1.49 (ddd, J = 9.5, 7.1, 4.0 Hz, 1H), 2.32 (dd, J = 14.4, 1.3 Hz, 1H), 2.41 (d, J = 14.4 Hz, 1H), 1H), 3.34 (s, 3H), 7.32-7.62 (m, 2H), 8.17 (d, J = 1.1 Hz, 1H), 8.19 (d, J = 8.1 Hz, 1H), 8.64-8.71 (m, 1H). m/z (ES⁺), [M + H]⁺ = 305; HPLC (C05) $t_R$ = 1.91 min (99.8%). ee = 96.9%. |
| 56 | Enantiomer A | 7-methoxy-4-oxo-7-(pyridin-2-yl)spiro[2.5]oct-5-ene-5-carbonitrile (Enantiomer A) | ¹H NMR (400 MHz, DMSO-d₆) δ ppm 0.34 (ddd, J = 8.9, 7.2, 3.5 Hz, 1H), 0.74-0.92 (m, 2H), 1.29 (ddd, J = 9.5, 7.2, 3.5 Hz, 1H), 2.20 (d, J = 13.8 Hz, 1H), 2.59 (d, J = 13.8 Hz, 1H), 3.18 (s, 3H), 7.42 (ddd, J = 7.5, 4.8, 1.1 Hz, 1H), 7.61 (dt, J = 8.0, 1.0 Hz, 1H), 7.93 (td, J = 7.7, 1.8 Hz, 1H), 8.53-8.60 (m, 2H). m/z (ES⁺), [M + H]⁺ = 255; HPLC (C05) $t_R$ = 1.26 min (98%). ee = 99%. |
| 57 | Enantiomer A | 7-methoxy-4-oxo-7-[3-(trifluoromethyl)pyridin-2-yl]spiro[2.5]oct-5-ene-5-carbonitrile (Enantiomer A) | ¹H NMR (400 MHz, DMSO-d₆) δ ppm 0.47 (ddd, J = 8.9, 7.2, 3.6 Hz, 1H), 0.96 (ddd, J = 8.9, 7.1, 3.6 Hz, 1H), 1.06 (ddd, J = 9.6, 7.1, 3.6 Hz, 1H), 1.26 (ddd, J = 10.4, 7.2, 3.5 Hz, 1H), 2.31 (d, J = 14.5 Hz, 1H), 2.52 (d, J = 14.5 Hz, 1H), 3.27 (s, 3H), 7.69 (dd, J = 8.1, 4.7 Hz, 1H), 8.35 (dd, J = 8.1, 1.6 Hz, 1H), 8.45 (s, 1H), 8.85 (dd, J = 4.8, 1.5 Hz, 1H). m/z (ES⁺), [M + H]⁺ = 323; HPLC (C05) $t_R$ = 2.71 min (99.9%). ee = 100%. |
| 59 | Enantiomer A | 7-methoxy-4-7-(4-methyl-1,3-thiazol-2-yl)-4-oxospiro[2.5]oct-5-ene-5-carbonitrile (Enantiomer A) | ¹H NMR (300 MHz, DMSO-d₆) δ ppm 0.52-0.66 (m, 1H), 0.82-0.96 (m, 2H), 1.24-1.38 (m, 1H), 2.17 (d, J = 13.7 Hz, 1H), 2.35 (d, J = 1.0 Hz, 3H), 2.75 (d, J = 13.7 Hz, 1H), 3.27 (s, 3H), 7.44 (s, 1H), 8.44 (s, 1H). m/z (ES⁺), [M + H]⁺ = 275; HPLC (C05) $t_R$ = 1.89 min (96%). ee = 98%. |
| 60 | Enantiomer A | 7-(3,5-difluoropyridin-2-yl)-7-methoxy-4-oxospiro[2.5]oct-5-ene-5-carbonitrile (Enantiomer A) | ¹H NMR (400 MHz, DMSO-d₆) δ ppm 0.39 (ddd, J = 9.0, 7.0, 3.6 Hz, 1H), 0.67 (ddd, J = 10.2, 7.4, 3.6 Hz, 1H), 0.88 (ddd, J = 9.1, 7.1, 3.7 Hz, 1H), 1.32 (ddd, J = 9.8, 7.1, 3.7 Hz, 1H), 2.28 (d, J = 13.8 Hz, 1H), 2.76 (d, J = 13.9 Hz, 1H), 3.19 (s, 3H), 8.10 (ddd, J = 11.3, 8.9, 2.4 Hz, 1H), 8.54-8.60 (m, 2H). m/z (ES⁺), [M + H]⁺ = 291; HPLC (C05) $t_R$ = 1.79 min (98%). ee = 99%. |

TABLE 4-continued

Compounds 55-57 and 59-65

| Cmpd # | Structure | Name | Analytical data |
|---|---|---|---|
| 61 | Enantiomer A | 7-(5-chloro-3-fluoropyridin-2-yl)-7-methoxy-4-oxospiro[2.5]oct-5-ene-5-carbonitrile (Enantiomer A) | 1H NMR (400 MHz, DMSO-d$_6$) δ ppm 0.42 (ddd, J = 9.1, 7.2, 3.6 Hz, 1H), 0.70 (ddd, J = 10.2, 7.2, 3.5 Hz, 1H), 0.88 (ddd, J = 9.1, 7.2, 3.8 Hz, 1H), 1.32 (ddd, J = 10.7, 7.1, 3.7 Hz, 1H), 2.28 (d, J = 13.2 Hz, 1H), 2.75 (d, J = 13.9 Hz, 1H), 3.20 (s, 3H), 8.23 (dd, J = 11.0, 2.0 Hz, 1H), 8.56 (s, 1H), 8.58 (dd, J = 1.9, 0.9 Hz, 1H). m/z (ES$^+$), [M + H]$^+$ = 307; HPLC (C05) t$_R$ = 5.77 min (99.1%). ee = 100%. |
| 62 | Enantiomer A | 7-[3-(difluoromethoxy)-5-fluoropyridin-2-yl]-7-methoxy-4-oxospiro[2.5]oct-5-ene-5-carbonitrile (Enantiomer A) | $^1$H NMR (400 MHz, CDCl$_3$) δ ppm 0.68 (ddd, J = 9.2, 7.3, 3.8 Hz, 1H), 0.89 (ddd, J = 9.2, 7.3, 3.8 Hz, 1H), 1.07 (ddd, J = 10.3, 7.3, 3.8 Hz, 1H), 1.57 (ddd, J = 10.3, 7.3, 3.8 Hz, 1H), 2.57 (dd, J = 13.9, 1.6 Hz, 1H), 2.69 (d, J = 13.9 Hz, 1H), 3.23 (s, 3H), 6.60 (dd, J = 73.4, 71.3 Hz, 1H), 7.46 (dd, J = 8.7, 2.4 Hz, 1H), 8.15 (d, J = 1.5 Hz, 1H), 8.35 (dd, J = 2.5, 1.0 Hz, 1H). m/z (ES$^+$), [M + H]$^+$ = 339; HPLC (C05) t$_R$ = 1.85 min (97%). ee = 100%. |
| 63 | Enantiomer A | 7-[3-(difluoromethyl)-5-fluoropyridin-2-yl]-7-methoxy-4-oxospiro[2.5]oct-5-ene-5-carbonitrile (Enantiomer A) | $^1$H NMR (400 MHz, DMSO-d6) δ ppm 0.33 (ddd, J = 9.0, 7.1, 3.7 Hz, 1H), 0.94 (ddd, J = 10.6, 7.1, 3.6 Hz, 1H), 1.04 (ddd, J = 8.9, 7.1, 3.6 Hz, 1H), 1.25 (ddd, J = 9.7, 7.2, 3.6 Hz, 1H), 2.18 (d, J = 14.2 Hz, 1H), 2.66 (d, J = 14.2 Hz, 1H), 3.27 (s, 3H), 7.58 (td, J = 53.8, 1.6 Hz, 1H), 8.24 (dd, J = 9.1, 2.8 Hz, 1H), 8.50 (s, 1H), 8.80 (d, J = 2.7 Hz, 1H). m/z (ES$^+$), [M + H]$^+$ = 323; HPLC (C05) t$_R$ = 2.87 min (99.3%). ee = 99.5%. |
| 64 | 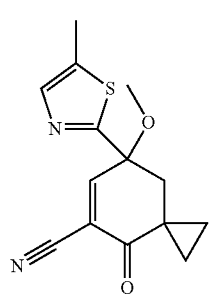 [SMILES: COC1(c2ncc(C)s2)C=C(C#N)C(=O)C2(CC2)C1] | 7-methoxy-7-(5-methyl-1,3-thiazol-2-yl)-4-oxospiro[2.5]oct-5-ene-5-carbonitrile | $^1$H NMR (400 MHz, DMSO-d$_6$) δ ppm 0.54-0.65 (m, 1H), 0.81-0.96 (m, 2H), 1.34 (ddd, J = 8.5, 7.2, 2.9 Hz, 1H), 2.06-2.17 (m, 1H), 2.48 (d, J = 1.2 Hz, 3H), 2.80 (d, J = 13.7 Hz, 1H), 3.28 (s, 3H), 7.51 (q, J = 1.3 Hz, 1H), 8.45 (d, J = 1.5 Hz, 1H). m/z (ES$^+$), [M + H]$^+$ = 275; HPLC (C05) t$_R$ = 1.46 min (98%). |

TABLE 4-continued

Compounds 55-57 and 59-65

| Cmpd # | Structure | Name | Analytical data |
|---|---|---|---|
| 65 | 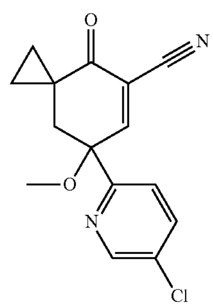 [SMILES: COC1(c2ccc(Cl)cn2)C=C(C#N)C(=O)C2(CC2)C1] | 7-(5-chloropyridin-2-yl)-7-methoxy-4-oxospiro[2.5]oct-5-ene-5-carbonitrile | $^1$H NMR (400 MHz, CDCl$_3$) δ ppm 0.54 (ddd, J = 9.2, 7.3, 4.0 Hz, 1H), 1.02-0.92 (m, 1H), 1.37-1.26 (m, 1H), 1.52 (ddd, J = 10.5, 7.2, 3.9 Hz, 1H), 2.33 (q, J =14.0 Hz, 2H), 3.28 (s, 3H), 7.51 (dd, J = 8.5, 0.8 Hz, 1H), 7.79 (dd, J = 8.4, 2.4 Hz, 1H), 8.02 (d, J = 0.9 Hz, 1H), 8.55 (d, J = 2.5 Hz, 1H). m/z (ES$^+$), [M + H]$^+$ = 289; HPLC (C05) t$_R$ = 2.25 min (99.3%). |

Compound 66: 9-methoxy-6-oxo-9-[3-(trifluoromethyl)pyridin-2-yl]spiro[4.5]dec-7-ene-7-carbonitrile (Enantiomer A)

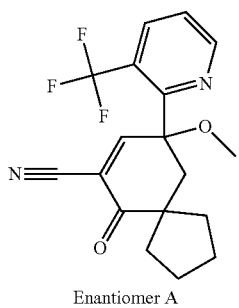 [SMILES: COC1(c2ncccc2C(F)(F)F)C=C(C#N)C(=O)C2(CCCC2)C1]

Enantiomer A

Compound 66, Step 1: 5-(3-(trifluoromethyl)pyridin-2-yl)-5,6-dihydro-4H-spiro[benzo[d]isoxazole-7,1'-cyclopentan]-5-ol

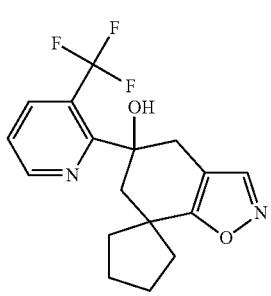 [SMILES: OC1(c2ncccc2C(F)(F)F)Cc2cnoc2C2(CCCC2)C1]

n-Butyllithium (2.20 mL, 5.49 mmol) was added dropwise to 2-bromo-3-(trifluoromethyl)pyridine (1182 mg, 5.23 mmol) in DCM (6 mL) at −78° C. under N$_2$. 4H-spiro[benzo[d]isoxazole-7,1'-cyclopentan]-5(6H)-one (500 mg, 2.61 mmol) in DCM (5 mL) was added dropwise to the mixture after it had been stirred for 30 min at −78° C. The resulting mixture was stirred at −78° C. for 1 h, quenched with sat. aq. NaHCO$_3$ (40 mL) and extracted with DCM (3×50 mL). The organic layers were combined and washed with sat. aq. NaCl (1×80 mL). The organic layer was dried over Na$_2$SO$_4$, filtered and evaporated to afford the crude product, which was purified by silica gel chromatography (0 to 12% EtOAc in petroleum ether) to afford 5-(3-(trifluoromethyl)pyridin-2-yl)-5,6-dihydro-4H-spiro[benzo[d]isoxazole-7,1'-cyclopentan]-5-ol (600 mg, 68%) as a yellow oil. $^1$H NMR (400 MHz, CDCl$_3$) δ ppm 1.43-1.55 (m, 1H), 1.66-1.84 (m, 2H), 1.83-2.04 (m, 2H), 2.00-2.19 (m, 4H), 2.34 (d, J=13.7 Hz, 1H), 2.74 (dd, J=15.9, 1.8 Hz, 1H), 3.08 (d, J=15.9 Hz, 1H), 7.42-7.55 (m, 2H), 8.10 (s, 1H), 8.43-8.49 (m, 1H). m/z (ES$^+$), [M+H]$^+$=339; HPLC (C05) t$_R$=1.50 min (87%).

Compound 66, Step 2: 5-methoxy-5-(3-(trifluoromethyl)pyridin-2-yl)-5,6-dihydro-4H-spiro[benzo[d]isoxazole-7,1'-cyclopentane]

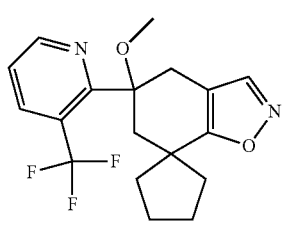 [SMILES: COC1(c2ncccc2C(F)(F)F)Cc2cnoc2C2(CCCC2)C1]

HMPA (0.617 mL, 3.55 mmol) in THF (5 mL) and NaHMDS (1.773 mL, 1.77 mmol) were added to 5-(3-(trifluoromethyl)pyridin-2-yl)-5,6-dihydro-4H-spiro[benzo[d]isoxazole-7,1'-cyclopentan]-5-ol (600 mg, 1.77 mmol) in THF (12 mL) at −78° C. under nitrogen. Methyl trifluoromethanesulfonate (582 mg, 3.55 mmol) was added after stirring for 5 min at −78° C. The mixture was stirred at −78° C. for 5 min and warmed up to r.t. for 15 min, diluted with water (10 mL), sat. aq. NH$_4$Cl (30 mL), and EtOAc (40 mL), and the aq. phase was extracted with EtOAc (2×40 mL). The combined organic phases were washed with brine (70 mL), dried (Na$_2$SO$_4$), filtered and evaporated to afford the crude product, which was purified by silica gel chromatography (elution gradient 0 to 8% EtOAc in petroleum ether). Pure fractions were evaporated to dryness to afford 5-methoxy-5-(3-(trifluoromethyl)pyridin-2-yl)-5,6-dihydro-4H-spiro[benzo[d]isoxazole-7,1'-cyclopentane] (190 mg, 30.4%) as a yellow oil. $^1$H NMR (300 MHz, CDCl$_3$) δ ppm 1.20-1.38 (m, 1H), 1.62-1.85 (m, 4H), 1.86-2.03 (m, 3H), 2.16-2.30 (m, 2H), 2.92 (dd, J=16.2, 1.5 Hz, 1H), 3.01 (s, 3H), 3.42 (d, J=16.2 Hz, 1H), 7.45 (td, J=8.6, 2.9 Hz, 1H), 7.60 (dd, J=8.8, 4.4 Hz, 1H), 8.11 (s, 1H), 8.41 (d, J=2.9 Hz, 1H). m/z (ES$^+$), [M+H]$^+$=353, HPLC (C05), $t_R$=1.45 min.

Compound 66, Step 3: 9-methoxy-6-oxo-9-(3-(trifluoromethyl)pyridin-2-yl)spiro[4.5]decane-7-carbonitrile

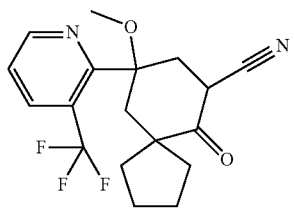 [SMILES: COC1(c2ncccc2C(F)(F)F)CC(C#N)C(=O)C2(CCCC2)C1]

Sodium methoxide in methanol (0.501 mL, 2.70 mmol) was added dropwise to 5-methoxy-5-(3-(trifluoromethyl)pyridin-2-yl)-5,6-dihydro-4H-spiro[benzo[d]isoxazole-7,1'-cyclopentane] (190 mg, 0.54 mmol) in Et$_2$O (7 mL) at 0° C. The mixture was stirred at 0° C. for 45 min, quenched with sat. aq. NH$_4$Cl (30 mL) and extracted with EtOAc (3×30 mL). The organic layer was dried over Na$_2$SO$_4$, filtered and evaporated to afford the crude product, which was purified by silica gel chromatography (0 to 13% EtOAc in petroleum ether). Pure fractions were evaporated to dryness to afford 9-methoxy-6-oxo-9-(3-(trifluoromethyl)pyridin-2-yl)spiro[4.5]decane-7-carbonitrile (170 mg, 89%) as a yellow oil. $^1$H NMR (300 MHz, CDCl$_3$) δ ppm 0.94 (dt, J=17.1, 6.0 Hz, 1H), 1.02-1.14 (m, 1H), 1.71 (dt, J=16.2, 7.6 Hz, 3H), 1.94 (d, J=14.5 Hz, 2H), 2.20 (dd, J=13.6, 7.1 Hz, 1H), 2.43 (dd, J=13.2, 5.3 Hz, 1H), 2.57 (dd, J=14.6, 4.1 Hz, 1H), 2.91 (dt, J=14.7, 4.2 Hz, 1H), 3.15 (d, J=1.1 Hz, 3H), 3.28 (t, J=14.5 Hz, 1H), 4.11-4.18 (m, 1H), 7.42 (dd, J=8.1, 4.6 Hz, 1H), 8.14 (d, J=8.4 Hz, 1H), 8.71 (d, J=4.7 Hz, 1H); m/z (ES$^+$), [M+H]$^+$=353; HPLC (C05) $t_R$=1.55 min (94%).

Compound 66, Step 4: 9-methoxy-6-oxo-9-[3-(trifluoromethyl)pyridin-2-yl]spiro[4.5]dec-7-ene-7-carbonitrile (Enantiomer A)

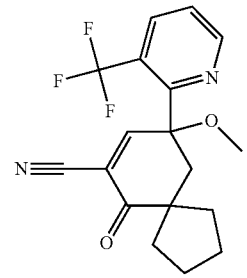

Enantiomer A

Pyridine (0.073 mL, 0.91 mmol) in DCM (2 mL) was added dropwise to phenylselenyl chloride (174 mg, 0.91 mmol) in DCM (4 mL) at 0° C. 9-Methoxy-6-oxo-9-(3-(trifluoromethyl)pyridin-2-yl)spiro[4.5]decane-7-carbonitrile (160 mg, 0.45 mmol) in DCM (8 mL) was added dropwise after stirring for 20 min. The mixture was stirred at 0° C. for 2 h, treated with 1M aq. HCl (3 mL) and water (5 mL), and the phases were separated. H$_2$O$_2$ (0.928 mL, 9.08 mmol) was added dropwise to the DCM layer at 0° C., and the mixture was vigorously stirred at 0° C. for 40 min. Water (20 mL) was added, and the mixture was extracted with DCM (3×20 mL). The combined organic phases were washed with brine (2×20 mL), dried (MgSO$_4$), filtered, and concentrated under reduced pressure. The crude product was purified by preparative HPLC under standard conditions to afford 9-methoxy-6-oxo-9-[3-(trifluoromethyl)pyridin-2-yl]spiro[4.5]dec-7-ene-7-carbonitrile (85 mg, 53.4%) as a pale yellow solid, followed by chiral separation as described in the Generic Procedure A to give the title compound (26 mg) and its enantiomer. $^1$H NMR (400 MHz, DMSO-d$_6$) δ ppm 1.02-1.11 (m, 1H), 1.47-1.68 (m, 4H), 1.84-2.02 (m, 3H), 2.24 (d, J=14.5 Hz, 1H), 2.56 (d, J=1.8 Hz, 1H), 3.21 (s, 3H), 7.69 (dd, J=8.1, 4.7 Hz, 1H), 8.36 (dd, J=8.1, 1.5 Hz, 1H), 8.48 (s, 1H), 8.87 (dd, J=4.8, 1.5 Hz, 1H). m/z (ES$^+$), [M+H]$^+$=351; HPLC (C05) $t_R$=2.41 min (98%). ee=100%.

The compounds provided in Table 5 have been prepared by analogy to the synthesis described for Compound 66, starting from Compound A4 (addition, alkylation, isoxazole opening, oxidation). All pure enantiomers in the following Table were separated as described in the Generic Procedure A for chiral separation of enantiomers (chiral HPLC). For compounds where the enantiomers were separated but for which absolute configuration was not assigned, data is given for the single enantiomer that was tested. For compounds drawn without specified stereochemistry and labeled as "Enantiomer A," all data provided throughout the application for that compound is for the more active enantiomer. For compounds drawn without specified stereochemistry and labeled as "Enantiomer B," all data provided throughout the application for that compound is for the less active enantiomer. For compounds drawn without specified stereochemistry and not labeled as "Enantiomer A" or "Enantiomer B," all data provided throughout the application for that compound is for the racemate.

TABLE 5

Compounds 67-68

| Cmpd # | Structure | Name | Analytical data |
|---|---|---|---|
| 67 | Enantiomer A | 9-(5-fluoropyridin-2-yl)-9-methoxy-6-oxospiro[4.5]dec-7-ene-7-carbonitrile (Enantiomer A) | $^1$H NMR (300 MHz, DMSO-d$_6$) δ ppm 0.80-0.93 (m, 1H), 1.38-1.65 (m, 5H), 1.65-1.78 (m, 1H), 1.92-2.05 (m, 1H), 2.30-2.46 (m, 2H), 3.12 (s, 3H), 7.67-7.78 (m, 1H), 7.88 (td, J = 8.8, 2.9 Hz, 1H), 8.50 (d, J = 0.9 Hz, 1H), 8.59 (d, J = 2.9 Hz, 1H). m/z (ES$^+$), [M + H]$^+$ = 301; HPLC (C05) t$_R$ = 2.14 min (98%). ee = 99%. |
| 68 | Enantiomer A | 9-(5-fluoro-3-methylpyridin-2-yl)-9-methoxy-6-oxospiro[4.5]dec-7-ene-7-carbonitrile (Enantiomer A) | $^1$H NMR (400 MHz, DMSO-d$_6$) δ ppm 0.68-0.81 (m, 1H), 1.38-1.52 (m, 3H), 1.52-1.69 (m, 3H), 1.96-2.11 (m, 1H), 2.40 (d, J = 14.2 Hz, 1H), 2.54 (d, J = 14.2 Hz, 1H), 2.55 (s, 3H), 3.15 (s, 3H), 7.70-7.78 (m, 1H), 8.43 (d, J = 2.8 Hz, 1H), 8.52 (s, 1H). m/z (ES$^+$), [M + H]$^+$ = 315; HPLC (C05) t$_R$ = 2.13 min (99%). ee = 100%. |

Compound 69: 3-[5-fluoro-3-(1-methyl-1H-pyrazol-4-yl)pyridin-2-yl]-3-methoxy-5,5-dimethyl-6-oxocyclohex-1-ene-1-carbonitrile (Enantiomer A)

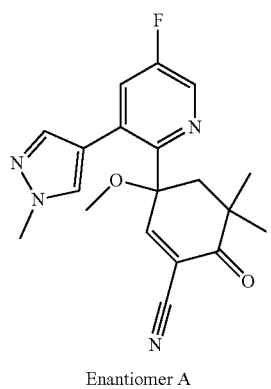 [SMILES: COC1(c2ncc(F)cc2-c2cnn(C)c2)C=C(C#N)C(=O)C(C)(C)C1]

Enantiomer A

Compound 69, Step 1: 5-(3-bromo-5-fluoropyridin-2-yl)-7,7-dimethyl-4,5,6,7-tetrahydrobenzo[d]isoxazol-5-ol

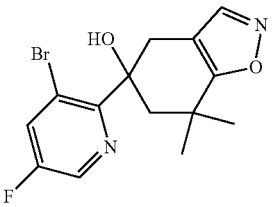 [SMILES: CC1(C)CC(O)(c2ncc(F)cc2Br)Cc2cnoc21]

n-Butyllithium (4.84 mL, 12.11 mmol) was added dropwise to 2,3-dibromo-5-fluoropyridine (2.78 g, 10.9 mmol) in DCM (20 mL) at −78° C. under N$_2$. 7,7-dimethyl-6,7-dihydrobenzo[d]isoxazol-5(4H)-one (1.00 g, 6.05 mmol) in DCM (10 mL) was added dropwise to the mixture after stirring for 10 min at −78° C. The mixture was stirred at −78° C. for 1 h, quenched with sat. aq. NH$_4$Cl (15 mL) and extracted with DCM (2×75 mL). The organic layers were combined and dried over Na$_2$SO$_4$, filtered and evaporated to afford the crude product, which was purified by silica gel chromatography (0 to 20% EtOAc in petroleum ether) to afford 5-(3-bromo-5-fluoropyridin-2-yl)-7,7-dimethyl-4,5,6,7-tetrahydrobenzo[d]isoxazol-5-ol (1.05 g, 51%) as a yellow oil which solidified on standing. $^1$H NMR (400 MHz, DMSO-d$_6$) δ 1.07 (s, 3H), 1.44 (s, 3H), 2.26-2.42 (m, 2H), 2.82 (d, J=15.7 Hz, 1H), 3.37 (d, J=5.9 Hz, 1H), 5.48 (s, 1H), 8.23 (dd, J=8.4, 2.6 Hz, 1H), 8.41 (s, 1H), 8.55 (d, J=2.6 Hz, 1H). m/z (ES$^+$), [M+H]$^+$=341/343; HPLC (C05) t$_R$=1.179 min.

Compound 69, Step 2: 5-(3-bromo-5-fluoropyridin-2-yl)-5-methoxy-7,7-dimethyl-4,5,6,7-tetrahydrobenzo[d]isoxazole

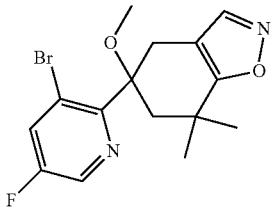 [SMILES: COC1(c2ncc(F)cc2Br)Cc2cnoc2C(C)(C)C1]

HMPA (1.07 mL, 6.16 mmol) in THF (3 mL) and NaHMDS (4.00 mL, 4.00 mmol) were added to 5-(3-bromo-5-fluoropyridin-2-yl)-7,7-dimethyl-4,5,6,7-tetrahydrobenzo[d]isoxazol-5-ol (1.05 g, 3.08 mmol) in THF (15.00 mL) at −78° C. under nitrogen. Methyl trifluoromethanesulfonate (1.010 g, 6.16 mmol) was added dropwise after stirring for 5 min at −78° C. The mixture was stirred at −78° C. for 5 min, warmed up to r.t. for 20 min, quenched with sat. aq. NH$_4$Cl (15 mL) and extracted with EtOAc (2×50 mL). The organic layer was dried over Na$_2$SO$_4$, filtered and evaporated to afford a yellow residue. The crude product was purified by silica gel chromatography (0 to 20% EtOAc in petroleum ether) to afford 5-(3-bromo-5-fluoropyridin-2-yl)-5-methoxy-7,7-dimethyl-4,5,6,7-tetrahydrobenzo[d]isoxazole (0.59 g, 54%) as a yellow oil. $^1$H NMR (DMSO-d$_6$, 400 MHz) δ 1.02 (s, 3H), 1.40 (s, 3H), 2.30 (d, J=14.3 Hz, 1H), 2.56 (d, J=1.7 Hz, 1H), 2.88 (s, 3H), 3.08 (dd, J=15.9, 1.6 Hz, 1H), 3.30 (dd, J=15.9, 1.6 Hz, 1H), 8.28 (dd, J=8.4, 2.6 Hz, 1H), 8.43 (s, 1H), 8.61 (dd, J=2.6, 0.7 Hz, 1H). m/z (ES$^+$), [M+H]$^+$=356; HPLC (C05) t$_R$=1.50 min.

Compound 69, Step 3: 5-(3-bromo-5-fluoropyridin-2-yl)-5-methoxy-3,3-dimethyl-2-oxocyclohexane-1-carbonitrile

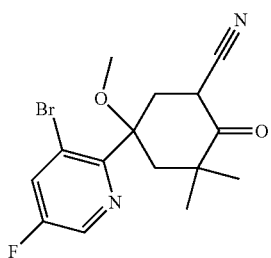 [SMILES: COC1(c2ncc(F)cc2Br)CC(C#N)C(=O)C(C)(C)C1]

Sodium methoxide in methanol (1.54 mL, 8.31 mmol) was added dropwise to 5-(3-bromo-5-fluoropyridin-2-yl)-5-methoxy-7,7-dimethyl-4,5,6,7-tetrahydrobenzo[d]isoxazole (590 mg, 1.66 mmol) in Et$_2$O (15 mL) at 0° C. The mixture was stirred at 0° C. for 45 min, quenched with sat. aq. NH$_4$Cl (25 mL) and extracted with EtOAc (3×25 mL). The organic layer was dried over Na$_2$SO$_4$, filtered and evaporated to afford 5-(3-bromo-5-fluoropyridin-2-yl)-5-methoxy-3,3-dimethyl-2-oxocyclohexane-1-carbonitrile (580 mg, 98%) as a yellow oil. $^1$H NMR (400 MHz, DMSO-d$_6$) δ 0.82 (s, 3H), 1.24 (s, 3H), 2.11-2.44 (m, 2H), 2.62-2.75 (m, 2H), 2.87 (s, 3H), 3.15-3.20 (m, 1H), 8.71 (s, 1H), 9.91 (s, 1H). m/z (ES$^+$), [M+H]$^+$=355; HPLC (C05) t$_R$=0.685 min.

Compound 69, Step 4: 3-(3-bromo-5-fluoropyridin-2-yl)-3-methoxy-5,5-dimethyl-6-oxocyclohex-1-ene-1-carbonitrile

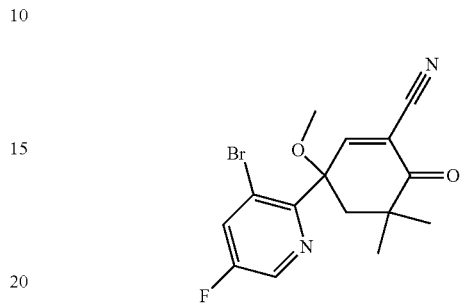

Pyridine (0.273 mL, 3.38 mmol) in DCM (2 mL) was added dropwise to phenylselenyl chloride (647 mg, 3.38 mmol) in DCM (7 mL) at 0° C. 5-(3-bromo-5-fluoropyridin-2-yl)-5-methoxy-3,3-dimethyl-2-oxocyclohexane-1-carbonitrile (600 mg, 1.69 mmol) in DCM (7 mL) was added dropwise after stirring for 20 min. The mixture was stirred at 0° C. for 2 h, treated with 1M aq. HCl (3 mL) and water (5 mL), and the phases were separated. H$_2$O$_2$ (3.45 mL, 33.78 mmol) was added dropwise to the DCM layer at 0° C. and the mixture was vigorously stirred at 0° C. for 40 min. Water (20 mL) was added and the mixture extracted with DCM (3×20 mL). The combined organic phases were washed with brine (2×20 mL), dried (Na$_2$SO$_4$), filtered, and concentrated under reduced pressure to afford 3-(3-bromo-5-fluoropyridin-2-yl)-3-methoxy-5,5-dimethyl-6-oxocyclohex-1-ene-1-carbonitrile (590 mg, 99%) as a yellow oil. $^1$H NMR (400 MHz, DMSO-d$_6$) δ 0.73 (s, 3H), 1.19 (s, 3H), 2.53-2.66 (m, 2H), 3.15 (s, 3H), 8.40 (dd, J=8.4, 2.5 Hz, 1H), 8.59 (s, 1H), 8.71 (d, J=2.6 Hz, 1H). m/z (ES$^+$), [M+H]$^+$=353; HPLC (C05) t$_R$=1.458 min.

Compound 69, Step 5: 3-[5-fluoro-3-(1-methyl-1H-pyrazol-4-yl)pyridin-2-yl]-3-methoxy-5,5-dimethyl-6-oxocyclohex-1-ene-1-carbonitrile (Enantiomer A)

Enantiomer A

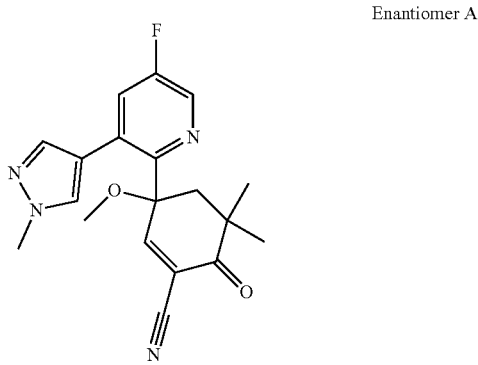 [SMILES: COC1(c2ncc(F)cc2-c2cnn(C)c2)C=C(C#N)C(=O)C(C)(C)C1]

Pd(Ph$_3$P)$_4$ (65.4 mg, 0.06 mmol) was added to Na$_2$CO$_3$ (150 mg, 1.42 mmol), (1-methyl-1H-pyrazol-4-yl)boronic acid (214 mg, 1.70 mmol) and 3-(3-bromo-5-fluoropyridin- 2-yl)-3-methoxy-5,5-dimethyl-6-oxocyclohex-1-ene-1-carbonitrile (200 mg, 0.57 mmol) in 1,4-dioxane (18 mL)/water (3 mL) at 25° C. under nitrogen. The mixture was stirred at 80° C. for 2 h. The solvent was removed under reduced pressure and the crude product purified by silica gel chromatography (0 to 50% EtOAc in petroleum ether) followed by preparative HPLC using standard conditions to afford 3-(5-fluoro-3-(1-methyl-1H-pyrazol-4-yl)pyridin-2-yl)-3-methoxy-5,5-dimethyl-6-oxocyclohex-1-ene-1-carbonitrile (102 mg, 51%) as a white solid, followed by chiral separation as described in the Generic Procedure A gave title compound (30 mg). $^1$H NMR (400 MHz, DMSO-d$_6$) δ 0.48 (s, 3H), 1.00 (s, 3H), 2.22 (d, J=14.2 Hz, 1H), 2.33 (dd, J=14.2, 1.8 Hz, 1H), 3.20 (s, 3H), 3.92 (s, 3H), 7.80 (s, 1H), 7.86 (dd, J=10.0, 2.8 Hz, 1H), 8.07 (s, 1H), 8.55 (d, J=2.8 Hz, 1H), 8.62 (d, J=1.5 Hz, 1H). m/z (ES$^+$), [M+H]$^+$=355; HPLC (C05) t$_R$=1.67 min. ee=100%.

The compounds provided in Table 6 have been prepared by analogy to the synthesis described for Compound 69, starting from Compound A1 (addition, alkylation, isoxazole opening, oxidation, Suzuki reaction). All pure enantiomers in the following Table were separated as described in the Generic Procedure A for chiral separation of enantiomers (chiral HPLC). The absolute configuration of compounds 74 and 80 were assigned based on the crystal structure of the compounds bound to the BTB domain of Keap1. For compounds where the enantiomers were separated but for which absolute configuration was not assigned, data is given for the single enantiomer that was tested. For compounds drawn without specified stereochemistry and labeled as "Enantiomer A," all data provided throughout the application for that compound is for the more active enantiomer. For compounds drawn without specified stereochemistry and labeled as "Enantiomer B," all data provided throughout the application for that compound is for the less active enantiomer. For compounds drawn without specified stereochemistry and not labeled as "Enantiomer A" or "Enantiomer B," all data provided throughout the application for that compound is for the racemate.

TABLE 6

Compounds 70-94 and 96

| Cmpd # | Structure | Name | Analytical data |
|---|---|---|---|
| 70 | *[structure image]* Enantiomer A | 3-[5-fluoro-3-(4-fluorophenyl)pyridin-2-yl]-3-methoxy-5,5-dimethyl-6-oxocyclohex-1-ene-1-carbonitrile (Enantiomer A) | $^1$H NMR (400 MHz, DMSO-d$_6$) δ ppm 0.66 (s, 3H), 0.97 (s, 3H), 2.03-2.18 (m, 2H), 3.10 (s, 3H), 7.31 (t, J = 8.8 Hz, 2H), 7.43-7.52 (m, 2H), 7.72 (dd, J = 9.3, 2.8 Hz, 1H), 8.46 (s, 1H), 8.68 (d, J = 2.8 Hz, 1H). m/z (ES$^+$), [M + H]$^+$ = 369; HPLC (C05) t$_R$ = 1.92 min (99.6%). ee = 99.6%. |
| 71 | *[structure image]* Enantiomer A | 3-[3-(1,5-dimethyl-1H-pyrazol-4-yl)-5-fluoropyridin-2-yl]-3-methoxy-5,5-dimethyl-6-oxocyclohex-1-ene-1-carbonitrile (Enantiomer A) | $^1$H NMR (400 MHz, DMSO-d$_6$) δ ppm 0.54 (s, 3H), 1.00 (s, 3H), 2.09-2.25 (m, 2H), 2.16 (s, 3H), 3.16 (s, 3H), 3.81 (s, 3H), 7.43 (s, 1H), 7.64 (dd, J = 9.5, 2.9 Hz, 1H), 8.43 (s, 1H), 8.62 (d, J = 2.8 Hz, 1H). m/z (ES$^+$), [M + H]$^+$ = 369; HPLC (C05) t$_R$ = 1.47 min (99.6%). ee = 100%. |

TABLE 6-continued

Compounds 70-94 and 96

| Cmpd # | Structure | Name | Analytical data |
|---|---|---|---|
| 72 | Enantiomer A | 3-[3-(1-cyclopropyl-1H-pyrazol-4-yl)-5-fluoropyridin-2-yl]-3-methoxy-5,5-dimethyl-6-oxocyclohex-1-ene-1-carbonitrile (Enantiomer A) | $^1$H NMR (400 MHz, DMSO-d$_6$) δ ppm 0.50 (s, 3H), 1.02 (s, 3H), 1.07 (t, J = 3.4 Hz, 2H), 1.09 (t, J = 3.4 Hz, 2H), 2.20-2.31 (m, 2H), 3.19 (s, 3H), 3.83 (tt, J = 7.2, 3.8 Hz, 1H), 7.79 (s, 1H), 7.88 (dd, J = 10.0, 2.7 Hz, 1H), 8.15 (s, 1H), 8.55 (d, J = 2.7 Hz, 1H), 8.60 (s, 1H). m/z (ES$^+$), [M + H]$^+$ = 381; HPLC (C05) t$_R$ = 1.61 min (100%). ee = 99.5%. |
| 73 | Enantiomer A | 3-[5-fluoro-3-(2-methyl-1,3-thiazol-5-yl)pyridin-2-yl]-3-methoxy-5,5-dimethyl-6-oxocyclohex-1-ene-1-carbonitrile (Enantiomer A) | $^1$H NMR (400 MHz, DMSO-d$_6$) δ ppm 0.59 (s, 3H), 1.02 (s, 3H), 2.17 (dd, J = 14.2, 1.5 Hz, 1H), 2.30 (d, J = 14.2 Hz, 1H), 2.72 (s, 3H), 3.19 (s, 3H), 7.83 (s, 1H), 7.95 (dd, J = 9.4, 2.8 Hz, 1H), 8.54 (d, J = 1.1 Hz, 1H), 8.70 (d, J = 2.8 Hz, 1H). m/z (ES$^+$), [M + H]$^+$ = 372; HPLC (C05) t$_R$ = 1.59 min (99.6%). ee = 100%. |
| 74 | 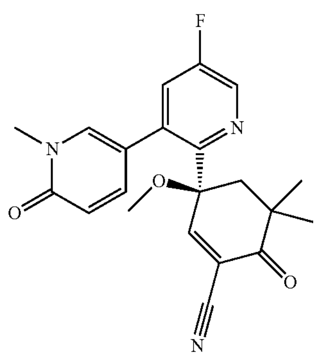 | (S)-3-[5-fluoro-3-(1-methyl-6-oxo-3-pyridyl)-2-pyridyl]-3-methoxy-5,5-dimethyl-6-oxo-cyclohexene-1-carbonitrile | $^1$H NMR (400 MHz, DMSO-d$_6$) δ ppm 0.69 (s, 3H), 1.08 (s, 3H), 2.21-2.34 (m, 2H), 3.12 (s, 3H), 3.49 (s, 3H), 6.45 (d, J = 9.4 Hz, 1H), 7.53 (dd, J = 9.4, 2.7 Hz, 1H), 7.76-7.86 (m, 2H), 8.48 (s, 1H), 8.67 (d, J = 2.8 Hz, 1H). m/z (ES$^+$), [M + H]$^+$ = 382; HPLC (C05) t$_R$ = 1.31 min (98.6%). ee = 100%. |
| 75 | Enantiomer A | 3-[5-fluoro-3-(1-methyl-2-oxo-3-pyridyl)-2-pyridyl]-3-methoxy-5,5-dimethyl-6-oxo-cyclohexene-1-carbonitrile (Enantiomer A) | $^1$H NMR (400 MHz, DMSO-d$_6$) δ ppm 0.79 (s, 3H), 1.07 (s, 3H), 2.35 (s, 2H), 3.03 (s, 3H), 3.34 (s, 3H), 6.36 (t, J = 6.8 Hz, 1H), 7.47 (dd, J = 7.0, 2.0 Hz, 1H), 7.63 (dd, J = 9.3, 2.9 Hz, 1H), 7.85 (dd, J = 6.7, 2.0 Hz, 1H), 8.29 (s, 1H), 8.65 (d, J = 2.8 Hz, 1H). m/z (ES$^+$), [M + H]$^+$ = 382; HPLC (C05) t$_R$ = 1.30 min (99.6%). ee = 99.5%. |

TABLE 6-continued

Compounds 70-94 and 96

| Cmpd # | Structure | Name | Analytical data |
|---|---|---|---|
| 76 | Enantiomer A | 3-[5-fluoro-3-(2-methyl-4-pyridyl)-2-pyridyl]-3-methoxy-5,5-dimethyl-6-oxo-cyclohexene-1-carbonitrile (Enantiomer A) | $^1$H NMR (400 MHz, DMSO-$d_6$) δ ppm 0.75 (s, 3H), 1.01 (s, 3H), 2.10 (d, J = 14.2 Hz, 1H), 2.21 (d, J = 14.2 Hz, 1H), 2.54 (s, 3H), 3.06 (s, 3H), 7.28 (d, J = 5.1 Hz, 1H), 7.33 (s, 1H), 7.76 (dd, J = 9.2, 2.8 Hz, 1H), 8.47 (s, 1H), 8.53 (d, J = 5.0 Hz, 1H), 8.72 (d, J = 2.8 Hz, 1H). m/z (ES$^+$), [M + H]$^+$ = 366; HPLC (C05) $t_R$ = 1.04 min (100%). ee = 99.8%. |
| 77 | Enantiomer A | 3-[3-(2,6-dimethyl-4-pyridyl)-5-fluoro-2-pyridyl]-3-methoxy-5,5-dimethyl-6-oxo-cyclohexene-1-carbonitrile (Enantiomer A) | $^1$H NMR (400 MHz, DMSO-$d_6$) δ ppm 0.74 (s, 3H), 1.01 (s, 3H), 2.08-2.25 (m, 2H), 2.49 (s, 6H), 3.07 (s, 3H), 7.12 (s, 2H), 7.73 (dd, J = 9.2, 2.8 Hz, 1H), 8.45 (s, 1H), 8.71 (d, J = 2.8 Hz, 1H). m/z (ES$^+$), [M + H]$^+$ = 380; HPLC (C05) $t_R$ = 0.944 min (99.1%). ee = 99.9%. |
| 78 | Enantiomer A | 3-[3-(1,3-dimethylpyrazol-4-yl)-5-fluoro-2-pyridyl]-3-methoxy-5,5-dimethyl-6-oxo-cyclohexene-1-carbonitrile (Enantiomer A) | $^1$H NMR (400 MHz, DMSO-$d_6$) δ ppm 0.53 (s, 3H), 0.99 (s, 3H), 2.09 (s, 3H), 2.15 (d, J = 5.5 Hz, 2H), 3.18 (s, 3H), 3.84 (s, 3H), 7.70 (s, 1H), 7.72 (dd, J = 9.7 Hz, 2.7 Hz, 1H), 8.47 (s, 1H), 8.60 (d, J = 2.6 Hz, 1H). m/z (ES$^+$), [M + H]$^+$ = 369; HPLC (C05) $t_R$ = 1.49 min (100%). ee = 100%. |

TABLE 6-continued

Compounds 70-94 and 96

| Cmpd # | Structure | Name | Analytical data |
|---|---|---|---|
| 79 | Enantiomer A | 3-[5-fluoro-3-(2-methyl-3-pyridyl)-2-pyridyl]-3-methoxy-5,5-dimethyl-6-oxo-cyclohexene-1-carbonitrile (Enantiomer A) | $^1$H NMR (400 MHz, DMSO-d$_6$, 2 rotamers observed) δ ppm 0.78 (s, 1.7H), 0.88 (s, 1.3H), 0.99 (s, 1.7H), 1.09 (s, 1.3H), 1.92-2.12 (m, 1H), 2.27 (s, 3H), 2.31 (s, 1H), 2.93 (s, 1.3H), 3.13 (s, 1.7H), 7.28-7.32 (m, 1H), 7.68 (ddd, J = 20.1, 7.7, 1.5 Hz, 1H), 7.80-7.85 (m, 1H), 8.11 (s, 0.4H), 8.35 (s, 0.6H), 8.53 (ddd, J = 11.4, 4.8, 1.6 Hz, 1H), 8.72 (t, J = 2.9 Hz, 1H). m/z (ES+), [M + H]$^+$ = 366; HPLC (C05) t$_R$ = 1.09 min (100%). ee = 100%. |
| 80 | 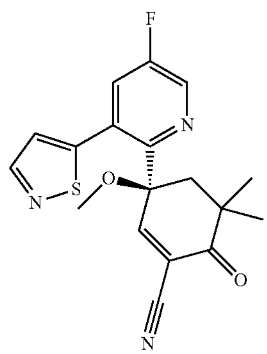 [SMILES: CO[C@]1(c2ncc(F)cc2-c2ccns2)C=C(C#N)C(=O)C(C)(C)C1] | (S)-3-(5-fluoro-3-isothiazol-5-yl-2-pyridyl)-3-methoxy-5,5-dimethyl-6-oxo-cyclohexene-1-carbonitrile | $^1$H NMR (400 MHz, DMSO-d$_6$) δ ppm 0.61 (s, 3H), 1.01 (s, 3H), 2.03 (dd, J = 14.3, 1.7 Hz, 1H), 2.37 (d, J = 14.2 Hz, 1H), 3.24 (s, 3H), 7.74 (d, J = 1.8 Hz, 1H), 8.04 (dd, J = 9.4, 2.8 Hz, 1H), 8.53 (s, 1H), 8.66 (d, J = 1.8 Hz, 1H), 8.74 (d, J = 2.8 Hz, 1H). m/z (ES$^+$), [M + H]$^+$ = 358; HPLC (C05) t$_R$ = 1.64 min (98.9%). ee = 100%. |
| 81 | Enantiomer A | 3-[5-fluoro-3-(1-phenylpyrazol-4-yl)-2-pyridyl]-3-methoxy-5,5-dimethyl-6-oxo-cyclohexene-1-carbonitrile (Enantiomer A) | $^1$H NMR (400 MHz, DMSO-d$_6$) δ ppm 0.56 (s, 3H), 1.02 (s, 3H), 2.33 (s, 2H), 3.24 (s, 3H), 7.38 (t, J = 7.4 Hz, 1H), 7.56 (t, J = 8.0 Hz, 2H), 7.91 (d, J = 7.7 Hz, 2H), 8.03 (dd, J = 9.9, 2.8 Hz, 1H), 8.11 (s, 1H), 8.60-8.66 (m, 2H), 8.84 (s, 1H). m/z (ES$^+$), [M + H]$^+$ = 417; HPLC (C05) t$_R$ = 1.87 min (99.8%). ee = 99.5%. |
| 82 | Enantiomer A | 3-[3-(2,3-dimethyl-4-pyridyl)-5-fluoro-2-pyridyl]-3-methoxy-5,5-dimethyl-6-oxo-cyclohexene-1-carbonitrile (Enantiomer A) | $^1$H NMR (400 MHz, DMSO-d$_6$, rotamers, observed) δ ppm 0.79 (s, 1.61H), 0.87 (s, 1.40H), 1.01 (s, 1.67H), 1.10 (s, 1.46H), 2.01 (d, J = 4.8 Hz, 3H), 2.03-2.12 (m, 1H), 2.30-2.44 (m, 1H), 2.53 (s, 3H), 2.96 (s, 1.46H), 3.12 (s, 1.60H), 7.13 (dd, J = 12.9, 5.0 Hz, 1H), 7.70 (dd, J = 9.1, 2.8 Hz, 1H), 8.05 (s, 0.46H), 8.31 (dd, J = 10.4, 5.1 Hz, 1H), 8.34 (s, 0.55H), 8.73 (d, J = 2.8 Hz, 1H). m/z (ES$^+$), [M + H]$^+$ = 380; HPLC (C05) t$_R$ = 1.49 min (99%). ee = 100%. |

TABLE 6-continued

Compounds 70-94 and 96

| Cmpd # | Structure | Name | Analytical data |
|---|---|---|---|
| 83 | Enantiomer A | 3-[3-(1-cyclopentylpyrazol-4-yl)-5-fluoro-2-pyridyl]-3-methoxy-5,5-dimethyl-6-oxo-cyclohexene-1-carbonitrile (Enantiomer A) | $^1$H NMR (400 MHz, DMSO-d$_6$) δ ppm 0.50 (s, 3H), 0.99 (s, 3H), 1.61-1.73 (m, 2H), 1.74-1.86 (m, 2H), 1.97 (dd, J = 12.8, 6.9 Hz, 2H), 2.10-2.15 (m, 2H), 2.17-2.33 (m, 2H), 3.19 (s, 3H), 4.78 (p, J = 7.2 Hz, 1H), 7.80 (s, 1H), 7.89 (dd, J = 10.0, 2.8 Hz, 1H), 8.12 (s, 1H), 8.55 (d, J = 2.8 Hz, 1H), 8.61 (s, 1H). m/z (ES$^+$), [M + H]$^+$ = 409; HPLC (C05) t$_R$ = 1.83 min (99.5%). ee = 99.3% |
| 84 | Enantiomer A | 3-[5-fluoro-3-(5-fluoro-3-pyridyl)-2-pyridyl]-3-methoxy-5,5-dimethyl-6-oxo-cyclohexene-1-carbonitrile (Enantiomer A) | $^1$H NMR (400 MHz, DMSO-d$_6$) δ ppm 0.80 (s, 3H), 1.03 (s, 3H), 2.08 (d, J = 14.5 Hz, 1H), 2.24 (d, J = 14.5 Hz, 1H), 3.03 (s, 3H), 7.84-7.97 (m, 2H), 8.47 (s, 1H), 8.54 (s, 1H), 8.69 (d, J = 2.7 Hz, 1H), 8.76 (d, J = 2.8 Hz, 1H). m/z (ES$^+$), [M + H]$^+$ = 370; HPLC (C05) t$_R$ = 1.59 min (99.4%). ee = 99.5% |
| 85 | Enantiomer A | 2'-(3-cyano-1-methoxy-5,5-dimethyl-4-oxocyclohex-2-enyl)-5'-fluoro-3,3'-bipyridine-5-carbonitrile (Enantiomer A) | $^1$H NMR (400 MHz, DMSO-d$_6$) δ ppm 0.85 (s, 3H), 1.06 (s, 3H), 2.08 (d, J = 14.5 Hz, 1H), 2.27 (d, J = 13.7 Hz, 1H), 2.95 (s, 3H), 7.91 (dd, J = 9.3, 2.8 Hz, 1H), 8.42 (s, 1H), 8.49 (t, J = 2.1 Hz, 1H), 8.77 (d, J = 2.8 Hz, 1H), 8.95 (d, J = 2.2 Hz, 1H), 9.11 (d, J = 1.9 Hz, 1H). m/z (ES$^+$), [M + H]$^+$ = 377; HPLC (C05) t$_R$ = 1.55 min (99.5%). ee = 99.7%. |

TABLE 6-continued

Compounds 70-94 and 96

| Cmpd # | Structure | Name | Analytical data |
|---|---|---|---|
| 86 | 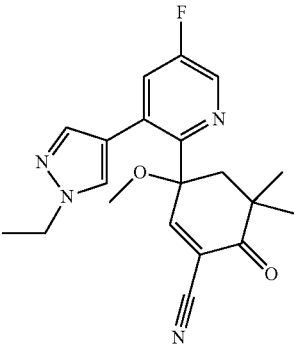 Enantiomer A | 3-[3-(1-ethylpyrazol-4-yl)-5-fluoro-2-pyridyl]-3-methoxy-5,5-dimethyl-6-oxo-cyclohexene-1-carbonitrile (Enantiomer A) | $^1$H NMR (400 MHz, DMOS-d$_6$) δ ppm 0.49 (s, 3H), 1.00 (s, 3H), 1.42 (t, J = 7.2 Hz, 3H), 2.21 (d, J = 14.2 Hz, 1H), 2.30 (dd, J = 14.3, 1.8 Hz, 1H), 3.20 (s, 3H), 4.22 (q, J = 7.3 Hz, 2H), 7.80 (s, 1H), 7.87 (dd, J = 10.0, 2.8 Hz, 1H), 8.11 (s, 1H), 8.55 (d, J = 2.8 Hz, 1H), 8.61 (d, J = 1.4 Hz, 1H). m/z (ES$^+$), [M + H]$^+$ = 369; HPLC (C05) t$_R$ = 1.57 min (99.3%). ee = 100%. |
| 87 | 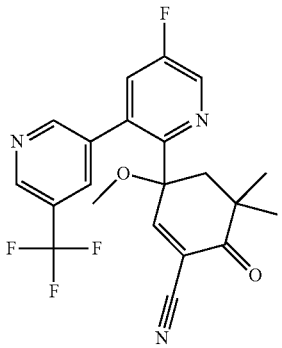 Enantiomer A | 3-[5-fluoro-3-[5-(trifluoromethyl)-3-pyridyl]-2-pyridyl]-3-methoxy-5,5-dimethyl-6-oxo-cyclohexene-1-carbonitrile (Enantiomer A) | $^1$H NMR (400 MHz, DMSO-d$_6$) δ ppm 0.84 (s, 3H), 1.02 (s, 3H), 2.06 (d, J = 14.5 Hz, 1H), 2.22 (d, J = 14.5 Hz, 1H), 2.97 (s, 3H), 7.96 (dd, J = 9.3, 2.8 Hz, 1H), 8.36 (d, J = 2.3 Hz, 1H), 8.44 (s, 1H), 8.77 (d, J = 2.8 Hz, 1H), 8.98 (d, J = 2.0 Hz, 1H), 9.07 (dd, J = 2.1, 1.0 Hz, 1H). m/z (ES$^+$), [M + H]$^+$ = 420; HPLC (C05) t$_R$ = 2.26 min (95.9%). ee = 100%. |
| 88 | 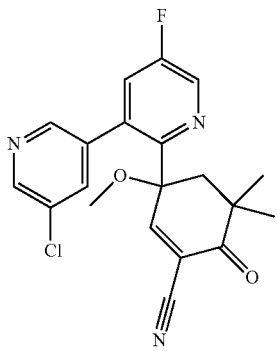 Enantiomer A | 3-[3-(5-chloro-3-pyridyl)-5-fluoro-2-pyridyl]-3-methoxy-5,5-dimethyl-6-oxo-cyclohexene-1-carbonitrile (Enantiomer A) | $^1$H NMR (400 MHz, DMSO-d$_6$) δ ppm 0.81 (s, 3H), 1.04 (s, 3H), 2.08 (d, J = 14.5 Hz, 1H), 2.24 (dd, J = 14.5, 1.2 Hz, 1H), 3.02 (s, 3H), 7.90 (dd, J = 9.3, 2.8 Hz, 1H), 8.10 (t, J = 2.1 Hz, 1H), 8.46 (s, 1H), 8.62 (d, J = 1.9 Hz, 1H), 8.74 (dd, J = 10.9, 2.6 Hz, 2H). m/z (ES$^+$), [M + H]$^+$ = 386; HPLC (C05) t$_R$ = 1.65 min (99.6%). ee = 99.7%. |

TABLE 6-continued

Compounds 70-94 and 96

| Cmpd # | Structure | Name | Analytical data |
|---|---|---|---|
| 89 | Enantiomer A | 3-[5-fluoro-3-(2-methylpyrimidin-5-yl)-2-pyridyl]-3-methoxy-5,5-dimethyl-6-oxo-cyclohexene-1-carbonitrile (Enantiomer A) | $^1$H NMR (400 MHz, DMSO-d$_6$) δ ppm 0.81 (s, 3H), 1.06 (s, 3H), 2.07 (d, J = 14.3 Hz, 1H), 2.26 (dd, J = 14.5, 1.3 Hz, 1H), 2.70 (s, 3H), 2.99 (s, 3H), 7.89 (dd, J = 9.3, 2.8 Hz, 1H), 8.45 (s, 1H), 8.74 (d, J = 2.8 Hz, 1H), 8.78 (s, 2H). m/z (ES$^+$), [M + H]$^+$ = 367; HPLC (C05) t$_R$ = 1.41 min (95.3%). ee = 100%. |
| 90 | Enantiomer A | 3-[5-fluoro-3-[6-(trifluoromethyl)-3-pyridyl]-2-pyridyl]-3-methoxy-5,5-dimethyl-6-oxo-cyclohexene-1-carbonitrile (Enantiomer A) | $^1$H NMR (400 MHz, DMSO-d$_6$) δ ppm 0.83 (s, 3H), 1.04 (s, 3H), 2.09 (d, J = 14.5 Hz, 1H), 2.26 (dd, J = 14.5, 1.3 Hz, 1H), 2.99 (s, 3H), 7.91 (dd, J = 9.2, 2.8 Hz, 1H), 8.03 (dd, J = 8.2, 0.8 Hz, 1H), 8.21 (dd, J = 8.1, 2.1 Hz, 1H), 8.45 (s, 1H), 8.78 (d, J = 2.8 Hz, 1H), 8.87 (d, J = 2.0 Hz, 1H). m/z (ES$^+$), [M + H]$^+$ = 420; HPLC (C05) t$_R$ = 1.80 min (100%). ee = 97.1%. |
| 91 | Enantiomer A | 3-[5-fluoro-3-([1,2,4]triazolo[1,5-a]pyridin-7-yl)-2-pyridyl]-3-methoxy-5,5-dimethyl-6-oxo-cyclohexene-1-carbonitrile (Enantiomer A) | $^1$H NMR (400 MHz, DMSO-d6) δ ppm 0.81 (s, 3H), 1.01 (s, 3H), 2.20 (d, J = 14.4 Hz, 1H), 2.29 (d, J = 14.8 Hz, 1H), 3.08 (s, 3H), 7.32 (dd, J = 7.1, 1.8 Hz, 1H), 7.89 (dd, J = 9.3, 2.8 Hz, 1H), 7.97 (dd, J = 1.9, 0.9 Hz, 1H), 8.48 (s, 1H), 8.60 (s, 1H), 8.76 (d, J = 2.8 Hz, 1H), 9.03 (dd, J = 7.1, 0.9 Hz, 1H). m/z (ES$^+$), [M + H]$^+$ = 392; HPLC (C05) t$_R$ = 1.383 min (99.5%). ee = 99.7%. |
| 92 | Enantiomer A | 3-[5-fluoro-3-(1,3,5-trimethylpyrazol-4-yl)-2-pyridyl]-3-methoxy-5,5-dimethyl-6-oxo-cyclohexene-1-carbonitrile (Enantiomer A) | $^1$H NMR (400 MHz, DMSO-d$_6$, rotamers observed) δ ppm 0.60 (s, 1.9H), 0.70 (s, 1.1H), 1.11 (s, 1.9H), 1.13 (s, 1.1H), 1.81 (s, 1.1H), 1.86 (s, 1.9H), 1.97 (s, 1.9H), 2.05 (s, 1.1H), 2.28 (dd, J = 13.8, 11.7 Hz, 1H), 2.54 (dd, J = 13.8, 1.7 Hz, 0.5H), 2.72 (dd, J = 13.8, 1.7 Hz, 0.5H), 3.11 (s, 1.1H), 3.13 (s, 1.H), 3.71 (s, 1.9H), 3.73 (s, 1.1H), 7.44 (d, J = 1.5 Hz, 0.6H), 7.58 (ddd, J = 16.6, 9.2, 2.9 Hz, 1H), 7.72 (s, 0.4H) 8.68 (dd, J = 5.7, 2.9 Hz, 1H). m/z (ES$^+$), [M + H]$^+$ = 383; HPLC (C05) t$_R$ = 1.53 min (99.4%). ee = 100%. |

TABLE 6-continued

Compounds 70-94 and 96

| Cmpd # | Structure | Name | Analytical data |
|---|---|---|---|
| 93 | 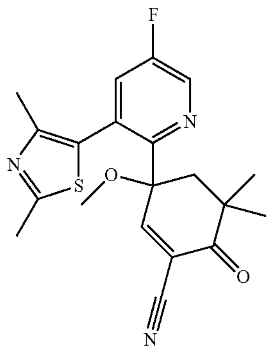 | 3-[3-(2,4-dimethylthiazol-5-yl)-5-fluoro-2-pyridyl]-3-methoxy-5,5-dimethyl-6-oxo-cyclohexene-1-carbonitrile (Enantiomer A) | $^1$H NMR (400 MHz, DMSO-d6) δ ppm 0.67 (s, 3H), 1.05 (s, 3H), 2.18-2.29 (m, 2H), 2.19 (s, 3H), 2.66 (s, 3H), 3.13 (s, 3H), 7.88 (dd, J = 9.2, 2.8 Hz, 1H), 8.41 (s, 1H), 8.72 (d, J = 2.8 Hz, 1H). m/z (ES$^+$), [M + H]$^+$ = 386; HPLC (C05) $t_R$ = 1.58 min (99.1%). ee 100%. |
| 94 | 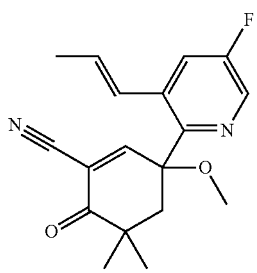 | 3-{5-fluoro-3-[(1E)-prop-1-en-1-yl]pyridin-2-yl}-3-methoxy-5,5-dimethyl-6-oxocyclohex-1-ene-1-carbonitrile (Enantiomer A) | $^1$H NMR (400 MHz, DMSO-d6) δ ppm 0.65 (s, 3H), 1.17 (s, 3H), 1.94 (dd, J = 6.7, 1.7 Hz, 3H), 2.34-2.48 (m, 2H), 3.14 (s, 3H), 6.46-6.60 (m, 1H), 7.04 (d, J = 15.8 Hz, 1H), 8.05 (dd, J = 10.4, 2.8 Hz, 1H), 8.45 (d, J = 2.7 Hz, 1H), 8.57 (s, 1H). m/z (ES$^+$), [M + H]$^+$ = 315; HPLC (C05) $t_R$ = 1.86 min (99%). ee = 99%. |
| 96 | 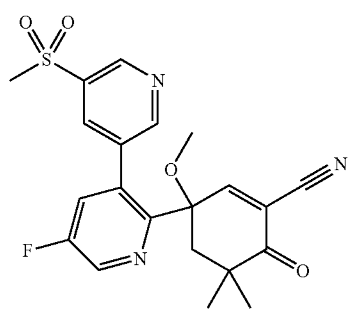 [SMILES: COC1(c2ncc(F)cc2-c2cncc(S(C)(=O)=O)c2)C=C(C#N)C(=O)C(C)(C)C1] | 3-(5-fluoro-5'-(methylsulfonyl)-[3,3'-bipyridin]-2-yl)-3-methoxy-5,5-dimethyl-6-oxocyclohex-1-ene-1-carbonitrile | $^1$H NMR (400 MHz, DMSO-d$_6$) δ ppm 0.85 (s, 3H), 1.04 (s, 3H), 2.07 (d, J = 14.5 Hz, 1H), 2.25 (d, J = 14.4 Hz, 1H), 2.97 (s, 3H), 3.39 (s, 3H), 7.96 (dd, J = 9.3, 2.8 Hz, 1H), 8.40-8.46 (m, 2H), 8.78 (d, J = 2.8 Hz, 1H), 9.01 (d, J = 2.0 Hz, 1H), 9.14 (d, J = 2.1 Hz, 1H). m/z (ES$^+$), [M + H]$^+$ = 430; HPLC (C05) $t_R$ = 1.60 min (98.9%). |

Compound 98: 3-(5-bromo-4-methyl-1,3-thiazol-2-yl)-3-methoxy-5,5-dimethyl-6-oxocyclohex-1-ene-1-carbonitrile (Enantiomer A)

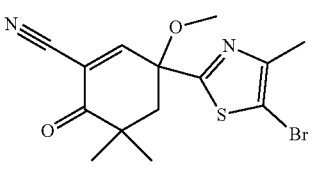

Enantiomer A

Compound 98, Step 1: 5-(5-bromo-4-methylthiazol-2-yl)-5-methoxy-7,7-dimethyl-4,5,6,7-tetrahydrobenzo[d]oxazole

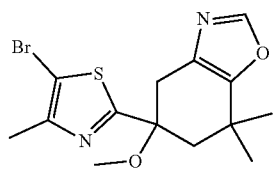

NBS (0.783 g, 4.40 mmol) was added to 5-methoxy-7,7-dimethyl-5-(4-methylthiazol-2-yl)-4,5,6,7-tetrahydrobenzo[d]oxazole (1.02 g, 3.66 mmol) in DMF (6 mL) at 25° C. under N$_2$. The resulting mixture was stirred at 50° C. for 2 h. The mixture was quenched with water (75 mL), extracted with EtOAc (3×50 mL), the organic layer was dried over Na₂SO₄, filtered and evaporated to afford a yellow solid. The crude product was purified by silica gel chromatography, elution gradient 0 to 7% EtOAc in petroleum ether. Pure fractions were evaporated to dryness to afford 5-(5-bromo-4-methylthiazol-2-yl)-5-methoxy-7,7-dimethyl-4,5,6,7-tetrahydrobenzo[d]oxazole (1.260 g, 96%) as a yellow solid. ¹H NMR (300 MHz, CDCl₃) δ ppm 1.28 (s, 3H), 1.48 (s, 3H), 2.10 (d, J=14.3 Hz, 1H), 2.23 (dd, J=14.3, 2.1 Hz, 1H), 2.37 (s, 3H), 3.05 (dd, J=16.6, 2.1 Hz, 1H), 3.12 (s, 3H), 3.24 (d, J=16.5 Hz, 1H), 8.10 (s, 1H); m/z (ES⁺), [M+H]⁺=357; HPLC (C05) $t_R$=1.11 min (97%).

Compound 98, Step 2: 5-(5-bromo-4-methylthiazol-2-yl)-5-methoxy-3,3-dimethyl-2-oxocyclohexane-1-carbonitrile

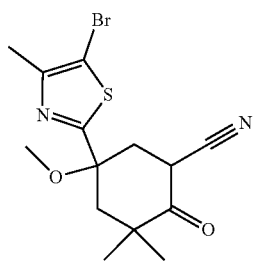 [SMILES: COC1(c2nc(C)c(Br)s2)CC(C#N)C(=O)C(C)(C)C1]

Sodium methoxide in methanol (0.702 mL, 3.15 mmol) was added dropwise to 5-(5-bromo-4-methylthiazol-2-yl)-5-methoxy-7,7-dimethyl-4,5,6,7-tetrahydrobenzo[d]isoxazole (225 mg, 0.63 mmol) in Et₂O (5 mL) at 0° C. The resulting mixture was stirred at 0° C. for 45 min, quenched with sat. aq. NH₄Cl (25 mL) and extracted with EtOAc (3×25 mL). The organic layer was dried over Na₂SO₄, filtered and evaporated to afford the crude product, which was purified by silica gel chromatography (0 to 15% EtOAc in petroleum ether) to afford 5-(5-bromo-4-methylthiazol-2-yl)-5-methoxy-3,3-dimethyl-2-oxocyclohexane-1-carbonitrile (215 mg, 96%) as a yellow oil. ¹H NMR (400 MHz, CDCl₃) δ ppm 1.19 (s, 3H), 1.43 (s, 3H), 2.19 (d, J=15.1 Hz, 1H), 2.38 (s, 3H), 2.63 (t, J=14.1, 14.1 Hz, 1H), 2.90 (dt, J=14.3, 4.4 Hz, 1H), 3.18 (d, J=9.4 Hz, 1H), 3.30 (s, 3H), 4.27 (dd, J=13.9, 4.7 Hz, 1H); m/z (ES⁺), [M+H]⁺=357; HPLC (C05) $t_R$=1.48 min (99%).

Compound 98, Step 3: 3-(5-bromo-4-methyl-1,3-thiazol-2-yl)-3-methoxy-5,5-dimethyl-6-oxocyclohex-1-ene-1-carbonitrile (Enantiomer A)

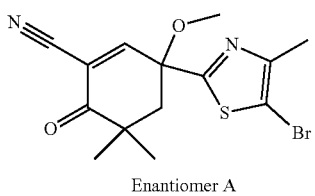 [SMILES: COC1(c2nc(C)c(Br)s2)C=C(C#N)C(=O)C(C)(C)C1]

Enantiomer A

Pyridine (0.100 mL, 1.23 mmol) in DCM (1 mL) was added dropwise to phenylselenyl chloride (236 mg, 1.23 mmol) in DCM (2 mL) at 0° C. 5-(5-Bromo-4-methylthiazol-2-yl)-5-methoxy-3,3-dimethyl-2-oxocyclohexane-1-carbonitrile (220 mg, 0.62 mmol) in DCM (4 mL) was added dropwise after stirring for 20 min. The mixture was stirred at 0° C. for 2 h, treated with 1M aq. HCl (3 mL) and water (5 mL) and the phases were separated. H₂O₂ (1.258 mL, 12.32 mmol) was added dropwise to the DCM layer at 0° C. and the mixture was vigorously stirred at 0° C. for 40 min. Water (20 mL) was added and the mixture was extracted with DCM (3×20 mL). The combined organic phases were washed with brine (2×20 mL), dried (MgSO₄), filtered, and concentrated under reduced pressure. The crude product was purified by preparative HPLC using standard conditions to afford 3-(5-bromo-4-methylthiazol-2-yl)-3-methoxy-5,5-dimethyl-6-oxocyclohex-1-ene-1-carbonitrile (120 mg, 55%) as light yellow solid, followed by chiral separation as described in the Generic Procedure A to give the title compound (40 mg) as a white solid. ¹H NMR (400 MHz, DMSO-d₆) δ ppm 0.96 (s, 3H), 1.24 (s, 3H), 2.34 (s, 3H), 2.39-2.44 (m, 2H), 3.26 (s, 3H), 8.36 (d, J=1.0 Hz, 1H). m/z (ES+), [M+H]+=357; HPLC (C05) $t_R$=1.93 min (92%). ee=99%.

Compound 99: 3-methoxy-5,5-dimethyl-3-[4-methyl-5-(pyridin-2-yl)-1,3-thiazol-2-yl]-6-oxocyclohex-1-ene-1-carbonitrile (Enantiomer A)

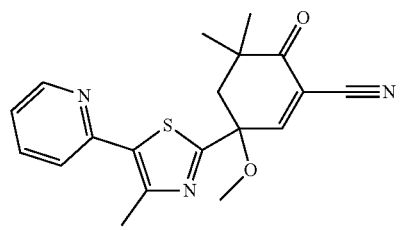

Enantiomer A

Pd(Ph₃P)₄ (140 mg, 0.12 mmol) was added to 2-(tributylstannyl)pyridine (1337 mg, 3.63 mmol) and 3-(5-bromo-4-methylthiazol-2-yl)-3-methoxy-5,5-dimethyl-6-oxocyclohex-1-ene-1-carbonitrile (430 mg, 1.21 mmol) in toluene (1 mL) at 25° C. under nitrogen. The resulting mixture was stirred at 95° C. for 18 h. The reaction mixture was filtered through celite. The crude product was purified by flash silica chromatography, elution gradient 0 to 25% EtOAc in petroleum ether. Pure fractions were evaporated to dryness to afford crude. The crude product was purified by preparative HPLC using standard conditions to afford 3-methoxy-5,5-dimethyl-3-(4-methyl-5-(pyridin-2-yl)thiazol-2-yl)-6-oxocyclohex-1-ene-1-carbonitrile (250 mg, 58.4%) as a yellow gum, followed by chiral separation as described in the Generic Procedure A to give the title compound (93 mg) as a white solid. ¹H NMR (400 MHz, DMSO-d₆) δ ppm 0.97 (s, 3H), 1.25 (s, 3H), 2.47-2.49 (m, 2H), 2.65 (s, 3H), 3.29 (s, 3H), 7.39 (ddd, J=7.6, 4.8, 1.1 Hz, 1H), 7.79 (dt, J=8.2, 1.1 Hz, 1H), 7.94 (td, J=7.8, 1.8 Hz, 1H), 8.47 (d, J=0.9 Hz, 1H), 8.64 (ddd, J=4.9, 1.8, 1.0 Hz, 1H). m/z (ES⁺), [M+H]⁺=354; HPLC (C05) $t_R$=1.72 min (97%). ee=99%.

Compound 100: 3-[5-fluoro-3-(3-methylbut-1-yn-1-yl)pyridin-2-yl]-3-methoxy-5,5-dimethyl-6-oxocyclohex-1-ene-1-carbonitrile (Enantiomer A)

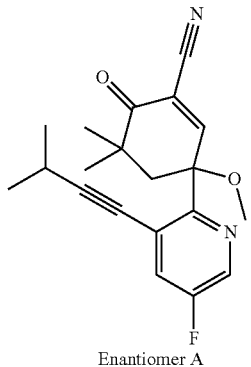 [SMILES: COC1(c2ncc(F)cc2C#CC(C)C)C=C(C#N)C(=O)C(C)(C)C1]

Enantiomer A

PdCl$_2$(PPh$_3$)$_2$ (23.9 mg, 0.03 mmol) was added to 3-(3-bromo-5-fluoropyridin-2-yl)-3-methoxy-5,5-dimethyl-6-oxocyclohex-1-ene-1-carbonitrile (120 mg, 0.34 mmol), 3-methylbut-1-yne (69.4 mg, 1.02 mmol) and copper(I) iodide (6.47 mg, 0.03 mmol) in TEA (3 mL) at 25° C. under nitrogen. The mixture was stirred at 50° C. for 3 h and solvent removed under reduced pressure. The crude product was purified by silica gel chromatography (0 to 20% EtOAc in petroleum ether) to afford a brown oil, which was purified by preparative HPLC using standard conditions to afford 3-(5-fluoro-3-(3-methylbut-1-yn-1-yl)pyridin-2-yl)-3-methoxy-5,5-dimethyl-6-oxocyclohex-1-ene-1-carbonitrile (46 mg, 39.8%) as a white solid, followed by chiral separation as described in the Generic Procedure A to give the title compound (15 mg) as a colourless oil. $^1$H NMR (400 MHz, CDCl$_3$) δ ppm 0.92 (s, 3H), 1.31 (d, J=6.9, 6H), 1.33 (s, 3H), 2.51-2.66 (m, 2H), 2.85 (h, J=7.0 Hz, 1H), 3.21 (s, 3H), 7.51 (dd, J=8.7, 2.8 Hz, 1H), 8.17 (s, 1H), 8.31 (d, J=2.8 Hz, 1H). m/z (ES$^+$), [M+H]$^+$=341; HPLC (C05) t$_R$=2.01 min (99.7%). ee=99.9%.

Compound 101: 3-methoxy-5,5-dimethyl-6-oxo-3-(3-propylpyridin-2-yl)cyclohex-1-ene-1-carbonitrile (Enantiomer A)

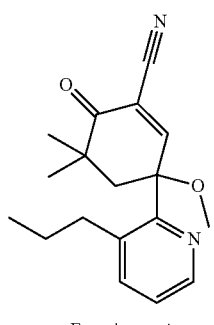

Enantiomer A

Compound 101, Step 1: (E)-5-methoxy-7,7-dimethyl-5-(3-(prop-1-en-1-yl)pyridin-2-yl)-4,5,6,7-tetrahydrobenzo[d]isoxazole

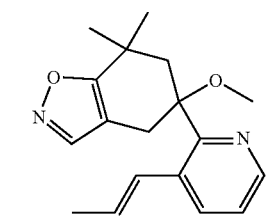 [SMILES: C/C=C/c1cccnc1C1(OC)Cc2cnoc2C(C)(C)C1]

Pd(Ph$_3$P)$_4$ (206 mg, 0.18 mmol) was added to a mixture of 5-(3-bromopyridin-2-yl)-5-methoxy-7,7-dimethyl-4,5,6,7-tetrahydrobenzo[d]isoxazole (600 mg, 1.78 mmol), (E)-4,4,5,5-tetramethyl-2-(prop-1-en-1-yl)-1,3,2-dioxaborolane (448 mg, 2.67 mmol) and cesium carbonate (1.16 g, 3.56 mmol) in 1,4-dioxane (4 mL) and water (0.4 mL) at r.t. under N$_2$. The resulting solution was stirred at 100° C. for 3 h and evaporated. The crude product was purified by silica gel chromatography (0 to 20% EtOAc in petroleum ether) to afford (E)-5-methoxy-7,7-dimethyl-5-(3-(prop-1-en-1-yl)pyridin-2-yl)-4,5,6,7-tetrahydrobenzo[d]isoxazole (280 mg, 52.7%) as a yellow solid. m/z (ES$^+$), [M+H]$^+$=299; HPLC (C05) t$_R$=0.96 min (97%).

Compound 101, Step 2: 5-methoxy-7,7-dimethyl-5-(3-propylpyridin-2-yl)-4,5,6,7-tetrahydrobenzo[d]isoxazole

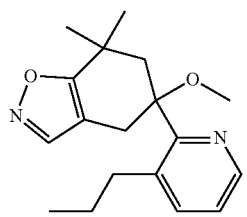 [SMILES: CCCc1cccnc1C1(OC)Cc2cnoc2C(C)(C)C1]

5% Pd on active carbon (9.27 mg, 0.09 mmol) was added dropwise to (E)-5-methoxy-7,7-dimethyl-5-(3-(prop-1-en-1-yl)pyridin-2-yl)-4,5,6,7-tetrahydrobenzo[d]isoxazole (260 mg, 0.87 mmol) in EtOAc (5 mL) at 20° C. The solution was stirred at 20° C. for 12 h under N$_2$ and filtered through Celite. The crude product was purified by silica gel chromatography (0 to 30% EtOAc in petroleum ether) to afford 5-methoxy-7,7-dimethyl-5-(3-propylpyridin-2-yl)-4,5,6,7-tetrahydrobenzo[d]isoxazole (185 mg, 71%) as a yellow oil. m/z (ES$^+$), [M+H]$^+$=301; HPLC (C05) t$_R$=0.97 min (67%).

Compound 101, Step 3: 5-methoxy-3,3-dimethyl-2-oxo-5-(3-propylpyridin-2-yl)cyclohexane-1-carbonitrile

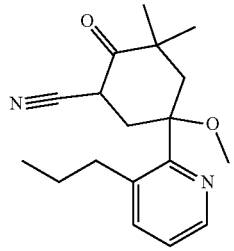 [SMILES: CCCc1cccnc1C1(OC)CC(C#N)C(=O)C(C)(C)C1]

Sodium methoxide in methanol (0.495 mL, 2.66 mmol) was added dropwise to 5-methoxy-7,7-dimethyl-5-(3-propylpyridin-2-yl)-4,5,6,7-tetrahydrobenzo[d]isoxazole (180 mg, 0.53 mmol) in Et$_2$O (5 mL) at 0° C. The mixture was stirred at 0° C. for 30 min, quenched with sat. aq. NH$_4$Cl (50 mL) and extracted with EtOAc (3×20 mL). The combined organic layers were washed with brine (100 mL), dried over Na$_2$SO$_4$, filtered and evaporated to afford 5-methoxy-3,3-dimethyl-2-oxo-5-(3-propylpyridin-2-yl)cyclohexane-1-carbonitrile (180 mg, 100%) as a pale yellow gum. $^1$H NMR (300 MHz, CDCl$_3$) δ ppm 1.09 (dd, J=16.3, 9.0 Hz, 6H), 1.26 (d, J=2.2 Hz, 1H), 1.45 (s, 3H), 1.64-1.73 (m, 2H), 2.05 (s, 1H), 2.42 (dd, J=14.9, 3.8 Hz, 1H), 2.91 (d, J=14.4 Hz, 1H), 3.05 (d, J=25.2 Hz, 5H), 4.28 (dd, J=13.6, 4.8 Hz, 1H), 7.15-7.26 (m, 1H), 7.61 (d, J=7.8 Hz, 1H), 8.36 (s, 1H), 1H missing. m/z (ES$^+$), [M+H]$^+$=301; HPLC (C05) t$_R$=0.98 min (89%).

Compound 101, Step 4: 3-methoxy-5,5-dimethyl-6-oxo-3-(3-propylpyridin-2-yl)cyclohex-1-ene-1-carbonitrile (Enantiomer A)

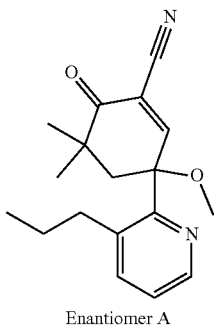 [SMILES: CCCc1cccnc1C1(OC)C=C(C#N)C(=O)C(C)(C)C1]

Enantiomer A

Pyridine (95 mg, 1.20 mmol) in DCM (2 mL) was added dropwise to phenyl hypochloroselenoite (230 mg, 1.20 mmol) in DCM (2 mL) at 0° C. 5-Methoxy-3,3-dimethyl-2-oxo-5-(3-propylpyridin-2-yl)cyclohexane-1-carbonitrile (180 mg, 0.60 mmol)) in DCM (4 mL) was added dropwise after stirring for 20 min. The mixture was stirred at 0° C. for 2 h, treated with 1M aq. HCl (3 mL) and water (5 mL) and the phases were separated. Hydrogen peroxide (1.22 mL, 11.9 mmol) was added dropwise to the DCM layer at 0° C., and the mixture was vigorously stirred at 0° C. for 40 min, quenched with water (20 mL) and extracted with DCM (3×25 mL). The organic layer was dried over Na$_2$SO$_4$, filtered and evaporated to afford yellow oil. The crude product was purified by preparative HPLC using standard conditions to afford 3-methoxy-5,5-dimethyl-6-oxo-3-(3-propylpyridin-2-yl)cyclohex-1-ene-1-carbonitrile (90 mg, 50.3%) as a white solid, followed by chiral separation as described in the Generic Procedure A to give the title compound (36 mg) as white solids. $^1$H NMR (400 MHz, DMSO-d$_6$) δ ppm 0.68 (s, 3H), 1.01 (t, J=7.3 Hz, 3H), 1.19 (s, 3H), 1.62-1.77 (m, 2H), 2.32 (d, J=14.2 Hz, 1H), 2.47 (d, J=14.2 Hz, 1H), 2.80-2.99 (m, 2H), 3.15 (s, 3H), 7.39 (dd, J=7.8, 4.6 Hz, 1H), 7.84 (dd, J=7.9, 1.6 Hz, 1H), 8.39 (dd, J=4.7, 1.6 Hz, 1H), 8.59 (s, 1H). m/z (ES$^+$), [M+H]$^+$=299; HPLC (C05) t$_R$=1.85 min (97%). ee=99%.

Compound 102: 7-methoxy-7-[4-methyl-5-(pyridin-2-yl)-1,3-thiazol-2-yl]-4-oxospiro[2.5]oct-5-ene-5-carbonitrile (Enantiomer A)

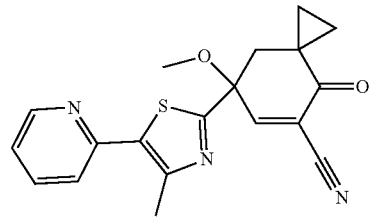

Enantiomer A

Compound 102, Step 1: 5-(4-methylthiazol-2-yl)-5,6-dihydro-4H-spiro[benzo[d]isoxazole-7,1'-cyclopropan]-5-ol

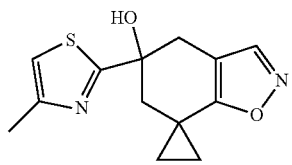 [SMILES: Cc1csc(C2(O)Cc3cnoc3C3(CC3)C2)n1]

n-Butyllithium (5.15 mL, 12.9 mmol) was added dropwise to 4-methylthiazole (1.215 g, 12.26 mmol) in DCM (6 mL) at −78° C. under N$_2$. 4H-spiro[benzo[d]isoxazole-7,1'-cyclopropan]-5(6H)-one (1 g, 6.13 mmol) in DCM (5 mL) was added dropwise to the mixture after stirring for 30 min at −78° C. The mixture was stirred at −78° C. for 1 h, quenched with sat. aq. NaHCO$_3$ (40 mL) and extracted with DCM (3×50 mL). The combined organic layers were washed with brine (80 mL), dried over Na$_2$SO$_4$, filtered and evaporated to afford the crude product, which was purified by silica gel chromatography (0 to 30% EtOAc in petroleum ether). Pure fractions were evaporated to dryness to afford 5-(4-methylthiazol-2-yl)-5,6-dihydro-4H-spiro[benzo[d]isoxazole-7,1'-cyclopropan]-5-ol (1.10 g, 68.4%) as a yellow solid. $^1$H NMR (400 MHz, CDCl$_3$) δ ppm 0.86 (ddd, J=9.4, 6.6, 4.5 Hz, 1H), 1.07 (ddd, J=9.8, 6.6, 4.3 Hz, 1H), 1.31-1.40 (m, 1H), 1.45 (ddd, J=10.0, 6.6, 4.6 Hz, 1H), 1.87 (dd, J=13.9, 1.6 Hz, 1H), 2.45 (d, J=1.0 Hz, 3H), 2.70 (d, J=13.8 Hz, 1H), 2.95 (dd, J=16.1, 1.6 Hz, 1H), 3.30 (d, J=16.1 Hz, 1H), 3.38 (s, 1H), 6.86 (q, J=1.0 Hz, 1H), 8.10 (s, 1H); m/z (ES$^+$), [M+H]$^+$=263; TFA, HPLC (C05) t$_R$=1.11 min (99%).

Compound 102, Step 2: 5-methoxy-5-(4-methylthiazol-2-yl)-5,6-dihydro-4H-spiro[benzo[d]isoxazole-7,1'-cyclopropane]

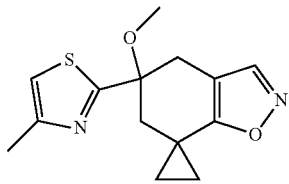 [SMILES: COC1(c2nc(C)cs2)Cc2cnoc2C2(CC2)C1]

HMPA (1.459 mL, 8.39 mmol) in THF (1.5 mL) and NaHMDS (4.61 mL, 4.61 mmol) were added to 5-(4-methylthiazol-2-yl)-5,6-dihydro-4H-spiro[benzo[d]isoxazole-7,1'-cyclopropan]-5-ol (1.1 g, 4.19 mmol) in THF (3 mL) at −78° C. under N₂. Methyl trifluoromethanesulfonate (1.376 g, 8.39 mmol) in THF (1.5 mL) was added after stirring for 5 min at −78° C. The mixture was stirred at −78° C. for 5 min, warmed up to r.t. for 10 min and diluted with water (6 mL), sat. aq. NH₄Cl (30 mL), and EtOAc (30 mL). The aq. phase was extracted with EtOAc (2×30 mL). The combined organic phases were washed with brine (40 mL), dried (Na₂SO₄), filtered and evaporated to afford the crude product, which was purified by silica gel chromatography (0 to 16% EtOAc in petroleum ether) to afford 5-methoxy-5-(4-methylthiazol-2-yl)-5,6-dihydro-4H-spiro[benzo[d] isoxazole-7,1'-cyclopropane] (1.10 g, 95%) as a yellow oil. ¹H NMR (300 MHz, CDCl₃) δ ppm 0.82-0.96 (m, 1H), 0.96-1.09 (m, 1H), 1.35 (tdd, J=11.1, 4.7, 1.9 Hz, 2H), 2.15 (dd, J=14.1, 1.7 Hz, 1H), 2.49 (d, J=1.0 Hz, 3H), 2.71 (d, J=14.1 Hz, 1H), 3.11 (dd, J=16.1, 1.7 Hz, 1H), 3.22 (s, 3H), 3.39 (d, J=16.0 Hz, 1H), 6.96 (q, J=1.0 Hz, 1H), 8.10 (s, 1H); m/z (ES⁺), [M+H]⁺=277; HPLC (C05) $t_R$=1.27 min (96%).

Compound 102, Step 3: 5-(5-bromo-4-methylthiazol-2-yl)-5-methoxy-5,6-dihydro-4H-spiro[benzo[d]oxazole-7,1'-cyclopropane]

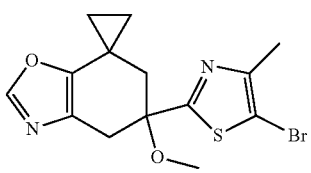 [SMILES: COC1(c2nc(C)c(Br)s2)Cc2ncoc2C2(CC2)C1]

NBS (0.850 g, 4.78 mmol) was added to 5-methoxy-5-(4-methylthiazol-2-yl)-5,6-dihydro-4H-spiro[benzo[d]oxazole-7,1'-cyclopropane] (1.1 g, 3.98 mmol) in DMF (8 mL) at 25° C. under N₂. The resulting mixture was stirred at 50° C. for 16 h, quenched with water (20 mL) and extracted with EtOAc (3×50 mL). The organic layer was dried over Na₂SO₄, filtered and evaporated to afford the crude product, which was purified by silica gel chromatography (0 to 20% EtOAc in petroleum ether) to afford 5-(5-bromo-4-methylthiazol-2-yl)-5-methoxy-5,6-dihydro-4H-spiro[benzo[d]oxazole-7,1'-cyclopropane] (1.40 g, 99%) as a yellow oil. ¹H NMR (400 MHz, CDCl₃) δ ppm 0.87 (ddd, J=10.5, 6.1, 3.8 Hz, 1H), 0.98-1.04 (m, 1H), 1.33 (ddd, J=13.7, 6.7, 3.5 Hz, 1H), 1.39 (ddd, J=9.7, 6.0, 3.6 Hz, 1H), 2.08-2.13 (m, 1H), 2.39 (s, 3H), 2.57 (d, J=14.1 Hz, 1H), 3.03 (dd, J=16.0, 1.7 Hz, 1H), 3.22 (s, 3H), 3.27 (d, J=16.0 Hz, 1H), 8.09 (s, 1H); m/z (ES⁺), [M+H]⁺=355; HPLC (C05) $t_R$=1.06 min (87%).

Compound 102, Step 4: 7-(5-bromo-4-methylthiazol-2-yl)-7-methoxy-4-oxospiro[2.5]octane-5-carbonitrile

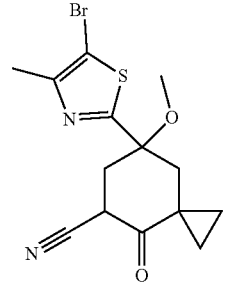 [SMILES: COC1(c2nc(C)c(Br)s2)CC(C#N)C(=O)C2(CC2)C1]

Sodium methoxide in methanol (4.39 mL, 19.7 mmol) was added dropwise to 5-(5-bromo-4-methylthiazol-2-yl)-5-methoxy-5,6-dihydro-4H-spiro[benzo[d]isoxazole-7,1'-cyclopropane] (1.4 g, 3.94 mmol) in Et₂O (5 mL) at 0° C. The mixture was stirred at 0° C. for 45 min, quenched with sat. aq. NH₄Cl (25 mL) and extracted with EtOAc (3×25 mL). The organic layer was dried over Na₂SO₄, filtered and evaporated to afford 7-(5-bromo-4-methylthiazol-2-yl)-7-methoxy-4-oxospiro[2.5]octane-5-carbonitrile (1.35 g, 96%) as a yellow oil. ¹H NMR (400 MHz, CDCl₃) δ ppm 0.66-0.81 (m, 1H), 1.03 (ddd, J=9.1, 7.2, 3.9 Hz, 1H), 1.12-1.23 (m, 1H), 1.76 (ddd, J=10.0, 7.1, 4.2 Hz, 1H), 2.01 (dd, J=15.0, 3.3 Hz, 1H), 2.40 (s, 3H), 2.68-2.79 (m, 1H), 2.89 (ddd, J=14.0, 5.5, 3.3 Hz, 1H), 3.28 (s, 3H), 3.40 (d, J=7.4 Hz, 1H), 4.03 (dd, J=13.4, 5.5 Hz, 1H); m/z (ES⁺), [M+H]⁺=355; HPLC (C05) $t_R$=0.63 min (92%).

Compound 102, Step 5: 7-(5-bromo-4-methylthiazol-2-yl)-7-methoxy-4-oxospiro[2.5]oct-5-ene-5-carbonitrile

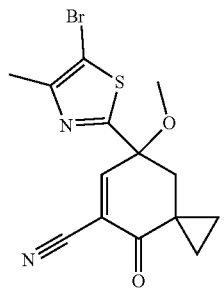 [SMILES: COC1(c2nc(C)c(Br)s2)C=C(C#N)C(=O)C2(CC2)C1]

Pyridine (0.63 mL, 7.77 mmol) in DCM (4 mL) was added dropwise to a solution of phenylselenyl chloride (1.49 g, 7.77 mmol) in DCM (8 mL) at 0° C. 7-(5-Bromo-4-methylthiazol-2-yl)-7-methoxy-4-oxospiro[2.5]octane-5-carbonitrile (1.38 g, 3.88 mmol) in DCM (8 mL) was added dropwise after stirring for 20 min. The mixture was stirred at 0° C. for 2 h and treated with 1M aq. HCl (3 mL) and water (5 mL). The phases were separated and $H_2O_2$ (7.94 mL, 77.7 mmol) was added dropwise to the DCM layer at 0° C. The mixture was vigorously stirred at 0° C. for 40 min. Water (20 mL) was added, and the mixture was extracted with DCM (3×20 mL). The combined organic phases were washed with brine (2×20 mL), dried ($MgSO_4$), filtered, and concentrated under reduced pressure. The crude product was purified by silica gel chromatography (0 to 20% EtOAc in petroleum ether) to afford 7-(5-bromo-4-methylthiazol-2-yl)-7-methoxy-4-oxospiro[2.5]oct-5-ene-5-carbonitrile (1.35 g, 98%) as a yellow oil. $^1$H NMR (400 MHz, $CDCl_3$) δ ppm 0.80 (ddd, J=9.2, 7.3, 4.0 Hz, 1H), 0.98 (ddd, J=9.3, 7.3, 4.0 Hz, 1H), 1.32-1.40 (m, 1H), 1.57 (ddd, J=9.9, 7.3, 3.9 Hz, 1H), 2.40 (s, 3H), 2.44 (d, J=12.0 Hz, 2H), 3.36 (s, 3H), 7.87 (d, J=1.1 Hz, 1H). m/z (ES$^+$), [M+H]$^+$=353; HPLC (C05) $t_R$=1.23 min (91%).

Compound 102, Step 6: 7-methoxy-7-[4-methyl-5-(pyridin-2-yl)-1,3-thiazol-2-yl]-4-oxospiro[2.5]oct-5-ene-5-carbonitrile (Enantiomer A)

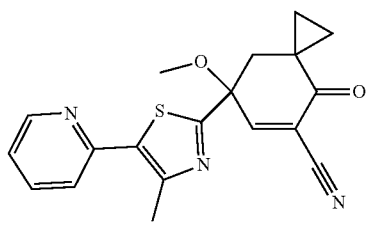

Enantiomer A

Pd(Ph$_3$P)$_4$ (164 mg, 0.14 mmol) was added to 2-(tributylstannyl)pyridine (1.56 g, 4.25 mmol) and 7-(5-bromo-4-methylthiazol-2-yl)-7-methoxy-4-oxospiro[2.5]oct-5-ene-5-carbonitrile (500 mg, 1.42 mmol) in toluene (10 mL) at 25° C. under N$_2$. The mixture was stirred at 100° C. for 18 h and filtered through Celite. The crude product was purified by silica gel chromatography (0 to 25% EtOAc in petroleum ether) and the crude product further purified by preparative HPLC using standard conditions to afford 7-methoxy-7-(4-methyl-5-(pyridin-2-yl)thiazol-2-yl)-4-oxospiro[2.5]oct-5-ene-5-carbonitrile (150 mg, 30%) as a beige solid. Chiral separation as described in the Generic Procedure A gave the title compound (53 mg) and its enantiomer as beige solids. $^1$H NMR (400 MHz, DMSO-d$_6$) δ ppm 0.67-0.75 (m, 1H), 0.92-1.02 (m, 2H), 1.31-1.40 (m, 1H), 2.26 (dd, J=13.8, 1.6, 1H), 2.63 (s, 3H), 2.79 (d, J=13.8, 1H), 3.34 (s, 3H), 7.38 (ddd, J=7.6, 4.8, 1.0, 1H), 7.78 (dd, J=8.0, 1.2, 1H), 7.93 (td, J=7.8, 1.8, 1H), 8.47 (d, J=1.2, 1H), 8.60-8.66 (m, 1H). m/z (ES$^+$), [M+H]$^+$=352; HPLC (C05) $t_R$=1.76 min (99%). ee=96%.

Compound 103: 3-Methoxy-5,5-dimethyl-6-oxo-3-(6-(prop-1-ynyl)pyridin-2-yl)cyclohex-1-enecarbonitrile

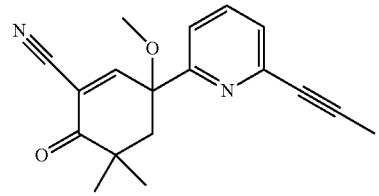 [SMILES: CC#Cc1cccc(C2(OC)C=C(C#N)C(=O)C(C)(C)C2)n1]

Trimethyl(prop-1-yn-1-yl)silane (0.049 mL, 0.33 mmol) was added to a mixture of 3-(6-bromopyridin-2-yl)-3-methoxy-5,5-dimethyl-6-oxocyclohex-1-ene-1-carbonitrile (0.08 g, 0.24 mmol), copper(I) iodide (10.91 mg, 0.06 mmol) and triphenylphosphine palladium chloride (0.017 g, 0.02 mmol) in degassed toluene (1 mL) under nitrogen at r.t. The mixture was treated with DIPEA (0.083 mL, 0.48 mmol) and tetra-n-butylammonium fluoride (1.0 M in THF) (0.334 mL, 0.33 mmol) and stirred at r.t. for 5 days. More catalyst (0.1 eq.) and alkyne (1 eq.) were added and the mixture was stirred for 3 additional days. The mixture was treated with sat. aq. NaHCO$_3$ (1 mL) and extracted with EtOAc (3×1 mL). The combined organic layers were washed with brine (1 mL), dried (Na$_2$SO$_4$), filtered and concentrated. Purification by HPLC under standard conditions yielded the title compound (11.8 mg, 12%). $^1$H NMR (600 MHz, DMSO) δ 8.53 (s, 1H), 7.91 (t, J=7.8, 7.8 Hz, 1H), 7.58 (dd, J=8.0, 0.8 Hz, 1H), 7.46 (dd, J=7.7, 0.8 Hz, 1H), 3.11 (s, 3H), 2.28 (s, 2H), 2.08 (s, 3H), 1.23 (s, 3H), 0.82 (s, 3H).

The compounds provided in Table 7 have been prepared by analogy to the synthesis described for Compound 13, starting from 3-(6-bromo-2-pyridyl)-3-methoxy-5,5-dimethyl-6-oxo-cyclohexene-1-carbonitrile (Compound 2, Suzuki reaction). All pure enantiomers in the following Table were separated as described in the Generic Procedure B for chiral separation of enantiomers (chiral HPLC). For compounds where the enantiomers were separated but for which absolute configuration was not assigned, data is given for the single enantiomer that was tested. For compounds drawn without specified stereochemistry and labeled as "Enantiomer A," all data provided throughout the applica tion for that compound is for the more active enantiomer. For compounds drawn without specified stereochemistry and labeled as "Enantiomer B," all data provided throughout the application for that compound is for the less active enantiomer. For compounds drawn without specified stereochemistry and not labeled as "Enantiomer A" or "Enantiomer B," all data provided throughout the application for that compound is for the racemate.

TABLE 7

Compounds 104-107

| Cmpd # | Structure | Name | Analytical data |
|---|---|---|---|
| 104 | Enantiomer A | 3-methoxy-5,5-dimethyl-6-oxo-3-(6-(pyrimidin-5-yl)pyridin-2-yl)cyclohex-1-ene-1-carbonitrile (Enantiomer A) | $^1$H NMR (500 MHz, CDCl$_3$) δ 1.06 (s, 3H), 1.40 (s, 3H), 2.32 (s, 2H), 3.26 (s, 3H), 7.64 (d, 1H), 7.79 (d, 1H), 7.98 (t, 1H), 8.11 (s, 1H), 9.31 (s, 3H). ee = 92.9%. |
| 105 | 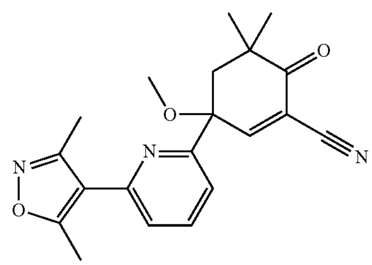 [SMILES: COC1(c2cccc(-c3c(C)noc3C)n2)C=C(C#N)C(=O)C(C)(C)C1] | 3-(6-(3,5-dimethylisoxazol-4-yl)pyridin-2-yl)-3-methoxy-5,5-dimethyl-6-oxocyclohex-1-ene-1-carbonitrile | $^1$H NMR (600 MHz, DMSO-d$_6$) δ 0.79 (s, 3H), 1.24 (s, 3H), 2.35 (s, 2H), 2.38 (s, 3H), 2.58 (s, 3H), 3.17 (s, 3H), 7.58 (t, J = 8.17, 8.17 Hz, 2H), 8.03 (t, J = 7.87, 7.87 Hz, 1H), 8.62 (s, 1H). |
| 106 | 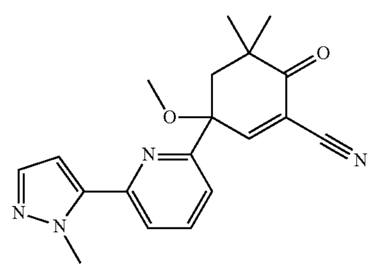 [SMILES: COC1(c2cccc(-c3ccnn3C)n2)C=C(C#N)C(=O)C(C)(C)C1] | 3-methoxy-5,5-dimethyl-3-(6-(1-methyl-1H-pyrazol-5-yl)pyridin-2-yl)-6-oxocyclohex-1-ene-1-carbonitrile | $^1$H NMR (500 MHz, DMSO-d$_6$) δ 0.80 (s, 3H), 1.24 (s, 3H), 2.37 (s, 2H), 3.18 (s, 3H), 4.11 (s, 3H), 6.89 (d, 1H), 7.49 (d, 1H), 7.60 (d, 1H), 7.84 (d, 1H), 8.04 (t, 1H), 8.70 (s, 1H). |
| 107 | Enantiomer A | 3-methoxy-5,5-dimethyl-3-(6-(1-methyl-1H-pyrazol-4-yl)pyridin-2-yl)-6-oxocyclohex-1-ene-1-carbonitrile (Enantiomer A) | $^1$H NMR (500 MHz, CDCl$_3$) δ 1.01 (s, 3H), 1.37 (s, 3H), 2.27 (d, 2H), 3.213 (s, 3H), 3.97 (s, 3H), 7.33 (d, 1H), 7.42 (d, 1H), 7.75 (t, 1H), 7.89 (d, 2H), 8.15 (s, 1H). ee = 99%. |

Compound 108: 3-(3-bromo-2-pyridyl)-3-methoxy-2,5,5-trimethyl-6-oxo-cyclohexene-1-carbonitrile

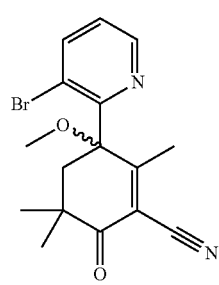 [SMILES: COC1(c2ncccc2Br)CC(C)(C)C(=O)C(C#N)=C1C]

Compound 108, Step 1: 3-(3-bromo-2-pyridyl)-3-methoxy-2,5,5-trimethyl-6-oxo-cyclohexanescarbonitrile

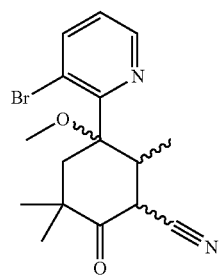 [SMILES: COC1(c2ncccc2Br)CC(C)(C)C(=O)C(C#N)C1C]

To a mixture of CuI (4.26 mg, 0.0200 mmol) in THF (1.00 mL) at −78° C. was added 3.0M MeMgBr in Et$_2$O (0.160 mL, 0.490 mmol). A solution of 3-(3-bromo-2-pyridyl)-3-methoxy-5,5-dimethyl-6-oxo-cyclohexene-1-carbonitrile (150 mg, 0.450 mmol) in THF (2 mL) was added dropwise. The mixture was stirred at −78° C. for 45 min and warmed to 0° C. Stirring was continued at 0° C. for 30 min. Sat. aq. NH$_4$Cl (20 mL) was added, and the aq. phase was extracted with EtOAc (3×20 mL). The combined organic phases were washed with brine (20 mL), dried (MgSO$_4$), filtered, and concentrated under reduced pressure. The product was purified by silica gel chromatography (12 g cartridge), eluting with hexanes and EtOAc (0-40%), to provide the title compound as a solid (39 mg, 25%). $^1$H NMR (500 MHz, CDCl$_3$) δ 8.51 (dd, J=4.5, 1.5 Hz, 1H), 7.97 (dd, J=8.0, 1.5 Hz, 1H), 7.14 (dd, J=8.0, 4.5 Hz, 1H), 4.89 (d, J=4.4 Hz, 1H), 3.79-3.65 (m, 1H), 3.14 (s, 3H), 2.81 (d, J=16.0 Hz, 1H), 2.44-2.29 (m, 1H), 1.42 (s, 3H), 1.24 (s, 3H), 0.69 (d, J=7.3 Hz, 3H). m/z (ES+), [M+H]$^+$: 351.3. HPLC (B05) $t_R$=1.21 min.

Compound 108, Step 2: 3-(3-bromo-2-pyridyl)-3-methoxy-2,5,5-trimethyl-6-oxo-cyclohexene-1-carbonitrile

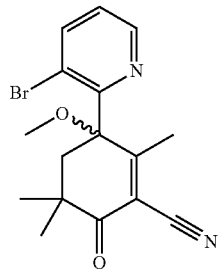 [SMILES: COC1(c2ncccc2Br)CC(C)(C)C(=O)C(C#N)=C1C]

As described for step 8 of Compound 11, the title compound was prepared from phenylselenium chloride (42.5 mg, 0.220 mmol), pyridine (18 uL, 0.220 mmol), 3-(3-bromo-2-pyridyl)-3-methoxy-2,5,5-trimethyl-6-oxo-cyclohexanescarbonitrile (39.0 mg, 0.110 mmol), and 35 wt % H$_2$O$_2$ in water (9.49 mL, 97.6 mmol) in DCM (2.50 mL). The product was purified by silica gel chromatography (4 g cartridge), eluting with hexanes and EtOAc (0-60%), to provide the title compound as a solid (25.7 mg, 66%). $^1$H NMR (500 MHz, CDCl$_3$) δ 8.40 (dd, J=4.6, 1.5 Hz, 1H), 7.98 (dd, J=8.0, 1.5 Hz, 1H), 7.14 (dd, J=8.0, 4.6 Hz, 1H), 3.34 (s, 3H), 2.89 (d, J=14.3 Hz, 1H), 2.48 (t, J=11.4 Hz, 1H), 2.33 (s, 3H), 1.22 (s, 3H), 0.60 (s, 3H). m/z (ES+), [M+H]$^+$: 349.2. HPLC (A05) $t_R$=2.39 min.

Compounds provided in Table 8 were prepared using procedures analogous to those above. For example, compounds 109-110, 113-115, 123-124, 134, 137, 139, 141-145, 147, 150-151, 154, 158, 174, 197-198, 204, 206, 208, 211, 214, 216, 224-225, and 239 have been prepared by analogy to the synthesis described for compound 3. Compounds 111-112, 116-120, 122, and 125 have been prepared by analogy to the synthesis described for compound 13. Compound 152 has been prepared by analogy to the synthesis described for compound 42. Compounds 126-130 have been prepared by analogy to the synthesis described for compound 49. Compounds 131-133, 135-136, 140, 156-157, 160, 162, 196, and 238 have been prepared by analogy to the synthesis described for compound 54. Compounds 146, 148-149, and 153 have been prepared by analogy to the synthesis described for compound 66. Compounds 161, 163-164, 166-168, 170-173, 175, 177-193, 195, 199-203, 205, 207, 209-210, 212-213, 215, 217-223, and 226-237 have been prepared by analogy to the synthesis described for compound 69. Compounds 155 and 194 have been prepared by analogy to the synthesis described for compound 99. For compounds where the enantiomers were separated but for which absolute configuration was not assigned, data is given for the single enantiomer that was tested. For compounds drawn without specified stereochemistry and labeled as "Enantiomer A," all data provided throughout the application for that compound is for the more active enantiomer. For compounds drawn without specified stereochemistry and labeled as "Enantiomer B," all data provided throughout the application for that compound is for the less active enantiomer. For compounds drawn without specified stereochemistry and not labeled as "Enantiomer A" or "Enantiomer B," all data provided throughout the application for that compound is for the racemate.

TABLE 8

Compounds 109-120, 122-137, 139-158, 160-212, and 214-240

| Cmpd # | Structure | Name | Analytical Data |
|---|---|---|---|
| 109 | 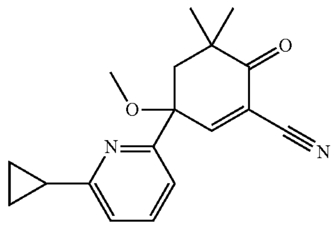 [SMILES: COC1(c2cccc(C3CC3)n2)C=C(C#N)C(=O)C(C)(C)C1] | 3-(6-cyclopropylpyridin-2-yl)-3-methoxy-5,5-dimethyl-6-oxocyclohex-1-ene-1-carbonitrile | 1H NMR (400 MHz, CDCl$_3$) δ 8.06 (s, 1H), 7.64 (t, J = 7.8 Hz, 1H), 7.31-7.26 (m, 1H), 7.13 (dd, J = 7.8, 0.9 Hz, 1H), 3.19 (s, 3H), 2.26 (s, 2H), 2.06-2.01 (m, 1H), 1.36 (s, 3H), 1.04-0.99 (m, 5H), 0.98 (s, 2H), 0.93 (ddd, J = 6.0, 4.6, 3.2 Hz, 1H). LCMS rt: 7.1 [M + H]+ = 297 |
| 110 | 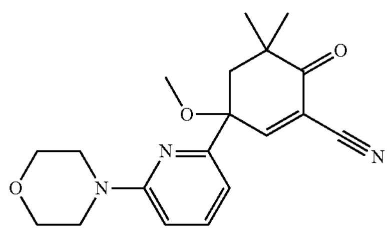 [SMILES: COC1(c2cccc(N3CCOCC3)n2)C=C(C#N)C(=O)C(C)(C)C1] | 3-methoxy-5,5-dimethyl-3-[6-(morpholin-4-yl)pyridin-2-yl]-6-oxocyclohex-1-ene-1-carbonitrile | m/z (ES+), [M + H]+ = 342 |
| 111 | 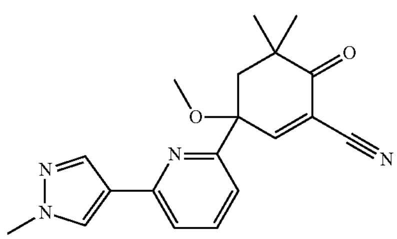 [SMILES: COC1(c2cccc(-c3cnn(C)c3)n2)C=C(C#N)C(=O)C(C)(C)C1] | 3-methoxy-5,5-dimethyl-3-[6-(1-methyl-1H-pyrazol-4-yl)pyridin-2-yl]-6-oxocyclohex-1-ene-1-carbonitrile | m/z (ES+), [M + H]+ = 337 |
| 112 | 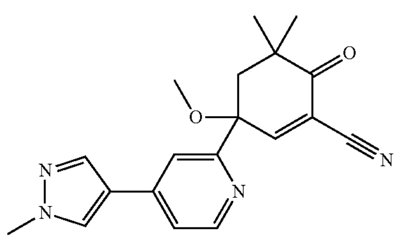 [SMILES: COC1(c2cc(-c3cnn(C)c3)ccn2)C=C(C#N)C(=O)C(C)(C)C1] | 3-methoxy-5,5-dimethyl-3-[4-(1-methyl-1H-pyrazol-4-yl)pyridin-2-yl]-6-oxocyclohex-1-ene-1-carbonitrile | m/z (ES+), [M + H]+ = 337 |
| 113 | 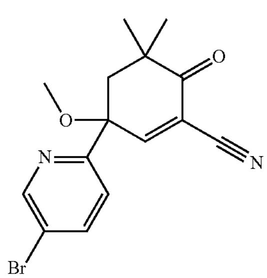 | 3-(5-bromopyridin-2-yl)-3-methoxy-5,5-dimethyl-6-oxocyclohex-1-ene-1-carbonitrile | m/z (ES+), [M + H]+ = 335 |

TABLE 8-continued

Compounds 109-120, 122-137, 139-158, 160-212, and 214-240

| Cmpd # | Structure | Name | Analytical Data |
|---|---|---|---|
| 114 | 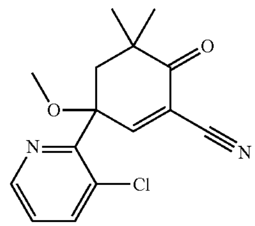 [SMILES: COC1(c2ncccc2Cl)C=C(C#N)C(=O)C(C)(C)C1] | 3-(3-chloropyridin-2-yl)-3-methoxy-5,5-dimethyl-6-oxocyclohex-1-ene-1-carbonitrile | m/z (ES+), [M + H]+ = 291 |
| 115 | 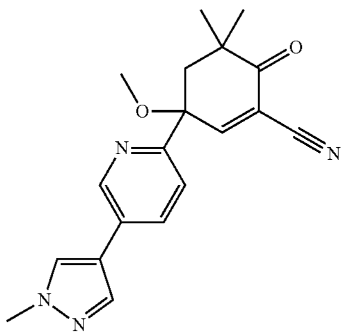 [SMILES: COC1(c2ccc(-c3cnn(C)c3)cn2)C=C(C#N)C(=O)C(C)(C)C1] | 3-methoxy-5,5-dimethyl-3-[5-(1-methyl-1H-pyrazol-4-yl)pyridin-2-yl]-6-oxocyclohex-1-ene-1-carbonitrile | m/z (ES+), [M + H]+ = 337 |
| 116 | 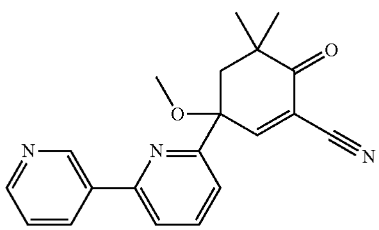 [SMILES: COC1(c2cccc(-c3cccnc3)n2)C=C(C#N)C(=O)C(C)(C)C1] | 3-([2,3'-bipyridin]-6-yl)-3-methoxy-5,5-dimethyl-6-oxocyclohex-1-ene-1-carbonitrile | m/z (ES+), [M + H]+ = 334 |
| 117 | 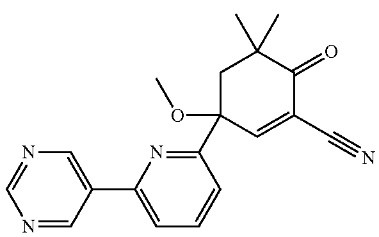 [SMILES: COC1(c2cccc(-c3cncnc3)n2)C=C(C#N)C(=O)C(C)(C)C1] | 3-methoxy-5,5-dimethyl-6-oxo-3-[6-(pyrimidin-5-yl)pyridin-2-yl]cyclohex-1-ene-1-carbonitrile | m/z (ES+), [M + H]+ = 335 |
| 118 | 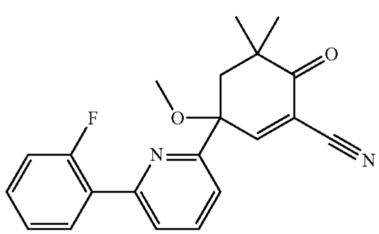 [SMILES: COC1(c2cccc(-c3ccccc3F)n2)C=C(C#N)C(=O)C(C)(C)C1] | 3-[6-(2-fluorophenyl)pyridin-2-yl]-3-methoxy-5,5-dimethyl-6-oxocyclohex-1-ene-1-carbonitrile | m/z (ES+), [M + H]+ = 351 |
| 119 | 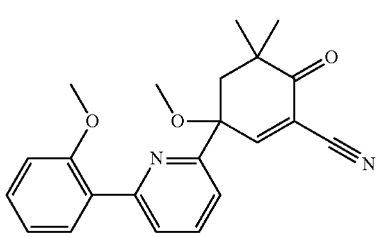 [SMILES: COc1ccccc1-c1cccc(C2(OC)C=C(C#N)C(=O)C(C)(C)C2)n1] | 3-methoxy-3-[6-(2-methoxyphenyl)pyridin-2-yl]-5,5-dimethyl-6-oxocyclohex-1-ene-1-carbonitrile | m/z (ES+), [M + H]+ = 363 |

TABLE 8-continued

Compounds 109-120, 122-137, 139-158, 160-212, and 214-240

| Cmpd # | Structure | Name | Analytical Data |
|---|---|---|---|
| 120 | Enantiomer A | 3-methoxy-3-[6-(2-methoxyphenyl)pyridin-2-yl]-5,5-dimethyl-6-oxocyclohex-1-ene-1-carbonitrile | |
| 122 | 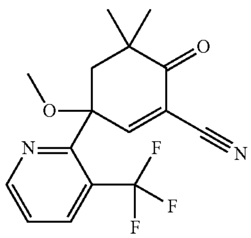 [SMILES: COC1(c2ncccc2C(F)(F)F)C=C(C#N)C(=O)C(C)(C)C1] | 3-methoxy-5,5-dimethyl-6-oxo-3-[3-(trifluoromethyl)pyridin-2-yl]cyclohex-1-ene-1-carbonitrile | m/z (ES+), [M + H]+ = 325 |
| 123 | 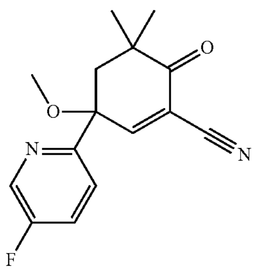 [SMILES: COC1(c2ccc(F)cn2)C=C(C#N)C(=O)C(C)(C)C1] | 3-(5-fluoropyridin-2-yl)-3-methoxy-5,5-dimethyl-6-oxocyclohex-1-ene-1-carbonitrile | m/z (ES+), [M + H]+ = 275; HPLC purity = 99.1%. |
| 124 | 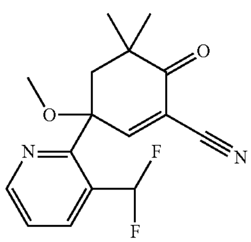 [SMILES: COC1(c2ncccc2C(F)F)C=C(C#N)C(=O)C(C)(C)C1] | 3-[3-(difluoromethyl)pyridin-2-yl]-3-methoxy-5,5-dimethyl-6-oxocyclohex-1-ene-1-carbonitrile | m/z (ES+), [M + H]+ = 307 |
| 125 | 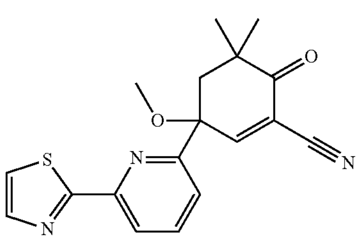 [SMILES: COC1(c2cccc(-c3nccs3)n2)C=C(C#N)C(=O)C(C)(C)C1] | 3-methoxy-5,5-dimethyl-6-oxo-3-[6-(1,3-thiazol-2-yl)pyridin-2-yl]cyclohex-1-ene-1-carbonitrile | m/z (ES+), [M + H]+ = 340 |
| 126 | 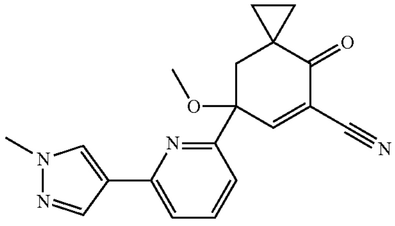 [SMILES: COC1(c2cccc(-c3cnn(C)c3)n2)C=C(C#N)C(=O)C2(CC2)C1] | 7-methoxy-7-[6-(1-methyl-1H-pyrazol-4-yl)pyridin-2-yl]-4-oxospiro[2.5]oct-5-ene-5-carbonitrile | m/z (ES+), [M + H]+ = 335; HPLC purity = 98.8%. |

TABLE 8-continued

Compounds 109-120, 122-137, 139-158, 160-212, and 214-240

| Cmpd # | Structure | Name | Analytical Data |
| --- | --- | --- | --- |
| 127 | 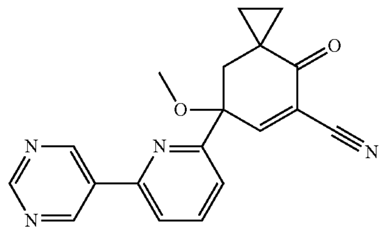 [SMILES: COC1(c2cccc(-c3cncnc3)n2)C=C(C#N)C(=O)C2(CC2)C1] | 7-methoxy-4-oxo-7-[6-(pyrimidin-5-yl)pyridin-2-yl]spiro[2.5]oct-5-ene-5-carbonitrile | m/z (ES$^+$), [M + H]$^+$ = 333; HPLC purity = 99.5%. |
| 128 | 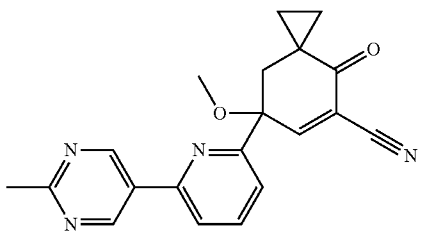 [SMILES: COC1(c2cccc(-c3cnc(C)nc3)n2)C=C(C#N)C(=O)C2(CC2)C1] | 7-methoxy-7-[6-(2-methylpyrimidin-5-yl)pyridin-2-yl]-4-oxospiro[2.5]oct-5-ene-5-carbonitrile | m/z (ES$^+$), [M + H]$^+$ = 347; HPLC purity = 99.4%. |
| 129 | 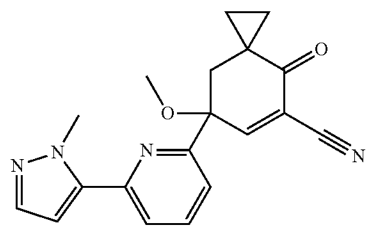 [SMILES: COC1(c2cccc(-c3ccnn3C)n2)C=C(C#N)C(=O)C2(CC2)C1] | 7-methoxy-7-[6-(1-methyl-1H-pyrazol-5-yl)pyridin-2-yl]-4-oxospiro[2.5]oct-5-ene-5-carbonitrile | m/z (ES$^+$), [M + H]$^+$ = 335; HPLC purity = 99.8%. |
| 130 | 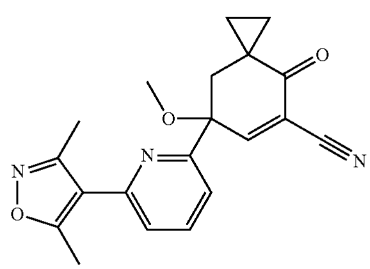 [SMILES: COC1(c2cccc(-c3c(C)noc3C)n2)C=C(C#N)C(=O)C2(CC2)C1] | 7-[6-(3,5-dimethyl-1,2-oxazol-4-yl)pyridin-2-yl]-7-methoxy-4-oxospiro[2.5]oct-5-ene-5-carbonitrile | m/z (ES$^+$), [M + H]$^+$ = 350; HPLC purity = 99.9%. |
| 131 | 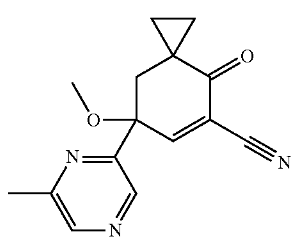 [SMILES: COC1(c2cncc(C)n2)C=C(C#N)C(=O)C2(CC2)C1] | 7-methoxy-7-(6-methylpyrazin-2-yl)-4-oxospiro[2.5]oct-5-ene-5-carbonitrile | m/z (ES$^+$), [M + H]$^+$ = 270; HPLC purity = 95.3%. |
| 132 | 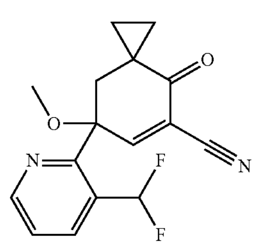 [SMILES: COC1(c2ncccc2C(F)F)C=C(C#N)C(=O)C2(CC2)C1] | 7-[3-(difluoromethyl)pyridin-2-yl]-7-methoxy-4-oxospiro[2.5]oct-5-ene-5-carbonitrile | m/z (ES$^+$), [M + H]$^+$ = 305; HPLC purity = 99.3%. |

TABLE 8-continued

Compounds 109-120, 122-137, 139-158, 160-212, and 214-240

| Cmpd # | Structure | Name | Analytical Data |
|---|---|---|---|
| 133 | 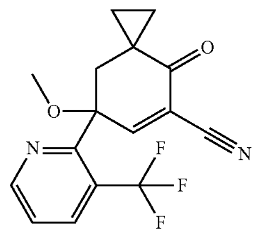 [SMILES: COC1(c2ncccc2C(F)(F)F)C=C(C#N)C(=O)C2(CC2)C1] | 7-methoxy-4-oxo-7-[3-(trifluoromethyl)pyridin-2-yl]spiro[2.5]oct-5-ene-5-carbonitrile | m/z (ES+), [M + H]+ = 323; HPLC purity = 97.1%. |
| 134 | 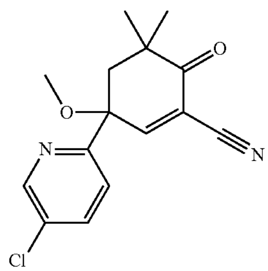 [SMILES: COC1(c2ccc(Cl)cn2)C=C(C#N)C(=O)C(C)(C)C1] | 3-(5-chloropyridin-2-yl)-3-methoxy-5,5-dimethyl-6-oxocyclohex-1-ene-1-carbonitrile | m/z (ES+), [M + H]+ = 291; HPLC purity = 99.2%. |
| 135 | 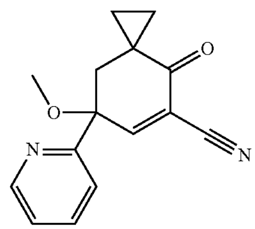 [SMILES: COC1(c2ccccn2)C=C(C#N)C(=O)C2(CC2)C1] | 7-methoxy-4-oxo-7-(pyridin-2-yl)spiro[2.5]oct-5-ene-5-carbonitrile | m/z (ES+), [M + H]+ = 255; HPLC purity = 98.0%). |
| 136 | 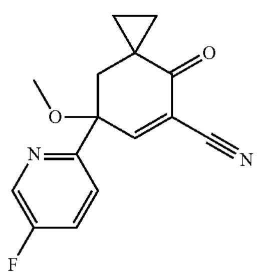 [SMILES: COC1(c2ccc(F)cn2)C=C(C#N)C(=O)C2(CC2)C1] | 7-(5-fluoropyridin-2-yl)-7-methoxy-4-oxospiro[2.5]oct-5-ene-5-carbonitrile | m/z (ES+), [M + H]+ = 273; HPLC purity = 98.4%. |
| 137 | 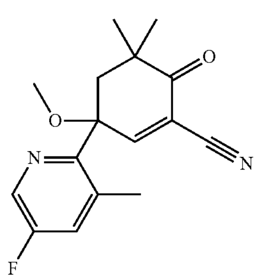 [SMILES: COC1(c2ncc(F)cc2C)C=C(C#N)C(=O)C(C)(C)C1] | 3-(5-fluoro-3-methylpyridin-2-yl)-3-methoxy-5,5-dimethyl-6-oxocyclohex-1-ene-1-carbonitrile | m/z (ES+), [M + H]+ = 289; HPLC purity = 99.6%. |
| 139 | 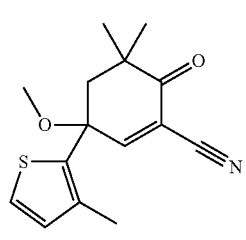 [SMILES: COC1(c2sccc2C)C=C(C#N)C(=O)C(C)(C)C1] | 3-methoxy-5,5-dimethyl-3-(3-methylthiophen-2-yl)-6-oxocyclohex-1-ene-1-carbonitrile | m/z (ES+), [M + H]+ = 276; HPLC purity = 97.0%. |

TABLE 8-continued

Compounds 109-120, 122-137, 139-158, 160-212, and 214-240

| Cmpd # | Structure | Name | Analytical Data |
|---|---|---|---|
| 140 | 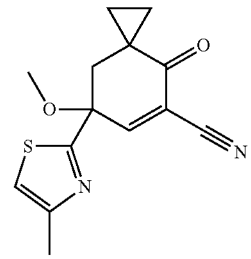 [SMILES: COC1(c2nc(C)cs2)C=C(C#N)C(=O)C2(CC2)C1] | 7-methoxy-7-(4-methyl-1,3-thiazol-2-yl)-4-oxospiro[2.5]oct-5-ene-5-carbonitrile | m/z (ES+), [M + H]+ = 275; HPLC purity = 92.3%. |
| 141 | 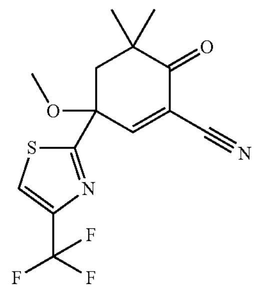 [SMILES: COC1(c2nc(C(F)(F)F)cs2)C=C(C#N)C(=O)C(C)(C)C1] | 3-methoxy-5,5-dimethyl-6-oxo-3-[4-(trifluoromethyl)-1,3-thiazol-2-yl]cyclohex-1-ene-1-carbonitrile | m/z (ES+), [M + H]+ = 331; HPLC purity = 97.1%. |
| 142 | 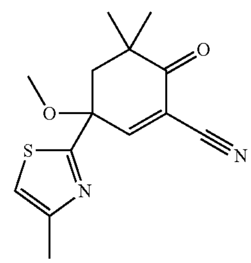 [SMILES: COC1(c2nc(C)cs2)C=C(C#N)C(=O)C(C)(C)C1] | 3-methoxy-5,5-dimethyl-3-(4-methyl-1,3-thiazol-2-yl)-6-oxocyclohex-1-ene-1-carbonitrile | m/z (ES+), [M + H]+ = 277; HPLC purity = 97.0%. |
| 143 | 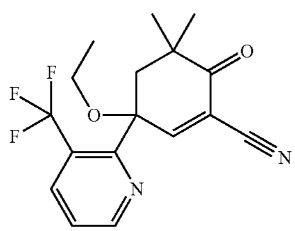 [SMILES: CCOC1(c2ncccc2C(F)(F)F)C=C(C#N)C(=O)C(C)(C)C1] | 3-ethoxy-5,5-dimethyl-6-oxo-3-[3-(trifluoromethyl)pyridin-2-yl]cyclohex-1-ene-1-carbonitrile | m/z (ES+), [M + H]+ = 339; HPLC purity = 99.6%. |
| 144 | 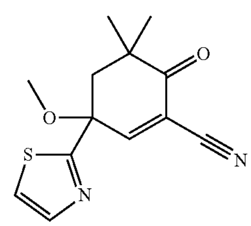 [SMILES: COC1(c2nccs2)C=C(C#N)C(=O)C(C)(C)C1] | 3-methoxy-5,5-dimethyl-6-oxo-3-(1,3-thiazol-2-yl)cyclohex-1-ene-1-carbonitrile | m/z (ES+), [M + H]+ = 263; HPLC purity = 96.8%. |
| 145 | 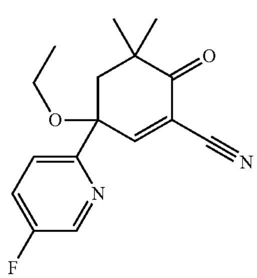 [SMILES: CCOC1(c2ccc(F)cn2)C=C(C#N)C(=O)C(C)(C)C1] | 3-ethoxy-3-(5-fluoropyridin-2-yl)-5,5-dimethyl-6-oxocyclohex-1-ene-1-carbonitrile | m/z (ES+), [M + H]+ = 289; HPLC purity = 98.9%. |

TABLE 8-continued

Compounds 109-120, 122-137, 139-158, 160-212, and 214-240

| Cmpd # | Structure | Name | Analytical Data |
|---|---|---|---|
| 146 | 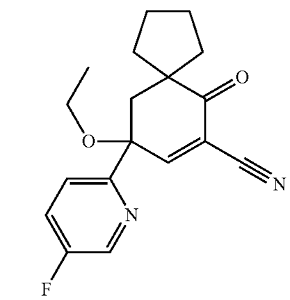 [SMILES: CCOC1(c2ccc(F)cn2)C=C(C#N)C(=O)C2(CCCC2)C1] | 9-ethoxy-9-(5-fluoropyridin-2-yl)-6-oxospiro[4.5]dec-7-ene-7-carbonitrile | |
| 147 | 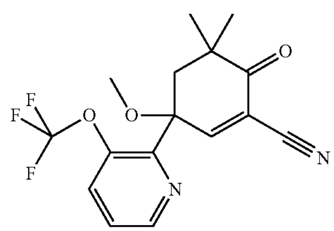 [SMILES: COC1(c2ncccc2OC(F)(F)F)C=C(C#N)C(=O)C(C)(C)C1] | 3-methoxy-5,5-dimethyl-6-oxo-3-[3-(trifluoromethoxy)pyridin-2-yl]cyclohex-1-ene-1-carbonitrile | m/z (ES$^+$), [M + H]$^+$ = 341; HPLC purity = 98.8%. |
| 148 | 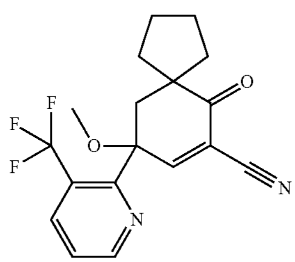 [SMILES: COC1(c2ncccc2C(F)(F)F)C=C(C#N)C(=O)C2(CCCC2)C1] | 9-methoxy-6-oxo-9-[3-(trifluoromethyl)pyridin-2-yl]spiro[4.5]dec-7-ene-7-carbonitrile | m/z (ES$^+$), [M + H]$^+$ = 351; HPLC purity = 98.8%. |
| 149 | 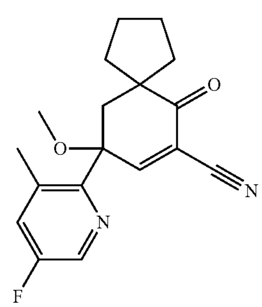 [SMILES: COC1(c2ncc(F)cc2C)C=C(C#N)C(=O)C2(CCCC2)C1] | 9-(5-fluoro-3-methylpyridin-2-yl)-9-methoxy-6-oxospiro[4.5]dec-7-ene-7-carbonitrile | m/z (ES$^+$), [M + H]$^+$ = 315; HPLC purity = 98.1%. |
| 150 | 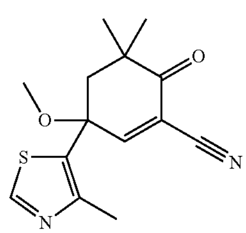 [SMILES: COC1(c2scnc2C)C=C(C#N)C(=O)C(C)(C)C1] | 3-methoxy-5,5-dimethyl-3-(4-methyl-1,3-thiazol-5-yl)-6-oxocyclohex-1-ene-1-carbonitrile | m/z (ES$^+$), [M + H]$^+$ = 277; HPLC purity = 95.4%. |

TABLE 8-continued

Compounds 109-120, 122-137, 139-158, 160-212, and 214-240

| Cmpd # | Structure | Name | Analytical Data |
|---|---|---|---|
| 151 | 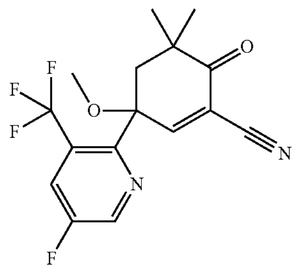 [SMILES: COC1(c2ncc(F)cc2C(F)(F)F)C=C(C#N)C(=O)C(C)(C)C1] | 3-[5-fluoro-3-(trifluoromethyl)pyridin-2-yl]-3-methoxy-5,5-dimethyl-6-oxocyclohex-1-ene-1-carbonitrile | m/z (ES$^+$), [M + H]$^+$ = 343; HPLC purity = 98.1%. |
| 152 | 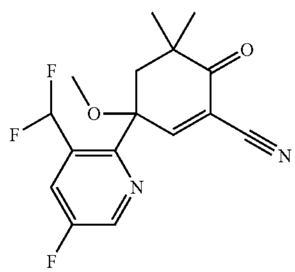 [SMILES: COC1(c2ncc(F)cc2C(F)F)C=C(C#N)C(=O)C(C)(C)C1] | 3-[3-(difluoromethyl)-5-fluoropyridin-2-yl]-3-methoxy-5,5-dimethyl-6-oxocyclohex-1-ene-1-carbonitrile | m/z (ES$^+$), [M + H]$^+$ = 325; HPLC purity = 99.5%. |
| 153 | Enantiomer B | 9-(5-fluoro-3-methylpyridin-2-yl)-9-methoxy-6-oxospiro[4.5]dec-7-ene-7-carbonitrile | m/z (ES$^+$), [M + H]$^+$ = 315; HPLC purity = 99.9%. ee = 99.5%. |
| 154 | 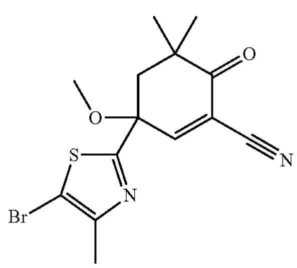 [SMILES: COC1(c2nc(C)c(Br)s2)C=C(C#N)C(=O)C(C)(C)C1] | 3-(5-bromo-4-methyl-1,3-thiazol-2-yl)-3-methoxy-5,5-dimethyl-6-oxocyclohex-1-ene-1-carbonitrile | m/z (ES$^+$), [M + H]$^+$ = 355; HPLC purity = 97.0%. |
| 155 | 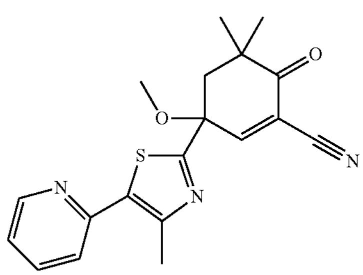 [SMILES: COC1(c2nc(C)c(-c3ccccn3)s2)C=C(C#N)C(=O)C(C)(C)C1] | 3-methoxy-5,5-dimethyl-3-[4-methyl-5-(pyridin-2-yl)-1,3-thiazol-2-yl]-6-oxocyclohex-1-ene-1-carbonitrile | m/z (ES$^+$), [M + H]$^+$ = 354; HPLC purity = 97.3%. |

TABLE 8-continued

Compounds 109-120, 122-137, 139-158, 160-212, and 214-240

| Cmpd # | Structure | Name | Analytical Data |
| --- | --- | --- | --- |
| 156 | 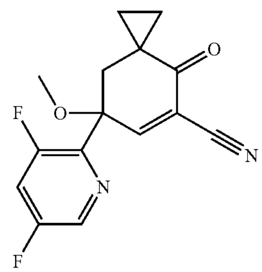 [SMILES: COC1(c2ncc(F)cc2F)C=C(C#N)C(=O)C2(CC2)C1] | 7-(3,5-difluoropyridin-2-yl)-7-methoxy-4-oxospiro[2.5]oct-5-ene-5-carbonitrile | m/z (ES$^+$), [M + H]$^+$ = 291; HPLC purity = 98.1%. |
| 157 | 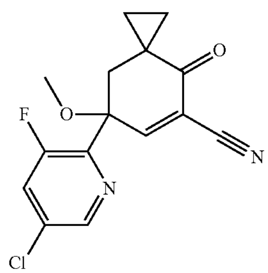 [SMILES: COC1(c2ncc(Cl)cc2F)C=C(C#N)C(=O)C2(CC2)C1] | 7-(5-chloro-3-fluoropyridin-2-yl)-7-methoxy-4-oxospiro[2.5]oct-5-ene-5-carbonitrile | m/z (ES$^+$), [M + H]$^+$ = 307; HPLC purity = 99.0%. |
| 158 | 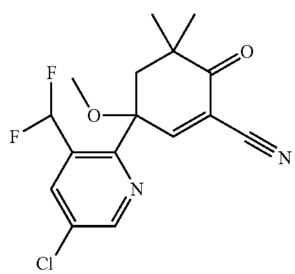 [SMILES: COC1(c2ncc(Cl)cc2C(F)F)C=C(C#N)C(=O)C(C)(C)C1] | 3-[5-chloro-3-(difluoromethyl)pyridin-2-yl]-3-methoxy-5,5-dimethyl-6-oxocyclohex-1-ene-1-carbonitrile | m/z (ES$^+$), [M + H]$^+$ = 341; HPLC purity = 99.7%. |
| 160 | 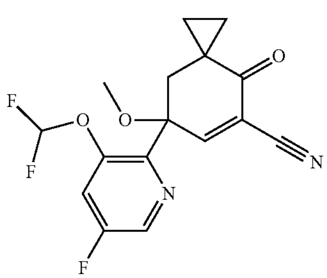 [SMILES: COC1(c2ncc(F)cc2OC(F)F)C=C(C#N)C(=O)C2(CC2)C1] | 7-[3-(difluoromethoxy)-5-fluoropyridin-2-yl]-7-methoxy-4-oxospiro[2.5]oct-5-ene-5-carbonitrile | m/z (ES$^+$), [M + H]$^+$ = 339; HPLC purity = 99.6%. |
| 161 | 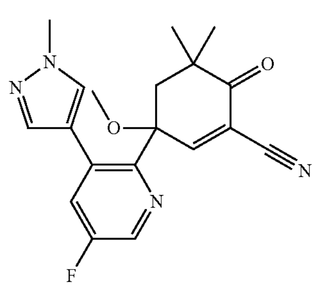 [SMILES: COC1(c2ncc(F)cc2-c2cnn(C)c2)C=C(C#N)C(=O)C(C)(C)C1] | 3-[5-fluoro-3-(1-methyl-1H-pyrazol-4-yl)pyridin-2-yl]-3-methoxy-5,5-dimethyl-6-oxocyclohex-1-ene-1-carbonitrile | m/z (ES$^+$), [M + H]$^+$ = 355; HPLC purity = 97.0%. |

TABLE 8-continued

Compounds 109-120, 122-137, 139-158, 160-212, and 214-240

| Cmpd # | Structure | Name | Analytical Data |
|---|---|---|---|
| 162 | 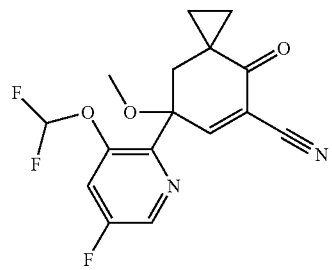 [SMILES: COC1(c2ncc(F)cc2OC(F)F)C=C(C#N)C(=O)C2(CC2)C1] | 7-[3-(difluoromethoxy)-5-fluoropyridin-2-yl]-7-methoxy-4-oxospiro[2.5]oct-5-ene-5-carbonitrile, Isomer 1 | m/z (ES+), [M + H]+ = 339; HPLC purity = 99.3%. ee = 100%. |
| 163 | 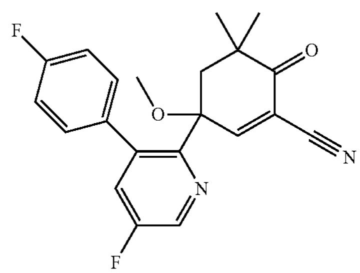 [SMILES: COC1(c2ncc(F)cc2-c2ccc(F)cc2)C=C(C#N)C(=O)C(C)(C)C1] | 3-[5-fluoro-3-(4-fluorophenyl)pyridin-2-yl]-3-methoxy-5,5-dimethyl-6-oxocyclohex-1-ene-1-carbonitrile | 1H NMR (400 MHz, DMSO-d6) δ ppm 0.66 (s, 3H), 0.97 (s, 3H), 2.02-2.16 (m, 2H), 3.10 (s, 3H), 7.25-7.36 (m, 2H), 7.42-7.53 (m, 2H), 7.72 (dd, J = 9.3, 2.8 Hz, 1H), 8.46 (s, 1H), 8.68 (d, J = 2.8 Hz, 1H); m/z (ES+), [M + H]+ = 369; HPLC purity = 99.1%. |
| 164 | 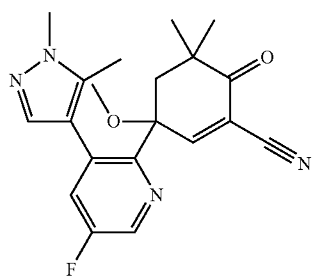 [SMILES: COC1(c2ncc(F)cc2-c2cnn(C)c2C)C=C(C#N)C(=O)C(C)(C)C1] | 3-[3-(1,5-dimethyl-1H-pyrazol-4-yl)-5-fluoropyridin-2-yl]-3-methoxy-5,5-dimethyl-6-oxocyclohex-1-ene-1-carbonitrile | m/z (ES+), [M + H]+ = 369; HPLC purity = 99.9%. |
| 165 | 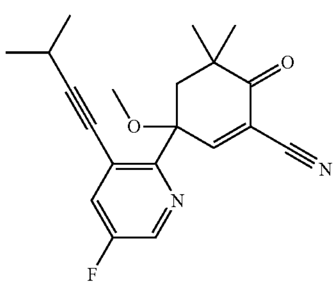 [SMILES: COC1(c2ncc(F)cc2C#CC(C)C)C=C(C#N)C(=O)C(C)(C)C1] | 3-[5-fluoro-3-(3-methylbut-1-yn-1-yl)pyridin-2-yl]-3-methoxy-5,5-dimethyl-6-oxocyclohex-1-ene-1-carbonitrile | m/z (ES+), [M + H]+ = 341; HPLC purity = 98.6%. |
| 166 | 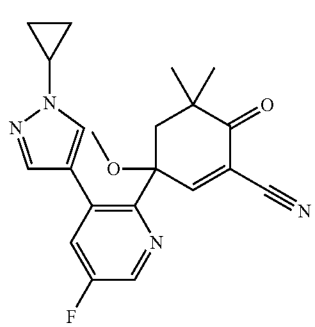 [SMILES: COC1(c2ncc(F)cc2-c2cnn(C3CC3)c2)C=C(C#N)C(=O)C(C)(C)C1] | 3-[3-(1-cyclopropyl-1H-pyrazol-4-yl)-5-fluoropyridin-2-yl]-3-methoxy-5,5-dimethyl-6-oxocyclohex-1-ene-1-carbonitrile | m/z (ES+), [M + H]+ = 381; HPLC purity = 99.6%. |

TABLE 8-continued

Compounds 109-120, 122-137, 139-158, 160-212, and 214-240

| Cmpd # | Structure | Name | Analytical Data |
|---|---|---|---|
| 167 | 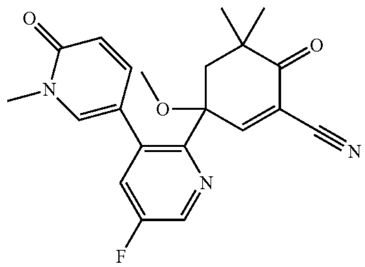 [SMILES: COC1(c2ncc(F)cc2-c2ccc(=O)n(C)c2)C=C(C#N)C(=O)C(C)(C)C1] | 3-(5-fluoro-1'-methyl-6'-oxo[1',6'-dihydro[3,3'-bipyridine]]-2-yl)-3-methoxy-5,5-dimethyl-6-oxocyclohex-1-ene-1-carbonitrile | m/z (ES$^+$), [M + H]$^+$ = 382; HPLC purity = 98.5%. |
| 168 | 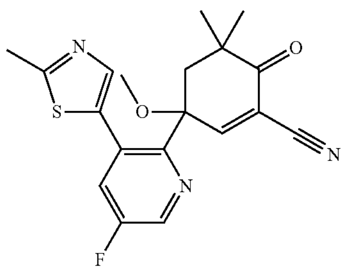 [SMILES: COC1(c2ncc(F)cc2-c2cnc(C)s2)C=C(C#N)C(=O)C(C)(C)C1] | 3-[5-fluoro-3-(2-methyl-1,3-thiazol-5-yl)pyridin-2-yl]-3-methoxy-5,5-dimethyl-6-oxocyclohex-1-ene-1-carbonitrile | m/z (ES$^+$), [M + H]$^+$ = 372; HPLC purity = 99.7%. |
| 169 | 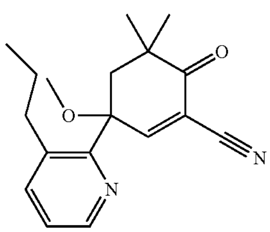 [SMILES: CCCc1cccnc1C1(OC)C=C(C#N)C(=O)C(C)(C)C1] | 3-methoxy-5,5-dimethyl-6-oxo-3-(3-propylpyridin-2-yl)cyclohex-1-ene-1-carbonitrile | m/z (ES$^+$), [M + H]$^+$ = 299; HPLC purity = 99.5%. |
| 170 | 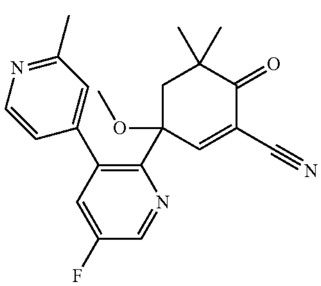 [SMILES: COC1(c2ncc(F)cc2-c2ccnc(C)c2)C=C(C#N)C(=O)C(C)(C)C1] | 3-(5-fluoro-2'-methyl[3,4'-bipyridin]-2-yl)-3-methoxy-5,5-dimethyl-6-oxocyclohex-1-ene-1-carbonitrile | m/z (ES$^+$), [M + H]$^+$ = 366; HPLC purity = 95.4%. |
| 171 | 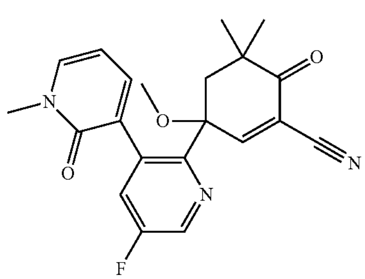 [SMILES: COC1(c2ncc(F)cc2-c2cccn(C)c2=O)C=C(C#N)C(=O)C(C)(C)C1] | 3-(5-fluoro-1'-methyl-2'-oxo[1',2'-dihydro[3,3'-bipyridine]]-2-yl)-3-methoxy-5,5-dimethyl-6-oxocyclohex-1-ene-1-carbonitrile | m/z (ES$^+$), [M + H]$^+$ = 382; HPLC purity = 99.5%. |

TABLE 8-continued

Compounds 109-120, 122-137, 139-158, 160-212, and 214-240

| Cmpd # | Structure | Name | Analytical Data |
|---|---|---|---|
| 172 | 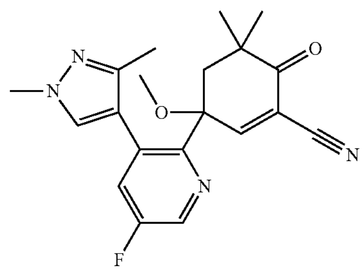 [SMILES: COC1(c2ncc(F)cc2-c2cn(C)nc2C)C=C(C#N)C(=O)C(C)(C)C1] | 3-[3-(1,3-dimethyl-1H-pyrazol-4-yl)-5-fluoropyridin-2-yl]-3-methoxy-5,5-dimethyl-6-oxocyclohex-1-ene-1-carbonitrile | m/z (ES$^+$), [M + H]$^+$ = 369; HPLC purity = 99.7%. |
| 173 | 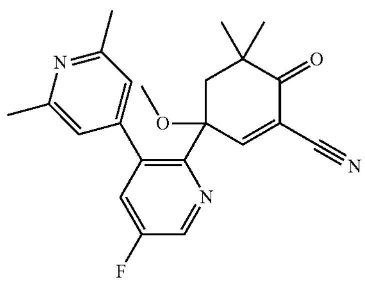 [SMILES: COC1(c2ncc(F)cc2-c2cc(C)nc(C)c2)C=C(C#N)C(=O)C(C)(C)C1] | 3-(5-fluoro-2',6'-dimethyl[3,4'-bipyridin]-2-yl)-3-methoxy-5,5-dimethyl-6-oxocyclohex-1-ene-1-carbonitrile | m/z (ES$^+$), [M + H]$^+$ = 380; HPLC purity = 99.4%. |
| 174 | 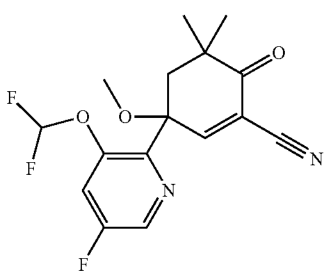 [SMILES: COC1(c2ncc(F)cc2OC(F)F)C=C(C#N)C(=O)C(C)(C)C1] | 3-[3-(difluoromethoxy)-5-fluoropyridin-2-yl]-3-methoxy-5,5-dimethyl-6-oxocyclohex-1-ene-1-carbonitrile | m/z (ES$^+$), [M + H]$^+$ = 341; HPLC purity = 99.2%. |
| 175 | 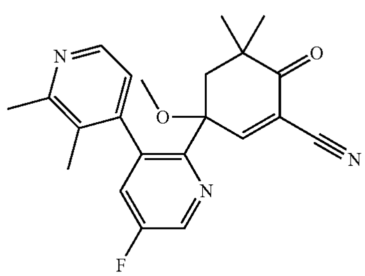 [SMILES: COC1(c2ncc(F)cc2-c2ccnc(C)c2C)C=C(C#N)C(=O)C(C)(C)C1] | 3-(5-fluoro-2',3'-dimethyl[3,4'-bipyridin]-2-yl)-3-methoxy-5,5-dimethyl-6-oxocyclohex-1-ene-1-carbonitrile | m/z (ES$^+$), [M + H]$^+$ = 380; HPLC purity = 98.7%. |
| 176 | 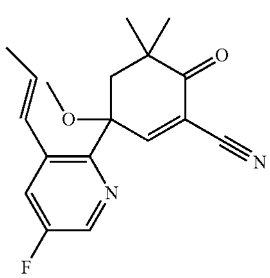 [SMILES: C/C=C/c1cc(F)cnc1C1(OC)C=C(C#N)C(=O)C(C)(C)C1] | 3-{5-fluoro-3-[(1E)-prop-1-en-1-yl]pyridin-2-yl}-3-methoxy-5,5-dimethyl-6-oxocyclohex-1-ene-1-carbonitrile | m/z (ES$^+$), [M + H]$^+$ = 315; HPLC purity = 99.5%. |

TABLE 8-continued

Compounds 109-120, 122-137, 139-158, 160-212, and 214-240

| Cmpd # | Structure | Name | Analytical Data |
|---|---|---|---|
| 177 | 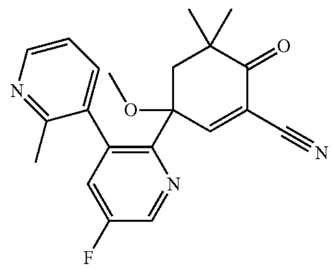 [SMILES: COC1(c2ncc(F)cc2-c2cccnc2C)C=C(C#N)C(=O)C(C)(C)C1] | 3-(5-fluoro-2'-methyl[3,3'-bipyridin]-2-yl)-3-methoxy-5,5-dimethyl-6-oxocyclohex-1-ene-1-carbonitrile | m/z (ES$^+$), [M + H]$^+$ = 366; HPLC purity = 97.5%. |
| 178 | 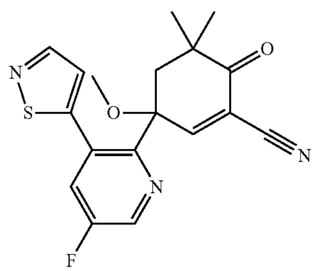 [SMILES: COC1(c2ncc(F)cc2-c2ccns2)C=C(C#N)C(=O)C(C)(C)C1] | 3-[5-fluoro-3-(1,2-thiazol-5-yl)pyridin-2-yl]-3-methoxy-5,5-dimethyl-6-oxocyclohex-1-ene-1-carbonitrile | m/z (ES$^+$), [M + H]$^+$ = 358; HPLC purity = 99.7%. |
| 179 | 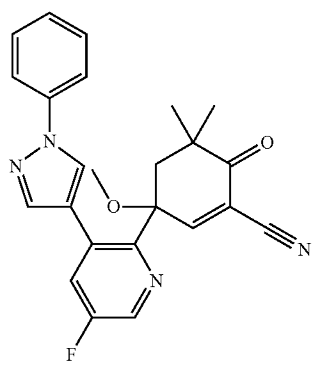 [SMILES: COC1(c2ncc(F)cc2-c2cnn(-c3ccccc3)c2)C=C(C#N)C(=O)C(C)(C)C1] | 3-[5-fluoro-3-(1-phenyl-1H-pyrazol-4-yl)pyridin-2-yl]-3-methoxy-5,5-dimethyl-6-oxocyclohex-1-ene-1-carbonitrile | m/z (ES$^+$), [M + H]$^+$ = 417; HPLC purity = 99.8%. |
| 180 | 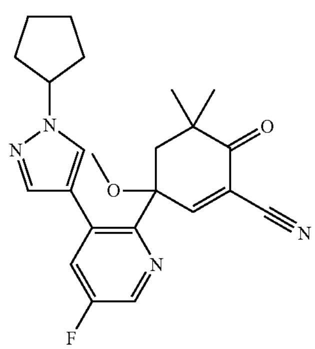 [SMILES: COC1(c2ncc(F)cc2-c2cnn(C3CCCC3)c2)C=C(C#N)C(=O)C(C)(C)C1] | 3-[3-(1-cyclopentyl-1H-pyrazol-4-yl)-5-fluoropyridin-2-yl]-3-methoxy-5,5-dimethyl-6-oxocyclohex-1-ene-1-carbonitrile | m/z (ES$^+$), [M + H]$^+$ = 409; HPLC purity = 99.7%. |
| 181 | 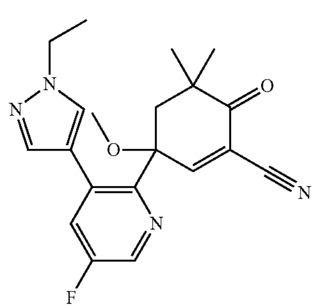 [SMILES: CCn1cc(-c2cc(F)cnc2C2(OC)C=C(C#N)C(=O)C(C)(C)C2)cn1] | 3-[3-(1-ethyl-1H-pyrazol-4-yl)-5-fluoropyridin-2-yl]-3-methoxy-5,5-dimethyl-6-oxocyclohex-1-ene-1-carbonitrile | m/z (ES$^+$), [M + H]$^+$ = 369; HPLC purity = 99.1%. |

TABLE 8-continued

Compounds 109-120, 122-137, 139-158, 160-212, and 214-240

| Cmpd # | Structure | Name | Analytical Data |
|---|---|---|---|
| 182 | 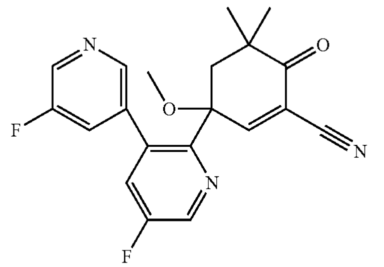 [SMILES: COC1(c2ncc(F)cc2-c2cncc(F)c2)C=C(C#N)C(=O)C(C)(C)C1] | 3-(5,5'-difluoro[3,3'-bipyridin]-2-yl)-3-methoxy-5,5-dimethyl-6-oxocyclohex-1-ene-1-carbonitrile | m/z (ES$^+$), [M + H]$^+$ = 370; HPLC purity = 99.6%. |
| 183 | 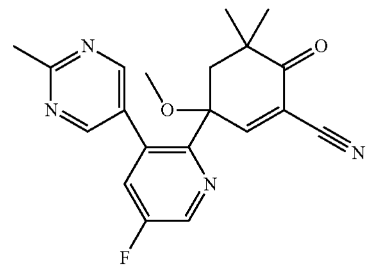 [SMILES: COC1(c2ncc(F)cc2-c2cnc(C)nc2)C=C(C#N)C(=O)C(C)(C)C1] | 3-[5-fluoro-3-(2-methylpyrimidin-5-yl)pyridin-2-yl]-3-methoxy-5,5-dimethyl-6-oxocyclohex-1-ene-1-carbonitrile | m/z (ES$^+$), [M + H]$^+$ = 367; HPLC purity = 97.4%. |
| 184 | 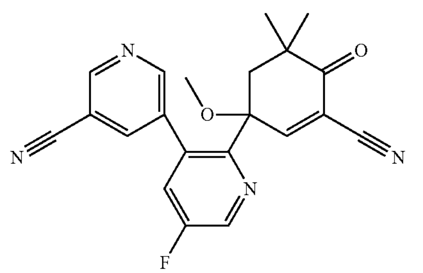 [SMILES: COC1(c2ncc(F)cc2-c2cncc(C#N)c2)C=C(C#N)C(=O)C(C)(C)C1] | 2'-(3-cyano-1-methoxy-5,5-dimethyl-4-oxocyclohex-2-en-1-yl)-5'-fluoro[3,3'-bypyridine]-5-carbonitrile | m/z (ES$^+$), [M + H]$^+$ = 377; HPLC purity = 99.2%. |
| 185 | 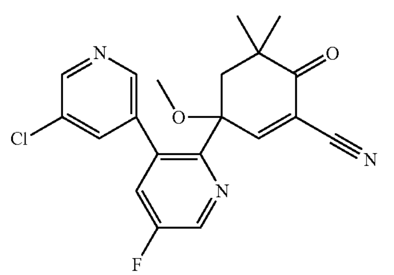 [SMILES: COC1(c2ncc(F)cc2-c2cncc(Cl)c2)C=C(C#N)C(=O)C(C)(C)C1] | 3-(5'-chloro-5-fluoro[3,3'-bypyridin]-2-yl)-3-methoxy-5,5-dimethyl-6-oxocyclohex-1-ene-1-carbonitrile | m/z (ES$^+$), [M + H]$^+$ = 386; HPLC purity = 99.1%. |
| 186 | 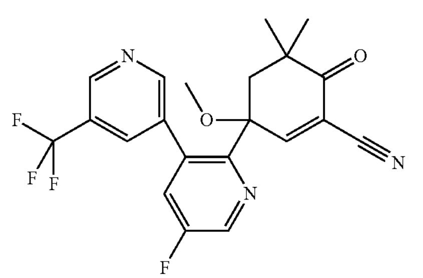 [SMILES: COC1(c2ncc(F)cc2-c2cncc(C(F)(F)F)c2)C=C(C#N)C(=O)C(C)(C)C1] | 3-[5-fluoro-5'-(trifluoromethyl)[3,3'-bypyridin]-2-yl]-3-methoxy-5,5-dimethyl-6-oxocyclohex-1-ene-1-carbonitrile | $^1$H NMR (400 MHz, DMSO-d$_6$) δ ppm 0.83 (s, 3H), 1.02 (s, 3H), 2.06 (d, J = 14.5 Hz, 1H), 2.22 (dd, J = 14.5, 1.3 Hz, 1H), 2.97 (s, 3H), 7.96 (dd, J = 9.3, 2.8 Hz, 1H), 8.36 (d, J = 2.3 Hz, 1H), 8.45 (s, 1H), 8.77 (d, J = 2.8 Hz, 1H), 8.98 (d, J = 2.0 Hz, 1H), 9.07 (dd, J = 2.2, 1.0 Hz, 1H); m/z (ES$^+$), [M + H]$^+$ = 420; |

TABLE 8-continued

Compounds 109-120, 122-137, 139-158, 160-212, and 214-240

| Cmpd # | Structure | Name | Analytical Data |
|---|---|---|---|
| | | | HPLC purity = 95.3%. |
| 187 | 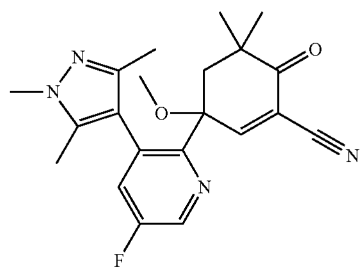 [SMILES: COC1(c2ncc(F)cc2-c2c(C)nn(C)c2C)C=C(C#N)C(=O)C(C)(C)C1] | 3-[5-fluoro-3-(1,3,5-trimethyl-1H-pyrazol-4-yl)pyridin-2-yl]-3-methoxy-5,5-dimethyl-6-oxocyclohex-1-ene-1-carbonitrile | m/z (ES+), [M + H]+ = 383; HPLC purity = 100%. |
| 188 | 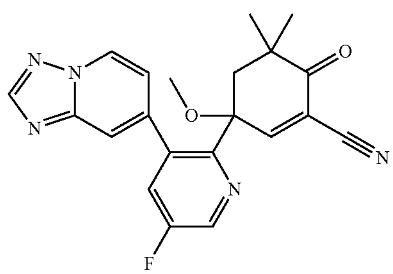 [SMILES: COC1(c2ncc(F)cc2-c2ccn3ncnc3c2)C=C(C#N)C(=O)C(C)(C)C1] | 3-[5-fluoro-3-([1,2,4]triazolo[1,5-a]pyridin-7-yl)pyridin-2-yl]-3-methoxy-5,5-dimethyl-6-oxocyclohex-1-ene-1-carbonitrile | m/z (ES+), [M + H]+ = 392; HPLC purity = 99.1%. |
| 189 | Enantiomer B (Isomer 1) | 3-[5-fluoro-3-(1,3,5-trimethyl-1H-pyrazol-4-yl)pyridin-2-yl]-3-methoxy-5,5-dimethyl-6-oxocyclohex-1-ene-1-carbonitrile | m/z (ES+), [M + H]+ = 383; HPLC purity = 100%. ee = 100%. |
| 190 | Enantiomer B (Isomer 1) | 3-[5-fluoro-3-([1,2,4]triazolo[1,5-a]pyridin-7-yl)pyridin-2-yl]-3-methoxy-5,5-dimethyl-6-oxocyclohex-1-ene-1-carbonitrile | m/z (ES+), [M + H]+ = 392; HPLC purity = 99.2%. ee = 99.8%. |
| 191 | 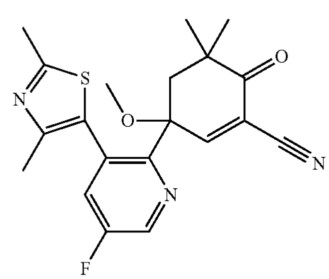 [SMILES: COC1(c2ncc(F)cc2-c2sc(C)nc2C)C=C(C#N)C(=O)C(C)(C)C1] | 3-[3-(2,4-dimethyl-1,3-thiazol-5-yl)-5-fluoropyridin-2-yl]-3-methoxy-5,5-dimethyl-6-oxocyclohex-1-ene-1-carbonitrile | m/z (ES+), [M + H]+ = 386; HPLC purity = 98.3%. |

TABLE 8-continued

Compounds 109-120, 122-137, 139-158, 160-212, and 214-240

| Cmpd # | Structure | Name | Analytical Data |
|---|---|---|---|
| 192 | 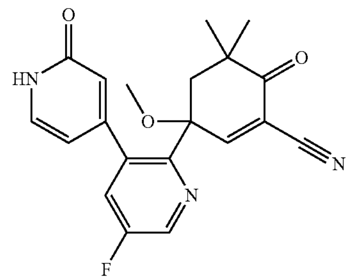 [SMILES: COC1(c2ncc(F)cc2-c2cc[nH]c(=O)c2)C=C(C#N)C(=O)C(C)(C)C1] | 3-(5-fluoro-2'-oxo[1',2'-dihydro[3,4'-bipyridine]]-2-yl)-3-methoxy-5,5-dimethyl-6-oxocyclohex-1-ene-1-carbonitrile | m/z (ES+), [M + H]+ = 368; HPLC purity = 96.3%. |
| 193 | 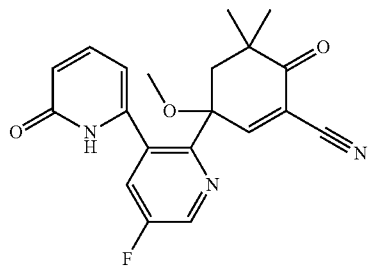 [SMILES: COC1(c2ncc(F)cc2-c2cccc(=O)[nH]2)C=C(C#N)C(=O)C(C)(C)C1] | 3-(5'-fluoro-6-oxo[1,6-dihydro[2,3'-bipyridine]]-2'-yl)-3-methoxy-5,5-dimethyl-6-oxocyclohex-1-ene-1-carbonitrile | m/z (ES+), [M + H]+ = 368; HPLC purity = 98.2%. |
| 194 | 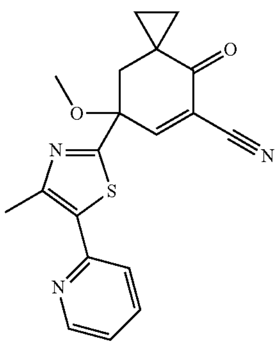 [SMILES: COC1(c2nc(C)c(-c3ccccn3)s2)C=C(C#N)C(=O)C2(CC2)C1] | 7-methoxy-7-[4-methyl-5-(pyridin-2-yl)-1,3-thiazol-2-yl]-4-oxospiro[2.5]oct-5-ene-5-carbonitrile | m/z (ES+), [M + H]+ = 352; HPLC purity = 97.0%. |
| 195 | Enantiomer B | 3-[3-(2,4-dimethyl-1,3-thiazol-5-yl)-5-fluoropyridin-2-yl]-3-methoxy-5,5-dimethyl-6-oxocyclohex-1-ene-1-carbonitrile | m/z (ES+), [M + H]+ = 386; HPLC purity = 99.3%. ee = 99.6%. |
| 196 | 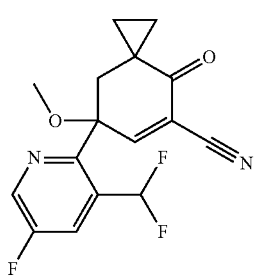 [SMILES: COC1(c2ncc(F)cc2C(F)F)C=C(C#N)C(=O)C2(CC2)C1] | 7-[3-(difluoromethyl)-5-fluoropyridin-2-yl]-7-methoxy-4-oxospiro[2.5]oct-5-ene-5-carbonitrile | m/z (ES+), [M + H]+ = 323; HPLC purity = 98.9%. |

TABLE 8-continued

Compounds 109-120, 122-137, 139-158, 160-212, and 214-240

| Cmpd # | Structure | Name | Analytical Data |
|---|---|---|---|
| 197 | 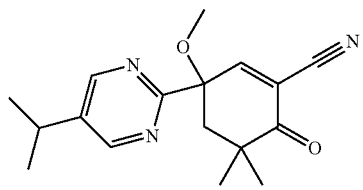 [SMILES: COC1(c2ncc(C(C)C)cn2)C=C(C#N)C(=O)C(C)(C)C1] | 3-methoxy-5,5-dimethyl-6-oxo-3-[5-(propan-2-yl)pyrimidin-2-yl]cyclohex-1-ene-1-carbonitrile, Isomer 1 | m/z (ES+), [M + H]+ = 300; HPLC purity = 98.6%. ee = 98.7%. |
| 198 | 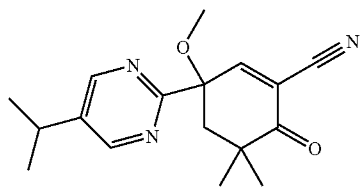 [SMILES: COC1(c2ncc(C(C)C)cn2)C=C(C#N)C(=O)C(C)(C)C1] | 3-methoxy-5,5-dimethyl-6-oxo-3-[5-(propan-2-yl)pyrimidin-2-yl]cyclohex-1-ene-1-carbonitrile, Isomer 2 | m/z (ES+), [M + H]+ = 300; HPLC purity = 99.2%. ee = 100%. |
| 199 | 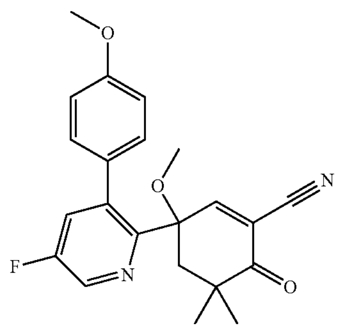 [SMILES: COc1ccc(-c2cc(F)cnc2C2(OC)C=C(C#N)C(=O)C(C)(C)C2)cc1] | 3-[5-fluoro-3-(4-methoxyphenyl)pyridin-2-yl]-3-methoxy-5,5-dimethyl-6-oxocyclohex-1-ene-1-carbonitrile, Isomer 1 | m/z (ES+), [M + H]+ = 381; HPLC purity = 96.5%. |
| 200 | 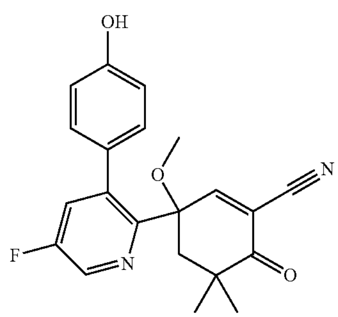 [SMILES: COC1(c2ncc(F)cc2-c2ccc(O)cc2)C=C(C#N)C(=O)C(C)(C)C1] | 3-[5-fluoro-3-(4-hydroxyphenyl)pyridin-2-yl]-3-methoxy-5,5-dimethyl-6-oxocyclohex-1-ene-1-carbonitrile, Isomer 1 | m/z (ES+), [M + H]+ = 367; HPLC purity = 99.7%. |
| 201 | (Enantiomer A) | 3-[5-fluoro-3-(2-methylimidazo[1,2-a]pyridin-6-yl)pyridin-2-yl]-3-methoxy-5,5-dimethyl-6-oxocyclohex-1-ene-1-carbonitrile (Enantiomer A) | m/z (ES+), [M + H]+ = 405; HPLC purity = 96.7%. |

TABLE 8-continued

Compounds 109-120, 122-137, 139-158, 160-212, and 214-240

| Cmpd # | Structure | Name | Analytical Data |
|---|---|---|---|
| 202 | 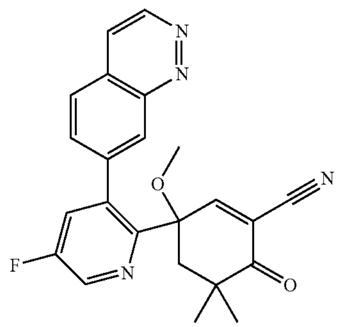 [SMILES: COC1(c2ncc(F)cc2-c2ccc3ccnnc3c2)C=C(C#N)C(=O)C(C)(C)C1] | 3-[3-(cinnolin-7-yl)-5-fluoropyridin-2-yl]-3-methoxy-5,5-dimethyl-6-oxocyclohex-1-ene-1-carbonitrile, Isomer 1 | m/z (ES+), [M + H]+ = 403; HPLC purity = 96.8%. |
| 203 | (Enantiomer A) | 3-[5-fluoro-3-(pyrazolo[1,5-a]pyridin-6-yl)pyridin-2-yl]-3-methoxy-5,5-dimethyl-6-oxocyclohex-1-ene-1-carbonitrile (Enantiomer A) | m/z (ES+), [M + H]+ = 403; HPLC purity = 95.0%. |
| 204 | (Enantiomer A) | 3-methoxy-5,5-dimethyl-3-(5-methylpyrimidin-2-yl)-6-oxocyclohex-1-ene-1-carbonitrile (Enantiomer A) | m/z (ES+), [M + H]+ = 272; HPLC purity = 96.8%. ee = 99.8%. |
| 205 | (Enantiomer A) | 3-[5-fluoro-3-(4-methyl-3,4-dihydro-2H-pyrido[3,2-b][1,4]oxazin-7-yl)pyridin-2-yl]-3-methoxy-5,5-dimethyl-6-oxocyclohex-1-ene-1-carbonitrile (Enantiomer A) | m/z (ES+), [M + H]+ = 423; HPLC purity = 96.2%. |
| 206 | (Enantiomer A) | 3-[5-chloro-3-(difluoromethyl)pyridin-2-yl]-3-methoxy-5,5-dimethyl-6-oxocyclohex-1-ene-1-carbonitrile (Enantiomer A) | m/z (ES+), [M + H]+ = 341; HPLC purity = 99.6%. ee = 98.13% |

TABLE 8-continued

Compounds 109-120, 122-137, 139-158, 160-212, and 214-240

| Cmpd # | Structure | Name | Analytical Data |
|---|---|---|---|
| 207 | (Enantiomer A) | 2-[3-cyano-1-methoxy-5,5-dimethyl-4-oxocyclohex-2-en-1-yl]-5-fluoro-N,N-dimethyl[3,4'-bipyridine]-2'-sulfonamide (Enantiomer A) | m/z (ES+), [M + H]+ = 459; HPLC purity = 93.1%. |
| 208 | (Enantiomer A) | 3-[5-chloro-3-(trifluoromethyl)pyridin-2-yl]-3-methoxy-5,5-dimethyl-6-oxocyclohex-1-ene-1-carbonitrile (Enantiomer A) | m/z (ES+), [M + H]+ = 359; HPLC purity = 99.8%. ee = 99.8% |
| 209 | (Enantiomer A) | 3-[5-fluoro-3-(6-methylpyridazin-4-yl)pyridin-2-yl]-3-methoxy-5,5-dimethyl-6-oxocyclohex-1-ene-1-carbonitrile (Enantiomer A) | m/z (ES+), [M + H]+ = 367; HPLC purity = 97.4%. |
| 210 | (Enantiomer A) | 3-{5-fluoro-3-[2-(trifluoromethyl)pyrimidin-5-yl]pyridin-2-yl}-3-methoxy-5,5-dimethyl-6-oxocyclohex-1-ene-1-carbonitrile (Enantiomer A) | m/z (ES+), [M + H]+ = 421; HPLC purity = 98.7%. |

TABLE 8-continued

Compounds 109-120, 122-137, 139-158, 160-212, and 214-240

| Cmpd # | Structure | Name | Analytical Data |
|---|---|---|---|
| 211 | (Enantiomer A) | 3-methoxy-5,5-dimethyl-6-oxo-3-[5-(trifluoromethyl)pyrimidin-2-yl]cyclohex-1-ene-1-carbonitrile (Enantiomer A) | m/z (ES$^+$), [M + H]$^+$ = 326; HPLC purity = 99.3%. ee = 99.3% |
| 212 | (Enantiomer A) | 3-[5-fluoro-3-([1,2,4]triazolo[1,5-a]pyridin-6-yl)pyridin-2-yl]-3-methoxy-5,5-dimethyl-6-oxocyclohex-1-ene-1-carbonitrile (Enantiomer A) | m/z (ES$^+$), [M + H]$^+$ = 392; HPLC purity = 99.6%. |
| 214 | 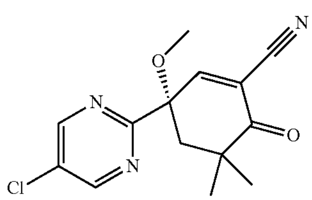 [SMILES: CO[C@]1(c2ncc(Cl)cn2)C=C(C#N)C(=O)C(C)(C)C1] | (3S)-3-(5-chloropyrimidin-2-yl)-3-methoxy-5,5-dimethyl-6-oxocyclohex-1-ene-1-carbonitrile | m/z (ES$^+$), [M + H]$^+$ = 292; HPLC purity = 99.0%. |
| 215 | (Enantiomer A) | 3-[5-fluoro-5'-(trifluoromethyl)[3,3'-bipyridin]-2-yl]-3-methoxy-5,5-dimethyl-6-oxocyclohex-1-ene-1-carbonitrile (Enantiomer A) | m/z (ES$^+$), [M + H]$^+$ = 420; HPLC purity = 99.7%. |
| 216 | (Enantiomer A) | 3-(5-fluoropyrimidin-2-yl)-3-methoxy-5,5-dimethyl-6-oxocyclohex-1-ene-1-carbonitrile (Enantiomer A) | m/z (ES$^+$), [M + H]$^+$ = 276; HPLC purity = 99.7%. ee = 99.7&. |

TABLE 8-continued

Compounds 109-120, 122-137, 139-158, 160-212, and 214-240

| Cmpd # | Structure | Name | Analytical Data |
|---|---|---|---|
| 217 | (Enantiomer A) | 2'-[3-cyano-1-methoxy-5,5-dimethyl-4-oxocyclohex-2-en-1-yl]-5'-fluoro[3,3'-bipyridine]-4-carbonitrile (Enantiomer A) | m/z (ES$^+$), [M + H]$^+$ = 377; HPLC purity = 99.5%. |
| 218 | (Enantiomer A) | 3-(5'-chloro-5-fluoro-2'-methoxy[3,4'-bipyridin]-2-yl)-3-methoxy-5,5-dimethyl-6-oxocyclohex-1-ene-1-carbonitrile (Enantiomer A) | m/z (ES$^+$), [M + H]$^+$ = 416; HPLC purity = 99.3%. |
| 219 | (Enantiomer A) | 3-[5-fluoro-3-(pyrazolo[1,5-a]pyridin-3-yl)pyridin-2-yl]-3-methoxy-5,5-dimethyl-6-oxocyclohex-1-ene-1-carbonitrile (Enantiomer A) | m/z (ES$^+$), [M + H]$^+$ = 391; HPLC purity = 99.6%. |
| 220 | (Enantiomer A) | 3-[5-fluoro-3-(pyridazin-4-yl)pyridin-2-yl]-3-methoxy-5,5-dimethyl-6-oxocyclohex-1-ene-1-carbonitrile (Enantiomer A) | m/z (ES$^+$), [M + H]$^+$ = 353; HPLC purity = 98.7%. |

TABLE 8-continued

Compounds 109-120, 122-137, 139-158, 160-212, and 214-240

| Cmpd # | Structure | Name | Analytical Data |
|---|---|---|---|
| 221 | (Enantiomer A) | 3-{5-fluoro-5'-[(propan-2-yl)sulfonyl][3,3'-bipyridin]-2-yl}-3-methoxy-5,5-dimethyl-6-oxocyclohex-1-ene-1-carbonitrile (Enantiomer A) | m/z (ES$^+$), [M + H]$^+$ = 458; HPLC purity = 97.0%. |
| 222 | (Enantiomer A) | 3-[5'-(2-cyanopropan-2-yl)-5-fluoro[3,3'-bipyridin]-2-yl]-3-methoxy-5,5-dimethyl-6-oxocyclohex-1-ene-1-carbonitrile (Enantiomer A) | m/z (ES$^+$), [M + H]$^+$ = 419; HPLC purity = 99.0%. |
| 223 | (Enantiomer A) | 3-[5'-(difluoromethoxy)-5-fluoro[3,3'-bipyridin]-2-yl]-3-methoxy-5,5-dimethyl-6-oxocyclohex-1-ene-1-carbonitrile (Enantiomer A) | m/z (ES$^+$), [M + H]$^+$ = 418; HPLC purity = 97.4%. |
| 224 | (Enantiomer A) | 3-(3-chloro-5-fluoropyridin-2-yl)-3-methoxy-5,5-dimethyl-6-oxocyclohex-1-ene-1-carbonitrile (Enantiomer A) | m/z (ES$^+$), [M + H]$^+$ = 309; HPLC purity = 99.0%. ee = 99.0%. |
| 225 | (Enantiomer A) | 3-(3,5-dichloropyridin-2-yl)-3-methoxy-5,5-dimethyl-6-oxocyclohex-1-ene-1-carbonitrile (Enantiomer A) | m/z (ES$^+$), [M + H]$^+$ = 325; HPLC purity = 99.8%. ee = 99.5%. |

TABLE 8-continued

Compounds 109-120, 122-137, 139-158, 160-212, and 214-240

| Cmpd # | Structure | Name | Analytical Data |
|---|---|---|---|
| 226 | (Enantiomer A) | 3-[5-fluoro-3-(imidazo[1,2-a]pyridin-6-yl)pyridin-2-yl]-3-methoxy-5,5-dimethyl-6-oxocyclohex-1-ene-1-carbonitrile (Enantiomer A) | m/z (ES$^+$), [M + H]$^+$ = 391; HPLC purity = 99.8%. |
| 227 | (Enantiomer A) | 2'-(3-cyano-1-methoxy-5,5-dimethyl-4-oxocyclohex-2-en-1-yl)-5'-fluoro-N,N-dimethyl[3,3'-bipyridine]-5-carboxamide (Enantiomer A) | m/z (ES$^+$), [M + H]$^+$ = 423; HPLC purity = 99.5%. ee = 99.8%. |
| 228 | (Enantiomer A) | 3-{5-fluoro-3-[1-(2,2,2-trifluoroethyl)-1H-pyrazol-4-yl]pyridin-2-yl}-3-methoxy-5,5-dimethyl-6-oxocyclohex-1-ene-1-carbonitrile (Enantiomer A) | m/z (ES$^+$), [M + H]$^+$ = 423; HPLC purity = 99.3%. ee = 99.2%. |
| 229 | (Enantiomer A) | 3-[5-fluoro-3-(2-methyl[1,2,4]triazolo[1,5-a]pyridin-7-yl)pyridin-2-yl]-3-methoxy-5,5-dimethyl-6-oxocyclohex-1-ene-1-carbonitrile (Enantiomer A) | m/z (ES$^+$), [M + H]$^+$ = 406; HPLC purity = 98.3%. ee = 95.7%. |

TABLE 8-continued

Compounds 109-120, 122-137, 139-158, 160-212, and 214-240

| Cmpd # | Structure | Name | Analytical Data |
|---|---|---|---|
| 230 | (Enantiomer A) | 3-(5,5'-difluoro-6'-methyl[3,3'-bipyridin]-2-yl)-3-methoxy-5,5-dimethyl-6-oxocyclohex-1-ene-1-carbonitrile (Enantiomer A) | m/z (ES$^+$), [M + H]$^+$ = 384; HPLC purity = 99.8%. ee = 97.5%. |
| 231 | (Enantiomer A) | 3-[3-(5,6-dihydro-4H-pyrrolo[1,2-v]pyrazol-3-yl)-5-fluoropyridin-2-yl]-3-methoxy-5,5-dimethyl-6-oxocyclohex-1-ene-1-carbonitrile (Enantiomer A) | m/z (ES$^+$), [M + H]$^+$ = 381; HPLC purity = 98.0%. ee = 98.0%. |
| 232 | (Enantiomer A) | 3-(5'-cyclopropyl-5-fluoro[3,3'-bipyridin]-2-yl)-3-methoxy-5,5-dimethyl-6-oxocyclohex-1-ene-1-carbonitrile (Enantiomer A) | m/z (ES$^+$), [M + H]$^+$ = 392; HPLC purity = 99.2%. ee = 99.0%. |
| 233 | (Enantiomer A) | 3-(5'-ethyl-5-fluoro[3,3'-bipyridin]-2-yl)-3-methoxy-5,5-dimethyl-6-oxocyclohex-1-ene-1-carbonitrile (Enantiomer A) | m/z (ES$^+$), [M + H]$^+$ = 380; HPLC purity = 99.2%. ee = 99.0%. |

TABLE 8-continued

Compounds 109-120, 122-137, 139-158, 160-212, and 214-240

| Cmpd # | Structure | Name | Analytical Data |
|---|---|---|---|
| 234 | (Enantiomer A) | 3-(5-fluoro-2'-methoxy-5'-methyl[3,3'-bipyridin]-2-yl)-3-methoxy-5,5-dimethyl-6-oxocyclohex-1-ene-1-carbonitrile (Enantiomer A) | m/z (ES$^+$), [M + H]$^+$ = 396; HPLC purity = 97.1%. ee = 99.7%. |
| 235 | (Enantiomer A) | 3-[5-fluoro-5'-(methylsulfonyl)[3,3'-bipyridin]-2-yl)-3-methoxy-5,5-dimethyl-6-oxocyclohex-1-ene-1-carbonitrile (Enantiomer A) | m/z (ES$^+$), [M + H]$^+$ = 430; HPLC purity = 99.3%. ee = 99.9%. |
| 236 | (Enantiomer A) | 3-[5-fluoro-2'-(trifluoromethyl)[3,4'-bipyridin]-2-yl]-3-methoxy-5,5-dimethyl-6-oxocyclohex-1-ene-1-carbonitrile (Enantiomer A) | m/z (ES$^+$), [M + H]$^+$ = 420; HPLC purity = 99.7%. ee = 98.8%. |
| 237 | (Enantiomer A) | 3-(5-fluoro-5'-methoxy[3,3'-bipyridin]-2-yl)-3-methoxy-5,5-dimethyl-6-oxocyclohex-1-ene-1-carbonitrile (Enantiomer A) | m/z (ES$^+$), [M + H]$^+$ = 382; HPLC purity = 99.4%. ee = 100%. |

TABLE 8-continued

Compounds 109-120, 122-137, 139-158, 160-212, and 214-240

| Cmpd # | Structure | Name | Analytical Data |
|---|---|---|---|
| 238 | (Enantiomer A) | 7-[5-chloro-3-(difluoromethyl)pyridin-2-yl]-7-methoxy-4-oxospiro[2.5]oct-5-ene-5-carbonitrile (Enantiomer A) | m/z (ES$^+$), [M + H]$^+$ = 339; HPLC purity = 99.8%. ee = 97.4%. |
| 239 | 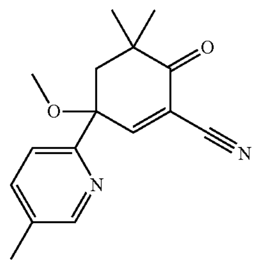 [SMILES: COC1(c2ccc(C)cn2)C=C(C#N)C(=O)C(C)(C)C1] | 3-methoxy-5,5-dimethyl-3-(5-methylpyridin-2-yl)-6-oxocyclohex-1-ene-1-carbonitrile | |
| 240 | 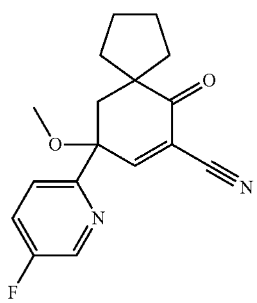 [SMILES: COC1(c2ccc(F)cn2)C=C(C#N)C(=O)C2(CCCC2)C1] | 9-(5-fluropyridin-2-yl)-9-methoxy-6-oxospiro[4.5]dec-7-ene-7-carbonitrile | m/z (ES$^+$), [M + H]$^+$ = 301; HPLC purity = 94.6%. |

Compound 159: 4-(6-bromo-2-pyridyl)-4-methoxy-1,1-dioxo-2,3-dihydrothiopyran-6-carbonitrile

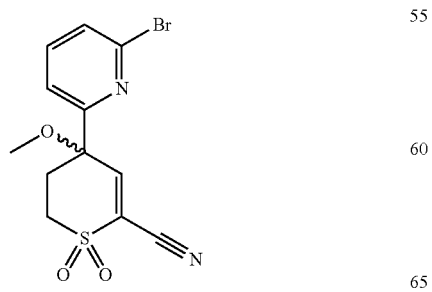

Compound 159, Step 1: 4-(6-bromo-2-pyridyl)-1,1-dioxo-thian-4-ol

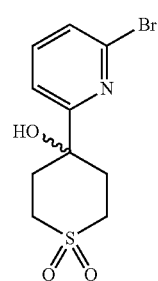 [SMILES: O=S1(=O)CCC(O)(c2cccc(Br)n2)CC1]

2.50M n-BuLi in hexanes (24.0 mL, 60.0 mmol) was added drop-wise over 30 m via a syringe-pump to a mixture of 2,6-dibromopyridine (13.0 g, 55.0 mmol) in DCM (65.0 mL) at −78° C. After the addition was complete, the mixture was stirred for 1 h at −78° C. 1,1-Dioxothian-4-one (7.41 g, 50.0 mmol) was added portion-wise. After the addition was complete, the mixture was stirred at −78° C. for 2 h. The mixture was warmed to 23° C. and stirred for 18 h. Sat. NaHCO₃ (150 mL) was added, and the aq. phase was extracted with DCM (3×100 mL). The combined organic phases were washed with brine (100 mL), dried (MgSO₄), filtered, and concentrated under reduced pressure. The product was purified by silica gel chromatography (220 g cartridge), eluting with DCM and EtOAc (0-100%), to provide the title compound as a solid (6.48 g; 42%). ¹H NMR (500 MHz, CDCl₃) δ 7.64 (t, J=7.8 Hz, 1H), 7.49 (dd, J=7.9, 0.7 Hz, 1H), 7.35 (dd, J=7.7, 0.7 Hz, 1H), 4.75 (s, 1H), 3.66 (td, J=13.8, 3.7 Hz, 2H), 3.04-2.95 (m, 2H), 2.61 (td, J=13.9, 3.5 Hz, 2H), 2.12-2.02 (m, 2H). m/z (ES+), [M+H]⁺: 306.0.

Compound 159, Step 2:
4-(6-bromo-2-pyridyl)-4-methoxy-thiane
1,1-dioxide

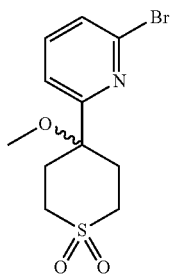 [SMILES: COC1(c2cccc(Br)n2)CCS(=O)(=O)CC1]

To a solution of 4-(6-bromo-2-pyridyl)-1,1-dioxo-thian-4-ol (3.06 g, 10.0 mmol) in THF (40.0 mL) at 0° C. was added 60 wt % NaH in mineral oil (0.48 g, 12.0 mmol) in portions. The mixture was warmed to 23° C. and stirred for 30 min. Iodomethane (0.750 mL, 12.0 mmol) was added, and the resulting mixture was stirred at 23° C. for 1.5 h. After cooling down to 0° C., water (50.0 mL) was slowly added. The aq. phase was extracted with EtOAc (3×75.0 mL). The combined organic phases were washed with brine (100 mL), dried (MgSO₄), filtered and concentrated under reduced pressure. The residue was purified by silica gel chromatography (80 g cartridge) eluting with DCM and EtOAc (0-20%) to provide the title compound as a solid (2.89 g; 90%). ¹H NMR (500 MHz, CDCl₃) δ 7.60 (t, J=7.8 Hz, 1H), 7.48-7.39 (m, 2H), 3.45-3.33 (m, 2H), 3.11 (s, 3H), 3.02-2.91 (m, 2H), 2.83-2.66 (m, 2H), 2.47-2.31 (m, 2H). m/z (ES+), [M+H]⁺: 320.2.

Compound 159, Step 3: 4-(6-bromo-2-pyridyl)-4-methoxy-1,1-dioxo-thiane-2-carbaldehyde

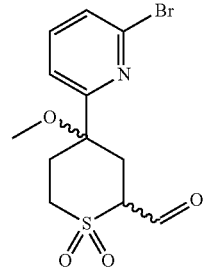 [SMILES: COC1(c2cccc(Br)n2)CCS(=O)(=O)C(C=O)C1]

1.0 M NaHMDS in THF (2.00 mL, 2.00 mmol) was added drop-wise to a solution of 4-(6-bromo-2-pyridyl)-4-methoxy-thiane 1,1-dioxide (500 mg, 1.56 mmol) in THF (5.00 mL) at −78° C. The mixture was stirred for 45 mat −78° C., and a solution of ethyl formate (0.140 mL, 1.72 mmol) in THF (1.00 mL) was added. The mixture was stirred at −78° C. for 45 m and warmed up to 23° C. Sat. NH₄Cl (20.0 mL) was added, and the aq. phase was extracted with EtOAc (3×20.0 mL). The combined organic phases were washed with brine (20.0 mL), dried (MgSO₄), filtered, and concentrated under reduced pressure. The product was purified by silica gel chromatography (4 g cartridge), eluting with hexanes and EtOAc (20-80%), to provide the title compound as a solid (152 mg, 28%). ¹H NMR (500 MHz, CDCl₃) δ 10.11-9.87 (m, 1H), 7.68-7.54 (m, 1H), 7.52-7.38 (m, 2H), 4.38-4.29 (m, 1H), 3.56-3.42 (m, 1H), 3.14-3.00 (m, 4H), 2.87-2.76 (m, 1H), 2.74-2.65 (m, 1H), 2.59-2.52 (m, 1H), 2.51-2.43 (m, 1H). m/z (ES+), [M+H]⁺: 348.2.

Compound 159, Step 4: (2E/2Z)-4-(6-bromo-2-pyridyl)-4-methoxy-1,1-dioxo-thiane-2-carbaldehyde oxime

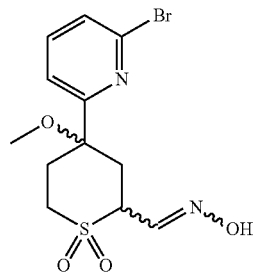 [SMILES: COC1(c2cccc(Br)n2)CCS(=O)(=O)C(C=NO)C1]

To a solution of 4-(6-bromo-2-pyridyl)-4-methoxy-1,1-dioxo-thiane-2-carbaldehyde (197 mg, 0.570 mmol) in EtOH (2.25 mL) were added hydroxylamine hydrochloride (78.7 mg, 1.13 mmol) and sodium acetate (92.9 mg, 1.13 mmol). The mixture was stirred at 23° C. for 1 h. The mixture was concentrated under reduced pressure. Water (20.0 mL) was added, and the aq. phase was extracted with EtOAc (3×20.0 mL). The combined organic phases were washed with brine (20.0 mL), dried (MgSO₄), filtered, and concentrated under reduced pressure to provide the title compound as a solid (157 mg, 76%). ¹H NMR (500 MHz, CDCl₃) δ 7.64-7.54 (m, 2H), 7.49-7.36 (m, 2H), 4.28 (ddd, J=12.9, 6.5, 3.1 Hz, 1H), 3.62-3.37 (m, 1H), 3.13 (s, 3H), 3.12-3.02 (m, 1H), 2.86-2.76 (m, 2H), 2.44 (dt, J=16.2, 3.6 Hz, 2H), 2.04 (s, 1H). m/z (ES+), [M+H]$^+$: 363.2.

Compound 159, Step 5: 4-(6-bromo-2-pyridyl)-4-methoxy-1,1-dioxo-thiane-2-carbonitrile

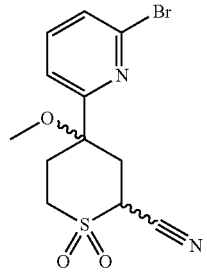 [SMILES: COC1(c2cccc(Br)n2)CCS(=O)(=O)C(C#N)C1]

To a stirred solution of (2E/2Z)-4-(6-bromo-2-pyridyl)-4-methoxy-1,1-dioxo-thiane-2-carbaldehyde oxime (153 mg, 0.420 mmol) in THF (4.00 mL) cooled to 0° C. were added NEt$_3$ (0.470 mL, 3.37 mmol) and a solution of 1.0 M SOCl$_2$ in DCM (1.68 mL, 1.68 mmol) drop-wise. The mixture was stirred at 0° C. for 1 h. Water (20.0 mL) was added, and the aq. phase was extracted with EtOAc (3×20.0 mL). The combined organic phases were washed with brine (20.0 mL), dried (MgSO$_4$), filtered, and concentrated under reduced pressure. The product was purified by silica gel chromatography (12 g cartridge), eluting with hexanes and EtOAc (0-70%), to provide the title compound as a solid (108 mg; 74%). $^1$H NMR (500 MHz, CDCl$_3$) δ 7.70-7.57 (m, 1H), 7.54-7.39 (m, 2H), 4.44 (dd, J=12.9, 3.3 Hz, 1H), 3.50-3.35 (m, 1H), 3.27-3.01 (m, 4H), 3.01-2.79 (m, 2H), 2.77-2.63 (m, 1H), 2.54-2.40 (m, 1H). m/z (ES+), [M+H]$^+$: 345.2.

Compound 159, Step 6: 4-(6-bromo-2-pyridyl)-4-methoxy-1,1-dioxo-2,3-dihydrothiopyran-6-carbonitrile

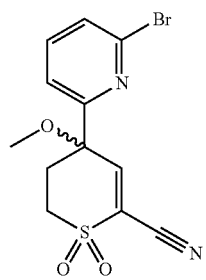 [SMILES: COC1(c2cccc(Br)n2)C=C(C#N)S(=O)(=O)CC1]

A solution of 4-(6-bromo-2-pyridyl)-4-methoxy-1,1-dioxo-thiane-2-carbonitrile (33.0 mg, 0.100 mmol) in THF (1.00 mL) was cooled to −78° C., and 1.0M KHMDS in THF (0.110 mL, 0.110 mmol) was added drop-wise. The mixture was stirred at −78° C. for 45 m. A solution of phenylselenium chloride (23.8 mg, 0.120 mmol) in THF (0.500 mL) was added drop-wise. After the addition complete, the mixture was warmed to 0° C. and stirred for 2.5 h. Sat. NH$_4$Cl (10 mL) was added, and the aq. phase was extracted with EtOAc (3×10.0 mL). The combined organic phases were washed with brine (10.0 mL), dried (MgSO$_4$), filtered and concentrated under reduced pressure. The residue was dissolved in DCM (1.00 mL) and cooled down to 0° C. 35 wt % H$_2$O$_2$ in water (0.190 mL, 1.91 mmol) was added drop-wise, and the mixture was vigorously stirred at 0° C. for 30 m. Water (20.0 mL) was added, and the aq. phase was extracted with EtOAc (3×20.0 mL). The combined organic phases were washed with brine (20.0 mL), dried (MgSO$_4$), filtered, and concentrated under reduced pressure. The product was purified by silica gel chromatography (4 g cartridge), eluting with hexanes and EtOAc (0-60%), to afford the title compound as a solid (7.90 mg, 24%). $^1$H NMR (500 MHz, CDCl$_3$) δ 7.68 (t, J=7.8 Hz, 1H), 7.53 (dd, J=7.9, 0.8 Hz, 1H), 7.50 (dd, J=7.7, 0.8 Hz, 1H), 7.34-7.31 (m, 1H), 3.68 (ddd, J=14.0, 9.7, 3.4 Hz, 1H), 3.56 (ddd, J=14.0, 8.1, 3.1 Hz, 1H), 3.29 (s, 3H), 2.80-2.63 (m, 2H). m/z (ES+), [M+H]$^+$: 343.2.

Example 2

Confirmation of Absolute Configuration of Compound 42

The Keap1 (G48-D180) [S172A] (referred to as 'Keap1N-BTB' hereinafter) plasmid fused to N-terminal hexa-histidine tag and TEV cleavge sequence was transformed in *Escherichia coli* (BL21 Gold DE3 competent cells), and grown in 50 ml Teriffic Broth (TB) supplemented with 100 μg/ml kanamycin and 50 μg/ml Tetracyclin at 37° C. overnight. This overnight culture was used to inoculate 3 L TB supplemented with 50 μg/mL kanamycin and 50 μg/mL Tetracyclin, and grown at 37° C. until OD$_{600}$ reached ~0.6, followed by induction with 0.2 mM IPTG. Expression was allowed to continue overnight at 18° C., and cells were harvested by centrifugation (4,400×g, 10 min, 4° C.). The resulting cell pellet (50 g cell weight) was resuspended in 200 mL of lysis buffer (40 mM HEPES pH 8.0, 300 mM NaCl, 20 mM Imidazole, 1 mM TCEP) supplemented with 2000 U Benzonase (Merck), four tablet of Complete EDTA-free protease inhibitor (Roche Applied Science), and 2.5 mg/mL lysozyme (Sigma Aldrich).

Cells were lysed by a single pass through a constant systems cell disrupter at 25 k psi. The lysate was clarified by centrifugation (69000×g, 1 hour, 4° C.) and incubated with 10 mL of Ni-NTA agarose resin (Qiagen) for 1 hour whilst rotating. The lysate was then passed through an Econocolumn (BioRad) and washed with 200 mL of lysis buffer. The protein was eluted by elution buffer (40 mM HEPES pH 8.0, 300 mM NaCl, 500 mM Imidazole, 1 mM TCEP). To cleave the hexa-histidine tag from the Keap1N-BTB, 0.1 mg of TEV protease was added per 10 mg of protein, and dialysed overnight against 5 L of dialysis buffer (40 mM HEPES pH 8.0, 300 mM NaCl, 10 mM Imidazole, 1 mM TCEP). After dialysing, the protein was passed through an Econocolumn containing 5 ml of Ni-NTA resin (Qiagen) to remove the uncleaned protein and the TEV protease. The flow through containing detagged Keap1N-BTB was collected and concentrated to 4 mL volume using centrifugal 10 k MWCO concentrator (Millipore). The concentrated protein was loaded on to HiLoad 26/60 Superdex 75 PG (GE Healthcare) pre-equilibrated in the storage buffer (25 mM Hepes pH 7.4, 150 mM NaCl, 1 mM TCEP). The fractions containing Keap1N-BTB protein from this size exclusion chromatography step were analysed on SDS PAGE, pooled, snap frozen, and stored at −80° C.

Keap1N-BTB protein in storage buffer at 11.5 mg/ml was mixed with compound stock solution to give final concentration of compound of 1 mM and left to incubate at 277K for 24 hours. The protein-compound complex was then crystallized using hanging-drop vapor diffusion method at 293K over reservoirs comprised of 12-20% (w/v) polyethylene glycol 3350 and 200 mM lithium acetate. Reservoir was supplemented with 20% (v/v) ethylene glycol for cryoprotection and crystals were frozen directly into liquid nitrogen. X-ray diffraction data were collected using synchrotron radiation (beamline i03, Diamond Light Source). The crystals belonged to space group $P6_522$ (a=b=42.7 Å, C=266.4 Å) and diffracted to 1.9 Å resolution. Data were scaled and merged using the Global Phasing Sofware autoPROC. The structure was phased by molecular replacement using the CCP4 suite of software and refined with BUSTER. The ligand was clearly defined in initial density maps and the protein inhibitor complex refined to give a final R-factor of 22% with good overall geometry. Data collection and refinement statistics are shown in Table 9.

TABLE 9

Crystallographic data collection and refinement statistics.

Data Collection

| | |
|---|---|
| Space Group | $P6_522$ |
| Cell (a, b, c, α, β, γ) | 42.71 Å, 42.71 Å, 266.39 Å, 90°, 90°, 120°. |
| Number of observations | 219222 |
| Number of unique reflections | 13062 |
| Resolution limits: overall (outer shell) | 36.9-18.7 Å (1.92-1.87 Å) |
| I/sigI | 17.2 (1.2) |
| Rmerge | 0.07 (2.36) |
| Redundancy | 16.8 (15.1 |
| Completeness | 99.8% (100%) |

Refinement

| | |
|---|---|
| Rwork/Rfree | 0.22/0.25 |
| RMSD (bonds) | 0.01 Å |
| RMSD (angles) | 1.04° |

Examination of Compound 42 covalently bound to Cys151 of Keap1N-BTB, established the S-configuration.

Example 3

Biological Activity

Purpose of the Assay

The purpose of this assay is to identify small molecule inhibitors of Keap1, preventing Keap1 binding to Nrf2, and thus activating the Nrf2 signalling pathway in HEK-293 ARE firefly luciferase transiently transfected cells. HEK-293 cells express wild-type Keap1 protein and therefore have low constitutive levels of Nrf2 protein and Nrf2-dependent transcription. The cell line was generated in house by transient transfection and possesses 2× tandem repeats of the ARE transcriptional response element upstream of firefly luciferase. When Keap1 is inhibited, Nrf2 signalling is activated, and there is an increase in luciferase expression and light emission.

Assay Workflow

Cryopreserved HEK ARE luciferase cells were rapidly thawed in a 37° C. water bath and resuspended in assay culture medium (DMEM, 10% FCS, 2 mM L-glutamine). The cell suspension was pelleted by centrifugation (5 mM; 300 g) using a Heraeus benchtop centrifuge. Supernatant was removed and the pellet was gently resuspended in 5 mL culture medium per vial. Cell viability and cell number was measured using an Invitrogen Countess automated cell counter (typical viability 80%), and cells were diluted to a density of $5.0 \times 10^5$ cells/mL.

Cells were then plated out into white 384-well plates (Greiner 781080) using a Multidrop Combi, 20 µL/well, to give 10,000 cells/well. As appropriate, test compounds had been added to wells prior to dispensing cells using an Echo 555 acoustic dispenser (Labcyte). Plates were left at room temperature for ~10 min to promote even cell settling across the plate before incubation for 18 h at 37° C., 95% humidity and 5% $CO_2$.

After 18 h incubation, plates were removed from the incubator and allowed to cool to room temperature for 30 min, before 10 µL per well SteadyGlo reagent detection reagent was added (as per manufacturer's instructions, 10 min before required 10 mL room temperature buffer was added to one vial of lyophilised substrate and inverted several times to fully dissolve). Plates were then incubated in the dark for 30 min before reading on an Envision plate reader.

Preparation of Compounds for Screening

Compounds were acoustically dispensed using a Labcyte Echo, using a 10 pt dose curve with a top concentration of 100 µM. Assay wells were backfilled with DMSO to a total of 60 nL to maintain 0.3% (v/v) DMSO through the assay.

Data Analysis Software and Calculation of Results

The Stimulator signal was defined using 30 µM tert-butyl hydroquinone (tBHQ) and the Neutral signal by DMSO vehicle control. All calculations were performed using GeneData.

In IBIS Column Calculations, Assay Type was set to 'Stimulator', and the Activity Threshold was set to 50.

Biological Results

Mean $EC_{50}$ values of compounds evaluated in the HEK293 luciferase assay are provided in Table 10. The mean values were calculated from anywhere from 1 to 20 individual measurements.

TABLE 10

EC50 values of compounds evaluated in the HEK293 luciferase assay

| Compound Number | HEK293 luciferase $EC_{50}$ (µM) |
|---|---|
| 1 | 0.408 |
| 2 | 0.228 |
| 3 | 0.424 |
| 4 | 1.144 |
| 5 | 0.010 |
| 6 | >10 |
| 7 | 0.082 |
| 8 | 0.186 |
| 9 | 0.269 |
| 10 | >30 |
| 11 | 0.085 |
| 12 | 0.119 |
| 13 | 10.000 |
| 14 | 0.012 |
| 15 | 0.024 |
| 16 | 0.660 |
| 17 | 0.309 |
| 18 | 0.265 |
| 19 | 1.242 |
| 20 | 0.126 |
| 21 | 0.452 |
| 22 | 0.045 |
| 23 | 0.056 |
| 24 | >10 |
| 25 | 0.070 |
| 26 | 0.024 |
| 27 | 0.180 |
| 28 | 0.036 |
| 29 | 0.091 |
| 30 | 0.458 |

TABLE 10-continued

EC50 values of compounds evaluated in the HEK293 luciferase assay

| Compound Number | HEK293 luciferase EC$_{50}$ (μM) |
|---|---|
| 31 | 0.019 |
| 32 | 0.055 |
| 33 | 0.383 |
| 34 | 0.012 |
| 35 | 0.039 |
| 36 | 0.096 |
| 37 | 0.086 |
| 38 | 0.132 |
| 39 | 0.125 |
| 40 | 0.038 |
| 41 | 0.011 |
| 42 | 0.033 |
| 43 | 0.129 |
| 44 | 0.037 |
| 45 | 0.028 |
| 46 | 0.304 |
| 47 | 0.008 |
| 48 | 0.006 |
| 49 | 0.138 |
| 50 | 0.030 |
| 51 | 0.048 |
| 52 | 0.074 |
| 53 | 0.133 |
| 54 | 0.363 |
| 55 | 0.014 |
| 56 | 0.179 |
| 57 | 0.047 |
| 59 | 0.261 |
| 60 | 0.153 |
| 61 | 0.079 |
| 62 | 0.015 |
| 63 | 0.018 |
| 64 | 0.145 |
| 65 | 0.247 |
| 66 | 0.126 |
| 67 | 0.239 |
| 68 | 0.070 |
| 69 | 0.002 |
| 70 | 0.015 |
| 71 | 0.009 |
| 72 | 0.006 |
| 73 | 0.007 |
| 74 | 0.015 |
| 75 | 0.036 |
| 76 | 0.003 |
| 77 | 0.004 |
| 78 | 0.002 |
| 79 | 0.074 |
| 80 | 0.002 |
| 81 | 0.002 |
| 82 | 0.052 |
| 83 | 0.070 |
| 84 | 0.006 |
| 85 | 0.006 |
| 86 | 0.009 |
| 87 | 0.017 |
| 88 | 0.009 |
| 89 | 0.011 |
| 90 | 0.011 |
| 92 | 0.067 |
| 93 | 0.005 |
| 94 | 0.021 |
| 96 | 0.007 |
| 98 | 0.079 |
| 99 | 0.066 |
| 100 | 0.077 |
| 101 | 0.033 |
| 102 | 0.073 |
| 103 | 0.077 |
| 104 | 0.045 |
| 105 | 0.036 |
| 106 | 0.120 |
| 107 | 0.037 |
| 108 | 1.896 |
| 109 | 0.185 |
| 110 | 0.109 |
| 111 | 0.065 |
| 112 | 0.371 |
| 113 | 0.343 |
| 114 | 0.235 |
| 115 | 0.106 |
| 116 | 0.382 |
| 117 | 0.034 |
| 118 | 0.355 |
| 119 | 0.141 |
| 120 | 0.245 |
| 122 | 0.043 |
| 123 | 0.061 |
| 124 | 0.027 |
| 125 | 0.236 |
| 126 | 0.085 |
| 127 | 0.267 |
| 128 | 0.145 |
| 129 | 0.136 |
| 130 | 0.153 |
| 131 | 0.464 |
| 132 | 0.150 |
| 133 | 0.076 |
| 135 | 0.244 |
| 137 | 0.047 |
| 139 | 0.381 |
| 140 | 0.140 |
| 141 | 0.335 |
| 142 | 0.060 |
| 143 | 0.139 |
| 144 | 0.389 |
| 145 | 0.065 |
| 147 | 0.022 |
| 148 | 0.252 |
| 149 | 0.201 |
| 150 | 0.147 |
| 151 | 0.034 |
| 152 | 0.047 |
| 153 | 7.089 |
| 154 | 0.053 |
| 155 | 0.161 |
| 156 | 0.249 |
| 157 | 0.448 |
| 158 | 0.021 |
| 160 | 0.020 |
| 161 | 0.014 |
| 163 | 0.054 |
| 164 | 0.028 |
| 165 | 0.151 |
| 166 | 0.014 |
| 167 | 0.018 |
| 168 | 0.012 |
| 169 | 0.173 |
| 170 | 0.012 |
| 171 | 0.136 |
| 172 | 0.008 |
| 173 | 0.015 |
| 174 | 0.041 |
| 175 | 0.174 |
| 176 | 0.019 |
| 177 | 0.103 |
| 178 | 0.052 |
| 179 | 0.007 |
| 180 | 0.115 |
| 181 | 0.068 |
| 182 | 0.105 |
| 183 | 0.121 |
| 184 | 0.121 |
| 185 | 0.008 |
| 186 | 0.075 |
| 187 | 0.077 |
| 188 | 0.023 |
| 189 | 1.531 |

TABLE 10-continued

EC50 values of compounds evaluated in the HEK293 luciferase assay

| Compound Number | HEK293 luciferase EC$_{50}$ (μM) |
|---|---|
| 190 | 1.682 |
| 191 | 0.012 |
| 192 | >10 |
| 193 | >10 |
| 194 | 0.203 |
| 195 | 1.298 |
| 196 | 0.046 |
| 201 | 0.182 |
| 203 | 0.006 |
| 204 | 0.009 |
| 205 | 0.052 |
| 206 | 0.159 |
| 207 | 0.048 |
| 208 | 0.231 |
| 209 | 0.015 |
| 210 | 0.020 |
| 211 | 0.004 |
| 212 | 0.007 |
| 214 | 0.020 |
| 215 | 0.015 |
| 216 | 0.021 |
| 217 | 0.012 |
| 218 | 0.023 |
| 219 | 0.005 |
| 220 | 0.010 |
| 221 | 0.008 |
| 222 | 0.006 |
| 223 | 0.014 |
| 224 | 0.014 |
| 225 | 0.012 |
| 226 | 0.013 |
| 227 | 0.015 |
| 228 | 0.015 |
| 229 | 0.010 |
| 230 | 0.016 |
| 231 | 0.016 |
| 232 | 0.023 |
| 233 | 0.006 |
| 234 | 0.009 |
| 235 | 0.079 |
| 236 | 0.017 |
| 237 | 0.020 |
| 238 | 0.044 |
| 239 | 0.050 |
| 240 | 0.838 |

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject application have been discussed, the above specification is illustrative and not restrictive. Many variations of the subject of the application will become apparent to those skilled in the art upon review of this specification and the claims below. The full scope of the application should be determined by reference to the claims, along with their full scope of equivalents, and the specification, along with such variations.

The invention claimed is:

1. A compound of formula (I')

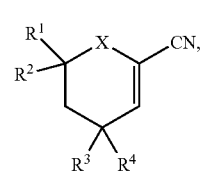

(I')

or a pharmaceutically acceptable salt thereof, wherein:
X is selected from —C(O)— and —S(O)$_2$—;
R$^1$ and R$^2$ each independently is selected from H and C$_{1-6}$ alkyl; or R$^1$ and R$^2$ taken together with the carbon to which they are attached form a spirocycloalkyl ring;
R$^3$ is selected from hydroxyl and optionally substituted alkoxy;
R$^4$ is selected from phenyl, pyridinyl, isoquinolinyl, pyrazinyl, thiophenyl, and thiazolyl; and
wherein R$^4$ is optionally substituted with one or more R$^5$; and
R$^5$, independently for each occurrence, is selected from halogen, optionally substituted alkyl, optionally substituted alkenyl, optionally substituted alkynyl, optionally substituted alkoxyl, optionally substituted cycloalkyl, optionally substituted cycloalkenyl, optionally substituted heterocycloalkyl, optionally substituted heterocycloalkenyl, optionally substituted phenyl, optionally substituted pyrazolyl, optionally substituted pyridinyl, optionally substituted thiazolyl, optionally substituted imidazolyl, optionally substituted pyrimidinyl, optionally substituted isoxazolyl, optionally substituted isothiazolyl, and optionally substituted triazolopyridinyl.

2. The compound of claim 1, or a pharmaceutically acceptable salt thereof, wherein X is —C(O)—.

3. The compound of claim 1, or a pharmaceutically acceptable salt thereof, wherein R$^4$ is pyridinyl optionally substituted with one or more R$^5$.

4. The compound of claim 1, or a pharmaceutically acceptable salt thereof, wherein:
R$^4$ is substituted with one or more R$^5$;
R$^5$, independently for each occurrence, is optionally substituted with one or more R$^6$; and
R$^6$, independently for each occurrence, is selected from halogen, CN, oxo, alkyl, alkenyl, alkynyl, alkoxy, alkyl sulfonyl, cycloalkyl, cycloalkenyl, heterocycloalkyl, heterocycloalkenyl, aryl, and heteroaryl.

5. The compound of claim 4, or a pharmaceutically acceptable salt thereof, wherein R$^6$, independently for each occurrence, is selected from halogen, CN, oxo, alkyl, alkoxy, alkyl sulfonyl, and cycloalkyl.

6. A compound of formula (Ia)

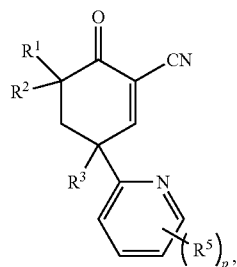

(Ia)

or a pharmaceutically acceptable salt thereof, wherein:

R¹ and R² each independently is selected from $C_{1-6}$ alkyl; or R¹ and R² taken together with the carbon to which they are attached form a spirocycloalkyl ring;

R³ is selected from hydroxyl and optionally substituted alkoxy;

R⁵, independently for each occurrence, is selected from halogen, CN, optionally substituted alkyl, optionally substituted alkenyl, optionally substituted alkynyl, optionally substituted alkylsulfonyl, optionally substituted alkoxyl, optionally substituted cycloalkyl, optionally substituted cycloalkenyl, optionally substituted heterocycloalkyl, optionally substituted heterocycloalkenyl, optionally substituted aryl, and optionally substituted heteroaryl; and p is selected from 0, 1, 2, 3, and 4.

7. The compound of claim 6, or a pharmaceutically acceptable salt thereof, wherein p is selected from 1 and 2.

8. The compound of claim 6, or a pharmaceutically acceptable salt thereof, wherein R⁵, independently for each occurrence, is selected from halogen, optionally substituted alkyl, optionally substituted alkenyl, optionally substituted alkynyl, optionally substituted alkoxyl, optionally substituted cycloalkyl, optionally substituted cycloalkenyl, optionally substituted heterocycloalkyl, optionally substituted heterocycloalkenyl, optionally substituted phenyl, optionally substituted pyrazolyl, optionally substituted pyridinyl, optionally substituted thiazolyl, optionally substituted imidazolyl, optionally substituted pyrimidinyl, optionally substituted isoxazolyl, optionally substituted isothiazolyl, and optionally substituted triazolopyridinyl.

9. The compound of claim 6, or a pharmaceutically acceptable salt thereof, wherein p is 2, and wherein one occurrence of R⁵ is —F and the other occurrence of R⁵ is —CH(F)₂.

10. The compound of claim 1 that is

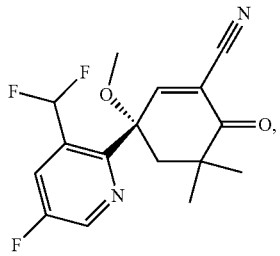 [SMILES: CO[C@]1(c2ncc(F)cc2C(F)F)C=C(C#N)C(=O)C(C)(C)C1]

or a pharmaceutically acceptable salt thereof.

11. The compound of claim 1 that is

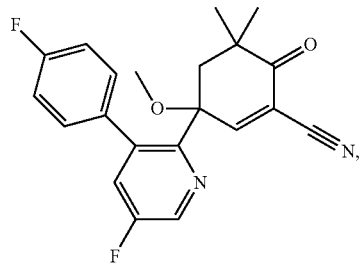 [SMILES: COC1(c2ncc(F)cc2-c2ccc(F)cc2)C=C(C#N)C(=O)C(C)(C)C1]

or a pharmaceutically acceptable salt thereof.

12. The compound of claim 1 that is

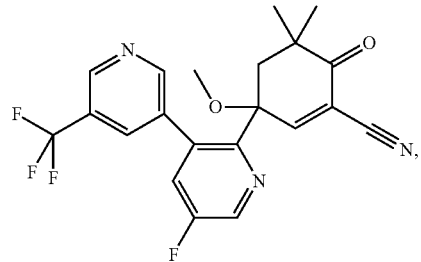 [SMILES: COC1(c2ncc(F)cc2-c2cncc(C(F)(F)F)c2)C=C(C#N)C(=O)C(C)(C)C1]

or a pharmaceutically acceptable salt thereof.

13. The compound of claim 1 that is

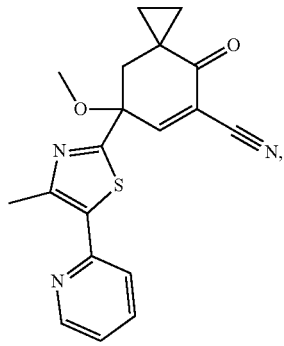 [SMILES: COC1(c2nc(C)c(-c3ccccn3)s2)C=C(C#N)C(=O)C2(CC2)C1]

or a pharmaceutically acceptable salt thereof.

14. A pharmaceutical composition comprising (a) a compound of claim 1; and (b) a pharmaceutically acceptable excipient.

15. A method of inhibiting a Keap1 protein, comprising contacting a cell with an effective amount of at least one compound of claim 1.

* * * * *